(12) United States Patent
Adams et al.

(10) Patent No.: US 9,856,204 B2
(45) Date of Patent: Jan. 2, 2018

(54) METHODS FOR INHIBITING MUSCLE ATROPHY

(75) Inventors: Christopher M. Adams, Iowa City, IA (US); Steven D. Kunkel, Iowa City, IA (US); Manish Suneja, Coralville, IA (US); Michael Welsh, Riverside, IA (US)

(73) Assignees: UNIVERSITY OF IOWA RESEARCH FOUNDATION, Iowa City, IA (US); THE UNITED STATES OF AMERICA AS REPRESENTED BY VETERANS AFFAIRS, Washington, DC (US)

( * ) Notice: Subject to any disclaimer, the term of this patent is extended or adjusted under 35 U.S.C. 154(b) by 1132 days.

(21) Appl. No.: 13/698,645

(22) PCT Filed: May 19, 2011

(86) PCT No.: PCT/US2011/037238
§ 371 (c)(1),
(2), (4) Date: Apr. 22, 2013

(87) PCT Pub. No.: WO2011/146768
PCT Pub. Date: Nov. 24, 2011

(65) Prior Publication Data
US 2013/0203712 A1 Aug. 8, 2013

Related U.S. Application Data

(60) Provisional application No. 61/346,813, filed on May 20, 2010, provisional application No. 61/445,488, filed on Feb. 22, 2011.

(51) Int. Cl.
| | |
|---|---|
| *C07C 61/29* | (2006.01) |
| *A61K 31/19* | (2006.01) |
| *A61K 31/191* | (2006.01) |
| *A61K 31/198* | (2006.01) |
| *A61K 31/215* | (2006.01) |
| *C07C 69/12* | (2006.01) |
| *C07C 69/757* | (2006.01) |
| *C07C 235/82* | (2006.01) |
| *C07D 265/30* | (2006.01) |
| *C07J 53/00* | (2006.01) |

(52) U.S. Cl.
CPC ........... *C07C 61/29* (2013.01); *A61K 31/19* (2013.01); *A61K 31/191* (2013.01); *A61K 31/198* (2013.01); *A61K 31/215* (2013.01); *C07C 69/12* (2013.01); *C07C 69/757* (2013.01); *C07C 235/82* (2013.01); *C07D 265/30* (2013.01); *C07J 53/002* (2013.01)

(58) Field of Classification Search
CPC ..... C07C 61/29; C07C 69/757; C07C 235/82; A61K 31/19; A61K 31/191; A61K 31/198; A61K 31/215; C07D 265/30; C07J 53/002
USPC ...... 514/169, 237.8, 510, 557, 623; 552/510
See application file for complete search history.

(56) References Cited

U.S. PATENT DOCUMENTS

| | | | |
|---|---|---|---|
| 2,910,470 A | 10/1959 | Baran et al. | |
| 3,466,279 A | 9/1969 | Marx | |
| 3,485,825 A | 12/1969 | Marx | |
| 3,539,449 A | 11/1970 | Marx | |
| 3,625,941 A | 12/1971 | Pappo et al. | |
| 3,903,089 A | 9/1975 | Vanstone | |
| 4,647,574 A | 3/1987 | Ienaga et al. | |
| 5,196,545 A | 3/1993 | Schermanz et al. | |
| 5,422,350 A | 6/1995 | Woolf | |
| 5,885,992 A * | 3/1999 | Ohgi .................... C07J 71/0005 514/245 |
| 5,985,924 A * | 11/1999 | Ishikawa ................ A61K 31/19 514/557 |
| 6,096,364 A | 8/2000 | Bok et al. | |
| 6,770,630 B2 | 8/2004 | Kashiwaba et al. | |
| 7,612,045 B2 | 11/2009 | Eldridge | |
| 2003/0153538 A1 | 8/2003 | Kuno et al. | |
| 2004/0086553 A1 | 5/2004 | Shinohara et al. | |
| 2004/0087557 A1 | 5/2004 | Steiner et al. | |
| 2004/0110663 A1 | 6/2004 | Dudek et al. | |
| 2005/0153968 A1 | 7/2005 | Bi et al. | |
| 2006/0025354 A1* | 2/2006 | Nair et al. ...................... 514/27 |
| 2006/0079562 A1 | 4/2006 | Ewing et al. | |
| 2007/0014719 A1 | 1/2007 | Reading et al. | |
| 2008/0119426 A1 | 5/2008 | Dale | |

(Continued)

FOREIGN PATENT DOCUMENTS

| | | |
|---|---|---|
| CN | 1582990 A | 2/2005 |
| EP | 0 774 255 A1 | 5/1997 |

(Continued)

OTHER PUBLICATIONS

Jayaprakasam et al. (J Agric Food Chem. Jan. 11, 2006; 54(1):243-8).*
Yasushiro Izumiya (Cell Metab. Feb. 2008; 7(2): 159-172).*
Baar, Keith et al. (Am. J. Physiol. 276 (Cell Physiol 45):C120-127, 1999).*
Belemtougri et al. (Journal of Zhejiang University Science B, 2006 7(1):56-63).*
Jei Liu (Journal of Ethnopharmacology 49 (1995) 57-68).*
Ramussen et al. (J. Appl. Physiol. 106: 1365-1366, 2009.*
Kunkel et al. (Cell metabolism 13, 627-638, Jun. 8, 2011).*
M. C. Dyle, et al., Systems-based Discovery of Tomatidine as a Natural Small Molecule Inhibitor of Skeletal Muscle Atrophy, Journal of Biological Chemistry, Apr. 9, 2014, pp. 14913-14924, vol. 289, No. 21.
Richard F. Keeler, et al., Cyclopamine and related steroidal alkaloid teratogens: Their occurrence, structural relationship, and biologic effects, Lipids, Oct. 1, 1978, pp. 708-715, vol. 13, No. 10.
Shalender Bhasin, The Brave New World of Function-Promoting Anabolic Therapies: Testosterone and Fraility, Journal of Clinical Endocrinology & Metabolism, Feb. 1, 2010, pp. 509-511, vol. 95, No. 2.
Extended European Search Report for PCT/US2012/041119 dated Mar. 25, 2015.

(Continued)

*Primary Examiner* — Sabiha N Qazi
(74) *Attorney, Agent, or Firm* — Heslin Rothenberg Farley & Mesiti P.C.

(57) ABSTRACT

In one aspect, the invention relates methods for inhibiting or preventing muscle atrophy or increasing muscle mass by providing to a subject in need thereof an effective amount of ursolic acid, a derivative thereof, or an analog of the ursane scaffold. This abstract is intended as a scanning tool for purposes of searching in the particular art and is not intended to be limiting of the present invention.

20 Claims, 15 Drawing Sheets

(56) References Cited

U.S. PATENT DOCUMENTS

| | | | |
|---|---|---|---|
| 2008/0145322 A1* | 6/2008 | Eldridge | A61K 8/63 424/55 |
| 2009/0143279 A1 | 6/2009 | Mootha et al. | |
| 2010/0104669 A1 | 4/2010 | Scheffler et al. | |
| 2010/0204121 A1 | 8/2010 | Romero et al. | |
| 2010/0305068 A1 | 12/2010 | Bulawa et al. | |
| 2011/0097427 A1 | 4/2011 | Ramakrishnan et al. | |

FOREIGN PATENT DOCUMENTS

| | | |
|---|---|---|
| EP | 1987827 A1 | 11/2008 |
| JP | H09143076 A | 6/1997 |
| JP | 2010-095459 A | 4/2010 |
| WO | 95/26330 A1 | 10/1995 |
| WO | 2006/007910 A1 | 1/2006 |
| WO | 2006/034586 A1 | 4/2006 |
| WO | WO-2007053915 A2 | 5/2007 |
| WO | WO-2008063318 A2 | 5/2008 |
| WO | 2010/132776 A1 | 11/2010 |
| WO | WO-2010124847 A1 | 11/2010 |
| WO | WO-2011046978 A2 | 4/2011 |
| WO | 2011/146768 A1 | 11/2011 |
| WO | WO-2011153315 A1 | 12/2011 |

OTHER PUBLICATIONS

R.R. Ortiz-Andrade, et al., Antidiabetic and Toxicological Evaluations of Naringenin in Normoglycaemic and NIDDM Rat Models and Its Implications on Extra-Pancreatic Glucose Regulation, Diabetes, Obesity and Metabolism, 2008, pp. 1097-1104, vol. 10.
Yamada, et al., Biol. Pharm. Bull., vol. 31, No. 4, pp. 651-655 (2008).
Amendment filed Sep. 27, 2013 for Australian Patent Application No. 2011255495, which claims priority to PCT/US2011/037238, which published as WO 2011/146768 on Nov. 24, 2011 (Applicant: University of Iowa Research Foundation // Inventor—Adams, et al) (10 pages).
Notice of Allowance of Amendment to the Specification dated Oct. 11, 2013 for for Australian Patent Application No. 2011255495, which claims priority to PCT/US2011/037238, which published as WO 2011/146768 on Nov. 24, 2011 (Applicant: University of Iowa Research Foundation // Inventor—Adams, et al) (1 page).
Amendment filed Aug. 2, 2013 for Chinese National Phase Patent Application No. 201180035480X, which claims priority to PCT/US2011/037238, which published as WO 2011/146768 on Nov. 24, 2011 (Applicant: University of Iowa Research Foundation // Inventor—Adams, et al) (7 pages).
Amendment filed Jul. 8, 2013 for European Patent Application No. 11784273.2, which claims priority to PCT/US2011/037238, which published as WO 2011/146768 on Nov. 24, 2011 (Applicant: University of Iowa Research Foundation // Inventor—Adams, et al) (5 pages).
Communication pursuant to Rules 161(2) and 162 EPC dated Jan. 7, 2013 for Jul. 8, 2013 for European Patent Application No. 11784273.2, which claims priority to PCT/US2011/037238, which published as WO 2011/146768 on Nov. 24, 2011 (Applicant: University of Iowa Research Foundation // Inventor—Adams, et al) (2 pages).
International Search Report dated Aug. 17, 2011 by the International Searching Authority for PCT Application No. PCT/US2011/037238, which published as WO 2011/146768 on Nov. 24, 2011 (Applicant: University of Iowa Research Foundation // Inventor—Adams, et al) (2 pages).
International Preliminary Report on Patentability dated Nov. 20, 2012 by the International Searching Authority for PCT Application No. PCT/US2011/037238, which published as WO 2011/146768 on Nov. 24, 2011 (Applicant: University of Iowa Research Foundation // Inventor—Adams, et al) (5 pages).
Written Opinion dated Aug. 17, 2011 by the International Searching Authority for PCT Application No. PCT/US2011/037238, which published as WO 2011/146768 on Nov. 24, 2011 (Applicant: University of Iowa Research Foundation // Inventor—Adams, et al) (4 pages).
International Search Report dated Nov. 5, 2012 by the International Searching Authority for PCT Application No. PCT/US2012/041119, which published as WO 2012/170546 on Dec. 13, 2012 (Applicant: University of Iowa Research Foundation // Inventor—Adams, et al) (5 pages).
International Search Report dated Feb. 8, 2013 by the International Searching Authority for PCT Application No. PCT/US2012/066341, which published as WO 2013/078372 on Nov. 24, 2011 (Applicant: University of Iowa Research Foundation // Inventor—Adams, et al) (5 pages).
Written Opinion dated Feb. 8, 2013 by the International Searching Authority for PCT Application No. PCT/US2012/066341, which published as WO 2013/078372 on Nov. 24, 2011 (Applicant: University of Iowa Research Foundation // Inventor—Adams, et al) (7 pages).
"Urosolic Acid Extract." http://www.ursolicare.com. Visited May 10, 2011.
Abbas T, et al. (2009). p21 in cancer: intricate networks and multiple; activities. Nat Rev Cancer 9: 400-414.
Abelian van Kan G. (2009) Epidemiology and consequences of sarcopenia. The Journal of Nutrition, Health & Aging 13: 708-712.
Acharyya S, et al. (2004) Cancer cachexia is regulated by selective targeting of skeletal muscle gene products. J Clin Investig 114: 370-378.
Acharyya S, et al. (2005) Dystrophin glycoprotein complex dysfunction: a regulatory link between musclular dystrophy and cancer cachexia. Cancer Cell 8(5): 421-432.
Adams CM, et al. (2011) Altered mRNA expression after long-term soleus electrical stimulation training in humans with paralysis. Muscle & Nerve 43(1): 65-75.ms.
Adams GR & Haddad F (1996) The relationships among IGF-1, DNA content, and protein accumulation during skeletal muscle hypertrophy. J Appl Physiol 81(6): 2509-2516.
Adams GR, et al. (1999) Time course of changes in markers of myogenesis in overloaded rat skeletal muscles. J Appl Physiol 87(5):1705-1712.
Adams V, et al. (2008) Induction of MuRF1 is essential for TNF-alpha-induced loss of muscle function in mice. Journal of molecular biology 384(1):48-59.
Adnyana, et al. (2001) Three new triterpenes from the seeds of combretum quadrangulare and their hepatoprotective activity. J Nat Prod 64: 360-363.
Almarasson O, et al. (2004) Crystal engineering of the composition of pharmaceutical phases. Do pharmaceutical co-crystals represent a new path to improved medicines? The Royal Science of Chemistry, 1889-1896.
Amthor H, et al. (2007) Lack of myostatin results in excessive muscle growth but impaired force generation. Proc Natl Acad Sci U.S.A., 104: 1835-1840.
Anderson R, et al. (2000). A simple method for the rapid generation of; recombinant adenovirus vectors. Gene therapy 7, 1034-1038.
Astley ST, et al. (1993) Hippeastrine synthesis: a comibined bio-dioxygenation/organoiron chirality relay approach. Tetrahedron Lett 34: 2035-2038.
Banduseela VC, et al. (2009) Gene expression and muscle fiber function in a porcine ICU model. Physiol. Genomics 39: 141-159.
Barres R, et al. (2009) Non-CpG methylation of the PGC-1 α promoter through DNMT3B controls mitochondrial density. Cell Metabolism 10: 189-198.
Barres R, et al. (2012) Acute exercise remodels promoter methylation in human skeletal muscle. Cell Metabolism 15: 405-411.
Barretto G, et al. (2007). Gadd45a promotes epigenetic gene activation by repair-mediated DNA demethylation. Nature 445: 671-675.
Barton-Davis ER, et al. (1998) Viral mediated expression of insulin-like growth factor I blocks the aging-related loss of skeletal muscle function. Proc Natl Acad Sci U.S.A. 95(26):15603-15607.

(56) References Cited

OTHER PUBLICATIONS

Bastida J, et al. (2011) Chemical and biological aspects of amaryllidacea alkaloids. Recent Advances in Pharmaceutical Sciences, 65-70.
Baumgartner RN, et al. (1998) Am J Epidemiol 147: 755-763.
Bennani-Baiti N and Walsh D, et al. (2011). Animal models of the cancer anorexia-cachexia syndrome. Support Care Cancer 19(9): 1451-1463.
Benson EK., et al. (2009) Single-vector inducible lentiviral RNAi system for oncology target validation. Cell cycle (Georgetown, Tex 8, 2002-2004.
Bird, A. (2002) Genes & Development 16, 6-21.
Bodine SC, et al. (2001a) Identification of ubiquitin ligases required for skeletal muscle atrophy. Science 294: 1704-1708.
Bodine SC, et al. (2001b) Akt/mTOR pathway is a crucial regulator of skeletal muscle hypertrophy and can prevent muscle atrophy in vivo. Nat Cell Biol 3(11):1014-1019.
Bradley, et al. (2008) Myostatin as a therapeutic target for musculoskeletal disease. Cell Mol Life Sci, 65: 2119-2124.
Brüning JC, et al. (1998) A muscle-specific insulin receptor knockout exhibits features of the metabolic syndrome of NIDDM without altering glucose tolerance. Mol Cell 2: 559-569.
Burks TN, et al. (2011) Losartan restores skeletal muscle remodeling and protects against disuse atrophy in sarcopenia. Sci. Translat. Med. 3: 82ra37.
Burridge S. (2011) Obesity and diabetes: lipid boosts muscle and shrinks fat. Nature Reviews Drug Discovery 10(8): 576.
Burton LA and Sumukadas D. (2010) Clin Interv Aging 5, 217-228.
Busquets S, et al. (2012) Myostatin blockage using actRIIB antabonsim in mice bearing the Lewis lung carcinoma results in the improvement of muscle wasting and physical performance. Journal of Cachexia, Sacropenia, and Muscle 3(1): 37-43.
Cai D, et al. (2004) IKKB/NF-kB activation causes severe muscle wasting in mice. Cell 119: 285-298.
Caron AZ, et al. (2009) A novel hindlimb immobilization procedure for studying skeletal muscle atrophy and recovery in mouse. J Appl Physiol. 106: 2049-2059.
Chadalapaka G, et al (2008) Structure-dependent inhibition of bladder and pancreatic cancer cell growth by 2-subsititued glycyrrhetinic and ursolic acid derivatives. Bioroganic and Medicinal Chemistry Letters 18(8): 2633-2639.
Chaturvedula, et al. (2004) A new ursane triterpene from Monochaetum vulcanicum that inhibits DNA polymerase beta lyase. J Nat Prod 67: 899-901.
Chedin F. (2011) Progress in molecular biology and translational science 101: 255-285.
Chen H, et al. (2010) Mitochondrial fusion is required for mtDNA stability in skeletal muscle and tolerance of mtDNA mutations. Cell 141: 280-289.
Chiu FL and Lin JK. (2008) Tomatidine inhibits iNOS and COX-2 through suppression of NF-kappaB and JNK pathways in LPS-stimulated mouse macrophages. FEBS letters 582(16): 2407-2412.
Choi SH, et al. (2012) Structure-activity relationships of alpha-, beta(1)-, gamma-, and delta-tomatine and tomatidine against human breast (MDA-MB-231), gastric (KATO-III), and prostate (PC3) cancer cells. Journal of Agricultural and Food Chemistry 60(15): 3891-3899.
Cohen S, et al. (2009) During muscle atrophy, thick, but not thin, filament components are degraded by MuRF1-dependent ubiquitylation. The Journal of Cell Biology 185(6):1083-1095.
Cohn RD, et al. (2002) Disruption of DAG1 in differentiated skeletal muscle reveals a role for dystroglycan in muscle regeneration. Cell 110: 639-648.
Coker RH and Wolfe RR. (2011) Bedrest and sarcopenia. Curr Opin Clin Nutr Metab Care 15, 7-11.
Cornelissen B, et al. (2008) The level of insulin growth factor-1 receptor expression is directly correlated with the tumor uptake of (111)IN-IGF-1(E3R) in vivo and the clonogenic survival of breast cancer cells exposed in vitro to trasuzumab (Herceptin). Nuclear Medicine and Biology 35(6): 645-653.

Cortellino S, et al. (2011) Thymine DNA glycosylase is essential for active DNA demethylation by linked deamination-base excision repair. Cell, 146: 67-79.
Coss CC, et al. (2011) Cancer cacexia therapy: a key weapon in the fight against cancer. Curr Opin Clin Nutr Metab Care 14(3): 268-273.
Das SK, et al. (2011) Adipose triglyceride lipase contributes to cancer-associated cachexia. Science 333(6039): 233-238.
De Angel RE, et al. (2010) Antitumor effects of ursolic acid in a mouse model of postmenopausal breast cancer. Nutrition and Cancer 62(8): 1074-1086.
de Melo CL, et al. (2010) Oleanolic acid, a natural triterpenoid improves blood glucose tolerance in normal mice and ameliorates visceral obesity in mice fed a high-fat diet. Chem Biol Interact 185(1): 59-65.
Dedkov EI, et al. (2003) Dynamics of post-denervation atrophy of young and old skeletal muscles. Differential responses of fiber types and muscle types. J Gerontol 58: 984-991.
Delibegovic M, et al. (2007) Improved glucose homeostasis in mice with muscle-specific deletion of protein-tyrosine phosphatase 1B. Molecular and Cellular Biology 27(21):7727-7734.
Deng Y, et al. (2000). Peg3/Pw1 promotes p53-mediated apoptosis by inducing Bax translocation from cytosol to mitochondria. Proc Natl Acad Sci U.S.A. 97: 12050-12055.
Dobrowolny G, et al. (2005) Muscle expression of a local Igf-1 isoform protects motor neurons in an ALS mouse model. The Journal of Cell Biology 168(2):193-199.
Doucet M, et al. (2007) Muscle atrophy and hypertrophy signaling in patients with chronic obstructive pulmonary disease. American Journal of Respiratory and Critical Care Medicine 176(3):261-269.
Dubowitz V, et al. (2007) Muscle biopsy : a practical approach (Saunders Elsevier, Philadelphia) 3rd Ed pp. XIII, 611 s.
Dupont J, et al. (2001) Insulin-like growth factor 1 (IGF-1)-induced twist expression is involved in the anti-apoptotic effects of the IGF-1 receptor. The Journal of Biological Chemistry 276(28): 26699-26707.
Easwaran H P, et al. (2010) Role of nuclear architecture in epigenetic alterations in cancer. Cold Spring Harbor Symp Quant Biol 75: 507-515.
Ebert SM, et al. (2010) The transcription factor ATF4 promotes skeletal myofiber atrophy during fasting. Molecular endocrinology 24(4):790-799.
Ebert SM, et al. (2012) Stress-induced skeletal muscle Gadd45a expression reprograms myonuclei and causes muscle atrophy. The Journal of Biological Chemistry, 287: 27290-27301.
Edwards, MG, et al. (2007) Gene expression profiling of aging reveals activation of a p53-mediated transcriptional program. BMC Genomics 8: 80.
Elchebly et al. (1999) Increased insulin sensitivity and obesity resistance in mice lacking the protein tyrosine phosphatase-1B gene. Science, 283: 1544-1548.
el-Deiry WS, et al. (1995) Cancer research 55: 2910-2919.
Evidente A, et al. (Apr. 2009) Biological evaluation of structurally diverse amaryllidaceae alkaloids and their synthetic derivatives: discovery of novel leads for anticancer drug design. Planta Med 75(5): 501-507.
Fearon KC. (2011) Cancer cachexia and fat-muscle physiology. The New England Journal of Medicine 365(6):565-567.
Fearon KC, et al. (2012) Cancer cachexia: mediators, signaling, and metabolic pathways. Cell metabolism 16: 153-166.
Flood M and Newman AM. (2007) Journal of Gerontological Nursing 33, 19-35; quiz 36-17.
Frame S, et al. (2001) GSK3 takes center stage more than 20 years after its discovery. Biochem J 359: 1-16.
Fry CS, et al. (2011) Skeletal Muscle Protein Balance and Metabolism in the Elderly. Current Aging Science 4: 260-268.
Gao Y, et al. (2010) The Synthesis of Glycyrrhetinic Acid Derivatives Containing a Nitrogen Heterocycle and Their Antiproliferative Effects in Human Leukemia Cells. Molecules 15: 4439-4449.
Genet C, et al. (2010). Structure-activity relationship study of betulinic acid, a novel and selective TGR5 agonist, and its synthetic derivatives: potential impact in diabetes. J. Med. Chem. 53: 178-190.

(56) References Cited

OTHER PUBLICATIONS

Gentile MA, et al. (2010) Androgen-mediated improvement of body composition and muscle function involves a novel early transcriptional program including IGF1, mechano growth factor, and induction of {beta}-catenin. Journal of Molecular Endocrinology 44(1):55-73.

Glass D, et al. (2010) Recent advances in the biology and therapy of muscle wasting. Ann N Y Acad Sci 1211: 25-36.

Glass DJ. (2005) Skeletal muscle hypertrophy and atrophy signaling pathways. The international journal of biochemistry & cell biology 37(10):1974-1984.

Gomes MD, et al. (2001) Atrogin-1, a muscle-specific F-box protein highly expressed during muscle atrophy. Proc Natl Acad Sci U.S.A. 98: 14440-14445.

Goncalves DA, et al. (2009). Mechanisms involved in 3',5'-cyclic adenosine monophosphate-mediated inhibition of the ubiquitin-proteasome system in skeletal; muscle. Endocrinology 150: 5395-5404.

Gonzalez de Aguilar JL, et al. (2008) Gene profiling of skeletal muscle in an amyotrophic lateral sclerosis mouse model. Physiol Genomics 32: 207-218.

Gundersen K, et al. (2008) Nuclear domains during muscle atrophy. Nuclei lost or paradigm lost? J Physiol 586: 2675-2681.

Hameed M, et al. (2004) The effect of recombinant human growth hormone and resistance training on IGF-I mRNA expression in the muscles of elderly men. The Journal of Physiology 555(Pt1):231-240.

Haning H, et al. (2011) Total synthesis of the amaryllidaceae alkaloid clivonine. Organic & Biomolecular Chemistry 9: 2809-2820.

Harding HP, et al. (2003) An integrated stress response regulates amino acid metabolism and resistance to oxidative stress. Mol Cell 11: 619-633.

Hirose M, et al. (2001) Long-term denervation impairs insulin receptor substrate-1-mediated insulin signaling in skeletal muscle. Metabolism: Clinical and Experimental 50(2): 216-222.

Hishiya A, et al. (2006) A novel ubiquitin-binding protein ZNF216 functioning in muscle atrophy. The EMBO journal 25(3):554-564.

Hu Z, et al. (2009) Endogenous glucocorticoids and impaired insulin signaling are both required to stimulate muscle wasting under pathophysiological conditions in mice. The Journal of Clinical Investigation 119(10): 3059-3069.

Ikuta, et al. (2003) Ursane- and Oleanane-Type Triterpenes from Ternstroemia gymnanthera Callus Tissues. J Nat Prod 66: 1051-1054.

Ishido M, et al. (2004) American Journal of Physiology 287: C484-493.

Izumiya Y, et al. (2008) Fast/Glycolytic muscle fiber growth reduces fat mass and improves metabolic parameters in obese mice. Cell Metabolism 7(2):159-172.

Jager S, et al. (2009) Pentacyclic Triterpene distribution in various plants-rich sources for a new group of multi-potent plant extracts. Molecules 14: 2016-2031.

Jagoe RT, et al. (2002) Patterns of gene expression in atrophying skeletal muscles: response to food deprivation. Faseb J 16(13):1697-1712.

Jang SM, et al. (2009) Ursolic acid enhances the cellular immune system and pancreatic beta-cell function in streptozotocin-induced diabetic mice fed a high-fat diet. Int Immunopharmacol 9(1):113-119.

Janssen I, et al. (2004) The healthcare costs of sarcopenia in the United States. J Am Geriatr Soc 52: 80-85.

Jayaprakasam B, et al. (2006) Amelioration of obesity and glucose intolerance in high-fat-fed C57BL/6 mice by anthocyanins and ursolic acid in Cornelian cherry (Cornus mas). J Agric Food Chem 54(1):243-248.

Jiang H, et al. (2007). The eukaryotic initiation factor-2 kinase pathway facilitates differential GADD45a expression in response to environmental stress. The Journal of Biological Chemistry 282: 3755-3765.

Jones (2010) Nature, 468: 752-753.

Jung SH, et al. (2007) Insulin-mimetic and insulin-sensitizing activities of a pentacyclic triterpenoid insulin receptor activator. The Biochemical journal 403(2):243-250.

Jung Y, et al. (2010). Examination of the expanding pathways for the regulation of p21 expression and activity. Cell Signal 22: 1003-1012.

Kajimura S, et al. (2010) Transcriptional control of brown fat development. Cell Metabolism 11(4): 257-262.

Kamei Y, et al. (2004) Potential role of microsomal prostaglandin in E synthase-1 in tumorigenesis. The Journal of Biological Chemistry 279: 41114-41123.

Kandarian SC and Jackman RW (2006) Intracellular signaling during skeletal muscle atrophy. Muscle & nerve 33(2):155-165.

Kaneko-Ishino T, et al. (1995). Peg1/Mest imprinted gene on chromosome 6 identified by cDNA subtraction hybridization. Nature Genetics 11: 52-59.

Kastan M, et al. (1992) A mammalian cell cycle checkpoint pathway utilizing p53 and GADD45 is defective in ataxia-telangiectasia. Cell 71: 587-597.

Kawamata Y, et al. (2003). A G protein-coupled receptor responsive to bile acids. J; Biol Chem 278: 9435-9440.

Kenner KA, et al. (1996). Protein-tyrosine phosphatase 1B is a negative regulator of insulin- and insulin-like growth factor-I-stimulated signaling J Biol Chem 271: 19810-19816.

Kessar, et al. (1971) Synthetic studies in steroidal sapogenins and alkaloids—X: Synthesis of tomatid-5-Ene-3-o1 and solasodine. Tetrahedron 27: 2869.

Klaman LD, et al. (2000) Increased energy expenditure, decreased adiposity, and tissue-specific insulin sensitivity in protein-tyrosine phosphatase 1B-deficient mice. Molecular and Cellular Biology 20(15): 5479-5489.

Koh SJ, et al. (2012) Sensitzation of ionizing radiation-induced apoptosis by ursolic acid. Free Radical Research 46(3): 339-345.

Korényi-Both AL. (1983) Muscle Pathology in Neuromuscular Disease, C.C. Thomas, Springfield, IL.

Kunkel S, et al. (2011) mRNA Expression Signatures of Human Skeletal; Muscle Atrophy Identify a Natural Compound that Increases Muscle Mass. Cell Metabolism; 13: 627-638.

Kunkel SD, et al. (2012) Ursolic Acid increases skeletal muscle and brown fat and decreases diet-induced obesity, glucose intolerance and Fatty liver disease. PloS one 7(6):e39332.

Kutner MH, et al. (2004) Applied Linear Regression Models, 4th ed., McGraw-Hill/Irwin, Boston.

Kwon SH, et al. (2010) Apoptotic action of ursolic acid isolated from corni fructus in RC-58T/h/SA#4 primary human prostate cancer cells. Bioorganic and Medicinal Chemistry Letters 20(22): 6435-6438.

Kwon TH, et al. (2009) Synthesis and NO production inhibitory activities of ursolic acid and oleanolic acid derivatives. Bull. Korean Chem. Soc. 30(1): 119-123.

Lagirand-Cantaloube J, et al. (2008) The initiation factor eIF3-f is a major target for atrogin1/MAFbx function in skeletal muscle atrophy. The EMBO Journal 27(8):1266-1276.

Lai KM, et al. (2004) Conditional activation of akt in adult skeletal muscle induces rapid hypertrophy. Molecular and Cellular Biology 24(21): 9295-9304.

Lal A and Gorospe M. (2006) Cell Cycle (Georgetown Tex) 5: 1422-1425.

Lamb J, et al. (2006) The Connectivity Map: using gene-expression signatures to connect small molecules, genes, and disease. Science 313(5795):1929-1935.

Laure L, et al. (2009) Cardiac ankyrin repeat protein is a marker of skeletal muscle pathological remodeling. FEBS J 276: 669-68.

Lauthier F, et al. (2000) Ursolic acid triggers calcium-dependent apoptosis in human Daudi cells. Anti-Cancer Drugs 11: 737-745.

Le May N, et al. (2010) NER factors are recruited to active promoters and facilitate chromatin modification for transcription in the absence of exogenous genotoxic attack.. Mol Cell 38: 54-66.

Lecker SH, et al. (2004) Multiple types of skeletal muscle atrophy involve a common program of changes in gene expression. FASEB J 18(1):39-51.

(56) References Cited

OTHER PUBLICATIONS

Lee SJ (2004) Regulation of muscle mass by myostatin. Annu Rev Cell Dev Biol 20:61-86.
Leger B, et al. (2006) Human skeletal muscle atrophy in amyotrophic lateral sclerosis reveals a reduction in Akt and an increase in atrogin-1. FASEB J 20(3):583-585.
Leinonen. (2006) Novel mass spectrometric analysis methods for anabolic androgenic steroids in sports drug testing. Department of Pharmaceutical Chemistry Faculty of Pharmacy University of Helsinki Finland.
Levine S, et al. (2008) Rapid disuse atrophy of diaphragm fibers in mechanically ventilated humans. The New England journal of medicine 358(13):1327-1335.
Li JB and Goldberg AL. (1976) Effects of food deprivation on protein synthesis and degradation in rat skeletal muscles. Am J Physiol 231: 441-448.
Liebermann DA and Hoffman B. (2008) Gadd45 in stress signaling. J. Mol. Signal 3, 15; Lin H, et al. (2010) Skp2 targeting suppresses tumorigenesis by Arf-p53-independent cellular senescence. Nature 464: 374-379.
Lin H, et al. Skp2 targeting suppresses tumorigenesis by Arf-p53-; independent cellular senescence. Nature 464, 374-379.
Liu J. (1995) Pharmacology of oleanolic acid and ursolic acid. Journal of ethnopharmacology 49(2):57-68.
Liu J. (2005) Oleanolic acid and ursolic acid: research perspectives. Journal of Ethnopharmacology 100(1-2): 92-94.
Llano-Diez M, et al. (2011) BMC Genomics 12: 602.
Lonning PE & Helle SI (2004) IGF-1 and breast cancer. Novartis Foundation Symposium 262: 205-212; discussion 212-204, 265-208.
Ma J, et al. (1999) Prospective study of colorectal cancer risk in men and plasma levels of insulin-like growth factor (IGF)-I and IGF-binding protein-3. Journal of the National Cancer Institute 91(7): 620-625.
Malmberg SE and Adams CM (2008) Insulin signaling and the general amino acid control response. Two distinct pathways to amino acid synthesis and uptake. J Biol Chem 283: 19229-19234.
Mammucari C, et al. (2007) FoxO3 controls autophagy in skeletal muscle in vivo. Cell Metab 6: 458-471.
Manas CG, et al. (2010) Total synthesis of the lycorenine-type amaryllidaceae alkaloid- (±)-clinonine via a biomimetric ring-switch from a lycorine-type progenitor. J Am Chem Soc, 132: 5176-5178.
Masuoka H, et al. (2002) Targeted disruption of the activating transcription factor 4 gene results in severe fetal anemia in mice. Blood 99: 736-745.
Mendez J and Keys A. (1960) Density and composition of mammalian muscle. Metabolism: Clinical and Experimental 9: 184-189.
Meng Y, et al. (2010) Molecules 15: 4033-4040.
Michael LF, et al. (2001) Restoration of insulin-sensitive glucose transporter (GLUT4) gene expression in muscle cells by the transcriptional coactivator PGC-1. Proc Natl Acad Sci U.S.A. 98: 3820-3825.
Miller RA and Nadon NL (2000) Principles of animal use for gerontological research.The Journals of Gerontology 55A: B117-123.
Moresi V, et al. (2010) Myogenin and class II HDACs control neurogenic muscle atrophy by inducing E3 ubiquitin ligases. Cell 143: 35-45.
Musarò A, et al. (2001) Localized Igf-1 transgene expression sustains hypertrophy and regeneration in senescent skeletal muscle. Nature Genetics 27(2): 195-200.
Nathanson L, et al. (1994) Chemohormone therapyof metastatic melanoma with megestrol acetate plus dacarbazine, carmustine, and cisplatin. Cancer 73(1):98-102.
Niehrs C and Schafer A. (2012) Active DNA demethylation by Gadd45 and DNA repairTrends Cell Biol 22: 220-227.
Nishimura, et al. (1999) Activity-Guided Isolation of Triterpenoid Acyl CoA Cholesteryl Acyl Transferase (ACAT) Inhibitors from Ilex kudincha. J Nat Prod 62: 1061-1064.

Novotny L, et al. (2001) Ursolic acid: an anti-tumorigenic and chemopreventive activity. Minireview. Neoplasma 48(4): 241-246.
Pallafacchina G, et al. (2002) A protein kinase B-dependent and rapamycin-sensitive pathway controls skeletal muscle growth but not fiber type specification. Proceedings of the National Academy of Sciences of the United States of America 99(14): 9213-9218.
Palus S, et al., (2011). Ghrelin and Its Analogues, BIM-28131 and BIM-; 28125, Improve Body Weight and Regulate the Expression of MuRF-1 and MAFbx in a Rat; Heart Failure Model. PLoS One, 6(11): e26865.
Pathak, et al. (2008) Expeditious microwave-assisted thionation with the system $PSCI3/H_2O/Et_3N$ under solvent-free condition. J Org Chem 73: 2890-2893.
Peterson JM, et al. (2011) NF-kB signaling in skeletal muscle health and disease. Curr Top Dev Biol 96: 85-119
Plant PJ, et al. (2009) Absence of caspase-3 protects against denervation-induced skeletal muscle atrophy. J Appl Physiol 107: 224-234.
Porter DC, et al. (2012) Cyclin-dependent kinase 8 mediates chemotherapyinduced tumor-promoting paracrine activities. Proc Natl Acad Sci U.S.A. 109: 13799-13804.
Powers SK, et al. (2012) Mitochondrial signaling contributes to disuse muscle atrophy. Am J Physiol Endocrinol Metab 303: E31-39.
Prasad S, et al. (2012) Ursolic acid inhibits growth and metastasis of human colorectal cancer in an orthotopic nude mouse model by targeting multiple cell signaling pathways: chemosensitization with capecitabine. Clin Cancer Res.
Proctor, et al. (2000) Synthesis of tacrine analogues and their structure-activity relationships. Curr Medical Chem 7: 295-302.
Qian S, et al. (2010) Synthesis and biological evaluation of oleanolic acid derivatives as inhibitors of protein tyrosine phosphatase 1B. J Nat Prod 73(11):1743-1750.
Reagan-Shaw S, et al. (2008) Dose translation from animal to human studies revisited. FASEB J 22(3):659-661.
Rodino-Klapac et al. (2009) Muscle Nerve 39: 283-296.
Sacheck J, et al. (2007). Rapid disuse and denervation atrophy involve; transcriptional changes similar to those of muscle wasting during systemic diseases. FASEB J; 21, 140-155.
Sacheck JM, et al. (2004) IGF-I stimulates muscle growth by suppressing protein breakdown and expression of atrophy-related ubiquitin ligases, atrogin-1 and MuRF1. Am J Physiol Endocrinol Metab 287(4):E591-601.
Sakuma K and Yamaguchi A. (2012) Novel intriguing strategies attenuating to sarcopenia. Journal of Aging Research 2012:251217.
Sandri M (2008) Signaling in muscle atrophy and hypertrophy. Physiology 23:160-170.
Sandri M, et al. (2004) Foxo transcription factors induce the atrophy-related ubiquitin ligase atrogin-1 and cuase skeletal muscle atrophy. Cell 117(3): 399-412.
Sandri M, et al. (2006) PGC-la protects skeletal muscle from atrophy by suppressing FoxO3 action and atrophy-specific gene transcription. Proc Natl Acad Sci U.S.A. 103: 16260-16265.
Sartori R, et al. (2009) Smad2 and 3 transcription factors control muscle mass in adulthood. American Journal of Physiology 296: C1248-1257.
Schiaffino S and Mammucari C. (2011) Regulation of skeletal muscle growth by the IGF1-Akt/PKB pathway. Insights from genetic models. Skelet Muscle 1: 4.
Schmitz KM, et al. (2009) TAF12 recruits Gadd45a and the nucleotide excision repair complex to the promoter of rRNA genes leading to active DNA demethylation.. Mol Cell 33: 344-353.
Schwarzkopf M, et al. (2006) Muscle cachexia is regulated by a p53-PW1/Peg3-dependent pathway. Genes Dev. 20: 3440-3452.
Scime A, et al. (2005) Rb and p107 regulate preadipocyte differentiation into white versus brown fat through repression of PGC-1alpha. Cell metabolism 2: 283-295.
Sen GL, et al. (2010) Nature 463: 563-567.
Shanmugam MK, et al. (2011) Ursolic acid inhibits multiple cell survival pathways leading to suppression of growth of prostate cancer xenograft in jude mice. Journal of Molecular Medicine 89(7): 713-727.

(56) References Cited

OTHER PUBLICATIONS

Shavlakadze T, et al. (2005) Insulin-like growth factor I slows the rate of denervation induced skeletal muscle atrophy. Neuromuscul Disord 15(2):139-146.
Siegel R, et al. (2011) Cancer statistics, 2011: the impact of eliminating socioeconomic and racial disparities on premature cancer deaths. CA Cancer J Clin 61(4): 212-236.
Sivakumar G, et al.(2009) Plant-based corosolic acid: future antidiabetic drug? Biotechnol J 4(12):1704-1711.
Skipworth RJ, et al. (2007) Pathophysiology of cancer cachexia: much more than host-tumor interaction. Clinical Nutrition 26(6): 667-676.
Sporn MB, et al (2011) New Synthetic triterpenoids: potent agents for prevention and treatment of tissue injury caused by inflammatory and oxidative stress. J Nat Prod 74: 537-545.
Stevenson E, et al. (2003). Global analysis of gene expression patterns during disuse atrophy in rat skeletal muscle. The Journal of Physiology 551, 33-48.
Stitt TN, et al. (2004) The IGF-1/PI3K/Akt pathway prevents expression of muscle atrophy-induced ubiquitin ligases by inhibiting FOXO transcription factors. Mol Cell 14(3): 395-403.
Subramanian A, et al. (2005). Gene set enrichment analysis: a knowledge-based approach for interpreting genome-wide expression profiles. Proc Nat Acad Sci U.S.A. 102: 15545-15550.
Sun H, et al. (2006) Structure-activity relationships of oleanane- and ursane-type triterpenoids. Botanical Studies 47: 339-368.
Suneja BL, et al. (2010). The transcription factor ATF4 promotes skeletal myofiber atrophy during fasting. Mol. Endocrinol. 24, 790-799.
Sytnikova YA, et al. (2011) Gadd45a is an RNA-binding protein and is localized in nuclear speckles. PloS One 6, e14500.
Tan BH and Fearon KC. (2008) Cachexia: prevalence and impact in medicine. Curr Opin Clin Nutr Metab Care 11(4): 400-407.
Tan BH, et al. (2009) Sarcopenia in an overweight or obese patient is an adverse prognositc factor in pancreatic cancer. Clin Cancer Res 15(22): 6973-6979.
Tian J, et al. (2011) Gadd45? is an inducible coactivator of transcription that facilitates rapid liver growth in mice. J Clin Investig 121: 4491-4502.
Tran H, et al. (2002) DNA repair pathway stimulated by the forkhead transcription factor FOXO3a through the Gadd45 protein. Science 296: 530-534.
Tureckova J, et al. (2001) Insulin-like growth factor-mediated muscle differentiation: collaboration between phosphatidylinositol 3-kinase-Akt-signaling pathways and myogenin. The Journal of Biological Chemistry 276(42):39264-39270.
Uhle. (1954) J Am Chem Soc 76: 6412.
Uhle. (1961) J Am Chem Soc 83: 1460.
Uldry M, et al. (2006) Complementary action of the PGC-1 coactivators in mitochondrial biogenesis and brown fat differentiation. Cell Metab 3: 333-341.
Verhees KJ, et al. (2011) Glycogen synthase kinase-3? is required for the induction of skeletal muscle atrophy. Am J Physiol Cell Physiol 301: C995-C1007.
Volk KA, et al. (2005) The Journal of Biological Chemistry 280: 18348-18354.
von Haeling S and Anker SD. (2010) Cachexia as a major under estimated and unmet medical need: facts and numbers. Journal of Cachexia, Sacropenia, and Muscle 1(1): 1-5.
Wang JS, et al. (2012) Ursolic acid induces apoptosis by suppressing the expression of FoxM1 in MCF-7 human breast cancer cells. Medical Oncology 29: 10-15.
Wang X, et al. (2005) Runx1 prevents wasting, myofibrillar disorganization, and autophagy of skeletal muscle. Genes Dev 19: 1715-1722.
Wang X, et al. (2011) Ursolic acid inhibits proliferation and induces apoptosis of cancer cells in vitro and in vivo. Journal of Biomedicine and Biotechnology 2011: 419343.
Wang ZH, et al. (2010) Anti-glycative effects of oleanolic acid and ursolic acid in kidney of diabetic mice. European Journal of Pharmacology 628(1-3):255-260.
Watanabe M, et al. (2006). Bile acids induce energy expenditure by; promoting intracellular thyroid hormone activation. Nature 439: 484-489.
Weber M, et al. (2005). Chromosome-wide and promoter-specific analyses identify sites of differential DNA methylation in normal and transformed human cells. Nature Genetics 37: 853-862.
Welle S, et al. (2003) Gene expression profile of aging in human muscle. Physiol Genomics 14: 149-159.
Welle S, et al. (2004) Skeletal muscle gene expression profiles in 20-29-year-old and 65-71-year-old women. Exp Gerontol 39: 369-377.
Wenz T, et al. (2009) Increased muscle PGC-1alpha expression protects from sarcopenia and metabolic disease during aging. Proc Nat Acad Sci U.S.A. 106(48): 20405-20410.
Yakar S, et al. (1999) Normal growth and development in the absence of hepatic insulin-like growth factor I. Proc Nat Acad Sci U.S.A. 96(13):7324-7329.
Yi YW, et al. (2000) Gadd45 family proteins are coactivators of nuclear hormone receptors. Biochem Biophys Res Commun 272: 193-198.
Ying QL, et al. (1991) Inhibition of human leucocyte elastase by ursolic acid. Biochem J, 277: 521-526.
Zabolotny JM, et al. (2004) Transgenic overexpression of protein-tyrosine phosphatase 1B in muscle causes insulin resistance, but overexpression with leukocyte antigen-related phosphatase does not additively impair insulin action. The Journal of Biological Chemistry 279(23):24844-24851.
Zeman R, et al. (2009). Differential skeletal muscle gene expression after; upper or lower motor neuron transection. Pflugers Arch 458: 525-535.
Zhan Q. (2005) Gadd45a, a p53- and BRCA1-regulated stress protein, in cellular response to DNA damage. Mutation Research 569: 133-143.
Zhang W, et al. (2006) Ursolic acid and its derivative inhibit protein tyrosine phosphatase 1B, enhancing insulin receptor phosphorylation and stimulating glucose uptake. Biochimica et Biophysica Acta 1760(10):1505-1512.
Zhang YN, et al. (2008) Oleanolic acid and its derivatives: new inhibitor of protein tyrosine phosphatase 1B with cellular activities. Bioorg Med Chem 16(18):8697-8705.
Zhang Z, et al. (2007) Sensitization of calcitonin gene-related peptide receptors by receptor activity-modifying protein-1 in the trigeminal ganglion. J Neurosci 27: 2693-270.
Zhao H, et al. (2000). The central region of Gadd45 is required for its interaction with p21/WAF1. Experimental Cell Research 258: 92-100.
Zhao J, et al. (2007) FoxO3 coordinately activates protein degradation by the autophagic/lysosomal and proteasomal pathways in atrophying muscle cells. Cell Metab 6: 472-483.
Zhou X, et al. (2010) Reversal of cancer cachexia and muscle wasting by ActRIIB antagonism leads to prolonged survival. Cell 142(4):531-43.

* cited by examiner

METHODS FOR INHIBITING MUSCLE ATROPHY

CROSS-REFERENCE TO RELATED APPLICATIONS

This application claims the benefit of U.S. Applications No. 61/346,813, filed on May 20, 2010, and No. 61/445,488, filed on Feb. 22, 2011, which are hereby incorporated by reference in entirety.

STATEMENT REGARDING FEDERALLY SPONSORED RESEARCH

This invention was made with government support under grant VA Career Development Award-2 to Christopher M. Adams, and support from a VA Research Enhancement Award Program to Steven D. Kunkel. The United States government has certain rights in the invention.

BACKGROUND

Skeletal muscle atrophy is characteristic of starvation and a common effect of aging. It is also a nearly universal consequence of severe human illnesses, including cancer, chronic renal failure, congestive heart failure, chronic respiratory disease, insulin deficiency, acute critical illness, chronic infections such as HIV/AIDS, muscle denervation, and many other medical and surgical conditions that limit muscle use. However, medical therapies to prevent or reverse skeletal muscle atrophy in human patients do not exist. As a result, millions of individuals suffer sequalae of muscle atrophy, including weakness, falls, fractures, opportunistic respiratory infections, and loss of independence. The burden that skeletal muscle atrophy places on individuals, their families, and society in general, is tremendous.

The pathogenesis of skeletal muscle atrophy is not well understood. Nevertheless, important advances have been made. For example, it has been described previously that insulin/IGF1 signaling promotes muscle hypertrophy and inhibits muscle atrophy, but is reduced by atrophy-inducing stresses such as fasting or muscle denervation (Bodine S C, et al. (2001) *Nat Cell Biol* 3(11):1014-1019; Sandri M, et al. (2004) *Cell* 117(3):399-4121; Stitt T N, et al. (2004) *Mol Cell* 14(3):395-403; Hu Z, et al. (2009) *The Journal of clinical investigation* 119(10):3059-3069; Dobrowolny G, et al. (2005) *The Journal of cell biology* 168(2):193-199; Kandarian S C & Jackman R W (2006) *Muscle & nerve* 33(2):155-165; Hirose M, et al. (2001) *Metabolism: clinical and experimental* 50(2):216-222; Pallafacchina G, et al. (2002) *Proceedings of the National Academy of Sciences of the United States of America* 99(14):9213-9218). The hypertrophic and anti-atrophic effects of insulin/IGF1 signaling are mediated at least in part through increased activity of phosphoinositide 3-kinase (PI3K) and its downstream effectors, including Akt and mammalian target of rapamycin complex 1 (mTORC1) Sandri M (2008) *Physiology (Bethesda)* 23:160-170; Glass D J (2005) *The international journal of biochemistry & cell biology* 37(10):1974-1984).

Another important advance came from microarray studies of atrophying rodent muscle (Lecker S H, et al. (2004) *Faseb J* 18(1):39-51; Sacheck J M, et al. (2007) *Faseb J* 21(1):140-155; Jagoe R T, et al. *Faseb J* 16(13):1697-1712). Those studies showed that several seemingly disparate atrophy-inducing stresses (including fasting, muscle denervation and severe systemic illness) generated many common changes in skeletal muscle mRNA expression. Some of those atrophy-associated changes promote muscle atrophy in mice; these include induction of the mRNAs encoding atroginI/MAFbx and MuRF1 (two E3 ubiquitin ligases that catalyze proteolytic events), and repression of the mRNA encoding PGC-1α (a transcriptional co-activator that inhibits muscle atrophy) (Sandri M, et al. (2006) *Proceedings of the National Academy of Sciences of the United States of America* 103(44):16260-16265; Wenz T, et al. *Proceedings of the National Academy of Sciences of the United States of America* 106(48):20405-20410; Bodine S C, et al. (2001) *Science* (New York, N.Y. 294(5547):1704-1708; Lagirand-Cantaloube J, et al. (2008) *The EMBO journal* 27(8):1266-1276; Cohen S, et al. (2009) *The Journal of cell biology* 185(6):1083-1095; Adams V, et al. (2008) *Journal of molecular biology* 384(1):48-59). However, the roles of many other mRNAs that are increased or decreased in atrophying rodent muscle are not yet defined. Data on the mechanisms of human muscle atrophy are even more limited, although atrogin-1 and MuRF1 are likely to be involved (Leger B, et al. (2006) *Faseb J* 20(3):583-585; Doucet M, et al. (2007) *American journal of respiratory and critical care medicine* 176(3):261-269; Levine S, et al. (2008) *The New England journal of medicine* 358(13):1327-1335).

Despite advances in understanding the physiology and pathophysiology of muscle atrophy, there is still a scarcity of compounds that are both potent, efficacious, and selective modulators of muscle growth and also effective in the treatment of muscle atrophy associated and diseases in which the muscle atrophy or the need to increase muscle mass is involved. These needs and other needs are satisfied by the present invention.

SUMMARY

In accordance with the purpose(s) of the invention, as embodied and broadly described herein, the invention, in one aspect, relates to compounds useful in methods to inhibit muscle atrophy and to increase muscle mass by providing to a subject in need thereof an effective amount of ursolic acid or a derivative thereof, and pharmaceutical compositions comprising compounds used in the methods.

In further aspects, the purpose(s) of the invention, as embodied and broadly described herein, the invention, in one aspect, relates to compounds useful in methods to modulate muscle growth, methods to inhibit muscle atrophy and to increase muscle mass, methods to induce skeletal muscle hypertrophy, methods to enhance tissue growth, and pharmaceutical compositions comprising compounds used in the methods.

Disclosed are methods for preventing or treating muscle atrophy in an animal, the method comprising administering to the animal a compound of the formula:

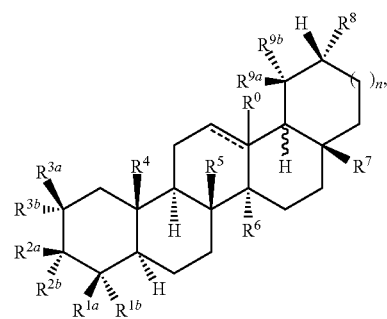

wherein ----- each is an optional covalent bond, and $R^0$ is optionally present; wherein n is 0 or 1; wherein $R^0$, when present, is hydrogen; wherein $R^{1a}$ is selected from C1-C6 alkyl and —C(O)ZR$^{10}$; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —OR$^{11}$, provided that at least one of $R^{2a}$ and $R^{2b}$ is —OR$^{11}$; or wherein $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of $R^4$, $R^5$, and $R^6$ is independently selected from C1-C6 alkyl; wherein $R^7$ is selected from C1-C6 alkyl, —CH$_2$OR$^{12}$, and —C(O)ZR$^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein $R^{10}$ is selected from hydrogen and C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

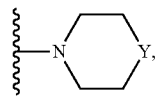

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to prevent or treat muscle atrophy in the animal, wherein the amount is greater than 1000 per day when the compound is ursolic acid, boswellic acid, corosolic acid, betulinic acid, or UA0713.

Also disclosed are methods for increasing muscle mass and/or muscular strength in an animal, the method comprising administering to the animal a compound of the formula:

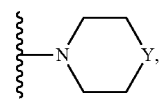

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)ZR$^{10}$; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —OR$^{11}$, provided that at least one of $R^{2a}$ and $R^{2b}$ is —OR$^{11}$; or wherein $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of $R^4$, $R^5$, and $R^6$ is independently selected from C1-C6 alkyl; wherein $R^7$ is selected from C1-C6 alkyl, —CH$_2$OR$^{12}$, and —C(O)ZR$^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein $R^{10}$ is selected from hydrogen and C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to increase muscle mass and/or muscular strength in the animal, wherein the amount is greater than about 1000 mg per day when the compound is ursolic acid, boswellic acid, corosolic acid, betulinic acid, or UA0713.

Also disclosed are methods for enhancing tissue growth in vitro, the method comprising administering to the tissue a compound of the formula:

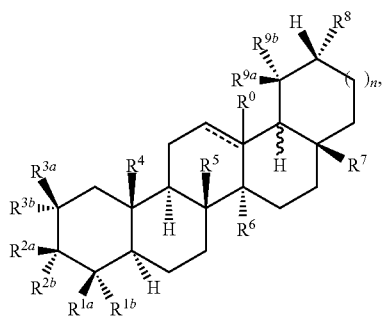

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)ZR$^{10}$; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —OR$^{11}$, provided that at least one of $R^{2a}$ and $R^{2b}$ is —OR$^{11}$; or wherein $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of $R^4$, $R^5$, and $R^6$ is independently selected from C1-C6 alkyl; wherein $R^7$ is selected from C1-C6 alkyl, —CH$_2$OR$^{12}$, and —C(O)ZR$^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein $R^{10}$ is selected from hydrogen and C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

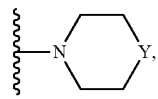

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to enhance growth of the tissue.

Also disclosed are methods for enhancing muscle formation in a mammal, the method comprising administering to the mammal a compound of the formula:

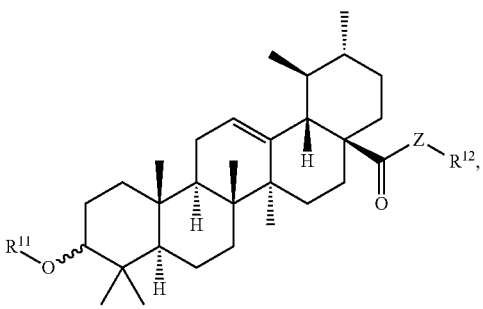

wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

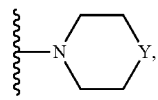

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount greater than about 1000 mg per day and effective to enhance muscle formation in the mammal.

Also disclosed are methods for testing for performance enhancing use of a ursolic acid analog in an animal, the method comprising: (a) obtaining a biological test sample from the animal; and (b) measuring the amount of a compound of formula:

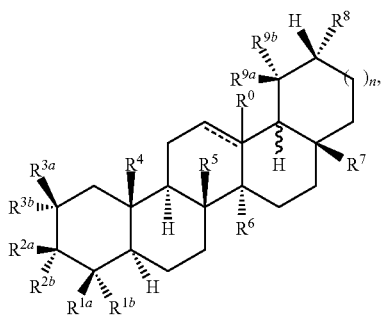

wherein each ----- is an optional covalent bond, and R⁰ is optionally present; wherein n is 0 or 1; wherein R⁰, when present, is hydrogen; wherein $R^{ha}$ is selected from C1-C6 alkyl and —C(O)ZR¹⁰; wherein $R^{1b}$ is selected from C1-C6 alkyl; wherein one of $R^{2a}$ and $R^{2b}$ is —OR¹¹, and the other is hydrogen; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; wherein each of R⁴, R⁵, and R⁶ is independently selected from C1-C6 alkyl; wherein R⁷ is selected from C1-C6 alkyl and —C(O)ZR¹²; wherein R⁸ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; wherein R¹⁰ is selected from hydrogen and C1-C6 alkyl; wherein R¹¹ is selected from hydrogen, C1-C6 alkyl, C1-C5 heteroalkyl, C3-C6 cycloalkyl, C4-C6 heterocycloalkyl, phenyl, heteroaryl, and —C(O)R¹⁴; wherein R¹¹, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein R¹² is selected from hydrogen and optionally substituted organic residue having from 1 to 20 carbons; wherein Z is selected from —O— and —NR¹³—; wherein R¹³ is selected from hydrogen and C1-C4 alkyl; and wherein R¹⁴ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in the test sample to determine whether a superphysiological amount of the compound is present in the test sample; wherein the superphysiological amount of the compound in the test sample is indicative of performance enhancing use of the compound.

Also disclosed are pharmaceutical compositions comprising a pharmaceutically acceptable carrier and an effective amount of a compound of the formula:

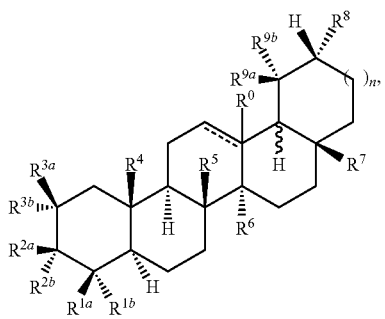

wherein each ----- is an optional covalent bond, and R⁰ is optionally present; wherein n is 0 or 1; wherein R⁰, when present, is hydrogen; wherein $R^{1a}$ is selected from C1-C6 alkyl and —C(O)ZR¹⁰; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —OR¹¹, provided that at least one of $R^{2a}$ and $R^{2b}$ is —OR¹¹; or wherein $R^{2a}$ and $R^{2b}$ together comprise =O; wherein each of $R^{1a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of R⁴, R⁵, and R⁶ is independently selected from C1-C6 alkyl; wherein R⁷ is selected from C1-C6 alkyl, —CH₂OR¹², and —C(O)ZR¹²; wherein R⁸ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein R¹⁰ is selected from hydrogen and C1-C6 alkyl; wherein each R¹¹ is independently selected from hydrogen, C1-C6 alkyl, C1-C5 heteroalkyl, C3-C6 cycloalkyl, C4-C6 heterocycloalkyl, phenyl, heteroaryl, and —C(O)R¹⁴; wherein R¹¹, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein R¹² is selected from hydrogen and optionally substituted organic residue having from 1 to 20 carbons; wherein Z is selected from —O— and —NR¹³—; wherein R¹³ is selected from hydrogen and C1-C4 alkyl; or, wherein Z is N, R¹² and R¹³ are covalently bonded and —NR¹²R¹³ comprises a moiety of the formula:

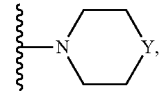

wherein Y is selected from —O—, —S—, —SO—, —SO₂—, —NH—, —NCH₃—; and wherein R¹⁴ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to prevent or treat muscle atrophy in the animal, wherein the amount is greater than about 1000 mg per day when the compound is ursolic acid, boswellic acid, corosolic acid, betulinic acid, or UA0713.

Also disclosed are kits comprising at least one compound having a structure represented by a formula:

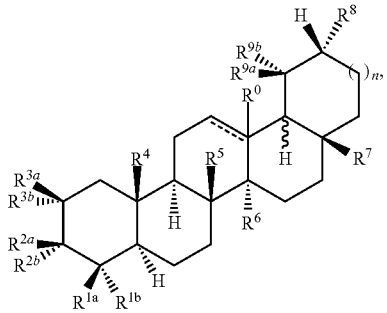

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)$ZR^{10}$; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —$OR^{11}$, provided that at least one of $R^{2a}$ and $R^{2b}$ is —$OR^{11}$; or wherein $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of $R^4$, $R^5$, and $R^6$ is independently selected from C1-C6 alkyl; wherein $R^7$ is selected from C1-C6 alkyl, —$CH_2OR^{12}$, and —C(O)$ZR^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein $R^{10}$ is selected from hydrogen and C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —C(O)$R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

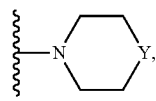

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, and one or more of: (a) a protein supplement; (b) an anabolic agent; (c) a catabolic agent; (d) a dietary supplement; (e) at least one agent known to treat a disorder associated with muscle wasting; (f) instructions for treating a disorder associated with cholinergic activity; or (g) instructions for using the compound to increase muscle mass and/or muscular strength.

Also disclosed are methods for manufacturing a medicament associated with muscle atrophy or the need to increase muscle mass comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with muscle atrophy or the need to increase muscle mass.

While aspects of the present invention can be described and claimed in a particular statutory class, such as the system statutory class, this is for convenience only and one of skill in the art will understand that each aspect of the present invention can be described and claimed in any statutory class.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
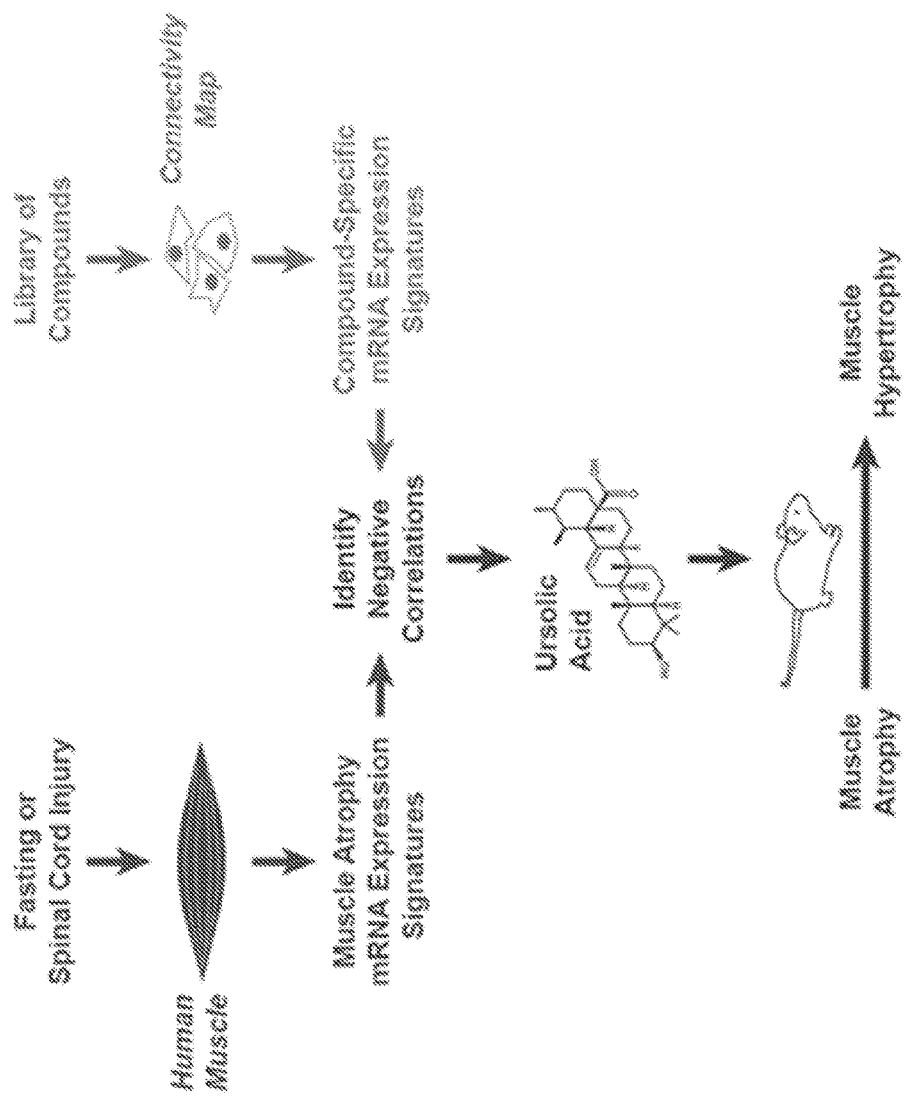
FIG. 1 shows a schematic overview of the discovery process leading to a pharmacological compound that promotes skeletal muscle growth and inhibits skeletal muscle atrophy.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, "ursolic acid" refers to ursolic acid, or extracts containing ursolic acid from plants such as apples, holy basil, bilberries, cranberries, elder flower, peppermint, lavender, oregano, thyme, sage, hawthorn, bearberry or prunes.

As used herein, "ursolic acid derivatives" refers to corosolic acid, betulinic acid, hederagenin, boswellic acids, UA0713, a substituted ursolic acid analog, an ursane compound or any other pentacyclic triterpene acids that prevents muscle atrophy, reduces muscle atrophy, increases muscle mass, increases muscle strength in an animal, including in humans, increases Akt phosphorylation, increases S6K phosphorylation, or stimulates biochemical events known to precede or follow Akt phosphorylation or S6K phosphorylation. For example, and not to be limiting, biochemical events known to precede or follow Akt phosphorylation or S6K phosphorylation can be events such as insulin receptor phosphorylation, IGF-I receptor phosphorylation, insulin receptor substrate (IRS) protein phosphorylation, phosphoinositide-3 kinase phosphorylation, phosphoinositide-3 kinase activation, phosphoinositide dependent kinase 1 activation, mammalian target of rapamycin complex 2 activation, adrenergic receptor activation, heterotrimeric G protein activation, adenylate cyclase activation, increased intracellular cyclic AMP, AMP kinase activation, protein kinase A activation, protein kinase C activation, CREB activation, mitogen activated protein kinase pathway activation, mammalian target of rapamycin complex 1 activation, 4E-BP1 phosphorylation, 4E-BP1 inactivation, GSK3β phosphorylation, GSK3 β inactivation, increased protein synthesis, increased glucose uptake, Foxo transcription factor phosphorylation, Foxo transcription factor inactivation, Cdkn1a phosphorylation, Cdkn1a inactivation, reduced atrogin-1 mRNA, reduced MuRF1 mRNA, increased VEGFA mRNA, or increased IGF1 mRNA.

As used herein, the term "subject" refers to the target of administration, e.g. an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for increasing muscle mass prior to the administering step. In some aspects of the disclosed method, the subject has been diagnosed with a need for increasing muscle mass prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a muscle atrophy disorder" means having been subjected to a physical examination by a person of skill, for example, a physician, and found to have a condition that can be diagnosed or treated by a compound or composition that can increase muscle mass. As a further example, "diagnosed with a need for increasing muscle mass" refers to having been subjected to a physical examination by a person of skill, for example, a physician, and found to have a condition characterized by muscle atrophy or other disease wherein increasing muscle mass would be beneficial to the subject. Such a diagnosis can be in reference to a disorder, such as muscle atrophy, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to muscle atrophy) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the a gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or $OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$ OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^o$; —(CH$_2$)$_{0-4}$OR$^o$; —O(CH$_2$)$_{0-4}$R$^o$, —O—(CH$_2$)$_{0-4}$C(O)OR$^o$; —(CH$_2$)$_{0-4}$CH(OR$^o$)$_2$; —(CH$_2$)$_{0-4}$SR$^o$; —(CH$_2$)$_{0-4}$Ph, which may be substituted with R$^o$; —(CH$_2$)$_{0-4}$O(CH$_2$)$_{0-1}$Ph which may be substituted with R$^o$; —CH=CHPh, which may be substituted with R$^o$; —(CH$_2$)$_{0-4}$O(CH$_2$)$_{0-1}$-pyridyl which may be substituted with R$^o$; —NO$_2$; —CN; —N$_3$; —(CH$_2$)$_{0-4}$N(R$^o$)$_2$; —(CH$_2$)$_{0-4}$N(R$^o$)C(O)R$^o$; —N(R$^o$)C(S)R$^o$; —(CH$_2$)$_{0-4}$N(R$^o$)C(O)NR$^o{}_2$; —N(R$^o$)C(S)NR$^o{}_2$; —(CH$_2$)$_{0-4}$ N(R$^o$)C(O)OR$^o$; —N(R$^o$)N(R$^o$)C(O)R$^o$; —N(R$^o$)N(R$^o$)C(O)NR$^o{}_2$; —N(R$^o$)N(R$^o$)C(O)OR$^o$; —(CH$_2$)$_{0-4}$C(O)R$^o$; —C(S)R$^o$; —(CH$_2$)$_{0-4}$ C(O)OR$^o$; —(CH$_2$)$_{0-4}$C(O)SR$^o$; —(CH$_2$)$_{0-4}$C(O)OSiR$^o{}_3$; —(CH$_2$)$_{0-4}$ OC(O)R$^o$; —OC(O)(CH$_2$)$_{0-4}$SR—, SC(S)SR$^o$; —(CH$_2$)$_{0-4}$ SC(O)R$^o$; —(CH$_2$)$_{0-4}$C(O)NR$^o{}_2$; —C(S)NR$^o{}_2$; —C(S)SR$^o$; —SC(S)SR$^o$, —(CH$_2$)$_{0-4}$OC(O)NR$^o{}_2$; —C(O)N(OR$^o$)R$^o$; —C(O)C(O)R$^o$; —C(O)CH$_2$C(O)R$^o$; —C(NOR$^o$)R$^o$; —(CH$_2$)$_{0-4}$SSR$^o$; —(CH$_2$)$_{0-4}$S(O)$_2$R$^o$; —(CH$_2$)$_{0-4}$S(O)$_2$ OR$^o$; —(CH$_2$)$_{0-4}$OS(O)$_2$R$^o$; —S(O)$_2$NR$^o{}_2$; —(CH$_2$)$_{0-4}$S(O) R$^o$; —N(R$^o$)S(O)$_2$NR$^o{}_2$; —N(R$^o$)S(O)$_2$R$^o$; N(OR$^o$)R$^o$; —C(NH)NR$^o{}_2$; —P(O)$_2$R$^o$; —P(O)R$^o{}_2$; —OP(O)R$^o{}_2$; —OP(O)(OR$^o$)$_2$; SiR$^o{}_3$; —(C$_{1-4}$ straight or branched)alkylene)O—N(R$^o$)$_2$; or —(C$_{1-4}$ straight or branched alkylene) C(O)O—N(R$^o$)$_2$, wherein each R$^o$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^o$ (or the ring formed by taking two independent occurrences of R$^o$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^o$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

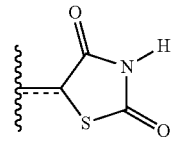

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

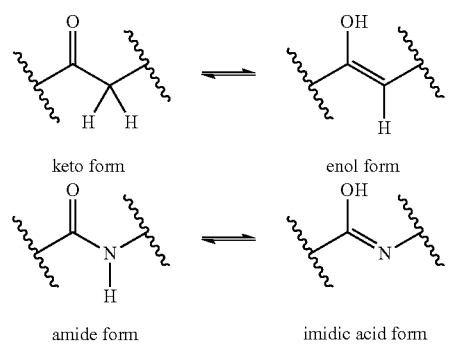

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

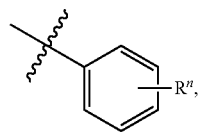

which is understood to be equivalent to a formula:

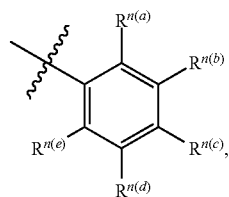

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in methods to inhibit muscle atrophy and to increase muscle mass by providing to a subject in need thereof an effective amount of ursolic acid or a derivative thereof, and pharmaceutical compositions comprising compounds used in the methods. In a further aspect, the invention relates to compounds useful in methods to modulate muscle growth, methods to inhibit muscle atrophy and to increase muscle mass, methods to induce skeletal muscle hypertrophy, methods to enhance tissue growth, and pharmaceutical compositions comprising compounds used in the methods.

In one aspect, the compounds of the invention are useful in the treatment of muscle disorders. In a further aspect, the muscle disorder can be skeletal muscle atrophy secondary to malnutrition, muscle disuse (secondary to voluntary or involuntary bedrest), neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Ursolic Acid Derivatives

Ursolic acid is a highly water-insoluble pentacyclic triterpene acid that possesses a wide range of biological effects, including anti-cancer, anti-oxidant, anti-inflammatory, anti-allergic, hepatoprotective, gastroprotective, hypolipidemic, hypoglycemic, lipolytic anti-obesity, anti-atherogenic and immunomodulatory effects (Liu J (1995) *Journal of ethnopharmacology* 49(2):57-68; Liu J (2005) *Journal of ethnopharmacology* 100(1-2):92-94; Wang Z H, et al. (2010) *European journal of pharmacology* 628(1-3):255-260; Jang S M, et al. (2009) *Int Immunopharmacol* 9(1):113-119). However, its effects on skeletal muscle were not known previously. At the molecular level, ursolic acid inhibits the STAT3 activation pathway, reduces matrix metalloproteinase-9 expression via the glucocorticoid receptor, inhibits protein tyrosine phosphatases, acts as an insulin mimetic, activates PPARα, inhibits NF-kB transcription factors, translocates hormone-sensitive lipase to stimulate lipolysis and inhibits the hepatic polyol pathway, among many other described effects. Its effects on skeletal muscle and IGF-I signaling were not previously known.

As medicine, ursolic acid is well tolerated and can be used topically and orally. Ursolic acid is present in many plants, including apples, basil, bilberries, cranberries, elder flower, peppermint, rosemary, lavender, oregano, thyme, hawthorn, prunes. Apple peels contain high quantity of ursolic acid and related compounds which are responsible for the anti-cancer activity of apple. Ursolic acid can also serve as a starting material for synthesis of more potent bioactive derivatives, such as anti-tumor agents.

Other names for ursolic acid include 3-β-hydroxy-urs-12-en-28-oic acid, urson, prunol, micromerol, and malol. The structure is shown below:

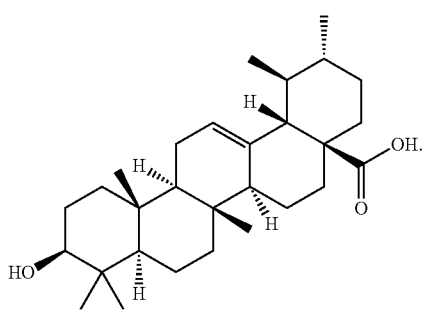 [SMILES: C[C@H]1[C@H](C)CC[C@]2(C(=O)O)CC[C@@H]3C(=CC[C@H]4[C@@]3(C)CC[C@H]3C(C)(C)[C@@H](O)CC[C@]43C)[C@H]12]

Other closely related pentacyclic triterpene acids with insulin sensitizing actions include oleanolic acid (Wang et at, 2010), corosolic acid (Sivakumar et at, 2009) and UA0713 (Zhang et at, 2006).

In one aspect, the invention relates to compounds of the formula:

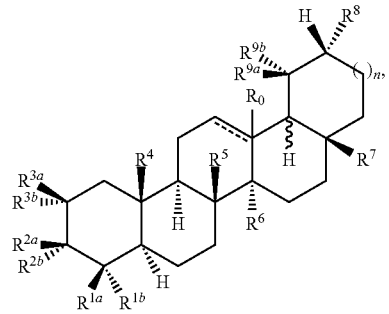

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)ZR$^{10}$; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —OR$^{11}$, and the other is hydrogen, or $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —CH$_2$OR$^{12}$ and —C(O)ZR$^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein $R^{10}$ is selected from hydrogen and C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

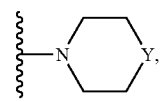

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof.

In a further aspect, the invention relates to compounds of a formula:

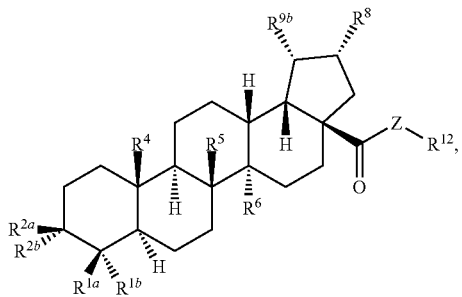

wherein each of $R^{1a}$ and $R^{1b}$ is C1-C6 alkyl; wherein one of $R^{2a}$ and $R^{2b}$ is —$OR^{11}$, and the other is hydrogen; wherein each of $R^4$, $R^5$, and $R^6$ is independently C1-C6 alkyl; wherein $R^8$ is selected from hydrogen and C1-C6 alkyl; wherein $R^{9b}$ is C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

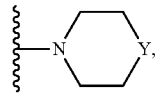

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, the invention relates to compounds of a formula:

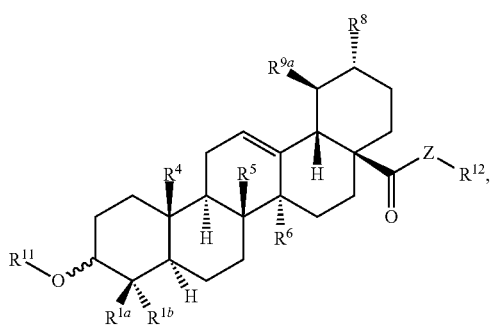

wherein $R^{1a}$ is selected from C1-C6 alkyl and —$C(O)ZR^{10}$; wherein $R^{1b}$ is selected from C1-C6 alkyl, or $R^{1a}$ and $R^{1b}$ are covalently bonded and, together with the intermediate carbon, comprise an optionally substituted 3- to 7-membered spirocycloalkyl; wherein $R^8$ is C1-C6 alkyl; wherein $R^{9a}$ is C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

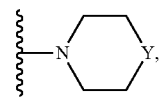

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, the invention relates to compounds of a formula:

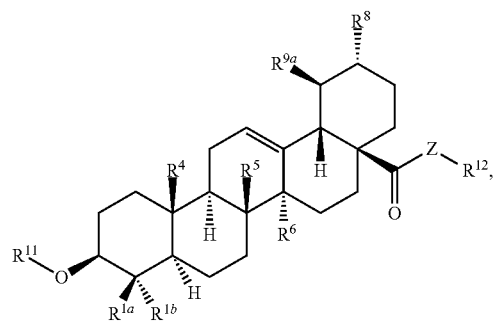

In a further aspect, the invention relates to compounds of a formula:

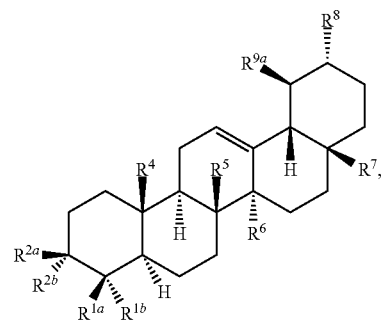

wherein $R^{1a}$ is —$C(O)ZR^{10}$; wherein $R^{1b}$ is C1-C6 alkyl; wherein one of $R^{2a}$ and $R^{2b}$ is —$OR^{11}$, and the other is hydrogen; wherein each of $R^4$, $R^5$, and $R^6$ is independently selected from C1-C6 alkyl; wherein $R^7$ is selected from C1-C6 alkyl; wherein $R^8$ is selected from hydrogen and C1-C6 alkyl; wherein $R^{9a}$ is selected from hydrogen and C1-C6 alkyl; wherein Z is selected from —O— and —$NR^{13}$—; wherein $R^{10}$ is selected from hydrogen and C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

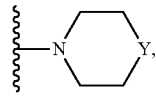

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, the invention relates to compounds of a formula:

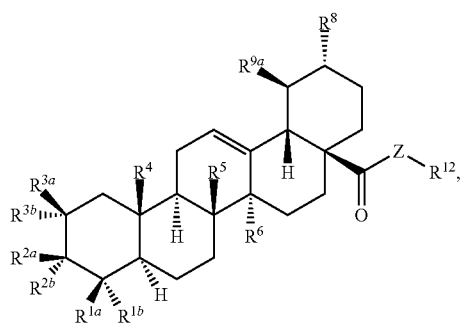

wherein each of $R^{1a}$ and $R^{1b}$ is independently C1-C6 alkyl; wherein one of $R^{2a}$ and $R^{2b}$ is —$OR^{11}$, and the other is hydrogen; wherein one of $R^{1a}$ and $R^{1b}$ is —$OR^{11}$, and the other is hydrogen; wherein each of $R^4$, $R^5$, and $R^6$ is independently selected from C1-C6 alkyl; wherein $R^8$ is C1-C6 alkyl; wherein $R^{9a}$ is C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

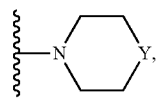

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, the invention relates to compounds of a formula:

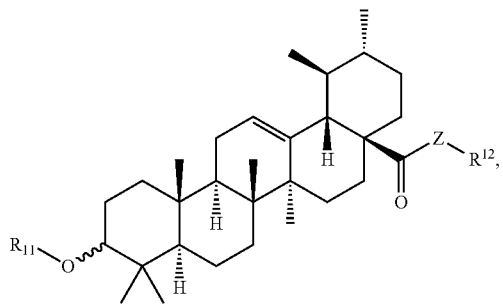

wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

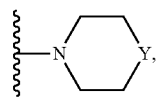

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof.

In a further aspect, the compound is administered in an amount effective to prevent or treat muscle atrophy in the animal. In a still further aspect, the compound is administered in amount is greater than about 1000 mg per day when the compound is ursolic acid, beta-boswellic acid, corosolic acid, betulinic acid, or UA0713. In a yet further aspect, the compound is administered in an amount greater than about 1000 mg per day and effective to enhance muscle formation in the mammal.

In a further aspect, the invention relates to compounds of a formula selected from:

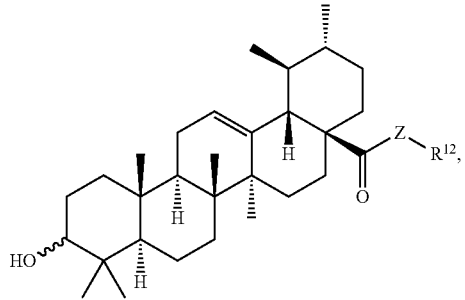

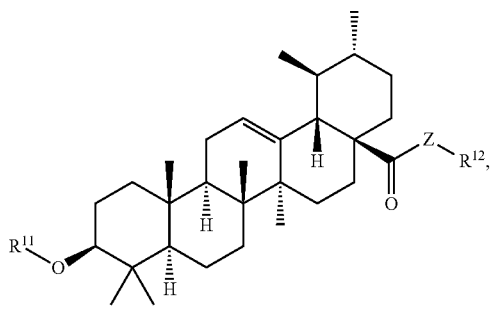

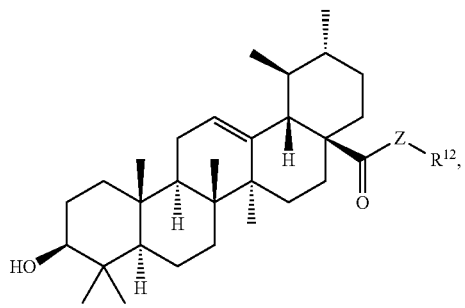

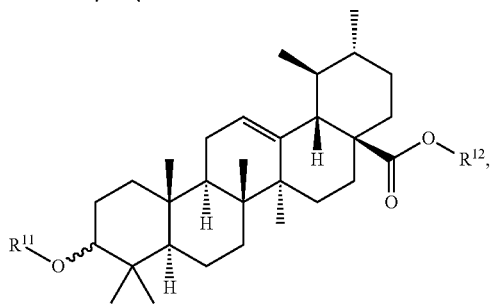

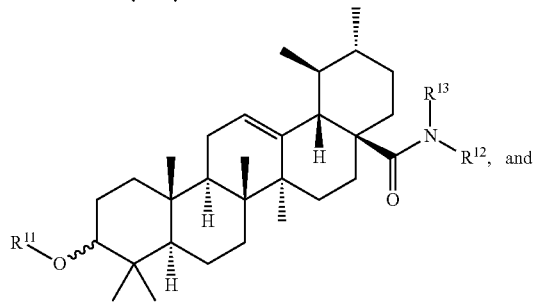

-continued

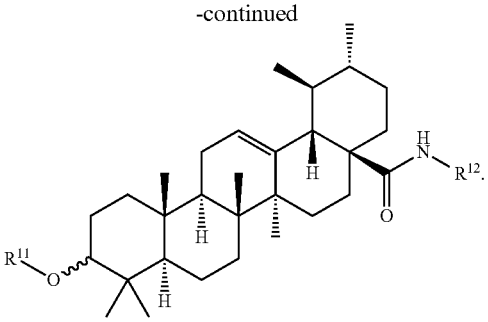

a. R⁰ Groups and Optional Bonds

In one aspect, an optional covalent bond can be represented by -----. Thus, in certain aspects, a particular bond is present, thereby providing a single covalent bond. In further aspects, a particular bond is present, thereby providing a double covalent bond. In further aspects, a particular bond is absent, thereby providing a double covalent bond.

In one aspect, $R^0$ is optionally present. That is, in certain aspects, $R^0$ is present. In further aspects, $R^0$ is absent. In a further aspect, $R^0$, when present, is hydrogen. It is understood that the presence and/or absence of $R^0$ Groups and optional bonds serve to satisfy valence of the adjacent chemical moieties.

b. $R^1$ Groups

In one aspect, $R^{1a}$ is selected from C1-C6 alkyl and —C(O)ZR¹⁰; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl. In a further aspect, $R^{1a}$ is —CO₂H. In a further aspect, $R^{1b}$ is methyl. In a further aspect, $R^{1a}$ and $R^{1b}$ are both methyl.

In one aspect, $R^{1a}$ is —C(O)ZR¹⁰. In a further aspect, $R^{1a}$ selected from C1-C6 alkyl, for example, methyl, ethyl, propyl, butyl, pentyl, or hexyl. In a further aspect, $R^{1b}$ is selected from C1-C6 alkyl, for example, methyl, ethyl, propyl, butyl, pentyl, or hexyl.

In a further aspect, $R^{1a}$ and $R^{1b}$ are covalently bonded and, along with the intermediate carbon, together comprise optionally substituted C3-C5 cycloalkyl or optionally substituted C2-C5 heterocycloalkyl.

c. $R^2$ Groups

In one aspect, $R^{2a}$ and $R^{2b}$ are independently selected from hydrogen and —OR¹¹, provided that at least one of $R^{2a}$ and $R^{2b}$ is —OR¹¹; or wherein $R^{2a}$ and $R^{2b}$ together comprise =O. In a further aspect, $R^{2a}$ is hydrogen, and $R^{2b}$ is —OR¹¹. In a further aspect, $R^{2a}$ is —OR¹¹, and $R^{2b}$ is hydrogen. In a further aspect, $R^{2a}$ and $R^{2b}$ together comprise =O.

In a further aspect, $R^{2a}$ is hydrogen. In a further aspect, $R^{2a}$ is —OR¹¹; wherein $R^{11}$ is selected from hydrogen, C1-C6 alkyl, and —C(O)R¹⁴; wherein $R^{14}$ is C1-C6 alkyl. In a further aspect, $R^{2b}$ is —OR¹¹; wherein $R^{11}$ is selected from hydrogen, C1-C6 alkyl, and —C(O)R¹⁴; and wherein $R^{14}$ is C1-C6 alkyl. In a further aspect, $R^{2b}$ is —OR¹¹; wherein $R^{11}$ is hydrogen.

In a further aspect, $R^{2b}$ is hydrogen. In a further aspect, $R^{2a}$ is —OR¹¹; wherein $R^{11}$ is selected from hydrogen, C1-C6 alkyl, and —C(O)R¹⁴; wherein $R^{14}$ is C1-C6 alkyl. In a further aspect, $R^{2a}$ is —OR¹¹; wherein $R^{11}$ is hydrogen.

d. $R^3$ Groups

In one aspect, each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl.

In a further aspect, $R^{3a}$ is hydrogen. In a further aspect, $R^{3b}$ is —$OR^{11}$; wherein $R^{11}$ is selected from hydrogen, C1-C6 alkyl, and —$C(O)R^{14}$; wherein $R^{14}$ is C1-C6 alkyl.

e. $R^4$ Groups

In one aspect, $R^4$ is independently selected from C1-C6 alkyl, for example, methyl, ethyl, propyl, butyl, pentyl, or hexyl. In a further aspect, $R^4$ is methyl. In a further aspect, $R^4$, $R^5$, and $R^6$ are all methyl.

f. $R^5$ Groups

In one aspect, $R^5$ is independently selected from C1-C6 alkyl, for example, methyl, ethyl, propyl, butyl, pentyl, or hexyl. In a further aspect, $R^5$ is methyl.

g. $R^6$ Groups

In one aspect, $R^6$ is independently selected from C1-C6 alkyl, for example, methyl, ethyl, propyl, butyl, pentyl, or hexyl. In a further aspect, $R^6$ is methyl.

h. $R^7$ Groups

In one aspect, $R^7$ is selected from C1-C6 alkyl, —$CH_2OR^{12}$, and —$C(O)ZR^{12}$. In a further aspect, $R^7$ is C1-C6 alkyl, for example, methyl, ethyl, propyl, butyl, pentyl, or hexyl. In a further aspect, $R^7$ is —$CH_2OR^{12}$. In a further aspect, $R^7$ is and —$C(O)ZR^{12}$.

i. $R^8$ Groups

In one aspect, $R^8$ is selected from hydrogen and C1-C6 alkyl. In a further aspect, $R^8$ is hydrogen. In a further aspect, $R^8$ is C1-C6 alkyl, for example, methyl, ethyl, propyl, butyl, pentyl, or hexyl.

j. $R^9$ Groups

In one aspect, each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl.

In a further aspect, $R^{9a}$ is hydrogen. In a further aspect, $R^{9a}$ is C1-C6 alkyl, for example, methyl, ethyl, propyl, butyl, pentyl, or hexyl. In a further aspect, $R^{9b}$ is hydrogen. In a further aspect, $R^{9b}$ is C1-C6 alkyl, for example, methyl, ethyl, propyl, butyl, pentyl, or hexyl. In a further aspect, $R^{9b}$ is selected from methyl, ethyl, vinyl, n-propyl, propen-2-yl, i-propyl, 2-propenyl, n-butyl, 1-buten-2-yl, 1-buten-3-yl, i-butyl, 1-buten-2-yl, 1-buten-3-yl, s-butyl, 2-buten-1-yl, 2-buten-2-yl, 2-buten-3-yl, and t-butyl.

In a further aspect, $R^{9a}$ and $R^{9b}$ are covalently bonded and, along with the intermediate carbon, together comprise optionally substituted C3-C5 cycloalkyl or optionally substituted C2-C5 heterocycloalkyl.

k. $R^{10}$ Groups

In one aspect, $R^{10}$ is selected from hydrogen and C1-C6 alkyl. In a further aspect, $R^{10}$ is hydrogen. In a further aspect, $R^{10}$ is C1-C6 alkyl, for example, methyl, ethyl, propyl, butyl, pentyl, or hexyl.

l. $R^{11}$ Groups

In one aspect, each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —$C(O)R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^{11}$ is hydrogen. In a further aspect, $R^{11}$ is selected from C1-C6 alkyl, C1-C5 heteroalkyl, C3-C6 cycloalkyl, C4-C6 heterocycloalkyl, phenyl, heteroaryl, and —$C(O)R^{14}$. In a further aspect, $R^{11}$ is C1-C6 alkyl. In a further aspect, $R^{11}$ is C1-C5 heteroalkyl. In a further aspect, $R^{11}$ is C3-C6 cycloalkyl. In a further aspect, $R^{11}$ is C4-C6 heterocycloalkyl. In a further aspect, $R^{11}$ is phenyl. In a further aspect, $R^{11}$ is heteroaryl. In a further aspect, $R^{11}$ is —$C(O)R^{14}$.

In a further aspect, $R^{11}$ is unsubstituted. In a further aspect, $R^{11}$, where permitted, is substituted with 0-2 groups. In a further aspect, $R^{11}$, where permitted, is substituted with 1 group. In a further aspect, $R^{11}$, where permitted, is substituted with 2 groups.

m. $R^{12}$ Groups

In one aspect, i R is selected from hydrogen and optionally substituted organic residue having from 1 to 20 carbons. In a further aspect, $R^{12}$ is hydrogen. In a further aspect, $R^{12}$ is optionally substituted organic residue having from 1 to 20 carbons. In a further aspect, $R^{12}$ is optionally substituted organic residue having from 3 to 12 carbons.

In a further aspect, $R^{12}$ is hydrogen. In a further aspect, $R^{12}$ is alkyl. In a further aspect, $R^{12}$ is heteroalkyl. In a further aspect, $R^{12}$ is cycloalkyl. In a further aspect, $R^{12}$ is heterocycloalkyl. In a further aspect, $R^{12}$ is aryl. In a further aspect, $R^{12}$ is heteroaryl. In a further aspect, $R^{12}$ is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^{12}$ comprises a group having a formula:

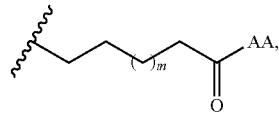

wherein m is an integer from 0 to 10 (e.g., 0, 1, 2, 3, 4, 5, 6, 7, 8, 9, or 10); and wherein AA represents an amino acid residue. In a further aspect, $R^{12}$ is AA is a phenylalanine residue. In a further aspect, $R^{12}$ comprises a group having a formula:

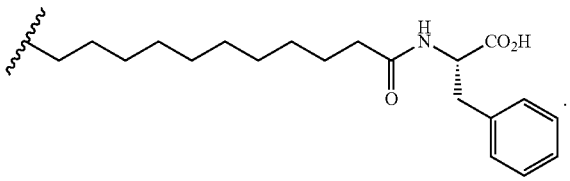 [SMILES: *CCCCCCCCCCC(=O)N[C@@H](Cc1ccccc1)C(=O)O]

n. $R^{13}$ Groups

In one aspect, $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

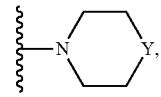

wherein Y is selected from —O—, —S—, —SO—, —SO₂—, —NH—, and —NCH₃—.

In a further aspect, $R^{13}$ is hydrogen. In a further aspect, $R^{13}$ is C1-C4 alkyl, for example, methyl, ethyl, propyl, or butyl. In a further aspect, Z is N, and —NR$^{12}$R$^{13}$ comprises a moiety of the formula:

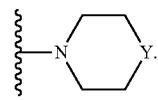

O. $R^{14}$ Groups

In one aspect, $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^{14}$ is C1-C6 alkyl, for example, methyl, ethyl, propyl, butyl, pentyl, or hexyl. In a further aspect, $R^{14}$ is unsubstituted. In a further aspect, $R^{14}$, where permitted, is substituted with 0-2 groups. In a further aspect, $R^{14}$, where permitted, is substituted with 1 group. In a further aspect, $R^{14}$, where permitted, is substituted with 2 groups.

p. AA GROUPS

In one aspect, AA represents an amino acid residue, for example, phenylalanine.

q. Y GROUPS

In one aspect, Y is selected from —O—, —S—, —SO—, —SO₂—, —NH—, and —NCH₃—.

r. Z GROUPS

In one aspect, Z is selected from —O— and —NR$^{13}$—. In a further aspect, Z is —O—. In a further aspect, Z is —NR$^{13}$—; wherein $R^{13}$ is hydrogen. In a further aspect, Z is —NR$^{13}$—; wherein $R^{13}$ is C1-C4 alkyl.

2. Example Compounds

In one aspect, a compound can be present as one or more of the following structures:

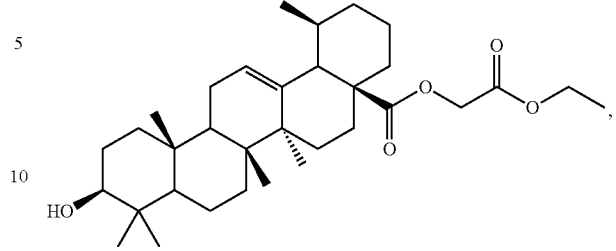

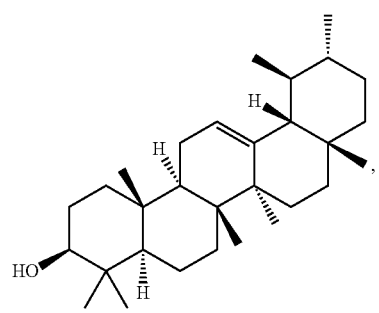

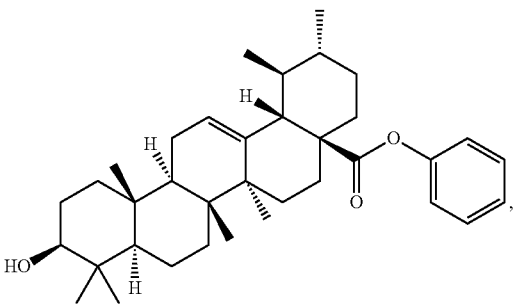

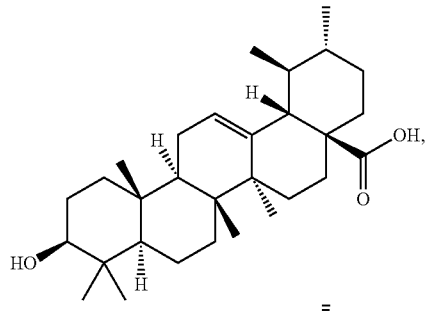

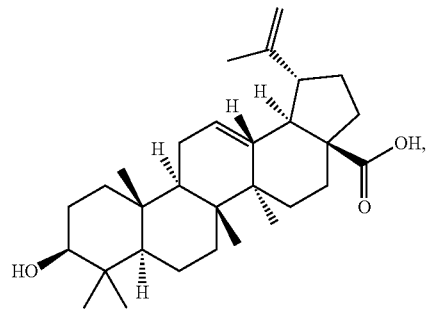

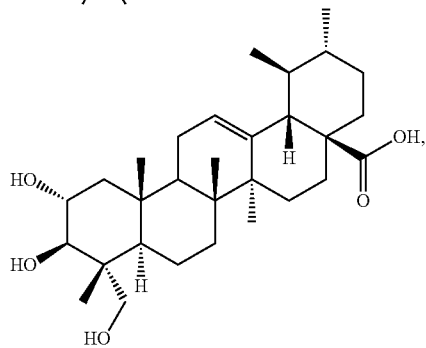

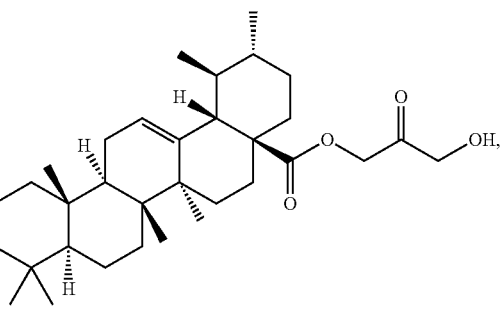

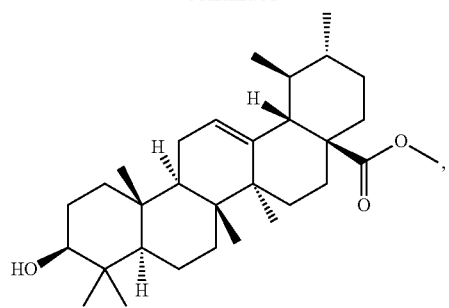
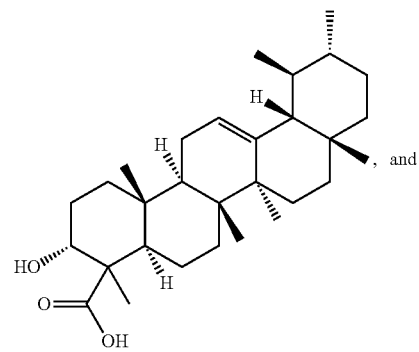
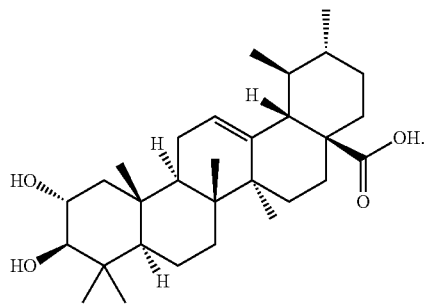
In a further aspect, a compound can be present as one or more of the following structures:
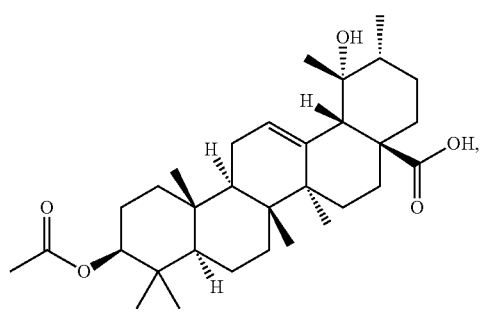
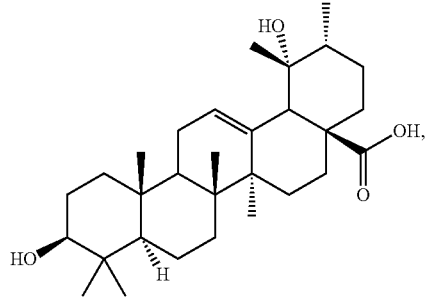
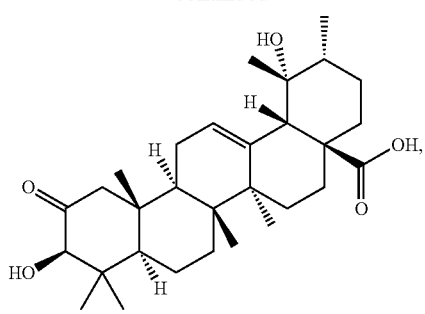
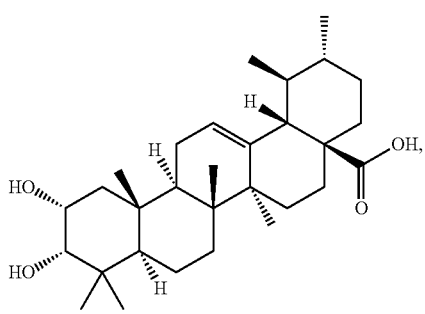
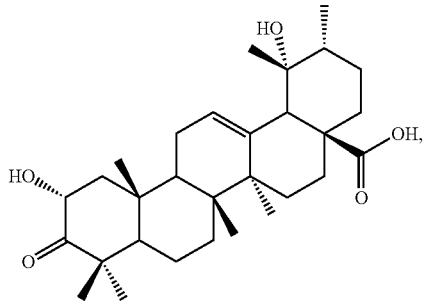
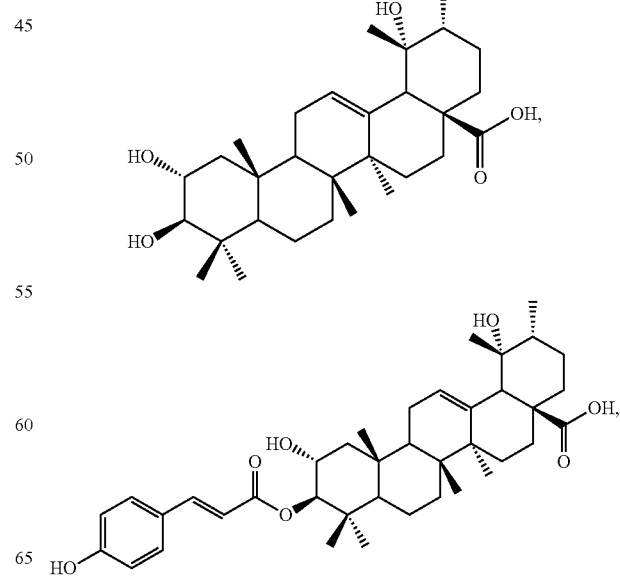

-continued
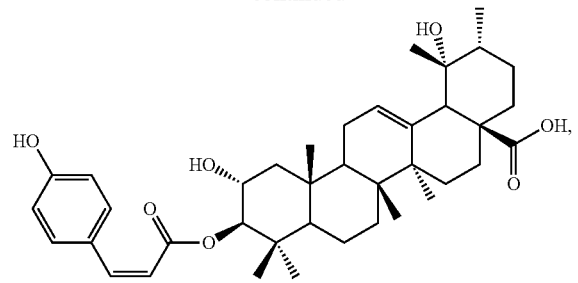
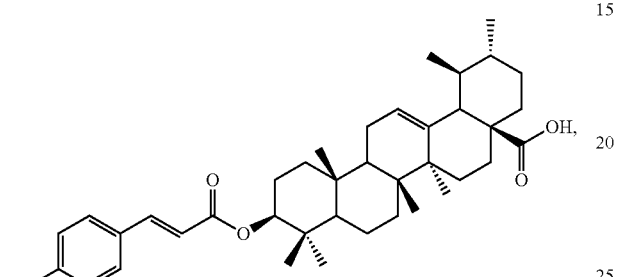
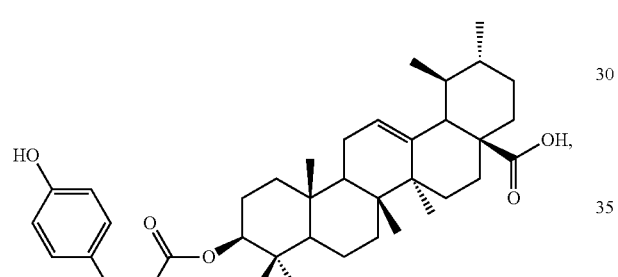
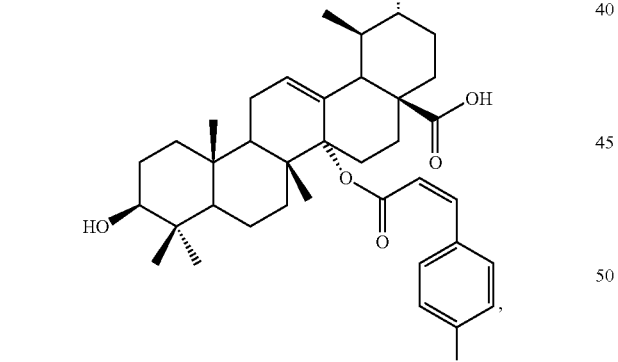
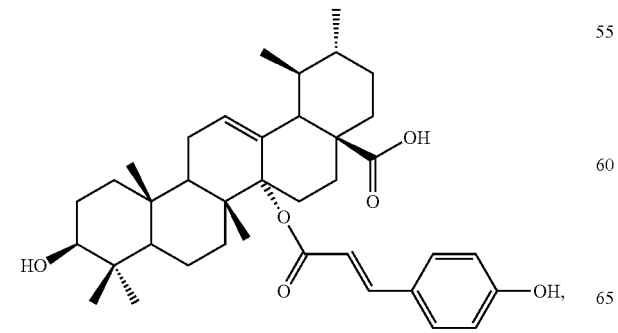
-continued
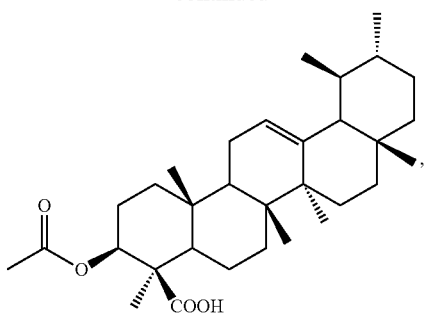
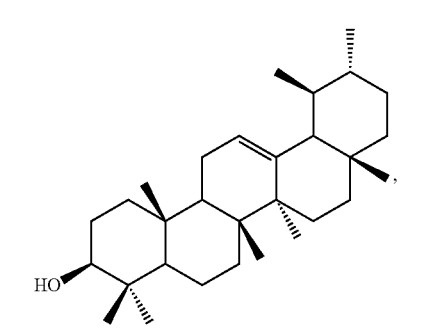
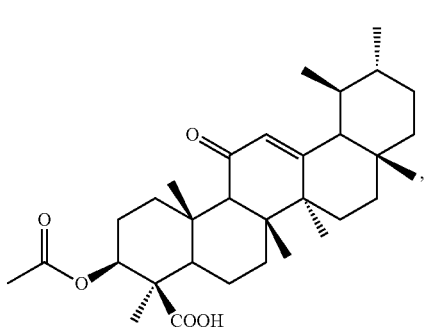
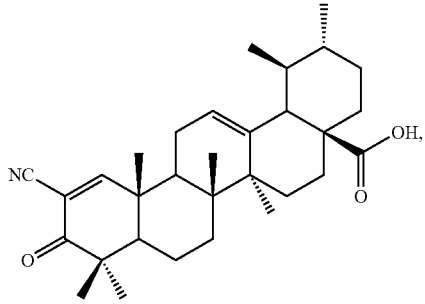
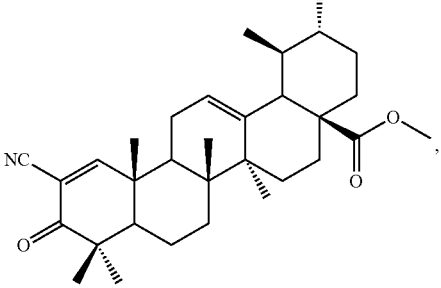

45
-continued
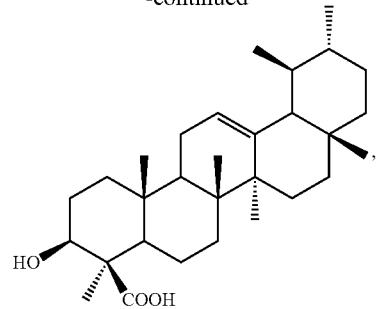
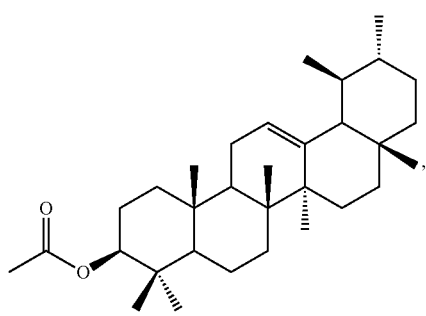
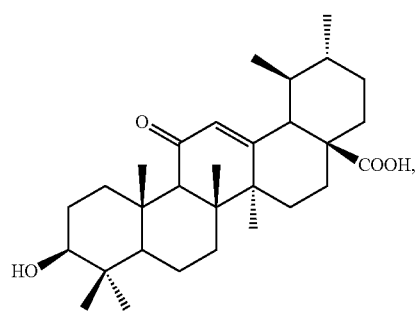
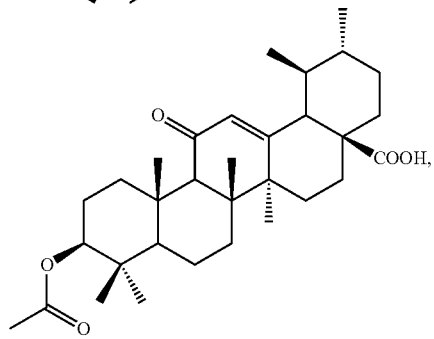
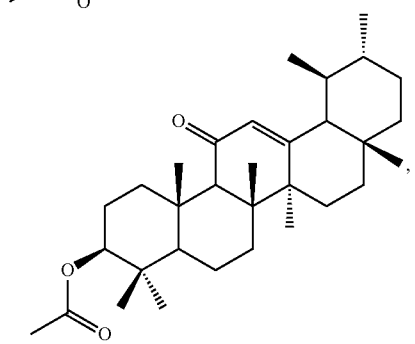
46
-continued
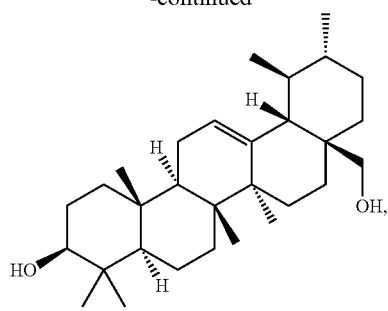
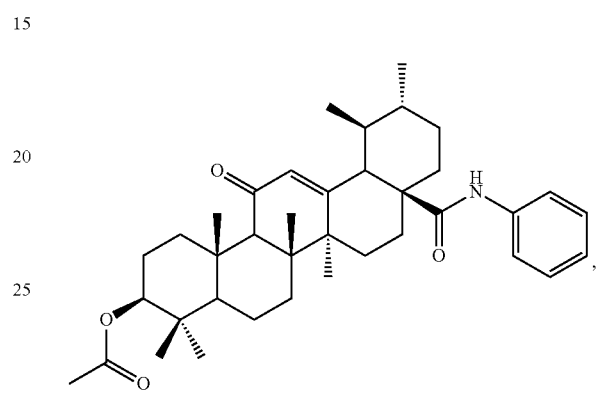
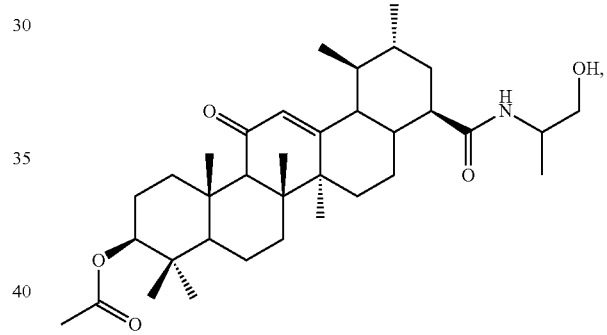
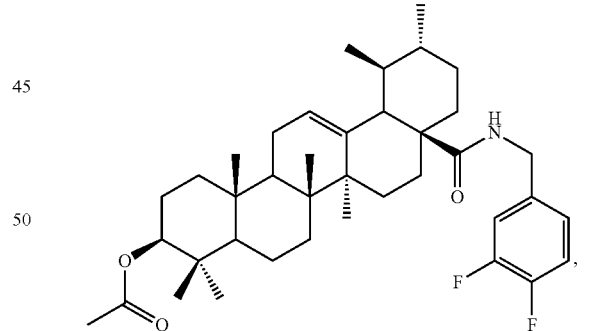
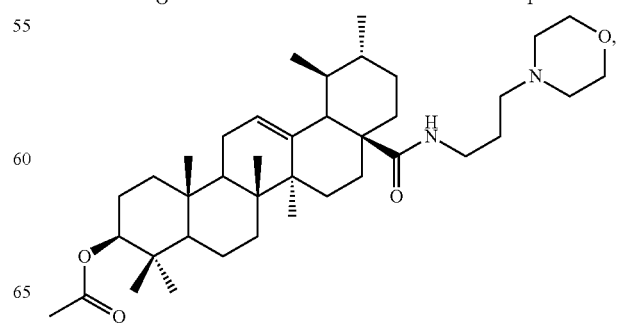

-continued
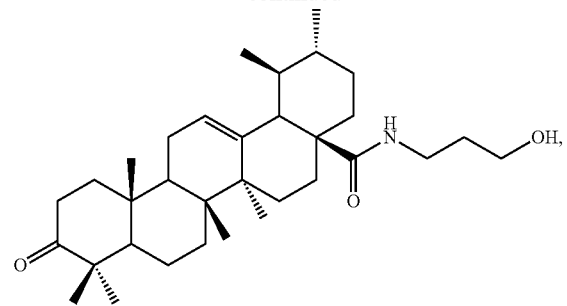
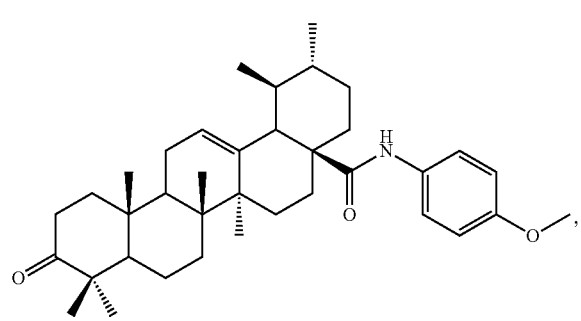
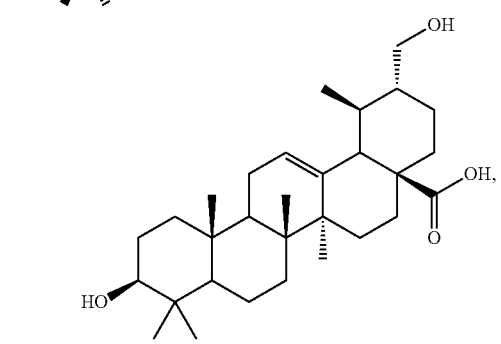
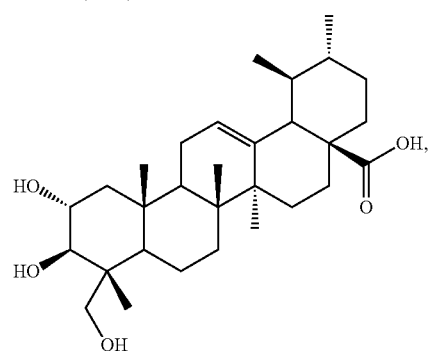
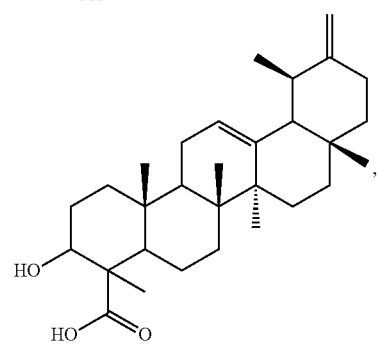
-continued
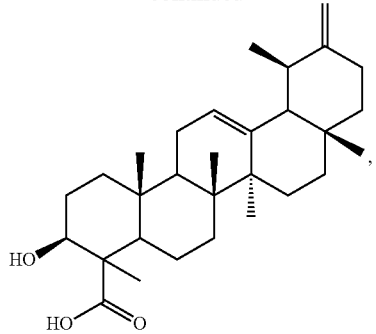
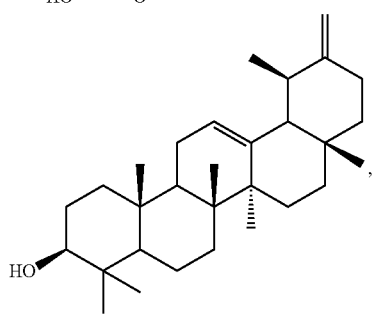
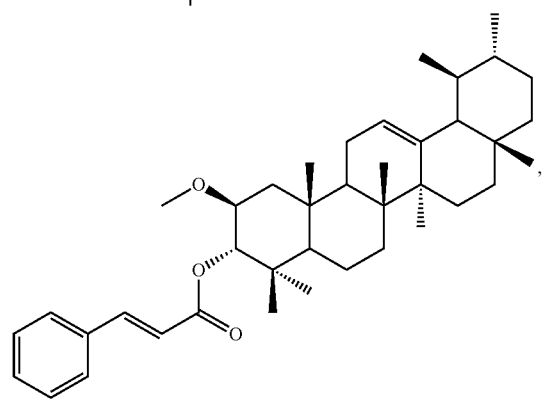
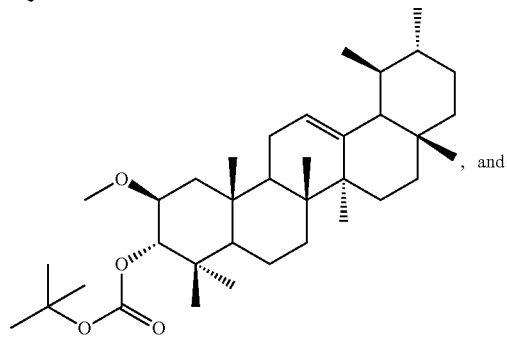, and
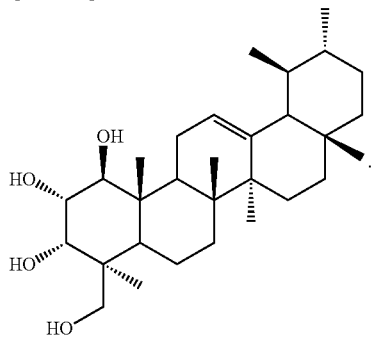.

3. Inhibition of Muscle Atrophy and Induction of Muscle Hypertrophy

In one aspect, the disclosed compounds inhibit muscle atrophy. In a further aspect, the disclosed compounds increase muscle mass. In a still further aspect, the disclosed compounds induce muscle hypertrophy. In a yet further aspect, the disclosed compounds inhibit of muscle atrophy and increase muscle mass. In an even further aspect, the disclosed compounds inhibit of muscle atrophy and induce muscle hypertrophy. In a further aspect, the inhibition of muscle atrophy is in an animal. In an even further aspect, the increase in muscle mass is in an animal. In a still further aspect, the animal is a mammal, In a yet further aspect, the mammal is a human. In a further aspect, the mammal is a mouse. In a yet further aspect, the mammal is a rodent.

In a further aspect, the disclosed compounds inhibit muscle atrophy when administered at an oral dose of greater than about 200 mg per day in a human. In a yet further aspect, the disclosed compounds inhibit muscle atrophy when administered at an oral dose of greater than about 300 mg per day in a human. In a still further aspect, the disclosed compounds inhibit muscle atrophy when administered at an oral dose of greater than about 400 mg per day in a human. In an even further aspect, the disclosed compounds inhibit muscle atrophy when administered at an oral dose of greater than about 500 mg per day in a human. In a further aspect, the disclosed compounds inhibit muscle atrophy when administered at an oral dose of greater than about 750 mg per day in a human. In a yet further aspect, the disclosed compounds inhibit muscle atrophy when administered at an oral dose of greater than about 1000 mg per day in a human. In a still further aspect, the disclosed compounds inhibit muscle atrophy when administered at an oral dose of greater than about mg per day in a human. In an even further aspect, the disclosed compounds inhibit muscle atrophy when administered at an oral dose of greater than about 2000 mg per day in a human.

In a further aspect, the disclosed compounds increase muscle mass when administered at an oral dose of greater than about 200 mg per day in a human. In a yet further aspect, the disclosed compounds increase muscle mass when administered at an oral dose of greater than about 300 mg per day in a human. In a still further aspect, the disclosed compounds increase muscle mass when administered at an oral dose of greater than about 400 mg per day in a human. In an even further aspect, the disclosed compounds increase muscle mass when administered at an oral dose of greater than about 500 mg per day in a human. In a further aspect, the disclosed compounds increase muscle mass when administered at an oral dose of greater than about 750 mg per day in a human. In a yet further aspect, the disclosed compounds increase muscle mass when administered at an oral dose of greater than about 1000 mg per day in a human. In a still further aspect, the disclosed compounds increase muscle mass when administered at an oral dose of greater than about mg per day in a human. In an even further aspect, the disclosed compounds increase muscle mass when administered at an oral dose of greater than about 2000 mg per day in a human.

It is contemplated that one or more compounds can optionally be omitted from the disclosed invention.

C. METHODS OF MAKING THE COMPOUNDS

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In one aspect, the invention relates to methods of making functionalized ursane compounds useful in methods of inhibiting muscle atrophy and increasing muscle mass. Such compounds can be useful in the treatment of various maladies associated with muscle wasting, useful for increasing muscle mass and/or muscle strength, as well as in enhancing muscle formation and/or muscular performance. The compounds of the invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein. The following examples are provided so that the invention might be more fully understood, are illustrative only, and should not be construed as limiting.

1. Route 1: Alkyl Etherification

In one aspect, functionalized ursane compounds of the present invention can be prepared generically as shown below.

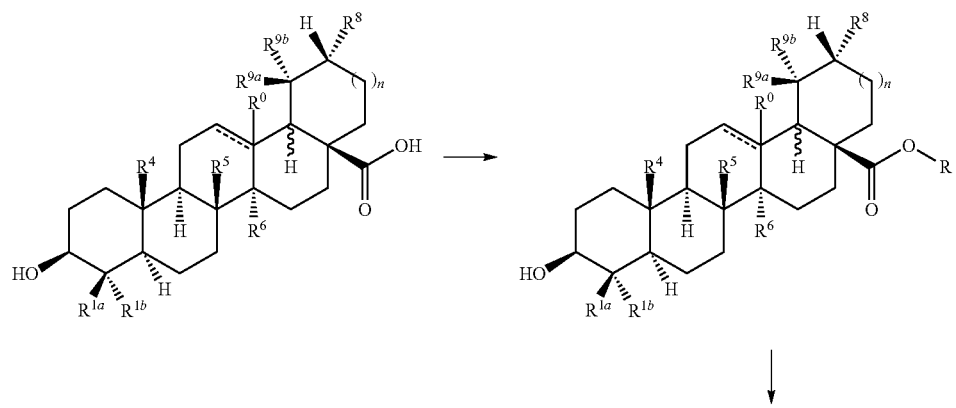

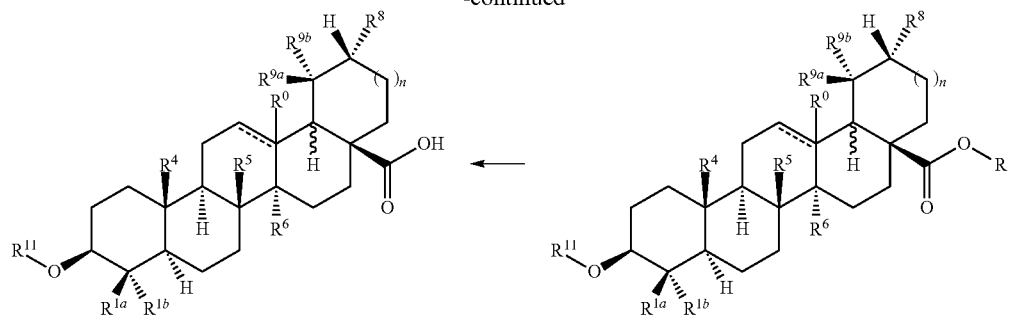

Compounds are represented in generic form, with substituents as noted in compound descriptions elsewhere herein. A more specific example is set forth below.

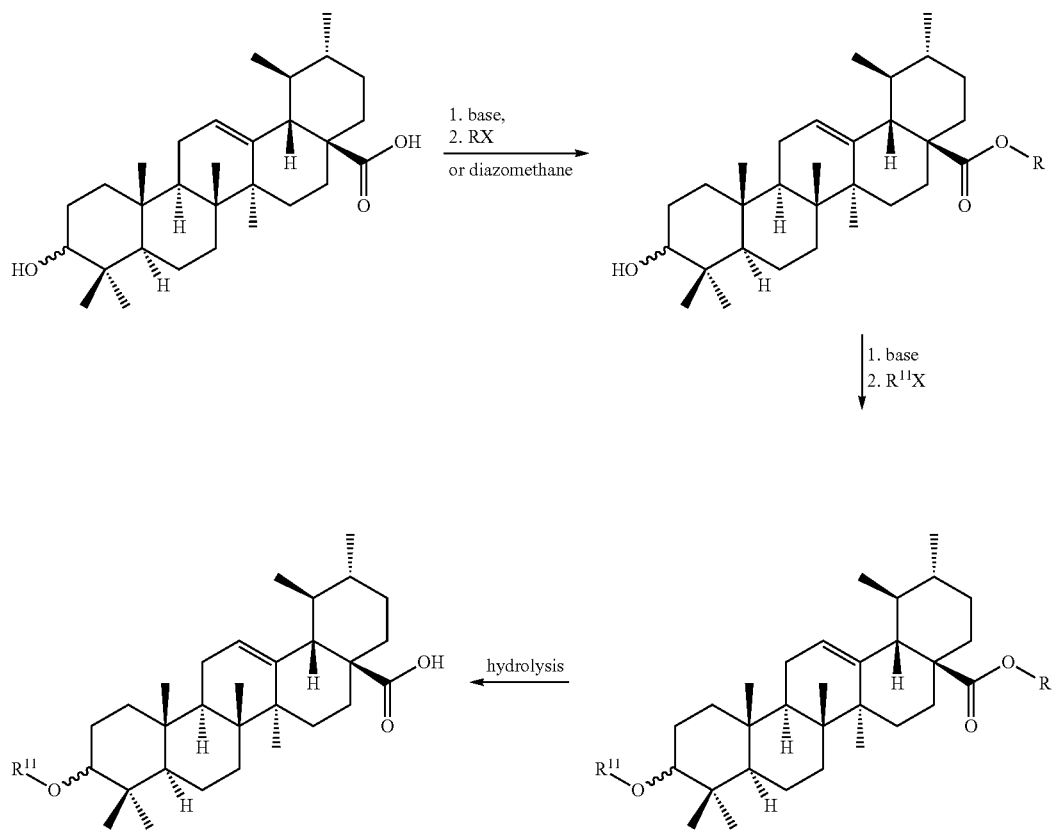

In one aspect, Route 1 step 1 begins with a free acid. In an appropriate solvent, a base (e.g., $K_2CO_3$, NaOH) strong enough to deprotonate the carboxylic acid, but not the alcohol, is added, and the reaction is conducted at a temperature effective and for a time effective to insure carboxylic acid deprotonation. An appropriate alkyl halide or halide equivalent is added to the reaction mixture, and the reaction is conducted at a temperature effective and for a time effective to insure alkylation of the carboxyl group. In a further aspect, an alternate Route 1 step 1 also begins with the free carboxylic acid. Diazomethane is added, and the reaction is conducted at a temperature effective and for a time effective to insure reaction.

In a further aspect, Route 1 step 2 the alkyl ester is dissolved in an appropriate dry solvent under anhydrous reaction conditions. A base is added, and the reaction is conducted at a temperature effective and for a time effective to insure deprotonation. Then, an appropriate alkyl, heteroalkyl, cycloalkyl, or heterocycloalkyl halide or halide equivalent (i.e., $R^{11}X$) is added to the reaction mixture. The reaction is conducted at a temperature effective and for a time effective insure complete reaction.

In a further aspect, in Route 1 step 3, the O-alkylated ursane compound alkyl ester is hydrolyzed with an appropriate base, such as LiOH, in an appropriate organic-aqueous mixed solvent system at a temperature effective and for a time effective to insure reaction. Then the reaction mixture can be acidified to a suitable pH with an appropriate aqueous acid of an sufficient concentration and at a temperature effective and for a time effective to insure reaction.

2. Route 2: Aryl Etherification
In one aspect, functionalized ursane compounds of the present invention can be prepared generically as shown below.
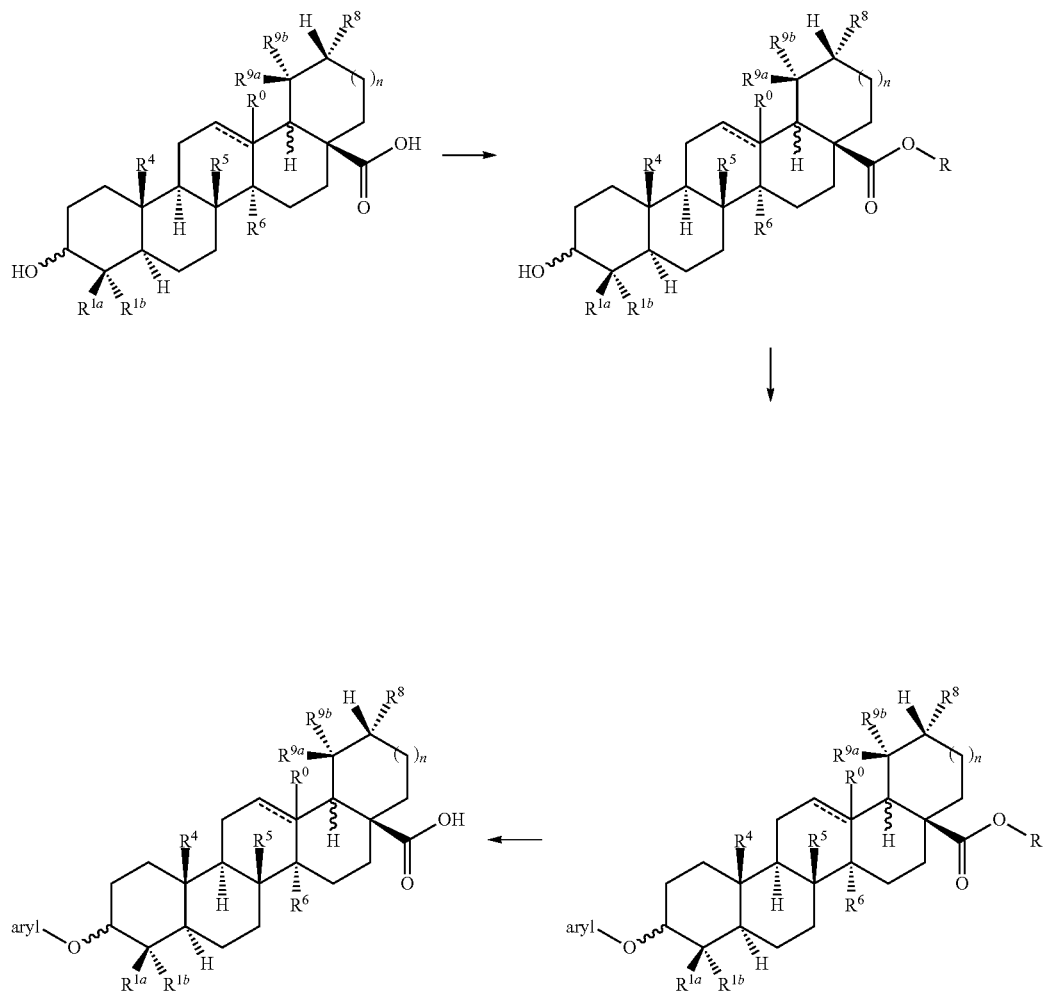
Compounds are represented in generic form, with substituents as noted in compound descriptions elsewhere herein. A more specific example is set forth below.
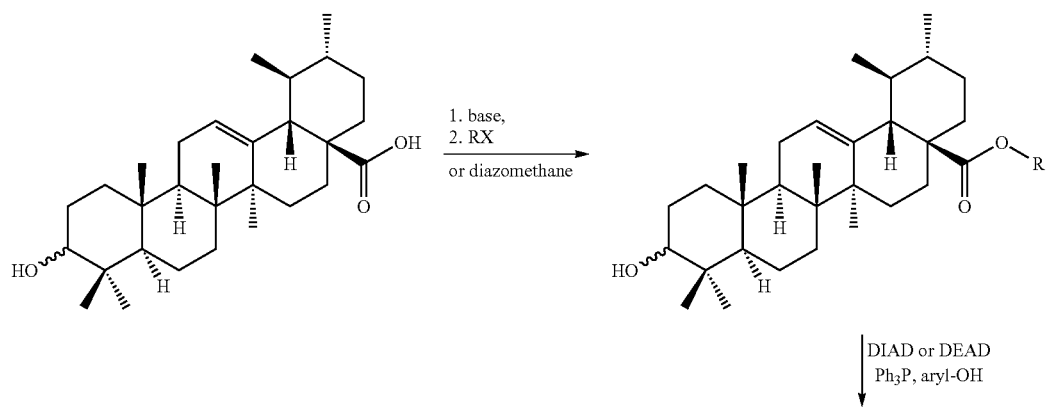

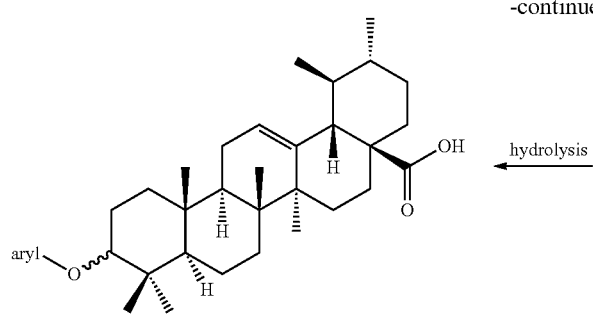 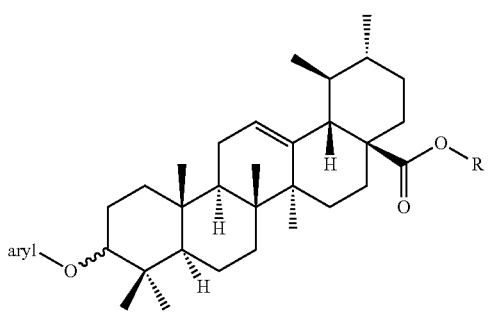

In one aspect, Route 2 step 1 begins with the ursane compound free carboxylic acid. In an appropriate solvent, a base (e.g., $K_2CO_3$, NaOH) strong enough to deprotonate the carboxylic acid, but not the alcohol group, is added, and the reaction is conducted at a temperature effective and for a time effective to insure deprotonation. Then, an appropriate alkyl halide or halide equivalent is added to the reaction mixture, and the reaction is conducted at a temperature effective and for a time effective to insure alkylation of the carboxyl group. In a further aspect, an alternate Route 2 step 1 begins with the ursane compound free carboxylic acid in an appropriate solvent. Diazomethane is added, and the reaction is conducted at a temperature effective and for a time effective to insure reaction.

In a further aspect, Route 2 step 2, the ursane compound alkyl ester is dissolved in an appropriate, dry solvent, along with phenol, an aryl alcohol, or appropriate heteroaryl alcohol, under anhydrous reaction conditions, followed by the addition of triphenylphosphine. The reaction is conducted at a effective temperature and for an effective time period. Then, an appropriate coupling agent, such as DIAD or DEAD, is added, and the reaction is conducted at a temperature effective and for a time effective to insure reaction. In a further aspect, in Route 2 step 3, the O-arylated or heteroarylated ursane compound alkyl ester can be treated with an appropriate base, such as LiOH, in an appropriate organic-aqueous mixed solvent system at a temperature effective and for a time effective to insure complete reaction. The reaction mixture can then be acidified to a suitable pH.

3. Route 3: Acylation

In one aspect, functionalized ursane compounds of the present invention can be prepared generically as shown below.

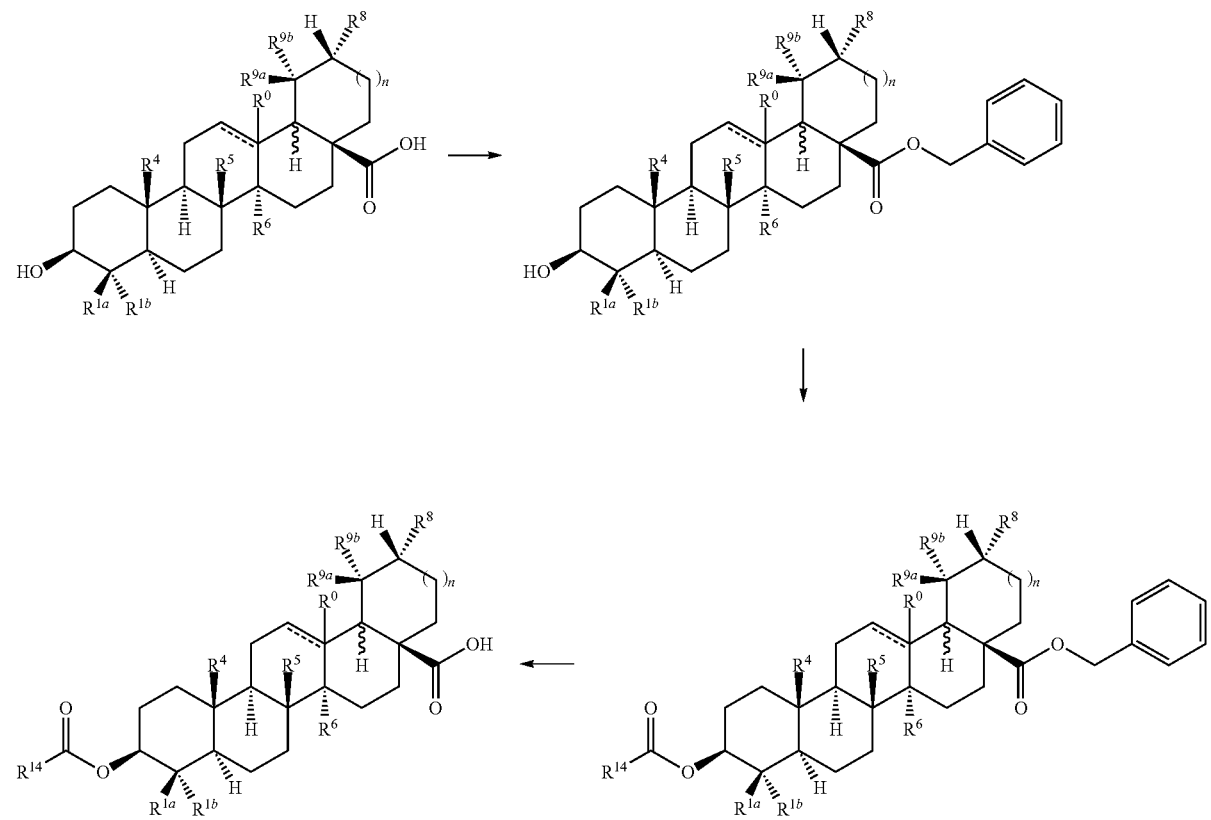

Compounds are represented in generic form, with substituents as noted in compound descriptions elsewhere herein. A more specific example is set forth below.

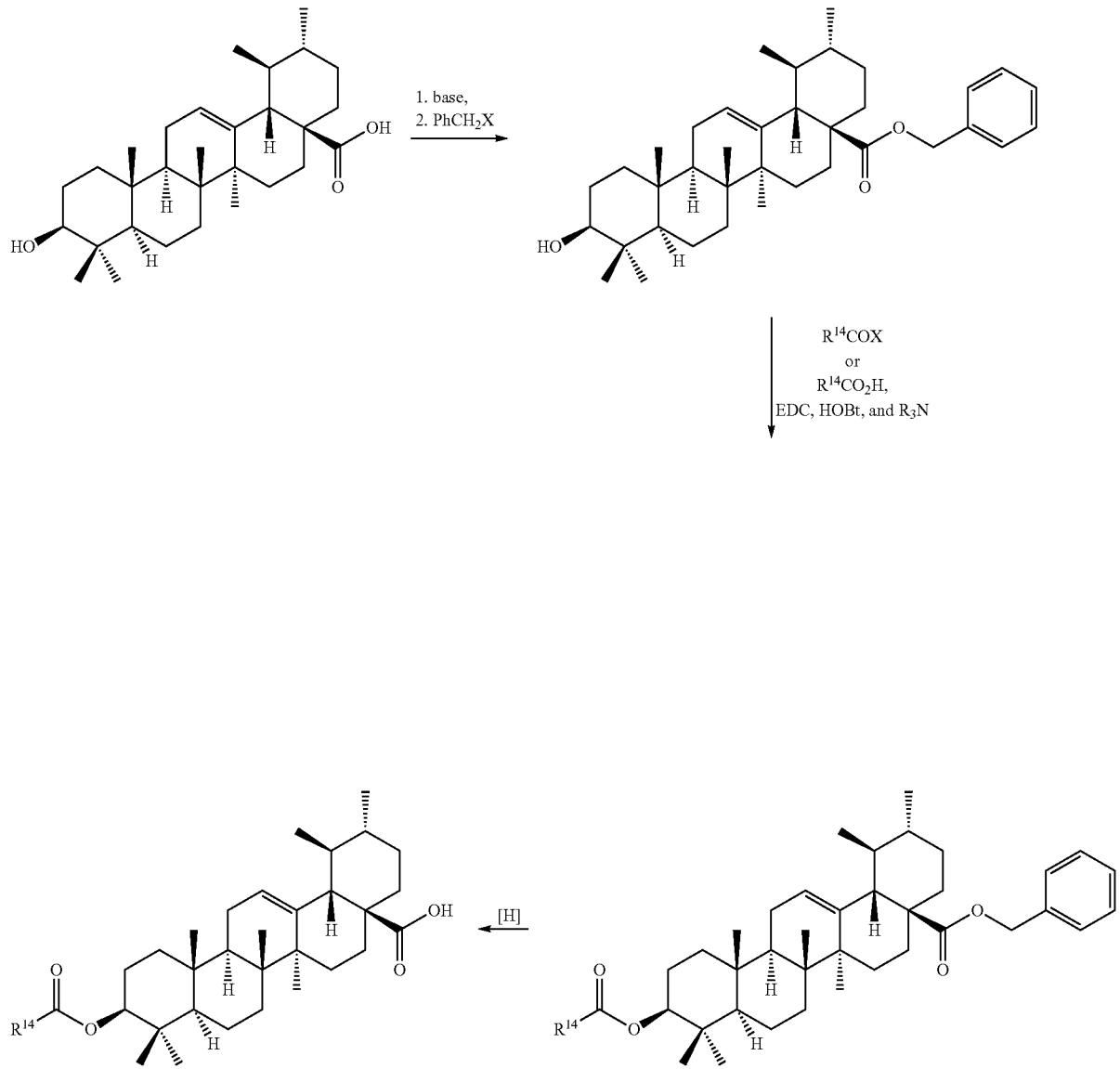

In one aspect, Route 3 step 1 begins with the ursane compound free carboxylic acid. In an appropriate solvent, a base (e.g., K$_2$CO$_3$, NaOH) strong enough to deprotonate the carboxylic acid, but not the alcohol group, is added, and the reaction is allowed to progress at a temperature effective and for a time effective to insure carboxylic acid deprotonation. Then, an appropriate benzyl halide or halide equivalent is added to the reaction mixture, and the reaction is conducted at a temperature effective and for a time effective to insure protection of the carboxyl group.

In Route 3 step 2, the ursane compound benzyl ester is dissolved in an appropriate, dry solvent under anhydrous reaction conditions, followed by the addition of an appropriate acid scavenger (weak base, e.g., K$_2$CO$_3$ or DIEA). The acyl halide (e.g., R$^{14}$COX) or equivalent acylating reagent is then added. The reaction is conducted at a temperature effective and for a time effective to insure reaction. In a further aspect, in an alternate Route 3 step 2, the ursane compound benzyl ester and a suitable carboxylic acid (e.g., R$^{14}$CO$_2$H) are dissolved in an appropriate, dry solvent under anhydrous reaction conditions. Ethyl-(N',N'-dimethylamino)propylcarbodiimide hydrochloride (EDC), 1-hydroxybenzotriazole (HOBt), and a trialkylamine (R$_3$N) are then added, and the reaction is conducted at a temperature effective and for a time effective to insure reaction.

In Route 3 step 3, the acylated ursane compound benzyl ester is reduced under standard conditions (e.g., hydrogenation with hydrogen gas in the presence of a suitable palladium catalyst), thereby liberating the ursane compound free carboxlic acid.

4. Route 4: Esterification

In one aspect, functionalized ursane compounds of the present invention can be prepared generically as shown below.

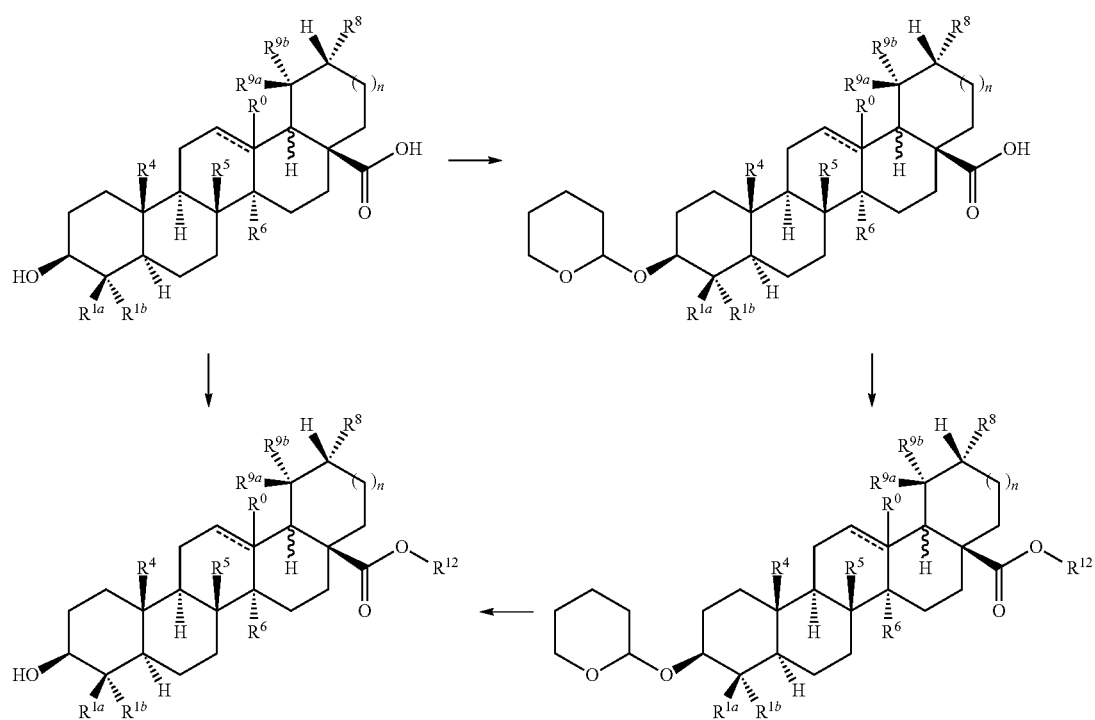
Compounds are represented in generic form, with substituents as noted in compound descriptions elsewhere herein. A more specific example is set forth below.
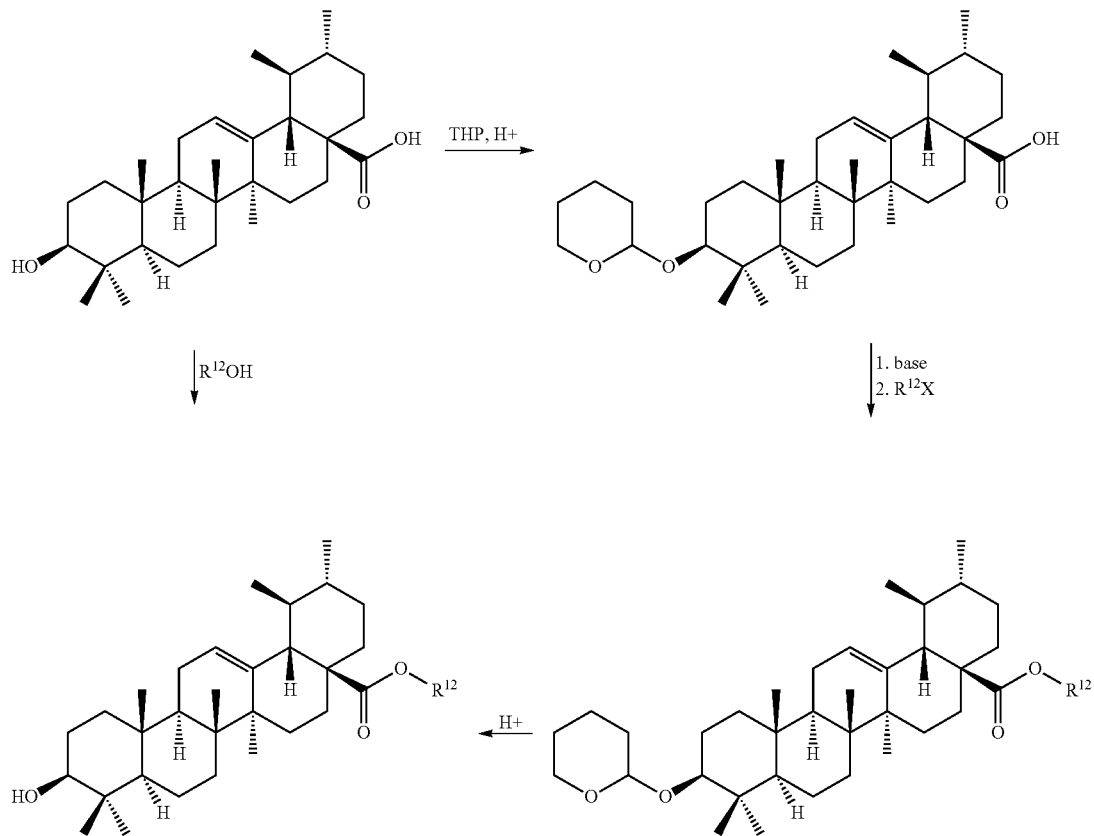

In one aspect, Route 4 step 1 begins with the ursane compound free carboxylic acid. An appropriate alcohol (e.g., $R^{12}OH$) is added, and the reaction is conducted at a temperature effective and for a time effective to time to insure reaction.

In a further aspect in an alternate synthesis, Route 4 step 1 begins with the ursane compound free carboxylic acid in a dry solvent under dry reaction conditions. Tetrahydropyran (THP) is added, along with an acid catalyst (e.g., pTsOH). The reaction is conducted at a temperature effective and for a time effective to insure protection of the hydroxyl group. A base (e.g., NaOH or NaH) is then added to the THP-protected ursane compound free carboxylic acid, in a dry solvent under anhydrous reaction conditions. The reaction is conducted at a temperature effective and for a time effective to insure carboxylic acid deprotonation. Then, an appropriate alkyl halide (i.e., $R^{12}X$) or equivalent is added to the reaction mixture, and the reaction is conducted at a temperature effective and for a time effective to insure alkylation of the carboxyl group. Route 4 step 3 begins with the THP-protected ursane compound alkyl ester in an alcohol solvent. An acid catalyst (e.g., pTsOH) is added, and the reaction is conducted at a temperature effective and for a time effective to insure deprotection.

5. Route 5: Amide Formation

In one aspect, functionalized ursane compounds of the present invention can be prepared generically as shown below.

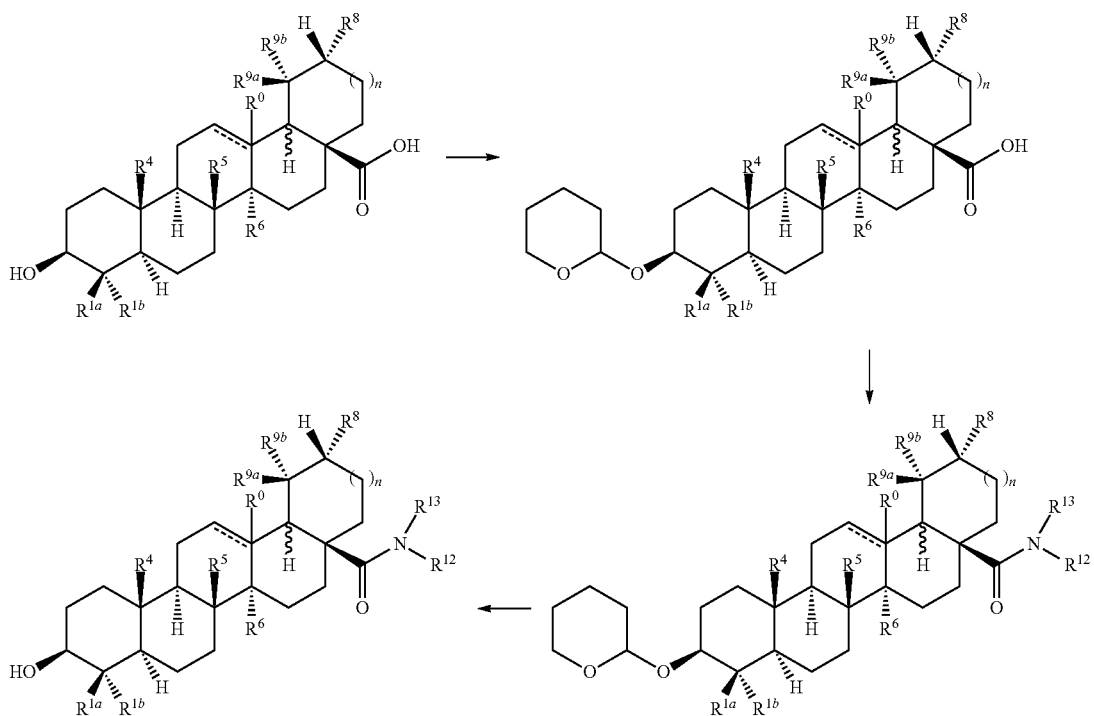

Compounds are represented in generic form, with substituents as noted in compound descriptions elsewhere herein. A more specific example is set forth below.

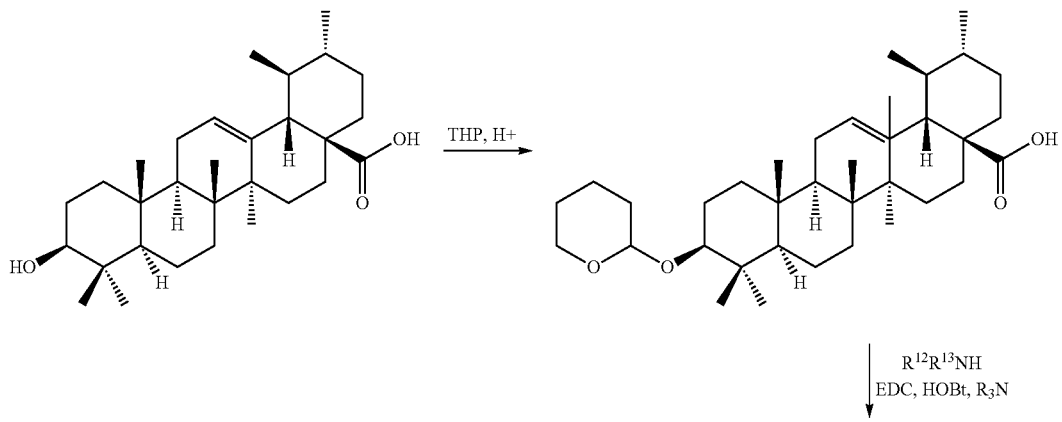

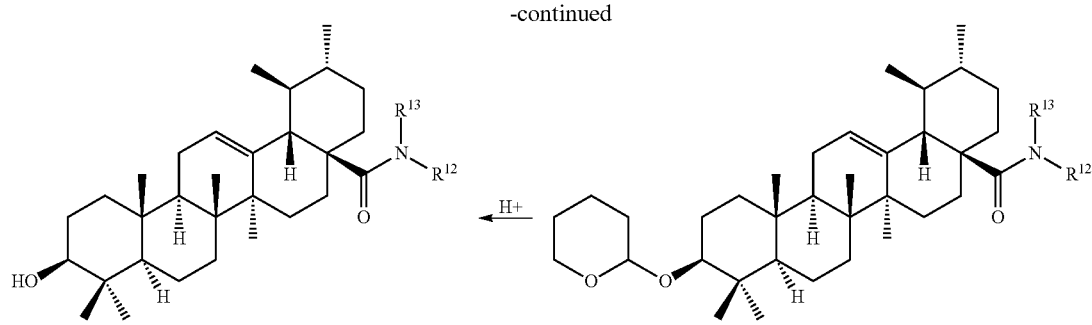

In one aspect, Route 5 step 1 begins with the ursane compound free carboxylic acid in a dry solvent. Under dry reaction conditions, tetrahydropyran (THP) and an acid catalyst (e.g., pTsOH) are added. The reaction is then conducted at a temperature effective and for a time effective to insure protection of the hydroxyl group. In Route 5 step 2, the THP-protected ursane compound free carboxylic acid is dissolved in an appropriate, dry solvent. Under anhydrous reaction conditions, a suitable amine (e.g., $R^{12}R^{13}NH$) is added, along with ethyl-(N',N'-dimethylamino)propylcarbodiimide hydrochloride (EDC), 1-hydroxybenzotriazole (HOBt), and a trialkylamine ($R_3N$), and the reaction is conducted at a temperature effective and for a time effective to time to insure complete reaction. In Route 5 step 3, the THP-protected ursane compound amide can then be deprotected by addition of an acid catalyst (e.g., pTsOH), and the reaction is conducted at a temperature effective and for a time effective to insure reaction.

6. Route 6: Reduction to Alcohol

In one aspect, functionalized ursane compounds of the present invention can be prepared generically as shown below.

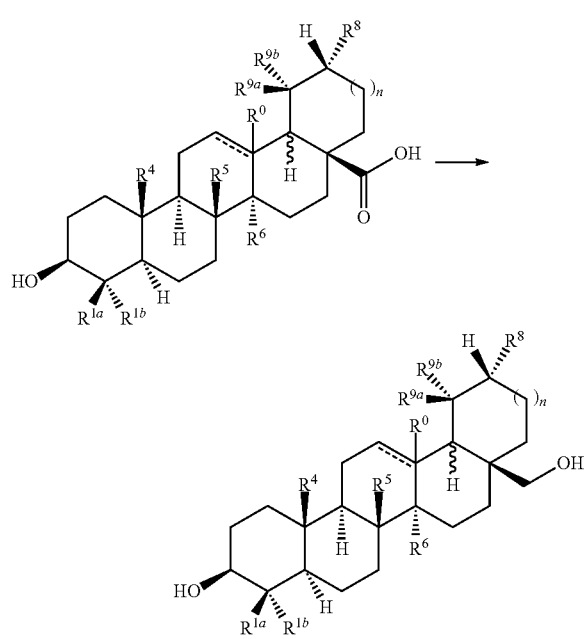

Compounds are represented in generic form, with substituents as noted in compound descriptions elsewhere herein. A more specific example is set forth below.

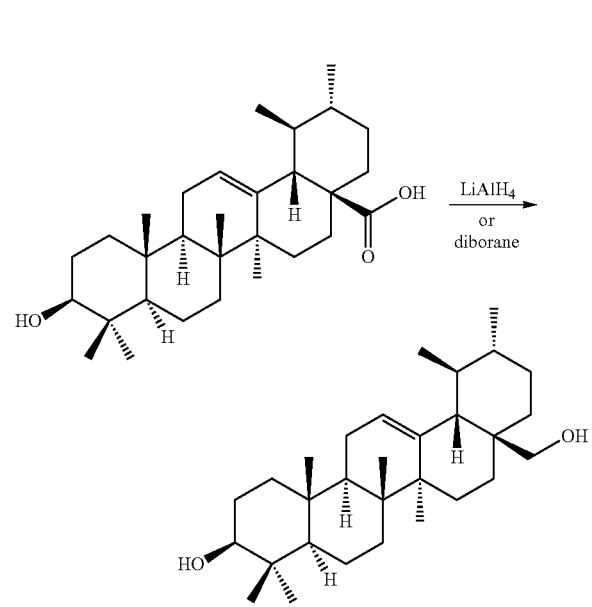

In one aspect, the ursane compound free carboxylic acid, in a dry solvent, can be reacted with lithium aluminum hydride ($LiAlH_4$) under dry reaction conditions to provide the corresponding primary alcohol. Alternatively, the ursane compound free carboxylic acid, in a dry solvent, can be reacted with diborane ($B_2H_6$) under dry reaction conditions to provide the corresponding primary alcohol. It is understood that protecting group chemistry, if needed, can also be used to protect sensitive remote functionality during these reaction steps.

7. Route 7: Hydroxyl Inversion

In one aspect, functionalized ursane compounds of the present invention can be prepared generically as shown below.

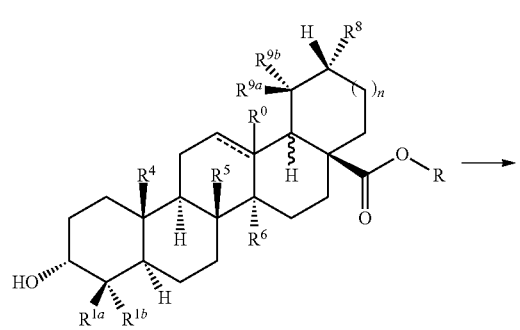

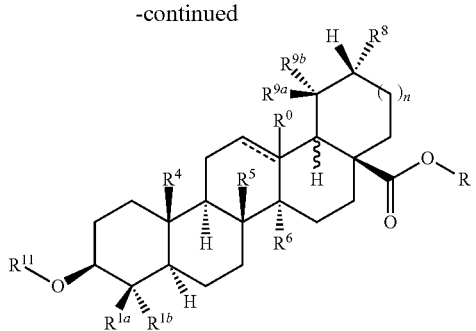

Compounds are represented in generic form, with substituents as noted in compound descriptions elsewhere herein. A more specific example is set forth below.

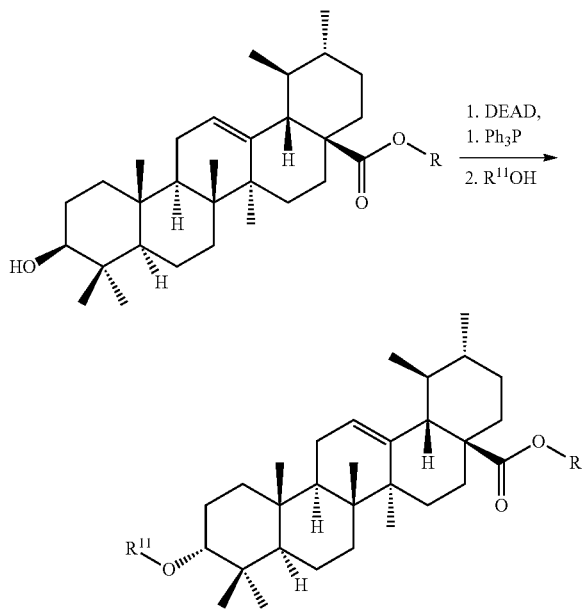

In one aspect, a hydroxyl functionality can be substituted with another group (e.g., alkoxyl, acyl, amino, etc.), while inverting the stereochemistry at the adjacent carbon, by reaction with an appropriate protic nucleophile in the presence of diethylazodicarboxylate (DEAD) and triphenylphosphine under Mitsunobu reaction conditions. While —$OR^{11}$ is shown, it is understood that additional moieties (e.g., acetoxyl, amino, etc.) can be substituted at that position by appropriate selection of protic nucleophile (e.g., acetic acid, ammonia, etc.).

8. Plant Sources of Ursolic Acid Derivatives

Many pentacyclic acid triterpenes useful as synthetic precursors to the ursolic acid derivatives in the synthetic methods described above may be isolated and purified from a natural source such as plants or materials derived from plants. Alternatively, certain known synthetic precursors useful in the preparation of ursolic acid derivatives can often be obtained from commercial sources. Ursolic Acid is a useful known synthetic precursor to ursolic acid derivatives that can be used as a synthetic precursor to prepare certain disclosed compounds. For example, ursolic acid can be isolated from plants such as Holy Basil (*Ocimum sanctum* L.), peppermint leaves (*Mentha piperita* L.), lavender (*Lavandula augustifolia* Mill.), oregano (*Origanum vulgare* L.), thyme (*Thymus vulgaris* L.), hawthorn (*Crataegus laevigata* (*Poir*) DC), cherry laurel leaves (*Prunus laurocerasus* L.), loquat leaves (*Eriobotrya japonica* L.), glossy privet leaves (*Ligustrum lucidum* Ait. L.), bilberry (*Vacciunum myrtillus* L.), Devil's Claw (*Harpagophytum procumbens* DC), Elder Flowers (European var.; *Sambucus nigra* L.), and periwinkle (*Vinca minor* L.).

A variety of methods that are generally applicable to purifying ursolic acid and ursolic acid derivatives. For example, Nishimura, et al. (J. Nat. Prod. 1999, 62, 1061-1064) described the identification of 2,3-dihydroxy-24-nor-urs-4(23),12-dien-28-oic acid and 23-hydroxyursolic acid. Nishimura described procedures to isolate these compounds. Procedures described herein demonstrate these compounds will be contained in flash chromatography fraction 3 (FCF3) as described in the examples. Similar HPLC procedures described herein can be used to further purify these compounds including using a gradient with water with 0.05% TFA and acetonitrile with 0.05% TFA, mobile phase A and B respectively, with a C18 BetaMax Neutral column (250×8 mm; 5 um). The gradient may consist of 40% β isocratic for 5 min, then from approximately 40% to 70% B in 30 min. A skilled artisan would recognize the general applicability of the methods described in Nishimura et al to efficiently isolate either the ursolic acid, ursolic acid derivatives or structurally related pentacyclic acid triterpenes from various plants.

Other illustrative methods that are generally applicable to purifying ursolic acid and ursolic acid derivatives are also known. For example, Chaturvedula, et al. (J. Nat. Prod. 2004, 67, p. 899-901) described the isolation of 3-acetoxy-2-hydroxy ursolic acid, 3-(p-coumaroyl)ursolic acid, and 2,3-diacetoxyursolic acid. Adnyana, et al. (J. Nat. Prod. 2001, 64, p. 360-363) described the isolation of 2,3,6,19-tetrahydroxyoleanolic acid, 2,3,19-trihydroxyoleanolic acid, 2,3,19,23-tetrahydroxyursolic acid, and 2,3,23-trihydroxyoleanolic acid. Ikuta, et al. (J. Nat. Prod. 2003, 66, p. 1051-1054) described the isolation of 2,3-dihydroxyurs-12-en-1'-on-28-oic acid and 2,3-dihydroxy-11-methoxyurs-12-en-28-oic acid. For example, similar HPLC procedures such as those described in U.S. Pat. No. 7,612,045 can be used to further purify these compounds including using a gradient with water with 0.05% TFA and acetonitrile with 0.05% TFA, mobile phase A and B respectively, with a C18 BetaMax Neutral column (250×8 mm; 5 um). The gradient may consist of 40% β isocratic for 5 min, then from approximately 40% to 70% B in 30 min.

Finally, another source of the known synthetic precursors useful in the synthetic methods described above to prepare ursolic acid derivatives are commercial sources or vendors. Purified forms of corosolic acid, ursolic acid, oleanolic acid, madecassic acid, asiatic acid, pygenic acid (A, B or C), caulophyllogenin and echinocystic acid may be obtained from a commercial source. For example, ursolic acid and oleanolic acid may be purchased from Sigma-Aldrich Chemical Company (St. Louis, Mo., USA) and corosolic acid, asiatic acid, madecassic acid, pygenic acid (A, B, or C), caulophyllogenin and echinocystic acid may be purchased from Chromadex (Santa Ana, Calif., USA). The compounds obtained from commercial sources may be furthered separated and purified as needed using methods such as column chromatography, high pressure liquid chromatography (HPLC), and/or recrystallization described herein. Additional methods of isolation of precursors are described in U.S. Pat. No. 7,612,045, U.S. patent application Ser. No. 10/355,201, and U.S. patent application Ser. No. 10/445,943.

It is further anticipated that the compounds of the invention can be obtained by direct synthesis. Direct synthesis may include either total synthesis or semi-synthesis. Exemplary synthetic methods for obtaining these compounds are described above. Additional synthetic procedures useful in the preparation of ursolic acid derivatives are described in U.S. Pat. No. 3,903,089, U.S. Pat. No. 7,612,045, and U.S. patent application Ser. No. 10/445,943, U.S. patent application Ser. No. 10/355,201. Further synthetic methods useful in the preparation of ursolic acid derivatives are Meng, Y., et al. (2010) *Molecules* 15:4033-4040; Gao, Y., et al. (2010) *Molecules* 15:4439-4449; Sporn, M. B., et al. (2011) *Journal of Natural Products* 74:537-545; Chadalapaka, G., et al. (2008) *Biorganic and Medicinal Chemistry Letters* 18(8): 2633-2639; and, Sun, H., et al. (2006) *Botanical Studies* 47:339-368.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In one aspect, the invention relates to a pharmaceutical composition comprising a pharmaceutically acceptable carrier and an effective amount of a compound having a structure represented by a formula:

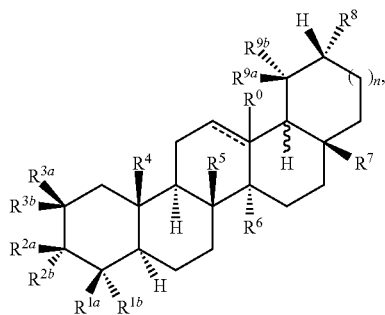

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)ZR$^{10}$; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —OR$^{11}$, and the other is hydrogen, or $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —CH$_2$OR$^{12}$ and —C(O)ZR$^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein $R^{10}$ is selected from hydrogen and C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —NR$^{13}$—; wherein $R^{13}$ is selected from hydrogen and C1-C4 alkyl; or, wherein Z is N, $R^{12}$ and $R^{13}$ are covalently bonded and —NR$^{12}$R$^{13}$ comprises a moiety of the formula:

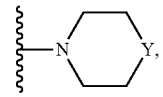

wherein Y is selected from —O—, —S—, —SO—, —SO$_2$—, —NH—, —NCH$_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to prevent or treat muscle atrophy in the animal, wherein the amount is greater than about 1000 mg per day when the compound is ursolic acid, boswellic acid, corosolic acid, betulinic acid, or UA0713.

In one aspect, the animal is an animal. In a further aspect, the animal is a mammal. In a yet further aspect, the mammal is a primate. In a still further aspect, the mammal is a human. In an even further aspect, the human is a patient.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, the muscle disorder is muscle atrophy. In an even further aspect, the muscle disorder is a condition in need of increasing muscle mass. In an even further aspect, the effective amount is greater than about 1000 mg per day when the compound is ursolic acid, beta-boswellic acid, corosolic acid, betulinic acid, or UA0713.

In a further aspect, the pharmaceutical composition is administered following identification of the mammal in need of treatment of muscle atrophy. In a still further aspect, the pharmaceutical composition is administered following identification of the mammal in need of prevention of muscle atrophy. In an even further aspect, the mammal has been diagnosed with a need for treatment of muscle atrophy prior to the administering step.

In a further aspect, the compound is not ursolic acid, beta-boswellic acid, corosolic acid, betulinic acid, or UA0713. In a yet further aspect, the compound is ursolic acid, beta-boswellic acid, corosolic acid, betulinic acid, or UA0713.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of cellular function related to muscle growth an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating cellular activity related to muscle growth (e.g., treatment of one or more disorders associated with muscle dysfunction or atrophy) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. METHODS OF USING THE COMPOUNDS AND COMPOSITIONS

1. Muscle Atrophy

Muscle atrophy is defined as a decrease in the mass of the muscle; it can be a partial or complete wasting away of muscle. When a muscle atrophies, this leads to muscle weakness, since the ability to exert force is related to mass. Muscle atrophy is a co-morbidity of several common diseases, and patients who have "cachexia" in these disease settings have a poor prognosis.

Muscle atrophy can also be skeletal muscle loss or weakness caused by malnutrition, aging, muscle disuse (such as voluntary and involuntary bedrest, neurologic disease (such as multiple sclerosis, amyotrophic lateral sclerosis, spinal muscular atrophy, critical illness neuropathy, spinal cord injury, peripheral neuropathy, or peripheral nerve injury), injury to the limbs or joints, casting, other post-surgical forms of limb immobilization, or spaceflight), chronic disease (such as cancer, congestive heart failure, chronic pulmonary disease, chronic renal failure, chronic liver disease, diabetes mellitus, glucocorticoid hypersecretion, and chronic infections such as HIV/AIDS or tuberculosis), burn injuries, sepsis, other illnesses requiring mechanical ventilation, drug-induced muscle disease (such as glucocorticoid-induced myopathy and statin-induced myopathy), genetic diseases that primarily affect skeletal muscle (such as muscular dystrophy, myotonic dystrophy and inclusion body myositis), or autoimmune diseases that affect skeletal muscle (such as polymyositis and dermatomyositis).

There are many diseases and conditions which cause muscle atrophy, including malnutrition, muscle disuse (secondary to voluntary or involuntary bedrest, neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization), chronic disease (including cancer, congestive heart failure, chronic pulmonary disease, chronic renal failure, chronic liver disease, diabetes mellitus, Cushing syndrome and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, and aging.

Muscle atrophy occurs by a change in the normal balance between protein synthesis and protein degradation. During atrophy, there is a down-regulation of protein synthesis pathways, and an activation of protein breakdown pathways. The particular protein degradation pathway which seems to be responsible for much of the muscle loss seen in a muscle undergoing atrophy is the ATP-dependent, ubiquitin/proteasome pathway. In this system, particular proteins are targeted for destruction by the ligation of at least four copies of a small peptide called ubiquitin onto a substrate protein. When a substrate is thus "poly-ubiquitinated," it is targeted for destruction by the proteasome. Particular enzymes in the ubiquitin/proteasome pathway allow ubiquitination to be directed to some proteins but not others—specificity is gained by coupling targeted proteins to an "E3 ubiquitin ligase." Each E3 ubiquitin ligase binds to a particular set of substrates, causing their ubiquitination. For example, in skeletal muscle, the E3 ubiquitin ligases atrogin-1 and MuRF1 are known to play essential roles protein degradation and muscle atrophy.

Muscle atrophy can be opposed by the signaling pathways which induce muscle hypertrophy, or an increase in muscle size. Therefore one way in which exercise induces an increase in muscle mass is to downregulate the pathways which have the opposite effect. One important rehabilitation tool for muscle atrophy includes the use of functional electrical stimulation to stimulate the muscles which has had limited success in the rehabilitation of paraplegic patients.

Ursolic acid or ursolic acid derivatives can be used as a therapy for illness- and age-related muscle atrophy. It can be useful as a monotherapy or in combination with other strategies that have been considered, such as myostatin inhibition (Zhou, X., et al. (2010) Cell 142(4): 531-543). Given its capacity to reduce adiposity, fasting blood glucose and plasma lipid levels, ursolic acid or ursolic acid derivatives can also be used as a therapy for obesity, metabolic syndrome and type 2 diabetes.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

Systemic administration of ursolic acid (by parenteral injection or by oral consumption) can be used to promote muscle growth and reduce muscle atrophy in all muscles, including those of the limbs and the diaphragm. Local administration of ursolic acid (by a topical route or localized injection) can be used to promote local muscle growth, as can be required following a localized injury or surgery.

In one aspect, the subject compounds can be coadministered with agents that stimulate insulin signaling, IGF1 signaling and/or muscle growth including insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type 1 (PTPN1a.k.a. PTP1B) inhibitors, myostatin signaling inhibitors, clenbuterol, and androgens including testosterone and 5-dehydroepiandrosterone. The derivative can be corosolic acid, UA0713, or other pentacyclic triterpene acids. The ursolic acid, derivative or salt thereof can be administered orally, intramuscularly, intravenously or intraarterially. The ursolic acid, derivative or salt thereof can be substantially pure. The ursolic acid, derivative or salt thereof can be administered at about 10 mg/day to 10 g/day.

In another aspect, the subject compounds can be administered in combination with agents that stimulate insulin signaling, IGF1 signaling and/or muscle growth including insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type 1 (PTPN1, which is also commonly referred to as PTP1B) inhibitors, myostatin signaling inhibitors, clenbuterol, and androgens including testosterone and 5-dehydroepiandrosterone. The derivative can be corosolic acid, UA0713, or other pentacyclic triterpene acids. The ursolic acid, derivative or salt thereof can be administered orally, intramuscularly, intravenously or intraarterially. The ursolic acid, derivative or salt thereof can be substantially pure. The ursolic acid, derivative or salt thereof can be administered at about 10 mg/day to 10 g/day.

The pharmaceutical compositions and methods of the present invention can further comprise other therapeutically active compounds as noted herein which are usually applied in the treatment of the above mentioned pathological conditions.

2. Treatment Methods

The compounds disclosed herein are useful for treating, preventing, ameliorating, controlling or reducing the risk of a variety of muscle disorders. Examples of such muscle disorders include, but are not limited to, skeletal muscle atrophy secondary to malnutrition, muscle disuse (secondary to voluntary or involuntary bedrest), neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia.

Thus, provided is a method for treating or preventing muscle atrophy, comprising: administering to a subject at least one disclosed compound; at least one disclosed pharmaceutical composition; and/or at least one disclosed product in a dosage and amount effective to treat the disorder in the subject.

Also provided is a method for increasing muscle mass, comprising: administering to a subject at least one disclosed compound; at least one disclosed pharmaceutical composition; and/or at least one disclosed product in a dosage and amount effective to treat the disorder in the subject.

a. Preventing or Treating Muscle Atrophy

In one aspect, the invention relates to a method for preventing or treating muscle atrophy in an animal, the method comprising administering to the animal a compound of the formula:

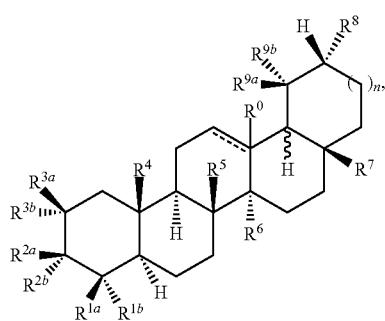

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)$ZR^{10}$; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —$OR^{11}$, and the other is hydrogen, or $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —$CH_2OR^{12}$ and —C(O)$ZR^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein $R^{10}$ is selected from hydrogen and C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)$R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

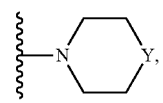

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to prevent or treat muscle atrophy in the animal, wherein the amount is greater than about 1000 mg per day when the compound is ursolic acid, beta-boswellic acid, corosolic acid, betulinic acid, or UA0713.

In a further aspect, the compound administered is a disclosed compound or a product of a disclosed method of making a compound.

In a further aspect, the animal is a mammal. In a yet further aspect, the mammal is a primate. In a still further aspect, the mammal is a human. In an even further aspect, the human is a patient.

In a further aspect. the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in a need of prevention of muscle atrophy. In an even further aspect, the mammal has been diagnosed with a need for treatment of muscle atrophy prior to the administering step.

In a further aspect, the compound is not ursolic acid, beta-boswellic acid, corosolic acid, betulinic acid, or UA0713. In a still further aspect, the compound is ursolic acid, beta-boswellic acid, corosolic acid, betulinic acid, or UA0713. In yet further aspect, the compound is not administered as a foodstuff.

b. Increasing Muscle Mass and/or Strength

In one aspect, the invention relates to a method for increasing muscle mass and/or muscular strength in an animal, the method comprising administering to the animal a compound of the formula:

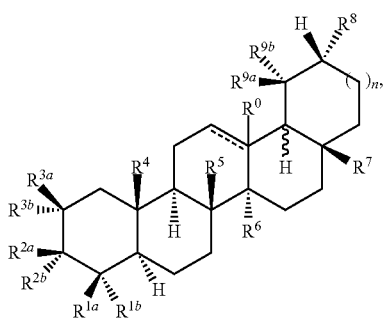

wherein each ----- is an optional covalent bond, and R⁰ is optionally present; wherein n is 0 or 1; wherein R⁰, when present, is hydrogen; wherein $R^{1a}$ is selected from C1-C6 alkyl and —C(O)ZR¹⁰; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —OR¹¹, and the other is hydrogen, or $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —CH₂OR¹², and —C(O)ZR¹²; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein R¹⁰ is selected from hydrogen and C1-C6 alkyl; wherein R¹¹ is selected from hydrogen, C1-C6 alkyl, C1-C5 heteroalkyl, C3-C6 cycloalkyl, C4-C6 heterocycloalkyl, phenyl, heteroaryl, and —C(O)R¹⁴; wherein R¹¹, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein R¹² is selected from hydrogen and optionally substituted organic residue having from 1 to 20 carbons; wherein Z is selected from —O— and —NR¹³—; wherein R¹³ is selected from hydrogen and C1-C4 alkyl; or, wherein Z is N, R¹² and R¹³ are covalently bonded and —NR¹²R¹³ comprises a moiety of the formula:

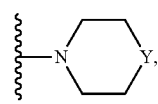

wherein Y is selected from —O—, —S—, —SO—, —SO₂—, —NH—, —NCH₃—; and wherein R¹⁴ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to prevent or treat muscle atrophy in the animal, wherein the amount is greater than about 1000 mg per day when the compound is ursolic acid, beta-boswellic acid, corosolic acid, betulinic acid, or UA0713. In a further aspect, the compound administered is a disclosed compound or a product of a disclosed method of making a compound.

In a further aspect, the compound administered is a disclosed compound or a product of a disclosed method of making a compound.

In a further aspect, the animal is a mammal. In a yet further aspect, the mammal is a primate. In a still further aspect, the mammal is a human. In an even further aspect, the human is a patient.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in need of prevention of muscle atrophy. In an even further aspect, the mammal has been diagnosed with a need for treatment of muscle atrophy prior to the administering step.

In a further aspect, the compound is not ursolic acid, beta-boswellic acid, corosolic acid, betulinic acid, or UA0713. In a still further aspect, the compound is ursolic acid, beta-boswellic acid, corosolic acid, betulinic acid, or UA0713. In yet further aspect, the compound is not administered as a foodstuff.

c. Enhancing Muscle Formation

In one aspect, the invention relates to a method of enhancing muscle formation in a mammal, the method comprising administering to the mammal a compound of the formula:

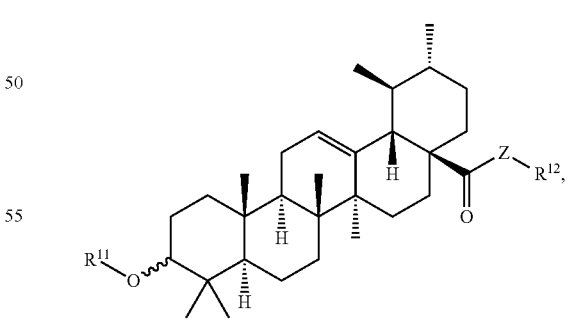

wherein R¹¹ is selected from hydrogen, C1-C6 alkyl, C1-C5 heteroalkyl, C3-C6 cycloalkyl, C4-C6 heterocycloalkyl, phenyl, heteroaryl, and —C(O)R¹⁴; wherein R¹¹, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein R¹² is selected from hydrogen and optionally substituted organic residue having from 1 to 20 carbons; wherein Z is selected from —O— and —NR$^{13}$—; wherein R$^{13}$ is selected from hydrogen and C1-C4 alkyl; or, R$^{12}$ and R$^{13}$, when present, are covalently bonded and —NR$^{12}$R$^{13}$ comprises a moiety represented by the formula:

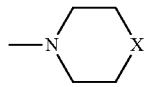

wherein X is selected from O, S, SO, SO$_2$, NH and NCH$_3$; and wherein R$^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount of at least about 200 mg/kg and effective to enhance muscle formation in the mammal.

In a further aspect, the compound administered is a disclosed compound or a product of a disclosed method of making a compound.

In a further aspect, the mammal is a human. In a still further aspect, the human is a patient. In a yet further aspect, administration of the compound prevents muscle atrophy in the mammal. In an even further aspect, administration of the compound treats muscle atrophy in the mammal. In a still further aspect, administration of the compound increases muscle mass in the mammal. In a yet further aspect, administration of the compound increases muscular strength in the mammal.

In a further aspect, the compound is administered in an effective amount. In a yet further aspect, the effective amount is a therapeutically effective amount. In a still further aspect, the effective amount is a prophylactically effective amount. In a still further aspect, the method further comprises the step of identifying the mammal in need of treatment of muscle atrophy. In a yet further aspect, the method further comprises the step of identifying the mammal in need of prevention of muscle atrophy. In an even further aspect, the mammal has been diagnosed with a need for treatment of muscle atrophy prior to the administering step.

In a further aspect, the mammal is a domesticated animal. In a yet further aspect, domesticated animal is livestock. In a yet further aspect, the livestock animal is selected from pig, cow, horse, goat, bison, and sheep.

In a further aspect, the compound is not ursolic acid. In a still further aspect, the compound is ursolic acid. In a further aspect, the compound is not ursolic acid, beta-boswellic acid, corosolic acid, betulinic acid, or UA0713. In a still further aspect, the compound is ursolic acid, beta-boswellic acid, corosolic acid, betulinic acid, or UA0713. In yet further aspect, the compound is not administered as a foodstuff.

3. Enhancing Tissue Growth In Vitro

In one aspect, the invention relates to a method of enhancing tissue growth in vitro, the method comprising administering to the tissue a compound of the formula:

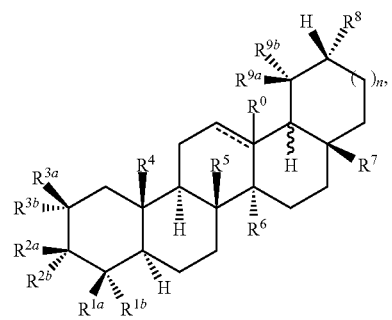

wherein each ----- is an optional covalent bond, and R$^0$ is optionally present; wherein n is 0 or 1; wherein R$^0$, when present, is hydrogen; wherein R$^{1a}$ is selected from C1-C6 alkyl and —C(O)ZR$^{10}$; wherein R$^{1b}$ is selected from C1-C6 alkyl, or wherein R$^{1a}$ and R$^{1b}$ are optionally covalently bonded and, together with the intermediate carbon, comprise an optionally substituted C3-C5 cycloalkyl or C2-C5 heterocycloalkyl; wherein one of R$^{2a}$ and R$^{2b}$ is —OR$^{11}$, and the other is hydrogen, or R$^{2a}$ and R$^{2b}$ together comprise =O; wherein each of R$^{1a}$ and R$^{3b}$ is independently selected from hydrogen, hydroxyl, C1-C6 alkyl, and C1-C6 alkoxyl, provided that R$^{3a}$ and R$^{3b}$ are not simultaneously hydroxyl, wherein R$^{3a}$ and R$^{3b}$ are optionally covalently bonded and, together with the intermediate carbon, comprise an optionally substituted C3-C5 cycloalkyl or C2-C5 heterocycloalkyl; wherein each of R$^4$, R$^5$, and R$^6$ is independently selected from C1-C6 alkyl; wherein R$^7$ is selected from C1-C6 alkyl, —CH$_2$OR$^{12}$ and —C(O)ZR$^{12}$; wherein R$^8$ is selected from hydrogen and C1-C6 alkyl; wherein each of R$^{9a}$ and R$^{9b}$ is independently selected from hydrogen and C1-C6 alkyl, provided that R$^{9a}$ and R$^{9b}$ are not simultaneously hydrogen; or wherein R$^{9a}$ and R$^{9b}$ are covalently bonded and, along with the intermediate carbon, together comprise C3-C5 cycloalkyl or C2-C5 heterocycloalkyl; wherein R$^{10}$ is selected from hydrogen and C1-C6 alkyl; wherein R$^{11}$ is selected from hydrogen, C1-C6 alkyl, C1-C5 heteroalkyl, C3-C6 cycloalkyl, C4-C6 heterocycloalkyl, phenyl, heteroaryl, and —C(O)R$^{14}$; wherein R$^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein R$^{12}$ is selected from hydrogen and optionally substituted organic residue having from 1 to 20 carbons; wherein Z is selected from —O— and —NR$^{13}$—; wherein R$^{13}$ is selected from hydrogen and C1-C4 alkyl; or, wherein Z is N, R$^{12}$ and R$^{13}$ are covalently bonded and —NR$^{12}$R$^{13}$ comprises a moiety of the formula:

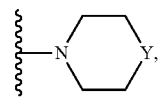

wherein Y is selected from —O—, —S—, —SO—, —SO$_2$—, —NH—, —NCH$_3$—; and wherein R$^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in an amount effective to enhance growth of the tissue.

In a further aspect, the compound administered is a disclosed compound or a product of a disclosed method of making a compound.

In a further aspect, the tissue comprises animal cells. In a still further aspect, the animal cells are muscle cells. In a yet further aspect, the muscle cells are myosatellite cells. In an even further aspect, the myosatellite cells are grown on a scaffold.

4. Manufacture of a Medicament

In one aspect, the invention relates to a method for the manufacture of a medicament for inhibiting muscle atrophy and for increasing muscle mass in a mammal comprising combining a therapeutically effective amount of a disclosed compound or product of a disclosed method with a pharmaceutically acceptable carrier or diluent.

In a further aspect, the medicament is modulates muscle growth. In a still further aspect, the medicament inhibits muscle atrophy. In a yet further aspect, the medicament increases muscle mass. In an even further aspect, the medicament induces skeletal muscle hypertrophy.

5. Methods of Testing for Performance Enhancing Use

In one aspect, the invention relates to a method of testing for performance enhancing use of a ursolic acid analog in an animal, the method comprising: (a) obtaining a biological test sample from the animal; and (b) measuring the amount of a compound of formula:

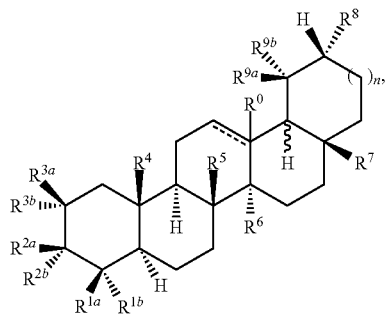

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)$ZR^{10}$; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —$OR^{11}$, and the other is hydrogen, or $R^{2a}$ and $R^{2b}$ together comprise=O; wherein each of $R^{1a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —$CH_2OR^{12}$ and —C(O)$ZR^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein $R^{10}$ is selected from hydrogen and C1-C6 alkyl;

wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)$R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

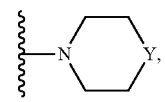

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, in the test sample to determine whether a superphysiological amount of the compound is present in the biological test sample; wherein the superphysiological amount of the compound in the biological test sample is indicative of performance enhancing use of the compound.

In a further aspect, the superphysiological amount is greater than the peak concentration from administration at a level of about 1000 mg per day. In a still further aspect, the superphysiological amount is the amount that results from administration of the compound at a level greater than 200 mg per day. In a still further aspect, the superphysiological amount is the amount resulting from administration of the compound at a level greater than 200 mg per day. In an even further aspect, the biological test sample is obtained about 12 hours to about 96 hours following administration of the compound.

In a further aspect, the animal is a mammal. In a yet further aspect, the animal is a domesticated animal. In a still further aspect, the mammal is a human.

In a further aspect, the biological sample is blood, urine, saliva, hair, muscle, skin, fat, or breath.

6. Use of Compounds

In one aspect, the invention relates to the use of a compound for increasing muscle mass in a mammal, the compound having a structure represented by a formula:

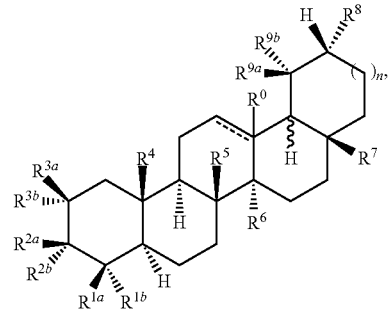

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)$ZR^{10}$; wherein $R^{1b}$ is selected from C1-C6 alkyl, or wherein $R^{1a}$ and $R^{1b}$ are optionally covalently bonded and, together with the intermediate carbon, comprise an optionally substituted C3-C5 cycloalkyl or C2-C5 heterocycloalkyl; wherein one of $R^{2a}$ and $R^{2b}$ is —$OR^{11}$, and the other is hydrogen, or $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl, wherein $R^{3a}$ and $R^{3b}$ are optionally covalently bonded and, together with the intermediate carbon, comprise an optionally substituted C3-C5 cycloalkyl or C2-C5 heterocycloalkyl; wherein each of $R^4$, $R^5$, and $R^6$ is independently selected from C1-C6 alkyl; wherein $R^7$ is selected from C1-C6 alkyl, —$CH_2OR^{12}$ and —C(O)$ZR^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise C3-C5 cycloalkyl or C2-C5 heterocycloalkyl; wherein $R^{10}$ is selected from hydrogen and C1-C6 alkyl; wherein $R^{11}$ is selected from hydrogen, C1-C6 alkyl, C1-C5 heteroalkyl, C3-C6 cycloalkyl, C4-C6 heterocycloalkyl, phenyl, heteroaryl, and —C(O)$R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, $R^{12}$ and $R^{13}$, when present, are covalently bonded and —$NR^{12}R^{13}$ comprises a moiety represented by the formula:

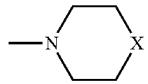

wherein X is selected from O, S, SO, $SO_2$, NH and $NCH_3$; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof.

In a further aspect, a use is the treatment of a mammal. In a yet further aspect, the mammal is a human. In a still further aspect, the human is a patient. In a yet further aspect, a use is administration of the compound to a mammal to prevent muscle atrophy. In a yet further aspect, a use is administration of the compound to increase muscular strength in the mammal. In a further aspect. the mammal is a domesticated animal. In a yet further aspect, domesticated animal is livestock. In a yet further aspect, the livestock animal is selected from pig, cow, horse, goat, bison, and sheep.

In a further aspect, a use is administration of the compound in an effective amount. In a yet further aspect, the effective amount is a therapeutically effective amount. In a still further aspect, the effective amount is a prophylactically effective amount. In a still further aspect, prior to use the mammal in need of treatment of muscle atrophy is identified.

In a yet further aspect, prior to use the mammal in need of prevention of muscle atrophy is identified. In an even further aspect, the mammal has been diagnosed with a need for treatment of muscle atrophy prior to the administering step.

In a further aspect, the compound is not ursolic acid. In a still further aspect, the compound is ursolic acid. In a further aspect, the compound is not ursolic acid, beta-boswellic acid, corosolic acid, betulinic acid, or UA0713. In a still further aspect, the compound is ursolic acid, beta-boswellic acid, corosolic acid, betulinic acid, or UA0713. In yet further aspect, the compound is not used as a foodstuff. In an even further aspect, the compound is used in an amount is greater than about 1000 mg per day when the compound is ursolic acid, beta-boswellic acid, corosolic acid, betulinic acid, or UA0713.

7. Kits

In one aspect, the invention relates to a kit comprising at least one compound having a structure represented by a formula:

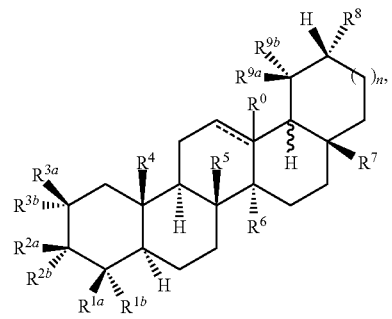

wherein each ----- is an optional covalent bond, and $R^0$ is optionally present; wherein n is 0 or 1; wherein $R^0$, when present, is hydrogen; wherein $R^{1a}$ is selected from C1-C6 alkyl and —C(O)$ZR^{10}$; wherein $R^{1b}$ is selected from C1-C6 alkyl; or wherein $R^{1a}$ and $R^{1b}$ are covalently bonded and, along with the intermediate carbon, together comprise optionally substituted C3-C5 cycloalkyl or optionally substituted C2-C5 heterocycloalkyl; wherein $R^{2a}$ and $R^{2b}$ are independently selected from hydrogen and —$OR^{11}$, provided that at least one of $R^{2a}$ and $R^{2b}$ is —$OR^{11}$; or wherein $R^{2a}$ and $R^{2b}$ together comprise =O; wherein each of $R^{3a}$ and $R^{3b}$ is independently selected from hydrogen, hydroxyl, C1-C6 alkyl, and C1-C6 alkoxyl, provided that $R^{3a}$ and $R^{3b}$ are not simultaneously hydroxyl; or wherein $R^{3a}$ and $R^{3b}$ are covalently bonded and, along with the intermediate carbon, together comprise optionally substituted C3-C5 cycloalkyl or optionally substituted C2-C5 heterocycloalkyl; wherein each of $R^4$, $R^5$, and $R^6$ is independently selected from C1-C6 alkyl; wherein $R^7$ is selected from C1-C6 alkyl, —$CH_2OR^{12}$, and —C(O)$ZR^{12}$; wherein $R^8$ is selected from hydrogen and C1-C6 alkyl; wherein each of $R^{9a}$ and $R^{9b}$ is independently selected from hydrogen and C1-C6 alkyl, provided that $R^{9a}$ and $R^{9b}$ are not simultaneously hydrogen; or wherein $R^{9a}$ and $R^{9b}$ are covalently bonded and, along with the intermediate carbon, together comprise optionally substituted C3-C5 cycloalkyl or optionally substituted C2-C5 heterocycloalkyl; wherein $R^{10}$ is selected from hydrogen and C1-C6 alkyl; wherein each $R^{11}$ is independently selected from hydrogen, C1-C6 alkyl, C1-C5 heteroalkyl, C3-C6 cycloalkyl, C4-C6 heterocycloalkyl, phenyl, heteroaryl, and —C(O)$R^{14}$; wherein $R^{11}$, where permitted, is substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; wherein $R^{12}$ is selected from hydrogen and optionally substituted organic residue having from 1 to 20 carbons; wherein Z is selected from —O— and —$NR^{13}$—; wherein $R^{13}$ is selected from hydrogen and C1-C4 alkyl; or, wherein Z is N, $R^{12}$ and $R^{13}$ are covalently bonded and —$NR^{12}R^{13}$ comprises a moiety of the formula:

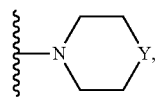

wherein Y is selected from —O—, —S—, —SO—, —$SO_2$—, —NH—, —$NCH_3$—; and wherein $R^{14}$ is C1-C6 alkyl and substituted with 0-2 groups selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl; or a pharmaceutically acceptable salt, hydrate, solvate, or polymorph thereof, and one or more of: (a) a protein supplement; (b) an anabolic agent; (c) a catabolic agent; (d) a dietary supplement; (e) at least one agent known to treat a disorder associated with muscle wasting; (f) instructions for treating a disorder associated with cholinergic activity; or (g) instructions for using the compound to increase muscle mass and/or muscular strength.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

8. Non-Medical Uses

Also provided are the uses of the disclosed compounds and products as pharmacological tools in the development and standardization of in vitro and in vivo test systems for the evaluation of the effects of modulators of muscle hypertrophy or inhibitors of muscle atrophy related activity in laboratory animals such as cats, dogs, rabbits, monkeys, rats and mice, as part of the search for new therapeutic agents of increase muscle mass and/or inhibit muscle hypertrophy.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Certain materials, reagents and kits were obtained from specific vendors as indicated below, and as appropriate the vendor catalog, part or other number specifying the item are indicated. Vendors indicated below are as follows: "Ambion" is Ambion, a division of Life Technologies Corporation, Austin, Tex., USA; "Applied Biosystems" is Applied Biosystems, a division of Life Technologies Corporation, Carlsbad, Calif., USA; "Boehringer Mannheim" is Boehringer Mannheim Corporation, Indianapolis, Ind., USA; "CardinalHealth" is Cardinal Health, Inc., Dublin, Ohio, USA; "Cell Signaling" is Cell Signaling Technology, Inc., Beverly, Mass., USA; "Columbus Inst" is Columbus Instruments International, Columbus, Ohio, USA; "Harlan" is Harlan Laboratories, Indianapolis, Ind., USA; "Instrumedics" is Instrumedics, Inc., Richmond, Ill., USA; "Invitrogen" is Invitrogen Corporation, Carlsbad, Calif., USA; "Microm" is the Microm division (Walldorf, Germany) of Thermo Fisher Scientific Inc., Rockford, Ill., USA; "Millipore" is Millipore Corporation, Billerica, Mass., USA; a division of Merck KGaA, Darmstadt, Germany; "Ortho" is Ortho Clinical Diagnostics, Rochester, N.Y., USA; "Pierce" is Pierce Biotechnology, Inc., Milwaukee, Wis., USA, a division of Thermo Fisher Scientific, Inc.; "R&D Systems" is R&D Systems Inc., Minneapolis, Minn., USA; "Roche Diagnostics" is Roche Diagnostics Corporation, Indianapolis, Ind., USA; "Sakura" is Sakura Finetek USA, Inc., Torrance, Calif., USA; "Santa Cruz" is Santa Cruz Biotechnology, Inc., Santa Cruz, Calif., USA; and, "Sigma" is Sigma-Aldrich Corporation, Saint Louis, Mo., USA.

1. General Methods a. Human Subject Protocol.

The study referred to herein was approved by the Institutional Review Board at the University of Iowa, and involved seven healthy adults who gave their informed consent before participating. One week prior to the fasting study, subjects made one visit to the Clinical Research Unit ("CRU") for anthropometric measurements, a dietary interview that established each subject's routine food intake and food preferences, and baseline determinations of blood hemoglobin ("Hb") A1c turbidimetric immunoinhibition using the BM/Hitachi 911 analyzer (Boehringer Mannheim); plasma triglycerides and plasma free T4 and TSH by electrochemiluminescence immunoassay using the Elecsys® System (Roche Diagnostics); plasma CRP by immunoturbidimetric assay using the Roche Cobas Integra® high-sensitivity assay (Roche Diagnostics); and, plasma TNF-α levels using the Quantikine® Kit (R&D Systems). To ensure that subjects were eating their routine diet prior to the fasting study, subjects ate only meals prepared by the CRU dietician (based on the dietary interview) for 48 hours before the fasting study. The fasting study began at t=0 hours, when subjects were admitted to the CRU and began fasting. While fasting, subjects remained in the CRU and were encouraged to maintain their routine physical activities. Water was allowed ad libitum, but caloric intake was not permitted. At about 40 hours, a percutaneous biopsy was taken from the vastus lateralis muscle using a Temno® Biopsy Needle (CardinalHealth; Cat #T1420) under ultrasound guidance.

Subjects then ate a CRU-prepared mixed meal, and at t=46 hours, a muscle biopsy was taken from the contralateral vastus lateralis muscle. Plasma glucose and insulin levels were measured at t=36, 40, 42 and 46 hours; the Elecsys® system was used to quantitate plasma insulin. Our study protocol of humans with spinal cord injury was described previously (Adams C M, et al. (2011) *Muscle Nerve.* 43(1): 65-75).

b. Microarray Analysis of Human Skeletal Muscle mRNA Levels.

Following harvest, skeletal muscle samples were immediately placed in RNAlater (Ambion) and stored at −80° C. until further use. Total RNA was extracted using TRIzol solution (Invitrogen), and microarray hybridizations were performed at the University of Iowa DNA Facility, as described previously (Lamb J, et al. (2006) *Science* (New York, N.Y. 313(5795):1929-1935). The $\log_2$ hybridization signals as shown herein reflect the mean signal intensity of all exon probes specific for an individual mRNA. To determine which human skeletal muscle mRNAs were significantly altered by fasting ($P \leq 0.02$), paired t-tests were used to compare fasted and fed $\log_2$ signals. To determine which mouse skeletal muscle mRNAs were significantly altered by ursolic acid ($P \leq 0.005$), unpaired t-tests were used to compare $\log_2$ signals in mice fed control diet or diet supplemented with ursolic acid. Highly expressed mRNAs were defined as those significantly altered mRNAs that were repressed from or induced to a $\log_2$ signal >8. These raw microarray data from humans and mice have been deposited in NCBI's Gene Expression Omnibus ("GEO") and are accessible through GEO Series accession numbers GSE28016 and GSE28017, respectively. Exon array studies of the effects of fasting on mouse skeletal muscle, and the effects of spinal cord injury on human skeletal muscle were described previously (Adams C M, et al. (2011) *Muscle & nerve* 43(1):65-75; Ebert S M, et al. (2010) *Molecular Endocrinology* 24(4):790-799).

C. Quantitative Real-Time Rt-PCR (qPCR).

TRIzol-extracted mRNA was treated with DNase I using the Turbo DNA free kit (Ambion). qPCR analysis of human mRNA and mouse IGF-I mRNA was performed using TaqMan Gene Expression Assays (Applied Biosystems). First strand cDNA was synthesized from 2 μg of RNA using the High Capacity cDNA Reverse Transcription Kit (Applied Biosystems, Part No. 4368814). The real time PCR contained, in a final volume of 20 μl, 20 ng of reverse transcribed RNA, 1 μl of 20×TaqMan Gene Expression Assay, and 10 μl of TaqMan Fast Universal PCR Master Mix (Applied Biosystems; Part No. 4352042). qPCR was carried out using a 7500 Fast Real-Time PCR System (Applied Biosystems) in 9600 emulation mode. qPCR analysis of mouse atrogin-1 and MuRF1 mRNA levels was performed as previously described (Ebert S M, et al. (2010) *Molecular Endocrinology* 24(4):790-799). All qPCR reactions were performed in triplicate and the cycle threshold (Ct) values were averaged to give the final results. To analyze the data, the ΔCt method was used, with the level of 36B4 mRNA serving as the invariant control.

d. Mouse Protocols.

Male C57BL/6 mice, ages 6-8 weeks, were obtained from NCI, housed in colony cages with 12 h light/12 h dark cycles, and used for experiments within 3 weeks of their arrival. Unless otherwise indicated, mice were maintained on standard chow (Harlan; Teklad Diet, Formula 7013, NIH-31 Modified Open Formula Mouse/Rat Sterilizable Diet). Metformin (Sigma) was dissolved in 0.9% NaCl at a concentration of 250 mg/ml. Ursolic acid (Enzo Life Sciences) was dissolved in corn oil at a concentration of 200 mg/ml (for i.p. injections); alternatively, the ursolic acid was added directly to standard chow (Harlan; Teklad Diet, Formula 7013) or standard high fat diet (Harlan; Teklad Diet, Formula TD.93075) as a customized chow. Oleanolic acid (Sigma) was dissolved in corn oil at a concentration of 200 mg/ml. Mice were fasted by removing food, but not water, for 24 hours. Fasting blood glucose levels were obtained from the tail vein with an ACCU-CHEK® Aviva glucose meter (Roche Diagnostics). Unilateral hindlimb muscle denervation was performed by transecting the sciatic nerve under anesthesia, and was followed by administration of ursolic acid (200 mg/kg) or vehicle alone (corn oil) via i.p injection twice daily for 7 days. Forelimb grip strength was determined using a grip strength meter equipped with a triangular pull bar (Columbus Inst). Each mouse was subjected to 5 consecutive tests to obtain the peak value. Plasma IGF-I and leptin levels were measured by RIA at the Vanderbilt University Hormone Assay Core Facility. Plasma cholesterol, triglyceride, creatinine, bilirubin and ALT were measured using the VITROS® 350 Chemistry System (Ortho). All animal procedures were approved by the Institutional Animal Care and Use Committee of the University of Iowa.

e. Histological Analysis.

Following harvest, tissues were immediately placed in isopentane that had been chilled to −160° C. with liquid $N_2$. Muscles were embedded in tissue freezing medium, and 10 μm sections from the mid-belly were prepared using a Microm HM 505 E cryostat equipped with a CryoJane sectioning system (Instrumedics). Adipose tissue was fixed in 10% neutral buffered formalin, embedded in paraffin, and then 4 μm sections were prepared using a Microm HM355 S motorized microtome (Microm). Hematoxylin and eosin stains were performed using a DRS-601 automatic slide stainer (Sakura), and examined on an Olympus IX-71 microscope equipped with a DP-70 camera. Image analysis was performed using ImageJ software (public domain, available from the National Institutes of Health, USA). Muscle fiber diameter was measured using the lesser diameter method, as described elsewhere (Dubowitz V, et al. (2007) *Muscle biopsy: a practical approach* (Saunders Elsevier, Philadelphia) 3rd Ed pp XIII, 611 s).

f. Analysis of IGF-I and Insulin-Mediated Protein Phosphorylation.

Mouse quadriceps muscles were snap frozen in liquid $N_2$, and Triton-X 100 soluble protein extracts were prepared as described previously (Ebert S M, et al. (2010) *Molecular endocrinology* 24(4):790-799). Mouse C2C12 myoblasts were obtained from American Type Culture Collection ("ATCC"), and maintained in Dulbecco's modified Eagle's medium (DMEM; ATCC #30-2002) containing antibiotics (100 units/ml penicillin, 100 μg/ml streptomycin sulfate) and 10% (v/v) fetal bovine serum (FBS). On day 0, myotubes were set-up in 6-well plates at a density of $2.5 \times 10^5$ cells/well. On day 2, differentiation into myotubes was induced by replacing 10% FBS with 2% horse serum. On day 7, myotubes were serum-starved by washing 2 times with phosphate buffered saline, and then adding fresh serum-free media. After 16 hours of serum-starvation, 10 μM ursolic acid (from a 10 mM stock prepared in DMSO), or an equal volume of DMSO, with or without 10 nM mouse IGF-I (Sigma; Cat. No. 18779) or 10 nM bovine insulin (Sigma; Cat. No. 16634) was directly added to the media. For analysis of Akt, S6K, ERK and FoxO phosphorylation, myotubes were incubated in the presence or absence of ursolic acid, IGF-I and/or insulin for 20 min, and then harvested into SDS lysis buffer (10 mM Tris-HCl, pH 7.6, 100 mM NaCl, 1% (w/v) SDS, 1 µg/ml pepstatin A, 2 µg/ml aprotonin, 10 µg/ml leupeptin, 200 µM phenylmethylsulfonyl fluoride and a 1:100 dilution of phosphatase inhibitor cocktail 3 (Sigma). An aliquot of each muscle extract or cell lysate was mixed with 0.25 volume of sample buffer (250 mM Tris-HCl, pH 6.8, 10% SDS, 25% glycerol, 0.2% (w/v) bromophenol blue, and 5% (w/v) 2-mercaptoethanol) and heated for 5 min at 95° C., whereas a separate aliquot was used to determine protein concentration by the BCA kit (Pierce). Samples (25 µg) were subjected to 8% SDS-PAGE, then transferred to Hybond-C extra nitrocellulose filters (Millipore). Immunoblots were performed at 4° C. for 16 h using a 1:2000 dilution of antibodies detecting total Akt, phospho-Akt(Ser473), total S6K, phospho-S6K(T421/S424), total ERK1/2, phospho-ERK(T202/Y204), FoxO3a, or phospho-FoxO1(T24)/FoxO3a(T32) (Cell Signaling). For analysis of IGF-1 receptor or insulin receptor phosphorylation, myotubes were incubated in the presence or absence of ursolic acid, IGF-I and/or insulin for 2 min, and then harvested into RIPA buffer (10 mM Tris-HCL, pH 7.4, 150 mM NaCl, 0.1% (w/v) SDS, 1% (w/v) Triton X-100, 1% Na deoxycholate, 5 mM EDTA, 1 mM NaF, 1 mM Na orthovanadate, 1 µg/ml pepstatin A, 2 µg/ml aprotonin, 10 µug/ml leupeptin, 200 µM phenylmethylsulfonyl fluoride, 1:100 dilution of phosphatase inhibitor cocktail 2 (Sigma) and a 1:100 dilution of phosphatase inhibitor cocktail 3 (Sigma). The protein concentration was measured using the BCA kit, after which the extract was diluted to a concentration of 1 mg/ml in RIPA buffer (final volume 500 µl). Then 2 µg anti-IGF-1 receptor β antibody (Cell Signaling) or 2 µg anti-insulin receptor β antibody (Santa Cruz) was added with 50 µl protein G plus Sepharose beads (Santa Cruz), and then the samples were rotated at 4° C. for 16 h. Immunoprecipitates were washed three times for 20 min with 1 ml RIPA buffer and then mixed with 100 µl sample buffer (50 mM Tris-HCl (pH 6.8), 2% SDS, 5% glycerol, 0.04% (w/v) bromophenol blue and 5% (w/v) 2-mercaptoethanol), then boiled for 5 min. Immunoprecipitates were subjected to 8% SDS-PAGE. For analysis of total IGF-1 receptor, phospho-insulin receptor and total insulin receptor, proteins were transferred to Hybond-C extra nitrocellulose filters (Millipore). For analysis of phospho-IGF-1 receptor, proteins were transferred to PVDF membranes (Bio-Rad). Immunoblots were performed at room temperature using a 1:2000 dilution of anti-IGF-1 receptor β antibody, 1:5000 dilution of mouse anti-phospho-tyrosine 4G10 monoclonal antibody (Millipore), a 1:2000 dilution of anti-insulin receptor β, or 1:2000 dilution of anti-phospho-insulin receptor β (Y1162/1163) (Santa Cruz).

g. PTP1B Inhibition Via RNA Interference.

The plasmids pCMV-miR-PTP1B #1 and pCMV-miR-PTP1B #2 were generated by ligating PTPN1-specific oligonucleotide duplexes (Invitrogen) into the pcDNA6.2GW/EmGFP miR plasmid (Invitrogen), which contains a CMV promoter driving co-cistronic expression of engineered pre-miRNAs and EmGFP. pCMV-miR-control encodes a non-targeting pre-miRNA hairpin sequence (miR-neg control; Invitrogen) in pcDNA6.2GW/EmGFP miR plasmid. Male C57BL/6 mice were obtained from NCI at ages 6-8 weeks, and used for experiments within 3 weeks of their arrival. Electroporation of mouse tibialis anterior muscles and isolation of skeletal muscle RNA was performed as described previously (Ebert S M, et al. (2010) *Molecular endocrinology* 24(4):790-799). First strand cDNA was synthesized in a 20 µl reaction that contained 2 µg of RNA, random hexamer primers and components of the High Capacity cDNA reverse transcription kit (Applied Biosystems). qPCR analysis of PTPN1 mRNA levels was performed using a Taqman expression assay as described previously (Ebert S M, et al. (2010) *Molecular endocrinology* 24(4):790-799). qPCR was carried out using a 7500 Fast Real-Time PCR System (Applied Biosystems). All qPCR reactions were performed in triplicate and the cycle threshold (Ct) values were averaged to give the final results. Fold changes were determined by the ΔCt method, with level of 36B4 mRNA serving as the invariant control. Skeletal muscle sections were prepared and transfected (EmGFP-positive) muscle fibers were identified and measured as described previously (Ebert S M, et al. (2010) *Molecular endocrinology* 24(4):790-799).

h. Measurement of Serum Ursolic Acid Levels.

Ursolic acid is extracted from serum using a 10:1 mixture of hexane:propanol (recovery >90%), and then conjugated via its carboxylic acid group to 2-(2,3-naphthalimino)ethyl trifluoromethanesulfonate (Invitrogen; Ne-OTf), a moiety that enhances TUV and fluorescence detection. Derivatized samples are then analyzed on a Waters Acquity UPLC equipped with a 100×2.1 mm C18 HSS column with 1.8 µm beads (Waters Part No. 186003533) and a TUV detector.

2. Identification of Therapeutics to Treat Muscle Atrophy

Skeletal muscle atrophy is common and debilitating condition that lacks a pharmacologic therapy. To identify and develop new therapeutic approaches to this pathophysiological condition (FIG. 1), an approach using gene expression signatures to connect small molecules, genes, and disease was used. Briefly, 63 mRNAs were identified that were regulated by fasting in both human and mouse muscle, and 29 mRNAs that were regulated by both fasting and spinal cord injury in human muscle. These two unbiased mRNA expression signatures of muscle atrophy were used to query the Connectivity Map, an algorithm that allows gene signature datasets to be used to find relationships between small molecules, genes, and disease.

Three complimentary studies to characterize global atrophy-associated changes in skeletal muscle mRNA levels in humans and mice were carried. These three studies determined the effects of: A) fasting on human skeletal muscle mRNA levels, B) spinal cord injury ("SCI") on human skeletal mRNA levels (Adams C M, et al. (2011) *Muscle & nerve* 43(1):65-75) and C) fasting on mouse skeletal muscle mRNA levels (Ebert S M, et al. (2010) *Molecular endocrinology* 24(4):790-799). In each study, exon expression arrays were used that quantitated levels of >16,000 mRNAs. Although there were many significant changes in each study, analysis focused on mRNAs whose levels were similarly altered in at least two atrophy models. Thus, by comparing the effects of fasting on human and mouse skeletal muscle, there were two sets of mRNAs identified: a) 31 mRNAs that were increased by fasting in both species, and b) 32 mRNAs that were decreased by fasting in both species. These evolutionarily conserved, fasting-regulated skeletal muscle mRNAs were termed "atrophy signature-1." Next, the effects of fasting and SCI on human skeletal muscle were determined and two sets of mRNAs were identified: a) 18 mRNAs that were increased by fasting and SCI, and b) 17 mRNAs that were decreased by fasting and SCI. This second group of mRNAs was termed "atrophy signature-2." Almost all of the mRNAs in atrophy signatures-1 and -2 have previously uncharacterized roles in normal or atrophied skeletal muscle. It was next hypothesized that pharmacologic compounds whose effects on cellular mRNA levels were opposite to atrophy signatures-1 and -2 might inhibit skeletal muscle atrophy. To identify candidate compounds, the Connectivity Map (Lamb J, et al. (2006) *Science* (New York, N.Y. 313(5795):1929-1935) was used to compare atrophy signatures-1 and -2 to mRNA expression signatures of >1300 bioactive small molecules. These results identified several predicted inhibitors of human skeletal muscle atrophy, including ursolic acid. As a proof-of-concept of the utility of atrophy signatures-1 and -2 described herein, the effects of ursolic acid were assessed in mice, and surprisingly it was discovered ursolic acid inhibited muscle atrophy and promoted muscle hypertrophy.

3. Effects of Fasting on Skeletal Muscle mRNA Expression in Humans.

Figure 2:
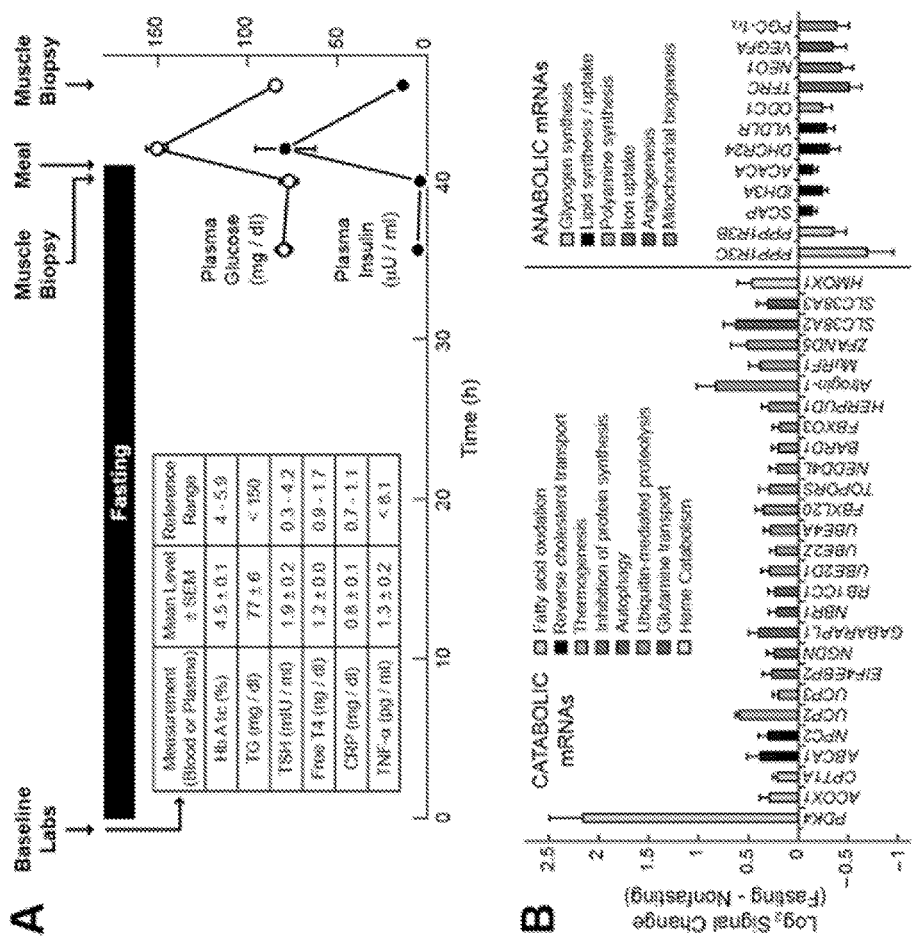
FIG. 2 shows representative data on the effect of fasting on skeletal muscle mRNA expression in healthy human adults.

Prolonged fasting induces muscle atrophy, but its effects on global mRNA expression in human skeletal muscle were not known heretofore. In order to determine the relationship between global mRNA expression and human skeletal muscle status, seven healthy adult human volunteers (3 male and 4 female) with ages ranging from 25 to 69 years (mean=46 years) were studied. The overall study design is shown in FIG. 2A. The mean body mass index of these subjects (±SEM) was 25±1. Their mean weight was 69.4±4.8 kg. Baseline circulating levels of hemoglobin A1c (HbA1c), triglycerides (TG), thyroid-stimulating hormone (TSH), free thyroxine (free T4), C-reactive protein (CRP) and tumor necrosis factor-α (TNF-α) were within normal limits (FIG. 2A). The table (FIG. 2A, insert) shows baseline circulating metabolic and inflammatory markers. The graph shows plasma glucose and insulin levels (FIG. 2A). Data are means±SEM from the seven study subjects. In some cases, the error bars are too small to see. While staying in the University of Iowa Clinical Research Unit, the subjects fasted for 40 h by forgoing food but not water. The mean weight loss during the fast was 1.7±0.1 kg (3±0% of the initial body weight).

After the 40 h fast, a muscle biopsy was obtained from the subjects' vastus lateralis (VL) muscle. Immediately after the muscle biopsy, the subjects ate a mixed meal. Five hours later (six hours after the first biopsy), a second muscle biopsy from their contralateral VL muscle. Thus, each subject had a muscle biopsy under fasting and nonfasting conditions. As expected, plasma glucose and insulin levels were low at the end of the 40 h fast, rose after the meal, and returned to baseline by the time of the second biopsy (FIG. 2A). These data indicate comparable levels of plasma glucose and insulin at the times of the first (fasting) and second (nonfasting) muscle biopsies.

To determine the effect of fasting on skeletal muscle mRNA expression, RNA was isolated from the paired muscle biopsies and then analyzed it with exon expression arrays. Using P≤0.02 (by paired t-test) as criteria for statistical significance, it was found that 281 mRNAs were higher in the fasting state and 277 were lower (out of >17,000 mRNAs measured; see FIG. 2B). A complete list of these fasting-responsive mRNAs is shown below in Table 1 ("Change" is the mean $\log_2$ change or difference between fasting and fed states). The data in Table 1 is for all mRNAs in this study whose levels were increased or decreased by fasting (P≤0.02 by paired t-test).

Representative fasting-responsive human skeletal muscle mRNAs, and the effect of fasting on their log 2 hybridization signals, as assessed by Affymetrix Human Exon 1.0 ST arrays are shown in FIG. 2B. In each subject, the fasting signal was normalized to the nonfasting signal from the same subject. Data are means±SEM from 7 subjects. P≤0.02 by paired t-test for all mRNAs shown. The complete set of 458 fasting-responsive mRNAs is shown in Table 1. Most of the differentially expressed mRNAs identified as altered by fasting surprisingly did not have previously known roles in muscle atrophy. However, fasting increased several mRNAs that encode proteins with known roles in catabolic processes such as fat oxidation, reverse cholesterol transport, thermogenesis, inhibition of protein synthesis, autophagy, ubiquitin-mediated proteolysis, glutamine transport and heme catabolism (FIG. 2B). Of these, atrogin-1, MuRF1 and ZFAND5 mRNAs encode proteins known to be required for skeletal muscle atrophy in mice (Bodine S C, et al. (2001) *Science* (New York, N.Y. 294(5547):1704-1708; Hishiya A, et al. (2006) *The EMBO journal* 25(3):554-564). Conversely, fasting significantly decreased several mRNAs encoding proteins with known roles in anabolic processes such as glycogen synthesis, lipid synthesis and uptake, polyamine synthesis, iron uptake, angiogenesis, and mitochondrial biogenesis (FIG. 2B). Of these, PGC-1αmRNA encodes a protein that inhibits atrophy-associated gene expression and skeletal muscle atrophy in mice (Sandri M, et al. (2006) *Proceedings of the National Academy of Sciences of the United States of America* 103(44):16260-16265).

Figure 3:
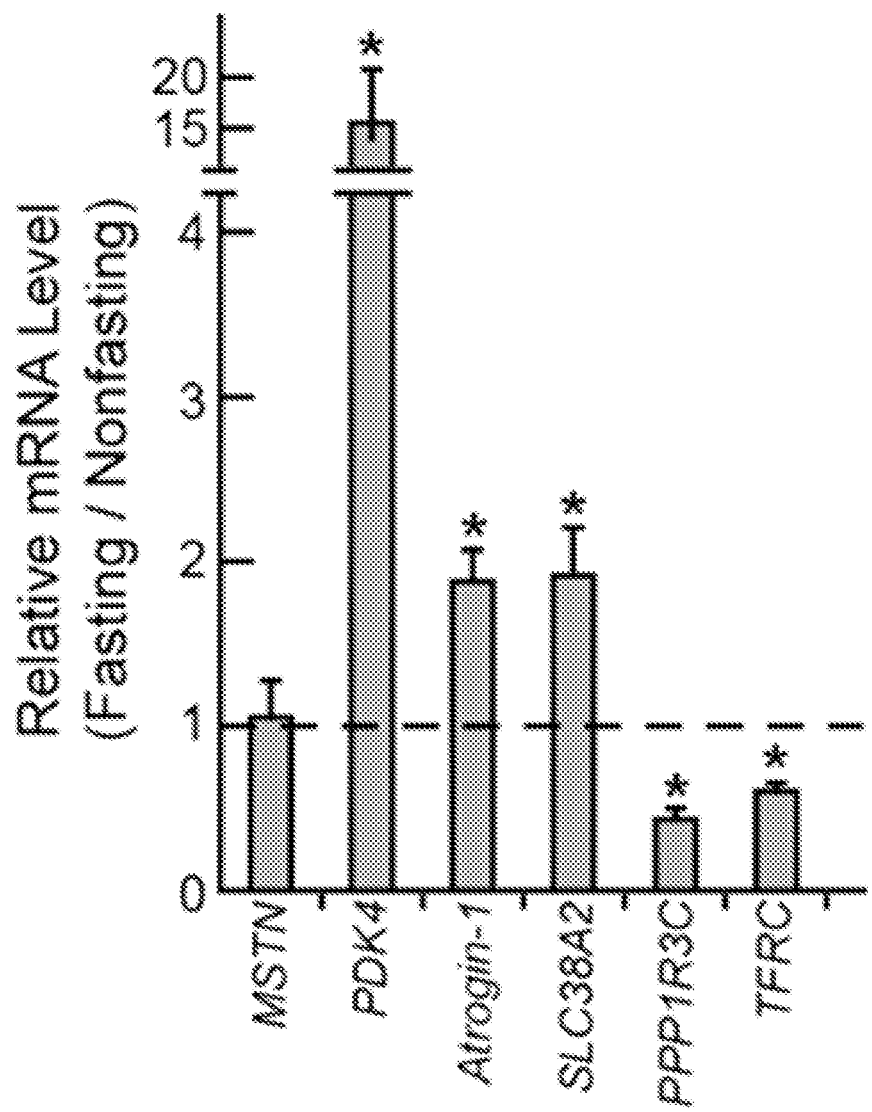
FIG. 3 shows qPCR analysis of representative fasting-responsive mRNAs from human skeletal muscle.

The results were further validated using qPCR to analyze RNA from paired fed and fasted skeletal muscle biopsy samples obtained from seven healthy human subjects (see FIG. 3; data are means±SEM; *P≤0.01 by paired t-test.). In each subject, the fasting mRNA level was normalized to the nonfasting level, which was set at 1. The mRNA encoding myostatin (MSTN) is a control transcript whose level was not altered by fasting, as assessed by exon expression arrays. Taken together, these data established an mRNA expression signature of fasting in human skeletal muscle.

TABLE 1

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3062082 | PDK4 | NM_002612 // PDK4 // pyruvate dehydrogenase kinase, isozyme 4 // 7q21.3 // 5166 | NM_002612 | 2.15 | 0.34 | 0.000 |
| 2319340 | SLC25A33 | NM_032315 // SLC25A33 // solute carrier family 25, member 33 // 1p36.22 // 84275 | NM_032315 | 1.42 | 0.41 | 0.007 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3165957 | IFNK | NM_020124 // IFNK // interferon, kappa //—// 56832 /// ENST00000276943 // IF | NM_020124 | 0.96 | 0.28 | 0.007 |
| 3424158 | MYF6 | NM_002469 // MYF6 // myogenic factor 6 (herculin) // 12q21 // 4618 /// ENST00000 | NM_002469 | 0.95 | 0.12 | 0.000 |
| 3422144 | LGR5 | NM_003667 // LGR5 // leucine-rich repeat-containing G protein-coupled receptor 5 | NM_003667 | 0.88 | 0.12 | 0.000 |
| 2356115 | TXNIP | NM_006472 // TXNIP // thioredoxin interacting protein // 1q21.1 // 10628 /// ENS | NM_006472 | 0.85 | 0.22 | 0.004 |
| 3233605 | PFKFB3 | NM_004566 // PFKFB3 // 6-phosphofructo-2-kinase/fructose-2,6-biphosphatase 3 // | NM_004566 | 0.84 | 0.18 | 0.002 |
| 3151607 | FBXO32 | NM_058229 // FBXO32 // F-box protein 32 // 8q24.13 // 114907 /// NM_148177 // FB | NM_058229 | 0.82 | 0.19 | 0.002 |
| 2745547 | GAB1 | NM_207123 // GAB1 // GRB2-associated binding protein 1 // 4q31.21 // 2549 /// NM | NM_207123 | 0.71 | 0.08 | 0.000 |
| 3173479 | FOXD4L3 | NM_199135 // FOXD4L3 // forkhead box D4-like 3 // 9q13 // 286380 /// NM_012184 / | NM_199135 | 0.68 | 0.25 | 0.017 |
| 3199500 | CER1 | NM_005454 // CER1 // cerberus 1, cysteine knot superfamily, homolog (*Xenopus* lae | NM_005454 | 0.64 | 0.24 | 0.019 |
| 3444309 | TAS2R9 | NM_023917 // TAS2R9 // taste receptor, type 2, member 9 // 12p13 // 50835 /// EN | NM_023917 | 0.63 | 0.22 | 0.015 |
| 3452323 | SLC38A2 | NM_018976 // SLC38A2 // solute carrier family 38, member 2 // 12q // 54407 /// E | NM_018976 | 0.62 | 0.13 | 0.001 |
| 3381843 | UCP3 | NM_003356 // UCP3 // uncoupling protein 3 (mitochondrial, proton carrier) // 11q | NM_003356 | 0.59 | 0.04 | 0.000 |
| 3147508 | KLF10 | NM_005655 // KLF10 // Kruppel-like factor 10 // 8q22.2 // 7071 /// NM_001032282 | NM_005655 | 0.58 | 0.11 | 0.001 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3982534 | LPAR4 | NM_005296 // LPAR4 // lysophosphatidic acid receptor 4 // Xq13-q21.1 // 2846 /// | NM_005296 | 0.57 | 0.17 | 0.008 |
| 3384321 | RAB30 | NM_014488 // RAB30 // RAB30, member RAS oncogene family // 11q12-q14 // 27314 // | NM_014488 | 0.56 | 0.21 | 0.019 |
| 3256192 | C10orf116 | NM_006829 // C10orf116 // chromosome 10 open reading frame 116 // 10q23.2 // 109 | NM_006829 | 0.55 | 0.19 | 0.013 |
| 2705690 | GHSR | NM_198407 // GHSR // growth hormone secretagogue receptor // 3q26.31 // 2693 /// | NM_198407 | 0.54 | 0.20 | 0.016 |
| 3326938 | LOC100130104 | AF274942 // LOC100130104 // PNAS-17 // 11p13 // 100130104 | AF274942 | 0.53 | 0.16 | 0.009 |
| 2318656 | PER3 | NM_016831 // PER3 // period homolog 3 (*Drosophila*) // 1p36.23 // 8863 /// ENST00 | NM_016831 | 0.52 | 0.16 | 0.009 |
| 3209623 | ZFAND5 | NM_001102420 // ZFAND5 // zinc finger, AN1-type domain 5 // 9q13-q21 // 7763 /// | NM_001102420 | 0.51 | 0.13 | 0.005 |
| 3741300 | OR1D4 | NM_003552 // OR1D4 // olfactory receptor, family 1, subfamily D, member 4 // 17p | NM_003552 | 0.50 | 0.19 | 0.019 |
| 2899176 | HIST1H2BD | NM_138720 // HIST1H2BD // histone cluster 1, H2bd // 6p21.3 // 3017 /// NM_02106 | NM_138720 | 0.49 | 0.16 | 0.010 |
| 3439256 | RPS11 | ENST00000270625 // RPS11 // ribosomal protein S11 // 19q13.3 // 6205 /// BC10002 | ENST00000270625 | 0.49 | 0.11 | 0.002 |
| 2973232 | KIAA0408 | NM_014702 // KIAA0408 // KIAA0408 // 6q22.33 // 9729 /// NM_001012279 // C6orf17 | NM_014702 | 0.49 | 0.14 | 0.006 |
| 3291151 | RHOBTB1 | NM_014836 // RHOBTB1 // Rho-related BTB domain containing 1 // 10q21.2 // 9886 / | NM_014836 | 0.48 | 0.09 | 0.001 |
| 2358136 | C1orf51 | BC027999 // C1orf51 // chromosome 1 open reading frame 51 // 1q21.2 // 148523 // | BC027999 | 0.48 | 0.17 | 0.016 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3948936 | — | — | — | 0.47 | 0.18 | 0.020 |
| 3944129 | HMOX1 | NM_002133 // HMOX1 // hemeoxygenase (decycling) 1 // 22q12|22q13.1 // 3162 /// | NM_002133 | 0.46 | 0.13 | 0.006 |
| 2968652 | SESN1 | NM_014454 // SESN1 // sestrin 1 // 6q21 // 27244 /// ENST00000302071 // SESN1 // | NM_014454 | 0.46 | 0.12 | 0.004 |
| 2951881 | PXT1 | NM_152990 // PXT1 // peroxisomal, testis specific 1 // 6p21.31 // 222659 /// ENS | NM_152990 | 0.45 | 0.14 | 0.008 |
| 2819747 | POLR3G | NM_006467 // POLR3G // polymerase (RNA) III (DNA directed) polypeptide G (32 kD) | NM_006467 | 0.45 | 0.13 | 0.007 |
| 2957384 | GSTA2 | NM_000846 // GSTA2 // glutathione S-transferase A2 // 6p12.1 // 2939 /// NM_1536 | NM_000846 | 0.44 | 0.10 | 0.002 |
| 4014387 | RPSA | NM_002295 // RPSA // ribosomal protein SA // 3p22.2 // 3921 /// NM_001012321 // | NM_002295 | 0.44 | 0.16 | 0.018 |
| 3021158 | C7orf58 | NM_024913 // C7orf58 // chromosome 7 open reading frame 58 // 7q31.31 // 79974 / | NM_024913 | 0.44 | 0.07 | 0.000 |
| 2976155 | OLIG3 | NM_175747 // OLIG3 // oligodendrocyte transcription factor 3 // 6q23.3 // 167826 | NM_175747 | 0.44 | 0.12 | 0.006 |
| 3261886 | C10orf26 | NM_017787 // C10orf26 // chromosome 10 open reading frame 26 // 10q24.32 // 5483 | NM_017787 | 0.44 | 0.17 | 0.019 |
| 2489169 | | — | — | 0.42 | 0.12 | 0.006 |
| 2790062 | TMEM154 | NM_152680 // TMEM154 // transmembrane protein 154 // 4q31.3 // 201799 /// ENST00 | NM_152680 | 0.42 | 0.14 | 0.012 |
| 3792656 | CCDC102B | NM_024781 // CCDC102B // coiled-coil domain containing 102B // 18q22.1 // 79839 | NM_024781 | 0.42 | 0.12 | 0.007 |
| 3554282 | INF2 | NM_022489 // INF2 // inverted formin, FH2 and WH2 domain containing // 14q32.33 | NM_022489 | 0.41 | 0.14 | 0.012 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2614142 | NR1D2 | NM_005126 // NR1D2 // nuclear receptor subfamily 1, group D, member 2 // 3p24.2 | NM_005126 | 0.39 | 0.15 | 0.019 |
| 3404636 | GABARAPL1 | NM_031412 // GABARAPL1 // GABA(A) receptor-associated protein like 1 // 12p13.2 | NM_031412 | 0.39 | 0.10 | 0.004 |
| 3063856 | tcag7.1177 | ENST00000292369 // tcag7.1177 // opposite strand transcription unit to STAG3 // | ENST00000292369 | 0.39 | 0.09 | 0.003 |
| 3461981 | TSPAN8 | NM_004616 // TSPAN8 // tetraspanin 8 // 12q14.1-q21.1 // 7103 /// ENST0000039333 | NM_004616 | 0.39 | 0.14 | 0.015 |
| 2908154 | C6orf206 | BC029519 // C6orf206 // chromosome 6 open reading frame 206 // 6p21.1 // 221421 | BC029519 | 0.39 | 0.09 | 0.003 |
| 3415046 | FLJ33996 | AK091315 // FLJ33996 // hypothetical protein FLJ33996 // 12q13.13 // 283401 /// | AK091315 | 0.39 | 0.15 | 0.019 |
| 3326400 | CAT | NM_001752 // CAT // catalase // 11p13 // 847 /// ENST00000241052 // CAT // catal | NM_001752 | 0.39 | 0.09 | 0.003 |
| 2390322 | OR2M5 | NM_001004690 // OR2M5 // olfactory receptor, family 2, subfamily M, member 5 // | NM_001004690 | 0.38 | 0.12 | 0.011 |
| 2402536 | TRIM63 | NM_032588 // TRIM63 // tripartite motif-containing 63 // 1p34-p33 // 84676 /// E | NM_032588 | 0.38 | 0.12 | 0.009 |
| 2976768 | CITED2 | NM_006079 // CITED2 // Cbp/p300-interacting transactivator, with Glu/Asp-rich ca | NM_006079 | 0.37 | 0.10 | 0.005 |
| 3218528 | ABCA1 | NM_005502 // ABCA1 // ATP-binding cassette, sub-family A (ABC1), member 1 // 9q3 | NM_005502 | 0.37 | 0.14 | 0.016 |
| 3377861 | DKFZp761E198 | NM_138368 // DKFZp761E198 // DKFZp761E198 protein // 11q13.1 // 91056 /// BC1091 | NM_138368 | 0.37 | 0.06 | 0.000 |
| 2961347 | FILIP1 | NM_015687 // FILIP1 // filamin A interacting protein 1 // 6q14.1 // 27145 /// EN | NM_015687 | 0.37 | 0.10 | 0.005 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3097580 | C8orf22 | NM_001007176 // C8orf22 // chromosome 8 open reading frame 22 // 8q11 // 492307 | NM_001007176 | 0.37 | 0.08 | 0.002 |
| 3755655 | FBXL20 | NM_032875 // FBXL20 // F-box and leucine-rich repeat protein 20 // 17q12 // 8496 | NM_032875 | 0.35 | 0.08 | 0.002 |
| 3057505 | CCL26 | NM_006072 // CCL26 // chemokine (C-C motif) ligand 26 // 7q11.23 // 10344 /// EN | NM_006072 | 0.35 | 0.12 | 0.012 |
| 3307795 | C10orf118 | NM_018017 // C10orf118 // chromosome 10 open reading frame 118 // 10q25.3 // 550 | NM_018017 | 0.35 | 0.13 | 0.020 |
| 3654699 | NUPR1 | NM_001042483 // NUPR1 // nuclear protein 1 // 16p11.2 // 26471 /// NM_012385 // | NM_001042483 | 0.35 | 0.10 | 0.007 |
| 3778252 | ANKRD12 | NM_015208 // ANKRD12 // ankyrin repeat domain 12 // 18p11.22 // 23253 /// NM_001 | NM_015208 | 0.34 | 0.08 | 0.002 |
| 2662560 | C3orf24 | NM_173472 // C3orf24 // chromosome 3 open reading frame 24 // 3p25.3 // 115795 / | NM_173472 | 0.34 | 0.08 | 0.002 |
| 3896370 | RP5-1022P6.2 | NM_019593 // RP5-1022P6.2 // hypothetical protein KIAA1434 // 20p12.3 // 56261 / | NM_019593 | 0.34 | 0.10 | 0.007 |
| 3389566 | KBTBD3 | NM_198439 // KBTBD3 // kelch repeat and BTB (POZ) domain containing 3 // 11q22.3 | NM_198439 | 0.34 | 0.08 | 0.003 |
| 3247818 | FAM133B | NM_152789 // FAM133B // family with sequence similarity 133, member B // 7q21.2 | NM_152789 | 0.34 | 0.11 | 0.010 |
| 2457988 | ZNF706 | AF275802 // ZNF706 // zinc finger protein 706 // 8q22.3 // 51123 /// BC015925 // | AF275802 | 0.34 | 0.12 | 0.016 |
| 3525234 | IRS2 | NM_003749 // IRS2 // insulin receptor substrate 2 // 13q34 // 8660 /// ENST00000 | NM_003749 | 0.34 | 0.09 | 0.004 |
| 2730281 | ODAM | NM_017855 // ODAM // odontogenic, ameloblast asssociated // 4q13.3 // 54959 /// | NM_017855 | 0.34 | 0.12 | 0.016 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3768969 | ABCA5 | NM_018672 // ABCA5 // ATP-binding cassette, sub-family A (ABC1), member 5 // 17q | NM_018672 | 0.33 | 0.10 | 0.008 |
| 3687494 | MAPK3 | NM_001040056 // MAPK3 // mitogen-activated protein kinase 3 // 16p11.2 // 5595 / | NM_001040056 | 0.33 | 0.09 | 0.004 |
| 3405396 | CREBL2 | NM_001310 // CREBL2 // cAMP responsive element binding protein-like 2 // 12p13 / | NM_001310 | 0.33 | 0.07 | 0.002 |
| 3647504 | PMM2 | NM_000303 // PMM2 // phosphomannomutase 2 // 16p13.3-p13.2 // 5373 /// ENST00000 | NM_000303 | 0.33 | 0.10 | 0.008 |
| 3392840 | BUD13 | NM_032725 // BUD13 // BUD13 homolog (*S. cerevisiae*) // 11q23.3 // 84811 /// ENST | NM_032725 | 0.33 | 0.07 | 0.002 |
| 3453837 | TUBA1A | NM_006009 // TUBA1A // tubulin, alpha 1a // 12q12-q14.3 // 7846 /// ENST00000301 | NM_006009 | 0.33 | 0.07 | 0.002 |
| 2409310 | ELOVL1 | NM_022821 // ELOVL1 // elongation of very long chain fatty acids (FEN1/Elo2, SUR | NM_022821 | 0.32 | 0.09 | 0.005 |
| 3837707 | ZNF114 | NM_153608 // ZNF114 // zinc finger protein 114 // 19q13.32 // 163071 /// ENST000 | NM_153608 | 0.31 | 0.09 | 0.007 |
| 3504434 | XPO4 | NM_022459 // XPO4 // exportin 4 // 13q11 // 64328 /// ENST00000255305 // XPO4 // | NM_022459 | 0.31 | 0.10 | 0.009 |
| 2431877 | — | — | — | 0.31 | 0.11 | 0.017 |
| 3837836 | PSCD2 | NM_017457 // PSCD2 // pleckstrin homology, Sec7 and coiled-coil domains 2 (cytoh | NM_017457 | 0.31 | 0.05 | 0.000 |
| 3869396 | ZNF432 | NM_014650 // ZNF432 // zinc finger protein 432 // 19q13.33 // 9668 /// ENST00000 | NM_014650 | 0.31 | 0.09 | 0.006 |
| 3981120 | OGT | NM_181672 // OGT // O-linked N-acetylglucosamine (GlcNAc) transferase (UDP-N-ace | NM_181672 | 0.31 | 0.10 | 0.013 |
| 2622607 | SLC38A3 | NM_006841 // SLC38A3 // solute carrier family 38, member 3 // 3p21.3 // 10991 // | NM_006841 | 0.30 | 0.11 | 0.016 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3978812 | FOXR2 | NM_198451 // FOXR2 // forkhead box R2 // Xp11.21 // 139628 /// ENST00000339140 / | NM_198451 | 0.30 | 0.09 | 0.008 |
| 3571904 | NPC2 | NM_006432 // NPC2 // Niemann-Pick disease, type C2 // 14q24.3 // 10577 /// NM_00 | NM_006432 | 0.30 | 0.10 | 0.011 |
| 2417945 | PTGER3 | NM_198715 // PTGER3 // prostaglandin E receptor 3 (subtype EP3) // 1p31.2 // 573 | NM_198715 | 0.30 | 0.11 | 0.017 |
| 3059393 | SEMA3E | NM_012431 // SEMA3E // sema domain, immunoglobulin domain (Ig), short basic doma | NM_012431 | 0.30 | 0.09 | 0.009 |
| 2336456 | MGC52498 | NM_001042693 // MGC52498 // hypothetical protein MGC52498 // 1p32.3 // 348378 // | NM_001042693 | 0.30 | 0.10 | 0.011 |
| 3726772 | CROP | NM_016424 // CROP // cisplatin resistance-associated overexpressed protein // 17 | NM_016424 | 0.30 | 0.11 | 0.016 |
| 2784265 | IL2 | NM_000586 // IL2 // interleukin 2 // 4q26-q27 // 3558 /// ENST00000226730 // IL2 | NM_000586 | 0.29 | 0.11 | 0.019 |
| 2495782 | LIPT1 | NM_145197 // LIPT1 // lipoyltransferase 1 // 2q11.2 // 51601 /// NM_145198 // LI | NM_145197 | 0.29 | 0.10 | 0.012 |
| 2377094 | PFKFB2 | NM_006212 // PFKFB2 // 6-phosphofructo-2-kinase/fructose-2,6-biphosphatase 2 // | NM_006212 | 0.29 | 0.10 | 0.012 |
| 2469213 | KLF11 | NM_003597 // KLF11 // Kruppel-like factor 11 // 2p25 // 8462 /// ENST00000305883 | NM_003597 | 0.29 | 0.10 | 0.011 |
| 3662387 | HERPUD1 | NM_014685 // HERPUD1 // homocysteine-inducible, endoplasmic reticulum stress-ind | NM_014685 | 0.29 | 0.07 | 0.003 |
| 3771215 | ACOX1 | NM_004035 // ACOX1 // acyl-Coenzyme A oxidase 1, palmitoyl // 17q24-q25| 17q25.1 | NM_004035 | 0.29 | 0.10 | 0.013 |
| 3203135 | TOPORS | NM_005802 // TOPORS // topoisomerase I binding, arginine/serine-rich // 9p21 // | NM_005802 | 0.28 | 0.11 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2805482 | — | — | — | 0.28 | 0.09 | 0.008 |
| 3247757 | UBE2D1 | NM_003338 // UBE2D1 // ubiquitin-conjugating enzyme E2D 1 (UBC4/5 homolog, yeast | NM_003338 | 0.28 | 0.08 | 0.007 |
| 3444147 | KLRC1 | NM_002259 // KLRC1 // killer cell lectin-like receptor subfamily C, member 1 // | NM_002259 | 0.28 | 0.10 | 0.015 |
| 3348891 | C11orf57 | NM_018195 // C11orf57 // chromosome 11 open reading frame 57 // 11q23.1 // 55216 | NM_018195 | 0.28 | 0.09 | 0.011 |
| 3906942 | SERINC3 | NM_006811 // SERINC3 // serine incorporator 3 // 20q13.1-q13.3 // 10955 /// NM_1 | NM_006811 | 0.28 | 0.07 | 0.003 |
| 2930418 | UST | NM_005715 // UST // uronyl-2-sulfotransferase // 6q25.1 // 10090 /// ENST0000036 | NM_005715 | 0.28 | 0.06 | 0.002 |
| 3188200 | OR1L1 | NM_001005236 // OR1L1 // olfactory receptor, family 1, subfamily L, member 1 // | NM_001005236 | 0.28 | 0.09 | 0.011 |
| 3856075 | ZNF682 | NM_033196 // ZNF682 // zinc finger protein 682 // 19p12 // 91120 /// NM_00107734 | NM_033196 | 0.28 | 0.10 | 0.017 |
| 3385951 | NOX4 | NM_016931 // NOX4 // NADPH oxidase 4 // 11q14.2-q21 // 50507 /// ENST00000263317 | NM_016931 | 0.28 | 0.06 | 0.002 |
| 3523881 | KDELC1 | NM_024089 // KDELC1 // KDEL (Lys-Asp-Glu-Leu) containing 1 // 13q33 // 79070 /// | NM_024089 | 0.28 | 0.06 | 0.002 |
| 2632778 | EPHA6 | NM_001080448 // EPHA6 // EPH receptor A6 // 3q11.2 // 285220 /// ENST00000389672 | NM_001080448 | 0.28 | 0.09 | 0.010 |
| 3373272 | OR5W2 | NM_001001960 // OR5W2 // olfactory receptor, family 5, subfamily W, member 2 // | NM_001001960 | 0.28 | 0.10 | 0.015 |
| 4017694 | IRS4 | NM_003604 // IRS4 // insulin receptor substrate 4 // Xq22.3 // 8471 /// ENST0000 | NM_003604 | 0.28 | 0.10 | 0.016 |
| 3545311 | KIAA1737 | NM_033426 // KIAA1737 // KIAA1737 // 14q24.3 // 85457 /// ENST00000361786 // KIA | NM_033426 | 0.28 | 0.07 | 0.003 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3753860 | CCL5 | NM_002985 // CCL5 // chemokine (C-C motif) ligand 5 // 17q11.2-q12 // 6352 /// E | NM_002985 | 0.28 | 0.05 | 0.001 |
| 3617312 | SLC12A6 | NM_001042496 // SLC12A6 // solute carrier family 12 (potassium/chloride transpor | NM_001042496 | 0.27 | 0.07 | 0.005 |
| 3351315 | UBE4A | NM_004788 // UBE4A // ubiquitination factor E4A (UFD2 homolog, yeast) // 11q23.3 | NM_004788 | 0.27 | 0.07 | 0.004 |
| 3755396 | CCDC49 | NM_017748 // CCDC49 // coiled-coil domain containing 49 // 17q12 // 54883 /// EN | NM_017748 | 0.27 | 0.09 | 0.013 |
| 2870889 | C5orf13 | NM_004772 // C5orf13 // chromosome 5 open reading frame 13 // 5q22.1 // 9315 /// | NM_004772 | 0.27 | 0.09 | 0.010 |
| 2775259 | RASGEF1B | NM_152545 // RASGEF1B // RasGEF domain family, member 1B // 4q21.21-q21.22 // 15 | NM_152545 | 0.27 | 0.10 | 0.015 |
| 3165624 | — | — | — | 0.27 | 0.06 | 0.003 |
| 2771654 | CENPC1 | NM_001812 // CENPC1 // centromere protein C 1 // 4q12-q13.3 // 1060 /// ENST0000 | NM_001812 | 0.27 | 0.09 | 0.013 |
| 3784670 | C18orf21 | NM_031446 // C18orf21 // chromosome 18 open reading frame 21 // 18q12.2 // 83608 | NM_031446 | 0.27 | 0.08 | 0.008 |
| 2364231 | DDR2 | NM_001014796 // DDR2 // discoidin domain receptor tyrosine kinase 2 // 1q23.3 // | NM_001014796 | 0.26 | 0.10 | 0.018 |
| 3921442 | SH3BGR | NM_007341 // SH3BGR // SH3 domain binding glutamic acid-rich protein // 21q22.3 | NM_007341 | 0.26 | 0.08 | 0.007 |
| 2627368 | C3orf49 | BC015210 // C3orf49 // chromosome 3 open reading frame 49 // 3p14.1 // 132200 | BC015210 | 0.26 | 0.06 | 0.003 |
| 3250699 | EIF4EBP2 | NM_004096 // EIF4EBP2 // eukaryotic translation initiation factor 4E binding pro | NM_004096 | 0.26 | 0.10 | 0.018 |
| 3237788 | PLXDC2 | NM_032812 // PLXDC2 // plexin domain containing 2 // 10p12.32-p12.31 // 84898 // | NM_032812 | 0.26 | 0.09 | 0.013 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3285926 | ZNF33B | NM_006955 // ZNF33B // zinc finger protein 33B // 10q11.2 // 7582 /// ENST000003 | NM_006955 | 0.26 | 0.10 | 0.018 |
| 3304475 | ARL3 | NM_004311 // ARL3 // ADP-ribosylation factor-like 3 // 10q23.3 // 403 /// ENST00 | NM_004311 | 0.26 | 0.08 | 0.008 |
| 3364306 | SOX6 | NM_017508 // SOX6 // SRY (sex determining region Y)-box 6 // 11p15.3 // 55553 // | NM_017508 | 0.26 | 0.08 | 0.010 |
| 3185498 | SLC31A2 | NM_001860 // SLC31A2 // solute carrier family 31 (copper transporters), member 2 | NM_001860 | 0.25 | 0.09 | 0.015 |
| 3998766 | KAL1 | NM_000216 // KAL1 // Kallmann syndrome 1 sequence // Xp22.32 // 3730 /// ENST000 | NM_000216 | 0.25 | 0.07 | 0.006 |
| 3143266 | PSKH2 | NM_033126 // PSKH2 // protein serine kinase H2 // 8q21.2 // 85481 /// ENST000002 | NM_033126 | 0.25 | 0.07 | 0.006 |
| 3458911 | CTDSP2 | NM_005730 // CTDSP2 // CTD (carboxy-terminal domain, RNA polymerase II, polypept | NM_005730 | 0.25 | 0.06 | 0.003 |
| 3195034 | PTGDS | NM_000954 // PTGDS // prostaglandin D2 synthase 21 kDa (brain) // 9q34.2-q34.3 // | NM_000954 | 0.25 | 0.08 | 0.010 |
| 3854066 | C19orf42 | NM_024104 // C19orf42 // chromosome 19 open reading frame 42 // 19p13.11 // 7908 | NM_024104 | 0.25 | 0.08 | 0.010 |
| 3819474 | ANGPTL4 | NM_139314 // ANGPTL4 // angiopoietin-like 4 // 19p13.3 // 51129 /// NM_001039667 | NM_139314 | 0.25 | 0.06 | 0.004 |
| 3944084 | TOM1 | NM_005488 // TOM1 // target of myb1 (chicken) // 22q13.1 // 10043 /// ENST000003 | NM_005488 | 0.25 | 0.07 | 0.006 |
| 3848243 | INSR | NM_000208 // INSR // insulin receptor // 19p13.3-p13.2 // 3643 /// NM_001079817 | NM_000208 | 0.24 | 0.09 | 0.014 |
| 3168415 | CLTA | NM_007096 // CLTA // clathrin, light chain (Lca) // 9p13 // 1211 /// NM_00107667 | NM_007096 | 0.24 | 0.08 | 0.009 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2609462 | CAV3 | NM_033337 // CAV3 // caveolin 3 // 3p25 // 859 /// NM_001234 // CAV3 // caveolin | NM_033337 | 0.24 | 0.07 | 0.007 |
| 3393834 | C11orf60 | BC022856 // C11orf60 // chromosome 11 open reading frame 60 // 11q23.3 // 56912 | BC022856 | 0.24 | 0.06 | 0.003 |
| 3755614 | STAC2 | NM_198993 // STAC2 // SH3 and cysteine rich domain 2 // 17q12 // 342667 /// ENST | NM_198993 | 0.24 | 0.07 | 0.009 |
| 3627363 | NARG2 | NM_024611 // NARG2 // NMDA receptor regulated 2 // 15q22.2 // 79664 /// NM_00101 | NM_024611 | 0.24 | 0.06 | 0.003 |
| 3212976 | ZCCHC6 | NM_024617 // ZCCHC6 // zinc finger, CCHC domain containing 6 // 9q21 // 79670 // | NM_024617 | 0.24 | 0.08 | 0.014 |
| 3275922 | PRKCQ | NM_006257 // PRKCQ // protein kinase C, theta // 10p15 // 5588 /// ENST000002631 | NM_006257 | 0.24 | 0.05 | 0.002 |
| 3023825 | C7orf45 | BC017587 // C7orf45 // chromosome 7 open reading frame 45 // 7q32.2 // 136263 // | BC017587 | 0.23 | 0.09 | 0.020 |
| 3832906 | IL29 | NM_172140 // IL29 // interleukin 29 (interferon, lambda 1) // 19q13.13 // 282618 | NM_172140 | 0.23 | 0.08 | 0.015 |
| 3529156 | NGDN | NM_015514 // NGDN // neuroguidin, EIF4E binding protein // 14q11.2 // 25983 /// | NM_015514 | 0.23 | 0.08 | 0.012 |
| 2620448 | CLEC3B | NM_003278 // CLEC3B // C-type lectin domain family 3, member B // 3p22-p21.3 // | NM_003278 | 0.23 | 0.08 | 0.014 |
| 3481296 | SGCG | NM_000231 // SGCG // sarcoglycan, gamma (35 kDa dystrophin-associated glycoprotei | NM_000231 | 0.23 | 0.09 | 0.019 |
| 3135184 | RB1CC1 | NM_014781 // RB1CC1 // RB1-inducible coiled-coil 1 // 8q11 // 9821 /// NM_001083 | NM_014781 | 0.23 | 0.07 | 0.008 |
| 2421843 | GBP3 | NM_018284 // GBP3 // guanylate binding protein 3 // 1p22.2 // 2635 /// ENST00000 | NM_018284 | 0.23 | 0.06 | 0.004 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3385003 | CREBZF | NM_001039618 // CREBZF // CREB/ATF bZIP transcription factor // 11q14 // 58487 / | NM_001039618 | 0.23 | 0.09 | 0.020 |
| 3610804 | IGF1R | NM_000875 // IGF1R // insulin-like growth factor 1 receptor // 15q26.3 // 3480 / | NM_000875 | 0.23 | 0.08 | 0.013 |
| 3606304 | AKAP13 | NM_006738 // AKAP13 // A kinase (PRKA) anchor protein 13 // 15q24-q25 // 11214 / | NM_006738 | 0.23 | 0.04 | 0.000 |
| 2565579 | ANKRD39 | NM_016466 // ANKRD39 // ankyrin repeat domain 39 // 2q11.2 // 51239 /// ENST0000 | NM_016466 | 0.23 | 0.05 | 0.003 |
| 2722151 | RBPJ | NM_005349 // RBPJ // recombination signal binding protein for immunoglobulin kap | NM_005349 | 0.22 | 0.07 | 0.008 |
| 3031533 | GIMAP4 | NM_018326 // GIMAP4 // GTPase, IMAP family member 4 // 7q36.1 // 55303 /// ENST0 | NM_018326 | 0.22 | 0.08 | 0.017 |
| 3725481 | UBE2Z | NM_023079 // UBE2Z // ubiquitin-conjugating enzyme E2Z // 17q21.32 // 65264 /// | NM_023079 | 0.22 | 0.06 | 0.004 |
| 3549575 | IFI27 | NM_005532 // IFI27 // interferon, alpha-inducible protein 27 // 14q32 // 3429 / | NM_005532 | 0.22 | 0.08 | 0.016 |
| 3725035 | NFE2L1 | NM_003204 // NFE2L1 // nuclear factor (erythroid-derived 2)-like 1 // 17q21.3 // | NM_003204 | 0.22 | 0.07 | 0.011 |
| 3348748 | C11orf1 | NM_022761 // C11orf1 // chromosome 11 open reading frame 1 // 11q13-q22 // 64776 | NM_022761 | 0.22 | 0.07 | 0.008 |
| 3722039 | RAMP2 | NM_005854 // RAMP2 // receptor (G protein-coupled) activity modifying protein 2 | NM_005854 | 0.22 | 0.05 | 0.003 |
| 3886704 | STK4 | NM_006282 // STK4 // serine/threonine kinase 4 // 20q11.2-q13.2 // 6789 /// ENST | NM_006282 | 0.22 | 0.07 | 0.012 |
| 3645901 | FLJ14154 | NM_024845 // FLJ14154 // hypothetical protein FLJ14154 // 16p13.3 // 79903 /// N | NM_024845 | 0.22 | 0.06 | 0.005 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3367673 | MPPED2 | NM_001584 // MPPED2 // metallophosphoesterase domain containing 2 // 11p13 // 74 | NM_001584 | 0.22 | 0.08 | 0.017 |
| 3219885 | PTPN3 | NM_002829 // PTPN3 // protein tyrosine phosphatase, non-receptor type 3 // 9q31 | NM_002829 | 0.22 | 0.05 | 0.003 |
| 3791466 | — | — | — | 0.22 | 0.06 | 0.007 |
| 3717635 | ZNF207 | NM_001098507 // ZNF207 // zinc finger protein 207 // 17q11.2 // 7756 /// NM_0034 | NM_001098507 | 0.22 | 0.08 | 0.015 |
| 2648141 | MBNL1 | NM_021038 // MBNL1 // muscleblind-like (*Drosophila*) // 3q25 // 4154 /// NM_20729 | NM_021038 | 0.22 | 0.07 | 0.009 |
| 2436938 | PBXIP1 | NM_020524 // PBXIP1 // pre-B-cell leukemia homeobox interacting protein 1 // 1q2 | NM_020524 | 0.21 | 0.05 | 0.002 |
| 3299705 | PANK1 | NM_148977 // PANK1 // pantothenate kinase 1 // 10q23.31 // 53354 /// NM_148978 / | NM_148977 | 0.21 | 0.06 | 0.007 |
| 3628923 | FAM96A | NM_032231 // FAM96A // family with sequence similarity 96, member A // 15q22.31 | NM_032231 | 0.21 | 0.05 | 0.003 |
| 2353669 | CD2 | NM_001767 // CD2 // CD2 molecule // 1p13 // 914 /// ENST00000369478 // CD2 // CD | NM_001767 | 0.21 | 0.06 | 0.006 |
| 3474450 | PLA2G1B | NM_000928 // PLA2G1B // phospholipase A2, group IB (pancreas) // 12q23-q24.1 // | NM_000928 | 0.21 | 0.08 | 0.016 |
| 3722417 | NBR1 | NM_031858 // NBR1 // neighbor of BRCA1 gene 1 // 17q21.31 // 4077 /// NM_005899 | NM_031858 | 0.21 | 0.08 | 0.017 |
| 3234760 | CUGBP2 | NM_001025077 // CUGBP2 // CUG triplet repeat, RNA binding protein 2 // 10p13 // | NM_001025077 | 0.21 | 0.06 | 0.004 |
| 3627422 | RORA | NM_134260 // RORA // RAR-related orphan receptor A // 15q21-q22 // 6095 /// NM_0 | NM_134260 | 0.21 | 0.06 | 0.006 |
| 3382061 | XRRA1 | NM_182969 // XRRA1 // X-ray radiation resistance associated 1 // 11q13.4// 1435 | NM_182969 | 0.21 | 0.08 | 0.017 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3015338 | STAG3 | NM_012447 // STAG3 // stromal antigen 3 // 7q22.1 // 10734 /// ENST00000317296 / | NM_012447 | 0.21 | 0.06 | 0.007 |
| 2665720 | ZNF385D | NM_024697 // ZNF385D // zinc finger protein 385D // 3p24.3 // 79750 /// ENST0000 | NM_024697 | 0.21 | 0.07 | 0.013 |
| 3154185 | TMEM71 | NM_144649 // TMEM71 // transmembrane protein 71 // 8q24.22 // 137835 /// ENST000 | NM_144649 | 0.21 | 0.06 | 0.009 |
| 3789947 | NEDD4L | NM_015277 // NEDD4L // neural precursor cell expressed, developmentally down-reg | NM_015277 | 0.21 | 0.08 | 0.016 |
| 2688933 | CD200R2 | ENST00000383679 // CD200R2 // CD200 cell surface glycoprotein receptor isoform 2 | ENST00000383679 | 0.21 | 0.08 | 0.016 |
| 3379644 | CPT1A | NM_001876 // CPT1A // carnitine palmitoyltransferase 1A (liver) // 11q13.1-q13.2 | NM_001876 | 0.21 | 0.04 | 0.001 |
| 3677795 | CREBBP | NM_004380 // CREBBP // CREB binding protein (Rubinstein-Taybi syndrome) // 16p13 | NM_004380 | 0.21 | 0.05 | 0.004 |
| 2358320 | TARS2 | NM_025150 // TARS2 // threonyl-tRNA synthetase 2, mitochondrial (putative) // 1q | NM_025150 | 0.21 | 0.06 | 0.007 |
| 3228373 | TSC1 | NM_000368 // TSC1 // tuberous sclerosis 1 // 9q34 // 7248 /// NM_001008567 // TS | NM_000368 | 0.20 | 0.06 | 0.006 |
| 3362795 | RNF141 | NM_016422 // RNF141 // ring finger protein 141 // 11p15.4 // 50862 /// ENST00000 | NM_016422 | 0.20 | 0.08 | 0.019 |
| 3673684 | CDT1 | NM_030928 // CDT1 // chromatin licensing and DNA replication factor 1 // 16q24.3 | NM_030928 | 0.20 | 0.07 | 0.015 |
| 3042881 | HOXA7 | NM_006896 // HOXA7 // homeobox A7 // 7p15-p14 // 3204 /// ENST00000396347 // HOX | NM_006896 | 0.20 | 0.02 | 0.000 |
| 3381817 | UCP2 | NM_003355 // UCP2 // uncoupling protein 2 (mitochondrial, proton carrier) // 11q | NM_003355 | 0.20 | 0.05 | 0.005 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3415068 | ANKRD33 | NM_182608 // ANKRD33 // ankyrin repeat domain 33 // 12q13.13 // 341405 /// ENST0 | NM_182608 | 0.20 | 0.06 | 0.006 |
| 3633403 | SIN3A | NM_015477 // SIN3A // SIN3 homolog A, transcription regulator (yeast) // 15q24.2 | NM_015477 | 0.20 | 0.07 | 0.014 |
| 3380901 | NUMA1 | NM_006185 // NUMA1 // nuclear mitotic apparatus protein 1 // 11q13 // 4926 /// E | NM_006185 | 0.19 | 0.04 | 0.002 |
| 2598099 | BARD1 | NM_000465 // BARD1 // BRCA1 associated RING domain 1 // 2q34-q35 // 580 /// ENST | NM_000465 | 0.19 | 0.07 | 0.015 |
| 3139722 | NCOA2 | NM_006540 // NCOA2 // nuclear receptor coactivator 2 // 8q13.3 // 10499 /// ENST | NM_006540 | 0.19 | 0.06 | 0.010 |
| 3641871 | LINS1 | NM_018148 // LINS1 // lines homolog 1 (*Drosophila*) // 15q26.3 // 55180 /// NM_00 | NM_018148 | 0.19 | 0.06 | 0.013 |
| 3401217 | TULP3 | NM_003324 // TULP3 // tubby like protein 3 // 12p13.3 // 7289 /// ENST0000022824 | NM_003324 | 0.19 | 0.06 | 0.008 |
| 3741997 | ANKFY1 | NM_016376 // ANKFY1 // ankyrin repeat and FYVE domain containing 1 // 17p13.3 // | NM_016376 | 0.19 | 0.06 | 0.008 |
| 2622742 | C3orf45 | BC028000 // C3orf45 // chromosome 3 open reading frame 45 // 3p21.31 // 132228 / | BC028000 | 0.19 | 0.06 | 0.013 |
| 3845352 | UQCR | NM_006830 // UQCR // ubiquinol-cytochrome c reductase, 6.4 kDa subunit // 19p13.3 | NM_006830 | 0.19 | 0.06 | 0.014 |
| 3960356 | BAIAP2L2 | NM_025045 // BAIAP2L2 // BAI1-associated protein 2-like 2 // 22q13.1 // 80115 // | NM_025045 | 0.19 | 0.07 | 0.018 |
| 3645947 | CLUAP1 | NM_015041 // CLUAP1 // clusterin associated protein 1 // 16p13.3 // 23059 /// NM | NM_015041 | 0.19 | 0.06 | 0.012 |
| 3835544 | ZNF227 | NM_182490 // ZNF227 // zinc finger protein 227 //— // 7770 /// ENST0000031304 | NM_182490 | 0.18 | 0.06 | 0.011 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3368748 | FBXO3 | NM_033406 // FBXO3 // F-box protein 3 // 11p13 // 26273 /// NM_012175 // FBXO3 / | NM_033406 | 0.18 | 0.07 | 0.020 |
| 3621623 | ELL3 | NM_025165 // ELL3 // elongation factor RNA polymerase II-like 3 // 15q15.3 // 80 | NM_025165 | 0.18 | 0.05 | 0.005 |
| 3430552 | PWP1 | NM_007062 // PWP1 // PWP1 homolog (*S. cerevisiae*) // 12q23.3 // 11137 /// ENST00 | NM_007062 | 0.18 | 0.07 | 0.016 |
| 2844908 | BTNL9 | NM_152547 // BTNL9 // butyrophilin-like 9 // 5q35.3 // 153579 /// ENST0000032770 | NM_152547 | 0.18 | 0.05 | 0.005 |
| 4021508 | ZNF280C | NM_017666 // ZNF280C // zinc finger protein 280C // Xq25 // 55609 /// ENST000003 | NM_017666 | 0.18 | 0.07 | 0.018 |
| 2489071 | TET3 | NM_144993 // TET3 // tet oncogene family member 3 // 2p13.1 // 200424 /// ENST00 | NM_144993 | 0.18 | 0.04 | 0.003 |
| 2516879 | HOXD8 | NM_019558 // HOXD8 // homeobox D8 // 2q31.1 // 3234 /// ENST00000313173 // HOXD8 | NM_019558 | 0.18 | 0.06 | 0.015 |
| 3740704 | SMYD4 | NM_052928 // SMYD4 // SET and MYND domain containing 4 // 17p13.3 // 114826 /// | NM_052928 | 0.18 | 0.06 | 0.012 |
| 3975467 | UTX | NM_021140 // UTX // ubiquitously transcribed tetratricopeptide repeat, X chromos | NM_021140 | 0.18 | 0.06 | 0.013 |
| 3699044 | RFWD3 | NM_018124 // RFWD3 // ring finger and WD repeat domain 3 // 16q22.3 // 55159 /// | NM_018124 | 0.18 | 0.06 | 0.011 |
| 3473083 | MED13L | NM_015335 // MED13L // mediator complex subunit 13-like // 12q24.21 // 23389 /// | NM_015335 | 0.18 | 0.02 | 0.000 |
| 2332711 | PPIH | NM_006347 // PPIH // peptidylprolyl isomerase H (cyclophilin H) // 1p34.1 // 104 | NM_006347 | 0.17 | 0.06 | 0.017 |
| 3556990 | JUB | NM_032876 // JUB // jub, ajuba homolog (*Xenopus laevis*) // 14q11.2 // 84962 /// | NM_032876 | 0.17 | 0.04 | 0.004 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2780143 | BDH2 | NM_020139 // BDH2 // 3-hydroxybutyrate dehydrogenase, type 2 // 4q24 // 56898 // | NM_020139 | 0.17 | 0.05 | 0.006 |
| 3899495 | C20orf12 | NM_001099407 // C20orf12 // chromosome 20 open reading frame 12 // 20p11.23 // 5 | NM_001099407 | 0.17 | 0.05 | 0.008 |
| 3290875 | ANK3 | NM_020987 // ANK3 // ankyrin 3, node of Ranvier (ankyrin G) // 10q21 // 288 /// | NM_020987 | 0.17 | 0.03 | 0.001 |
| 3576014 | C14orf102 | NM_017970 // C14orf102 // chromosome 14 open reading frame 102 // 14q32.11 // 55 | NM_017970 | 0.17 | 0.04 | 0.002 |
| 3644887 | ATP6V0C | NM_001694 // ATP6V0C // ATPase, H+ transporting, lysosomal 16 kDa, V0 subunit c / | NM_001694 | 0.17 | 0.06 | 0.017 |
| 2648378 | RAP2B | NM_002886 // RAP2B // RAP2B, member of RAS oncogene family // 3q25.2 // 5912 /// | NM_002886 | 0.17 | 0.06 | 0.017 |
| 2362892 | ATP1A2 | NM_000702 // ATP1A2 // ATPase, Na+/K+ transporting, alpha 2 (+) polypeptide // 1 | NM_000702 | 0.16 | 0.06 | 0.015 |
| 2361488 | RHBG | NM_020407 // RHBG // Rh family, B glycoprotein // 1q21.3 // 57127 /// ENST000003 | NM_020407 | 0.16 | 0.06 | 0.014 |
| 3415915 | PFDN5 | NM_002624 // PFDN5 // prefoldin subunit 5 // 12q12 // 5204 /// NM_145897 // PFDN | NM_002624 | 0.16 | 0.05 | 0.011 |
| 3433796 | PEBP1 | NM_002567 // PEBP1 // phosphatidylethanolamine binding protein 1 // 12q24.23 // | NM_002567 | 0.16 | 0.04 | 0.004 |
| 3788302 | SMAD4 | NM_005359 // SMAD4 // SMAD family member 4 // 18q21.1 // 4089 /// ENST0000039841 | NM_005359 | 0.16 | 0.05 | 0.012 |
| 3436236 | ZNF664 | NM_152437 // ZNF664 // zinc finger protein 664 // 12q24.31 // 144348 /// ENST000 | NM_152437 | 0.16 | 0.06 | 0.016 |
| 3441542 | TMEM16B | NM_020373 // TMEM16B // transmembrane protein 16B // 12p13.3 // 57101 /// ENST00 | NM_020373 | 0.16 | 0.06 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3456353 | CALCOCO1 | NM_020898 // CALCOCO1 // calcium binding and coiled-coil domain 1 // 12q13.13 // | NM_020898 | 0.16 | 0.05 | 0.010 |
| 3888721 | PTPN1 | NM_002827 // PTPN1 // protein tyrosine phosphatase, non-receptor type 1 // 20q13 | NM_002827 | 0.16 | 0.06 | 0.020 |
| 3138204 | CYP7B1 | NM_004820 // CYP7B1 // cytochrome P450, family 7, subfamily B, polypeptide 1 // | NM_004820 | 0.15 | 0.05 | 0.014 |
| 3278401 | FRMD4A | NM_018027 // FRMD4A // FERM domain containing 4A // 10p13 // 55691 /// ENST00000 | NM_018027 | 0.15 | 0.05 | 0.009 |
| 3904226 | RBM39 | NM_184234 // RBM39 // RNA binding motif protein 39 // 20q11.22 // 9584 /// NM_00 | NM_184234 | 0.15 | 0.05 | 0.015 |
| 3791850 | SERPINB13 | NM_012397 // SERPINB13 // serpin peptidase inhibitor, clade B (ovalbumin), membe | NM_012397 | 0.15 | 0.04 | 0.005 |
| 3665603 | CTCF | NM_006565 // CTCF // CCCTC-binding factor (zinc finger protein) // 16q21-q22.3 / | NM_006565 | 0.15 | 0.04 | 0.004 |
| 3969802 | BMX | NM_203281 // BMX // BMX non-receptor tyrosine kinase // Xp22.2 // 660 /// NM_001 | NM_203281 | 0.15 | 0.05 | 0.016 |
| 3621276 | HISPPD2A | NM_014659 // HISPPD2A // histidine acid phosphatase domain containing 2A // 15q1 | NM_014659 | 0.14 | 0.04 | 0.005 |
| 2325113 | C1orf213 | NM_138479 // C1orf213 // chromosome 1 open reading frame 213 // 1p36.12 // 14889 | NM_138479 | 0.14 | 0.05 | 0.012 |
| 3681956 | KIAA0430 | NM_014647 // KIAA0430 // KIAA0430 // 16p13.11 // 9665 /// ENST00000396368 // KIA | NM_014647 | 0.14 | 0.05 | 0.018 |
| 3415193 | GRASP | NM_181711 // GRASP // GRP1 (general receptor for phosphoinositides 1)-associated | NM_181711 | 0.14 | 0.05 | 0.019 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3249369 | LRRTM3 | NM_178011 // LRRTM3 // leucine rich repeat transmembrane neuronal 3 // 10q21.3 / | NM_178011 | 0.14 | 0.05 | 0.011 |
| 3874023 | PTPRA | NM_002836 // PTPRA // protein tyrosine phosphatase, receptor type, A // 20p13 // | NM_002836 | 0.14 | 0.04 | 0.004 |
| 3809621 | FECH | NM_001012515 // FECH // ferrochelatase (protoporphyria) // 18q21.3 // 2235 /// N | NM_001012515 | 0.14 | 0.04 | 0.009 |
| 3351385 | MLL | NM_005933 // MLL // myeloid/lymphoid or mixed-lineage leukemia (trithorax homolo | NM_005933 | 0.14 | 0.05 | 0.016 |
| 3288707 | ERCC6 | NM_000124 // ERCC6 // excision repair cross-complementing rodent repair deficien | NM_000124 | 0.14 | 0.05 | 0.016 |
| 3624607 | MYO5A | NM_000259 // MYO5A // myosin VA (heavy chain 12, myoxin) // 15q21 // 4644 /// EN | NM_000259 | 0.14 | 0.04 | 0.006 |
| 3353859 | OR4D5 | NM_001001965 // OR4D5 // olfactory receptor, family 4, subfamily D, member 5 // | NM_001001965 | 0.14 | 0.05 | 0.017 |
| 2823797 | TSLP | NM_033035 // TSLP // thymic stromal lymphopoietin // 5q22.1 // 85480 /// NM_1385 | NM_033035 | 0.14 | 0.05 | 0.013 |
| 2414366 | PPAP2B | NM_003713 // PPAP2B // phosphatidic acid phosphatase type 2B // 1pter-p22.1 // 8 | NM_003713 | 0.13 | 0.04 | 0.007 |
| 3878308 | CSRP2BP | NM_020536 // CSRP2BP // CSRP2 binding protein // 20p11.23 // 57325 /// NM_177926 | NM_020536 | 0.13 | 0.05 | 0.019 |
| 4025771 | CD99L2 | NM_031462 // CD99L2 // CD99 molecule-like 2 // Xq28 // 83692 /// NM_134446 // CD | NM_031462 | 0.13 | 0.04 | 0.007 |
| 3414776 | LETMD1 | NM_015416 // LETMD1 // LETM1 domain containing 1 // 12q13.13 // 25875 /// NM_001 | NM_015416 | 0.13 | 0.05 | 0.014 |
| 3645253 | SRRM2 | NM_016333 // SRRM2 // serine/arginine repetitive matrix 2 // 16p13.3 // 23524 // | NM_016333 | 0.13 | 0.04 | 0.007 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2440700 | ADAMTS4 | NM_005099 // ADAMTS4 // ADAM metallopeptidase with thrombospondin type 1 motif, | NM_005099 | 0.13 | 0.03 | 0.005 |
| 2609870 | BRPF1 | NM_001003694 // BRPF1 // bromodomain and PHD finger containing, 1 // 3p26-p25 // | NM_001003694 | 0.13 | 0.04 | 0.012 |
| 3632298 | ADPGK | NM_031284 // ADPGK // ADP-dependent glucokinase // 15824.1 // 83440 /// ENST0000 | NM_031284 | 0.13 | 0.04 | 0.007 |
| 3184940 | GNG10 | NM_001017998 // GNG10 // guanine nucleotide binding protein (G protein), gamma 1 | NM_001017998 | 0.13 | 0.04 | 0.011 |
| 3223776 | C5 | NM_001735 // C5 // complement component 5 // 9q33-q34 // 727 /// ENST00000223642 | NM_001735 | 0.13 | 0.04 | 0.008 |
| 3922100 | MX1 | NM_002462 // MX1 // myxovirus (influenza virus) resistance 1, interferon-inducib | NM_002462 | 0.12 | 0.04 | 0.015 |
| 3960478 | CSNK1E | NM_001894 // CSNK1E // casein kinase 1, epsilon // 22q13.1 // 1454 /// NM_152221 | NM_001894 | 0.12 | 0.04 | 0.018 |
| 3715703 | SUPT6H | NM_003170 // SUPT6H // suppressor of Ty 6 homolog (*S. cerevisiae*) // 17q11.2 // | NM_003170 | 0.11 | 0.03 | 0.005 |
| 2322818 | PADI3 | NM_016233 // PADI3 // peptidyl arginine deiminase, type III // 1p36.13 // 51702 | NM_016233 | 0.11 | 0.03 | 0.006 |
| 2393740 | KIAA0562 | NM_014704 // KIAA0562 // KIAA0562 // 1p36.32 // 9731 /// ENST00000378230 // KIAA | NM_014704 | 0.11 | 0.03 | 0.009 |
| 3784509 | ZNF271 | NM_001112663 // ZNF271 // zinc finger protein 271 // 18q12 // 10778 /// NM_00662 | NM_001112663 | 0.11 | 0.04 | 0.020 |
| 3372253 | CUGBP1 | NM_006560 // CUGBP1 // CUG triplet repeat, RNA binding protein 1 // 11p11 // 106 | NM_006560 | 0.11 | 0.04 | 0.011 |
| 2948259 | TRIM26 | NM_003449 // TRIM26 // tripartite motif-containing 26 // 6p21.3 // 7726 /// ENST | NM_003449 | 0.11 | 0.03 | 0.006 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3191900 | NUP214 | NM_005085 // NUP214 // nucleoporin 214 kDa // 9q34.1 // 8021 /// ENST00000359428 | NM_005085 | 0.11 | 0.03 | 0.003 |
| 3105581 | CA3 | NM_005181 // CA3 // carbonic anhydrase III, muscle specific // 8q13-q22 // 761 / | NM_005181 | 0.11 | 0.03 | 0.003 |
| 3832457 | RYR1 | NM_000540 // RYR1 // ryanodine receptor 1 (skeletal) // 19q13.1 // 6261 /// NM_0 | NM_000540 | 0.11 | 0.03 | 0.006 |
| 3936256 | BCL2L13 | NM_015367 // BCL2L13 // BCL2-like 13 (apoptosis facilitator) // 22q11 // 23786 / | NM_015367 | 0.10 | 0.02 | 0.002 |
| 3599280 | PIAS1 | NM_016166 // PIAS1 // protein inhibitor of activated STAT, 1 // 15q // 8554 /// | NM_016166 | 0.10 | 0.04 | 0.017 |
| 3755976 | MED24 | NM_014815 // MED24 // mediator complex subunit 24 // 17q21.1 // 9862 /// NM_0010 | NM_014815 | 0.10 | 0.04 | 0.019 |
| 3656418 | SRCAP | NM_006662 // SRCAP // Snf2-related CREBBP activator protein // 16p11.2 // 10847 | NM_006662 | 0.10 | 0.04 | 0.017 |
| 3943101 | DEPDC5 | NM_014662 // DEPDC5 // DEP domain containing 5 // 22q12.3 // 9681 /// NM_0010071 | NM_014662 | 0.09 | 0.01 | 0.000 |
| 3960685 | DMC1 | NM_007068 // DMC1 // DMC1 dosage suppressor of mck1 homolog, meiosis-specific ho | NM_007068 | 0.09 | 0.03 | 0.013 |
| 2434776 | CDC42SE1 | NM_001038707 // CDC42SE1 // CDC42 small effector 1 // 1q21.2 // 56882 /// NM_020 | NM_001038707 | 0.08 | 0.03 | 0.014 |
| 3438417 | SFRS8 | NM_004592 // SFRS8 // splicing factor, arginine/serine-rich 8 (suppressor-of-whi | NM_004592 | 0.08 | 0.03 | 0.016 |
| 3457696 | PAN2 | NM_014871 // PAN2 // PAN2 polyA specific ribonuclease subunit homolog (S. cerevi | NM_014871 | 0.08 | 0.02 | 0.008 |
| 2534615 | SCLY | NM_016510 // SCLY // selenocysteine lyase // 2q37.3 // 51540 /// ENST00000254663 | NM_016510 | 0.08 | 0.02 | 0.004 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2765865 | RELL1 | NM_001085400 // RELL1 // RELT-like 1 // 4p14 // 768211 /// NM_001085399 // RELL1 | NM_001085400 | 0.07 | 0.02 | 0.002 |
| 3765642 | INTS2 | NM_020748 // INTS2 // integrator complex subunit 2 // 17q23.2 // 57508 /// ENST0 | NM_020748 | 0.05 | 0.01 | 0.005 |
| 2906607 | NFYA | NM_002505 // NFYA // nuclear transcription factor Y, alpha // 6p21.3 // 4800 /// | NM_002505 | −0.07 | 0.02 | 0.011 |
| 3168102 | CREB3 | NM_006368 // CREB3 // cAMP responsive element binding protein 3 // 9pter-p22.1 / | NM_006368 | −0.07 | 0.02 | 0.010 |
| 3939365 | SMARCB1 | NM_003073 // SMARCB1 // SWI/SNF related, matrix associated, actin dependent regu | NM_003073 | −0.07 | 0.02 | 0.013 |
| 3415229 | NR4A1 | NM_002135 // NR4A1 // nuclear receptor subfamily 4, group A, member 1 // 12q13 / | NM_002135 | −0.07 | 0.03 | 0.015 |
| 2437801 | ARHGEF2 | NM_004723 // ARHGEF2 // rho/rac guanine nucleotide exchange factor (GEF) 2 // 1q | NM_004723 | −0.09 | 0.02 | 0.002 |
| 3645565 | THOC6 | NM_024339 // THOC6 // THO complex 6 homolog (*Drosophila*) // 16p13.3 // 79228 /// | NM_024339 | −0.10 | 0.04 | 0.018 |
| 2406766 | MRPS15 | NM_031280 // MRPS15 // mitochondrial ribosomal protein S15 // 1p35-p34.1 // 6496 | NM_031280 | −0.11 | 0.03 | 0.003 |
| 3553141 | KIAA0329 | NM_014844 // KIAA0329 // KIAA0329 // 14q32.31 // 9895 /// ENST00000359520 // KIA | NM_014844 | −0.11 | 0.04 | 0.018 |
| 3297666 | DYDC1 | NM_138812 // DYDC1 // DPY30 domain containing 1 // 10823.1 // 143241 /// ENST000 | NM_138812 | −0.11 | 0.02 | 0.000 |
| 3625674 | RFXDC2 | NM_022841 // RFXDC2 // regulatory factor X domain containing 2 // 15q21.3 // 648 | NM_022841 | −0.12 | 0.04 | 0.012 |
| 2926969 | PDE7B | NM_018945 // PDE7B // phosphodiesterase 7B // 6q23-q24 // 27115 /// ENST00000308 | NM_018945 | −0.12 | 0.04 | 0.013 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3525313 | COL4A1 | NM_001845 // COL4A1 // collagen, type IV, alpha 1 // 13q34 // 1282 /// ENST00000 | NM_001845 | −0.12 | 0.04 | 0.014 |
| 2438892 | FCRL5 | NM_031281 // FCRL5 // Fc receptor-like 5 // 1q21 // 83416 /// ENST00000361835 // | NM_031281 | −0.12 | 0.04 | 0.009 |
| 3220846 | SUSD1 | NM_022486 // SUSD1 // sushi domain containing 1 // 9q31.3-q33.1 // 64420 /// ENS | NM_022486 | −0.12 | 0.03 | 0.006 |
| 3598430 | SLC24A1 | NM_004727 // SLC24A1 // solute carrier family 24 (sodium/potassium/calcium excha | NM_004727 | −0.12 | 0.05 | 0.019 |
| 3506431 | RNF6 | NM_005977 // RNF6 // ring finger protein (C3H2C3 type) 6 // 13q12.2 // 6049 /// | NM_005977 | −0.12 | 0.04 | 0.011 |
| 3696057 | SLC12A4 | NM_005072 // SLC12A4 // solute carrier family 12 (potassium/chloride transporter | NM_005072 | −0.12 | 0.02 | 0.001 |
| 2519577 | COL3A1 | NM_000090 // COL3A1 // collagen, type III, alpha 1 (Ehlers-Danlos syndrome type | NM_000090 | −0.12 | 0.04 | 0.012 |
| 3734479 | TMEM104 | NM_017728 // TMEM104 // transmembrane protein 104 // 17q25.1 // 54868 /// ENST00 | NM_017728 | −0.13 | 0.04 | 0.015 |
| 3345157 | PIWIL4 | NM_152431 // PIWIL4 // piwi-like 4 (*Drosophila*) // 11q21 // 143689 /// ENST00000 | NM_152431 | −0.13 | 0.05 | 0.015 |
| 2949471 | NEU1 | NM_000434 // NEU1 // sialidase 1 (lysosomal sialidase) // 6p21.3 // 4758 /// ENS | NM_000434 | −0.13 | 0.04 | 0.013 |
| 2599670 | CRYBA2 | NM_057093 // CRYBA2 // crystallin, beta A2 // 2q34-q36 // 1412 /// NM_005209 // | NM_057093 | −0.13 | 0.04 | 0.014 |
| 3922444 | ABCG1 | NM_207628 // ABCG1 // ATP-binding cassette, sub-family G (WHITE), member 1 // 21 | NM_207628 | −0.13 | 0.03 | 0.003 |
| 2760371 | WDR1 | NM_017491 // WDR1 // WD repeat domain 1 // 4p16.1 // 9948 /// NM_005112 // WDR1 | NM_017491 | −0.14 | 0.05 | 0.019 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2835440 | TCOF1 | NM_001008656 // TCOF1 // Treacher Collins-Franceschetti syndrome 1 // 5q32-q33.1 | NM_001008656 | −0.14 | 0.04 | 0.007 |
| 2451544 | MYOG | NM_002479 // MYOG // myogenin (myogenic factor 4) // 1q31-q41 // 4656 /// ENST00 | NM_002479 | −0.14 | 0.05 | 0.018 |
| 3745504 | SCO1 | NM_004589 // SCO1 // SCO cytochrome oxidase deficient homolog 1 (yeast) // 17p12 | NM_004589 | −0.14 | 0.03 | 0.003 |
| 2835213 | PPARGC1B | NM_133263 // PPARGC1B // peroxisome proliferator-activated receptor gamma, coact | NM_133263 | −0.14 | 0.04 | 0.006 |
| 3704567 | CBFA2T3 | NM_005187 // CBFA2T3 // core-binding factor, runt domain, alpha subunit 2; trans | NM_005187 | −0.14 | 0.05 | 0.020 |
| 2893562 | RREB1 | NM_002955 // RREB1 // ras responsive element binding protein 1 // 6p25 // 6239 / | NM_002955 | −0.14 | 0.04 | 0.006 |
| 2672712 | SCAP | NM_012235 // SCAP // SREBF chaperone // 3p21.31 // 22937 /// ENST00000265565 // | NM_012235 | −0.14 | 0.04 | 0.009 |
| 2768197 | CORIN | NM_006587 // CORIN // corin, serine peptidase // 4p13-p12 // 10699 /// ENST00000 | NM_006587 | −0.14 | 0.05 | 0.011 |
| 2495279 | VWA3B | NM_144992 // VWA3B // von Willebrand factor A domain containing 3B // 2q11.2 // | NM_144992 | −0.14 | 0.04 | 0.006 |
| 2903588 | PFDN6 | NM_014260 // PFDN6 // prefoldin subunit 6 // 6p21.3 // 10471 /// ENST00000399112 | NM_014260 | −0.14 | 0.05 | 0.014 |
| 3031383 | REPIN1 | NM_013400 // REPIN1 // replication initiator 1 // 7q36.1 // 29803 /// NM_014374 | NM_013400 | −0.15 | 0.05 | 0.018 |
| 3754469 | ACACA | NM_198839 // ACACA // acetyl-Coenzyme A carboxylase alpha // 17q21 // 31 /// NM_ | NM_198839 | −0.15 | 0.05 | 0.010 |
| 3767480 | AXIN2 | NM_004655 // AXIN2 // axin 2 (conductin, axil) // 17q23-q24 // 8313 /// ENST0000 | NM_004655 | −0.15 | 0.05 | 0.013 |
| 2954506 | CRIP3 | NM_206922 // CRIP3 // cysteine-rich protein 3 // 6p21.1 // 401262 /// ENST000003 | NM_206922 | −0.15 | 0.06 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3845263 | ADAMTSL5 | NM_213604 // ADAMTSL5 // ADAMTS-like 5 // 19p13.3 // 339366 /// ENST00000330475 | NM_213604 | −0.15 | 0.06 | 0.016 |
| 2565143 | STARD7 | NM_020151 // STARD7 // StAR-related lipid transfer (START) domain containing 7 / | NM_020151 | −0.15 | 0.06 | 0.016 |
| 2321960 | PLEKHM2 | NM_015164 // PLEKHM2 // pleckstrin homology domain containing, family M (with RU | NM_015164 | −0.16 | 0.05 | 0.009 |
| 3829174 | GPATCH1 | NM_018025 // GPATCH1 // G patch domain containing 1 // 19q13.11 // 55094 /// ENS | NM_018025 | −0.16 | 0.03 | 0.001 |
| 2798586 | AHRR | NM_020731 // AHRR // aryl-hydrocarbon receptor repressor // 5p15.3 // 57491 /// | NM_020731 | −0.16 | 0.05 | 0.011 |
| 2362991 | CASQ1 | NM_001231 // CASQ1 // calsequestrin 1 (fast-twitch, skeletal muscle) // 1q21 // | NM_001231 | −0.16 | 0.06 | 0.015 |
| 3954525 | ZNF280B | NM_080764 // ZNF280B // zinc finger protein 280B // 22q11.22 // 140883 /// ENST0 | NM_080764 | −0.16 | 0.04 | 0.005 |
| 4020991 | ACTRT1 | NM_138289 // ACTRT1 // actin-related protein T1 // Xq25 // 139741 /// ENST000003 | NM_138289 | −0.16 | 0.05 | 0.007 |
| 3982975 | POU3F4 | NM_000307 // POU3F4 // POU class 3 homeobox 4 // Xq21.1 // 5456 /// ENST00000373 | NM_000307 | −0.16 | 0.05 | 0.013 |
| 3963990 | PKDREJ | NM_006071 // PKDREJ // polycystic kidney disease (polycystin) and REJ homolog (s | NM_006071 | −0.16 | 0.03 | 0.001 |
| 2436401 | JTB | NM_006694 // JTB // jumping translocation breakpoint // 1q21 // 10899 /// NM_002 | NM_006694 | −0.16 | 0.06 | 0.014 |
| 2759654 | ABLIM2 | NM_032432 // ABLIM2 // actin binding LIM protein family, member 2 // 4p16-p15 // | NM_032432 | −0.16 | 0.05 | 0.007 |
| 2437329 | CLK2 | NM_003993 // CLK2 // CDC-like kinase 2 // 1q21 // 1196 /// NR_002711 // CLK2P // | NM_003993 | −0.16 | 0.06 | 0.016 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3401119 | ITFG2 | NM_018463 // ITFG2 // integrin alpha FG-GAP repeat containing 2 // 12p13.33 // 5 | NM_018463 | −0.16 | 0.04 | 0.004 |
| 3599709 | GLCE | NM_015554 // GLCE // glucuronic acid epimerase // 15q23 // 26035 /// ENST0000026 | NM_015554 | −0.16 | 0.06 | 0.014 |
| 3882413 | C20orf114 | NM_033197 // C20orf114 // chromosome 20 open reading frame 114 // 20q11.21 // 92 | NM_033197 | −0.16 | 0.06 | 0.020 |
| 3712922 | C17orf39 | NM_024052 // C17orf39 // chromosome 17 open reading frame 39 // 17p11.2 // 79018 | NM_024052 | −0.16 | 0.06 | 0.017 |
| 2473376 | EFR3B | BC049384 // EFR3B // EFR3 homolog B (S. cerevisiae) // 2p23.3 // 22979 /// ENST0 | BC049384 | −0.17 | 0.05 | 0.009 |
| 2607262 | STK25 | NM_006374 // STK25 // serine/threonine kinase 25 (STE20 homolog, yeast) // 2q37. | NM_006374 | −0.17 | 0.06 | 0.015 |
| 3755580 | CACNB1 | NM_199247 // CACNB1 // calcium channel, voltage-dependent, beta 1 subunit // 17q | NM_199247 | −0.17 | 0.06 | 0.013 |
| 3402150 | NTF3 | NM_001102654 // NTF3 // neurotrophin 3 // 12p13 // 4908 /// NM_002527 // NTF3 // | NM_001102654 | −0.17 | 0.06 | 0.020 |
| 3014714 | ARPC1B | NM_005720 // ARPC1B // actin related protein 2/3 complex, subunit 1B, 41 kDa // 7 | NM_005720 | −0.17 | 0.06 | 0.020 |
| 3723071 | DBF4B | NM_145663 // DBF4B // DBF4 homolog B (S. cerevisiae) // 17q21.31|17q21 // 80174 | NM_145663 | −0.17 | 0.04 | 0.002 |
| 2371255 | SMG7 | NM_173156 // SMG7 // Smg-7 homolog, nonsense mediated mRNA decay factor (C. eleg | NM_173156 | −0.17 | 0.06 | 0.014 |
| 3217487 | ALG2 | NM_033087 // ALG2 // asparagine-linked glycosylation 2 homolog (S. cerevisiae, a | NM_033087 | −0.17 | 0.06 | 0.011 |
| 3352159 | LOC100130353 | AK130019 // LOC100130353 // hypothetical protein LOC100130353 // 11q23.3 // 1001 | AK130019 | −0.17 | 0.06 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3401259 | TEAD4 | NM_003213 // TEAD4 // TEA domain family member 4 // 12p13.3-p13.2 // 7004 /// NM | NM_003213 | −0.17 | 0.07 | 0.020 |
| 3114618 | RNF139 | NM_007218 // RNF139 // ring finger protein 139 // 8q24 // 11236 /// ENST00000303 | NM_007218 | −0.17 | 0.06 | 0.015 |
| 2991150 | TSPAN13 | NM_014399 // TSPAN13 // tetraspanin 13 // 7p21.1 // 27075 /// ENST00000262067 // | NM_014399 | −0.18 | 0.05 | 0.006 |
| 2875193 | P4HA2 | NM_004199 // P4HA2 // procollagen-proline, 2-oxoglutarate 4-dioxygenase (proline | NM_004199 | −0.18 | 0.05 | 0.007 |
| 4011743 | SLC7A3 | NM_032803 // SLC7A3 // solute carrier family 7 (cationic amino acid transporter, | NM_032803 | −0.18 | 0.06 | 0.009 |
| 3194015 | LCN9 | NM_001001676 // LCN9 // lipocalin 9 // 9q34.3 // 392399 /// ENST00000277526 // L | NM_001001676 | −0.18 | 0.06 | 0.011 |
| 3741040 | MNT | NM_020310 // MNT // MAX binding protein // 17p13.3 // 4335 /// ENST00000174618 / | NM_020310 | −0.18 | 0.04 | 0.003 |
| 3901851 | ABHD12 | NM_001042472 // ABHD12 // abhydrolase domain containing 12 // 20p11.21 // 26090 | NM_001042472 | −0.18 | 0.05 | 0.004 |
| 2324919 | EPHB2 | NM_017449 // EPHB2 // EPH receptor B2 // 1p36.1-p35 // 2048 /// NM_004442 // EPH | NM_017449 | −0.18 | 0.06 | 0.010 |
| 3185976 | COL27A1 | NM_032888 // COL27A1 // collagen, type XXVII, alpha 1 // 9q32 // 85301 /// ENST0 | NM_032888 | −0.18 | 0.06 | 0.009 |
| 2855434 | C5orf39 | NM_001014279 // C5orf39 // chromosome 5 open reading frame 39 // 5p12 // 389289 | NM_001014279 | −0.18 | 0.05 | 0.007 |
| 2334476 | MAST2 | NM_015112 // MAST2 // microtubule associated serine/threonine kinase 2 // 1p34.1 | NM_015112 | −0.18 | 0.02 | 0.000 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3962734 | TTLL1 | NM_001008572 // TTLL1 // tubulin tyrosine ligase-like family, member 1 // 22q13. | NM_001008572 | −0.18 | 0.03 | 0.001 |
| 4017538 | COL4A6 | NM_033641 // COL4A6 // collagen, type IV, alpha 6 // Xq22 // 1288 /// NM_001847 | NM_033641 | −0.18 | 0.03 | 0.000 |
| 3141589 | IL7 | NM_000880 // IL7 // interleukin 7 // 8q12-q13 // 3574 /// ENST00000263851 // IL7 | NM_000880 | −0.19 | 0.05 | 0.006 |
| 2436826 | KCNN3 | NM_002249 // KCNN3 // potassium intermediate/small conductance calcium-activated | NM_002249 | −0.19 | 0.06 | 0.008 |
| 3521174 | ABCC4 | NM_005845 // ABCC4 // ATP-binding cassette, sub-family C (CFTR/MRP), member 4 // | NM_005845 | −0.19 | 0.07 | 0.017 |
| 3768280 | C17orf58 | NM_181656 // C17orf58 // chromosome 17 open reading frame 58 // 17q24.2 // 28401 | NM_181656 | −0.19 | 0.07 | 0.017 |
| 2363784 | HSPA6 | NM_002155 // HSPA6 // heat shock 70 kDa protein 6 (HSP70B') // 1q23 // 3310 /// E | NM_002155 | −0.19 | 0.06 | 0.011 |
| 3928211 | GRIK1 | NM_175611 // GRIK1 // glutamate receptor, ionotropic, kainate 1 // 21q22.11 // 2 | NM_175611 | −0.19 | 0.06 | 0.011 |
| 2758978 | EVC2 | NM_147127 // EVC2 // Ellis van Creveld syndrome 2 (limbin) // 4p16.2-p16.1 // 13 | NM_147127 | −0.19 | 0.06 | 0.012 |
| 3740664 | C17orf91 | NM_032895 // C17orf91 // chromosome 17 open reading frame 91 // 17p13.3 // 84981 | NM_032895 | −0.19 | 0.07 | 0.015 |
| 2782267 | NEUROG2 | NM_024019 // NEUROG2 // neurogenin 2 // 4q25 // 63973 /// ENST00000313341 // NEU | NM_024019 | −0.20 | 0.06 | 0.010 |
| 3826542 | ZNF738 | BC034499 // ZNF738 // zinc finger protein 738 // 19p12 // 148203 /// AK291002 // | BC034499 | −0.20 | 0.05 | 0.003 |
| 3966000 | TYMP | NM_001113756 // TYMP // thymidine phosphorylase // 22q13\|22q13.33 // 1890 /// NM | NM_001113756 | −0.20 | 0.05 | 0.003 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3607447 | ABHD2 | NM_007011 // ABHD2 // abhydrolase domain containing 2 // 15q26.1 // 11057 /// NM | NM_007011 | −0.20 | 0.05 | 0.005 |
| 3236448 | SUV39H2 | NM_024670 // SUV39H2 // suppressor of variegation 3-9 homolog 2 (*Drosophila*) // | NM_024670 | −0.20 | 0.07 | 0.011 |
| 2528504 | SPEG | NM_005876 // SPEG // SPEG complex locus // 2q35 // 10290 /// ENST00000312358 // | NM_005876 | −0.20 | 0.06 | 0.009 |
| 2730746 | SLC4A4 | NM_001098484 // SLC4A4 // solute carrier family 4, sodium bicarbonate cotranspor | NM_001098484 | −0.20 | 0.06 | 0.007 |
| 2544662 | DNMT3A | NM_175629 // DNMT3A // DNA (cytosine-5-)-methyltransferase 3 alpha // 2p23 // 17 | NM_175629 | −0.20 | 0.06 | 0.007 |
| 2937625 | C6orf208 | BC101251 // C6orf208 // chromosome 6 open reading frame 208 // 6q27 // 80069 /// | BC101251 | −0.20 | 0.06 | 0.007 |
| 3233157 | UCN3 | NM_053049 // UCN3 // urocortin 3 (stresscopin) // 10p15.1 // 114131 /// ENST0000 | NM_053049 | −0.20 | 0.08 | 0.017 |
| 2548172 | FEZ2 | NM_001042548 // FEZ2 // fasciculation and elongation protein zeta 2 (zygin II) / | NM_001042548 | −0.21 | 0.03 | 0.000 |
| 3877809 | OTOR | NM_020157 // OTOR // otoraplin // 20p12.1-p11.23 // 56914 /// ENST00000246081 // | NM_020157 | −0.21 | 0.08 | 0.019 |
| 3839400 | C19orf63 | NM_175063 // C19orf63 // chromosome 19 open reading frame 63 // 19q13.33 // 2843 | NM_175063 | −0.21 | 0.04 | 0.002 |
| 3875108 | C20orf196 | AK292708 // C20orf196 // chromosome 20 open reading frame 196 // 20p12.3 // 1498 | AK292708 | −0.21 | 0.06 | 0.006 |
| 2970985 | TSPYL4 | NM_021648 // TSPYL4 // TSPY-like 4 // 6q22.1 // 23270 /// ENST00000368611 // TSP | NM_021648 | −0.21 | 0.07 | 0.011 |
| 3189580 | ZBTB43 | NM_014007 // ZBTB43 // zinc finger and BTB domain containing 43 // 9q33-q34 // 2 | NM_014007 | −0.21 | 0.08 | 0.017 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3407926 | CMAS | NM_018686 // CMAS // cytidine monophosphate N-acetylneuraminic acid synthetase / | NM_018686 | −0.21 | 0.03 | 0.000 |
| 3249886 | TET1 | NM_030625 // TET1 // tet oncogene 1 // 10q21 // 80312 /// ENST00000373644 // TET | NM_030625 | −0.21 | 0.06 | 0.007 |
| 3151970 | MTSS1 | NM_014751 // MTSS1 // metastasis suppressor 1 // 8p22 // 9788 /// ENST0000032506 | NM_014751 | −0.21 | 0.07 | 0.009 |
| 3937183 | DGCR8 | NM_022720 // DGCR8 // DiGeorge syndrome critical region gene 8 // 22q11.2 // 544 | NM_022720 | −0.21 | 0.06 | 0.008 |
| 3958253 | C22orf28 | BC016707 // C22orf28 // chromosome 22 open reading frame 28 // 22q12 // 51493 // | BC016707 | −0.22 | 0.08 | 0.019 |
| 3607503 | ABHD2 | NM_007011 // ABHD2 // abhydrolase domain containing 2 // 15q26.1 // 11057 /// NM | NM_007011 | −0.22 | 0.07 | 0.010 |
| 2799030 | SLC6A19 | NM_001003841 // SLC6A19 // solute carrier family 6 (neutral amino acid transport | NM_001003841 | −0.22 | 0.06 | 0.007 |
| 3870611 | LILRB3 | NM_001081450 // LILRB3 // leukocyte immunoglobulin-like receptor, subfamily B (w | NM_001081450 | −0.22 | 0.08 | 0.016 |
| 3857811 | C19orf12 | NM_031448 // C19orf12 // chromosome 19 open reading frame 12 // 19q12 // 83636 / | NM_031448 | −0.22 | 0.08 | 0.019 |
| 2500667 | FBLN7 | NM_153214 // FBLN7 // fibulin 7 // 2q13 // 129804 /// ENST00000331203 // FBLN7 / | NM_153214 | −0.22 | 0.08 | 0.019 |
| 3523156 | TMTC4 | NM_032813 // TMTC4 // transmembrane and tetratricopeptide repeat containing 4 // | NM_032813 | −0.22 | 0.07 | 0.010 |
| 2612371 | EAF1 | NM_033083 // EAF1 // ELL associated factor 1 // 3p24.3 // 85403 /// ENST00000396 | NM_033083 | −0.22 | 0.07 | 0.008 |
| 3988638 | LONRF3 | NM_001031855 // LONRF3 // LON peptidase N-terminal domain and ring finger 3 // X | NM_001031855 | −0.23 | 0.08 | 0.012 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3114240 | C8orf32 | BC008781 // C8orf32 // chromosome 8 open reading frame 32 // 8q24.13 // 55093 // | BC008781 | −0.23 | 0.08 | 0.016 |
| 2460368 | TTC13 | NM_024525 // TTC13 // tetratricopeptide repeat domain 13 // 1q42.2 // 79573 /// | NM_024525 | −0.23 | 0.08 | 0.014 |
| 2428425 | PPM1J | NM_005167 // PPM1J // protein phosphatase 1J (PP2C domain containing) // 1p13.2 | NM_005167 | −0.23 | 0.06 | 0.003 |
| 3194986 | LCN12 | NM_178536 // LCN12 // lipocalin 12 // 9q34.3 // 286256 /// ENST00000371633 // LC | NM_178536 | −0.23 | 0.06 | 0.004 |
| 3642875 | RAB11FIP3 | NM_014700 // RAB11FIP3 // RAB11 family interacting protein 3 (class II) // 16p13 | NM_014700 | −0.23 | 0.07 | 0.010 |
| 2532378 | CHRND | NM_000751 // CHRND // cholinergic receptor, nicotinic, delta // 2q33-q34 // 1144 | NM_000751 | −0.23 | 0.08 | 0.018 |
| 2995667 | ADCYAP1R1 | NM_001118 // ADCYAP1R1 // adenylate cyclase activating polypeptide 1 (pituitary) | NM_001118 | −0.23 | 0.05 | 0.002 |
| 3390641 | ARHGAP20 | NM_020809 // ARHGAP20 // Rho GTPase activating protein 20 // 11q22.3-q23.1 // 57 | NM_020809 | −0.23 | 0.05 | 0.003 |
| 2830465 | MYOT | NM_006790 // MYOT // myotilin // 5q31 // 9499 /// ENST00000239926 // MYOT // myo | NM_006790 | −0.23 | 0.07 | 0.007 |
| 2452069 | PIK3C2B | NM_002646 // PIK3C2B // phosphoinositide-3-kinase, class 2, beta polypeptide // | NM_002646 | −0.23 | 0.02 | 0.000 |
| 3744127 | HES7 | NM_032580 // HES7 // hairy and enhancer of split 7 (Drosophila) // 17p13.1 // 84 | NM_032580 | −0.23 | 0.09 | 0.019 |
| 3327057 | FLJ14213 | NM_024841 // FLJ14213 // protor-2 // 11p13-p12 // 79899 /// ENST00000378867 // F | NM_024841 | −0.23 | 0.07 | 0.007 |
| 2664332 | COLQ | NM_005677 // COLQ // collagen-like tail subunit (single strand of homotrimer) of | NM_005677 | −0.23 | 0.07 | 0.006 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3829160 | C19orf40 | NM_152266 // C19orf40 // chromosome 19 open reading frame 40 // 19q13.11 // 9144 | NM_152266 | −0.23 | 0.08 | 0.012 |
| 3708798 | SENP3 | NM_015670 // SENP3 // SUMO1/sentrin/SMT3 specific peptidase 3 // 17p13 // 26168 | NM_015670 | −0.23 | 0.06 | 0.005 |
| 2358700 | MGC29891 | NM_144618 // MGC29891 // hypothetical protein MGC29891 // 1q21.2 // 126626 /// E | NM_144618 | −0.23 | 0.09 | 0.019 |
| 2755111 | KLKB1 | NM_000892 // KLKB1 // kallikrein B, plasma (Fletcher factor) 1 // 4q34-q35 // 38 | NM_000892 | −0.24 | 0.08 | 0.012 |
| 2568968 | UXS1 | NM_025076 // UXS1 // UDP-glucuronate decarboxylase 1 // 2q12.2 // 80146 /// BC00 | NM_025076 | −0.24 | 0.08 | 0.011 |
| 2748923 | GUCY1B3 | NM_000857 // GUCY1B3 // guanylate cyclase 1, soluble, beta 3 // 4q31.3-q33 // 29 | NM_000857 | −0.24 | 0.07 | 0.007 |
| 3816509 | GADD45B | NM_015675 // GADD45B // growth arrest and DNA-damage-inducible, beta // 19p13.3 | NM_015675 | −0.24 | 0.09 | 0.016 |
| 3376410 | SLC22A24 | BC034394 // SLC22A24 // solute carrier family 22, member 24 // 11q12.3 // 283238 | BC034394 | −0.24 | 0.07 | 0.007 |
| 3286393 | ZNF32 | NM_006973 // ZNF32 // zinc finger protein 32 // 10q22-q25 // 7580 /// NM_0010053 | NM_006973 | −0.24 | 0.08 | 0.010 |
| 2540157 | ODC1 | NM_002539 // ODC1 // ornithine decarboxylase 1 // 2p25 // 4953 /// ENST000002341 | NM_002539 | −0.24 | 0.09 | 0.020 |
| 2994835 | CHN2 | NM_004067 // CHN2 // chimerin (chimaerin) 2 // 7p15.3 // 1124 /// NM_001039936 / | NM_004067 | −0.24 | 0.09 | 0.017 |
| 3603199 | IDH3A | NM_005530 // IDH3A // isocitrate dehydrogenase 3 (NAD+) alpha // 15q25.1-q25.2 / | NM_005530 | −0.24 | 0.05 | 0.001 |
| 3040454 | TWISTNB | NM_001002926 // TWISTNB // TWIST neighbor // 7p15.3 // 221830 /// ENST0000022256 | NM_001002926 | −0.24 | 0.09 | 0.017 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2497301 | TMEM182 | NM_144632 // TMEM182 // transmembrane protein 182 // 2q12.1 // 130827 /// ENST00 | NM_144632 | −0.24 | 0.07 | 0.007 |
| 3766716 | TEX2 | NM_018469 // TEX2 // testis expressed 2 // 17q23.3 // 55852 /// ENST00000258991 | NM_018469 | −0.25 | 0.07 | 0.007 |
| 3458819 | CYP27B1 | NM_000785 // CYP27B1 // cytochrome P450, family 27, subfamily B, polypeptide 1 / | NM_000785 | −0.25 | 0.08 | 0.009 |
| 3368940 | ABTB2 | NM_145804 // ABTB2 // ankyrin repeat and BTB (POZ) domain containing 2 // 11p13 | NM_145804 | −0.25 | 0.08 | 0.010 |
| 3298924 | MMRN2 | NM_024756 // MMRN2 // multimerin 2 // 10q23.2 // 79812 /// ENST00000372027 // MM | NM_024756 | −0.25 | 0.07 | 0.006 |
| 3529951 | KIAA1305 | NM_025081 // KIAA1305 // KIAA1305 // 14q12 // 57523 /// BC008219 // KIAA1305 // | NM_025081 | −0.25 | 0.08 | 0.011 |
| 3006572 | AUTS2 | NM_015570 // AUTS2 // autism susceptibility candidate 2 // 7q11.22 // 26053 /// | NM_015570 | −0.25 | 0.09 | 0.017 |
| 3025500 | BPGM | NM_001724 // BPGM // 2,3-bisphosphoglycerate mutase // 7q31-q34 // 669 /// NM_19 | NM_001724 | −0.25 | 0.10 | 0.018 |
| 2494709 | CNNM4 | NM_020184 // CNNM4 // cyclin M4 // 2p12-p11.2 // 26504 /// ENST00000377075 // CN | NM_020184 | −0.26 | 0.09 | 0.016 |
| 3329983 | PTPRJ | NM_002843 // PTPRJ // protein tyrosine phosphatase, receptor type, J // 11p11.2 | NM_002843 | −0.26 | 0.08 | 0.010 |
| 2769346 | LNX1 | NM_032622 // LNX1 // ligand of numb-protein X 1 // 4q12 // 84708 /// ENST0000030 | NM_032622 | −0.26 | 0.09 | 0.015 |
| 3867195 | FAM83E | NM_017708 // FAM83E // family with sequence similarity 83, member E // 19q13.32- | NM_017708 | −0.26 | 0.09 | 0.013 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3790529 | GRP | NM_002091 // GRP // gastrin-releasing peptide // 18q21.1-q21.32 // 2922 /// NM_0 | NM_002091 | −0.26 | 0.05 | 0.001 |
| 3987029 | TMEM164 | NM_032227 // TMEM164 // transmembrane protein 164 // Xq22.3 // 84187 /// ENST000 | NM_032227 | −0.26 | 0.10 | 0.018 |
| 3526454 | GRTP1 | NM_024719 // GRTP1 // growth hormone regulated TBC protein 1 // 13q34 // 79774 / | NM_024719 | −0.26 | 0.09 | 0.015 |
| 2438344 | GPATCH4 | NM_182679 // GPATCH4 // G patch domain containing 4 // 1q22 // 54865 /// NM_0155 | NM_182679 | −0.26 | 0.07 | 0.006 |
| 3132927 | NKX6-3 | NM_152568 // NKX6-3 // NK6 homeobox 3 // 8p11.21 // 157848 /// ENST00000343444 / | NM_152568 | −0.27 | 0.09 | 0.014 |
| 2672376 | TESSP2 | NM_182702 // TESSP2 // testis serine protease 2 // 3p21.31 // 339906 /// ENST000 | NM_182702 | −0.27 | 0.09 | 0.013 |
| 2730347 | C4orf35 | NM_033122 // C4orf35 // chromosome 4 open reading frame 35 // 4q13.3 // 85438 // | NM_033122 | −0.27 | 0.10 | 0.019 |
| 3921068 | ETS2 | NM_005239 // ETS2 // v-ets erythroblastosis virus E26 oncogene homolog 2 (avian) | NM_005239 | −0.27 | 0.03 | 0.000 |
| 2532894 | DGKD | NM_152879 // DGKD // diacylglycerol kinase, delta 130 kDa // 2q37.1 // 8527 /// N | NM_152879 | −0.27 | 0.07 | 0.003 |
| 4018454 | AMOT | NM_133265 // AMOT // angiomotin // Xq23 // 154796 /// NM_001113490 // AMOT // an | NM_133265 | −0.27 | 0.09 | 0.012 |
| 3070507 | RNF148 | NM_198085 // RNF148 // ring finger protein 148 // 7q31.33 // 378925 /// BC029264 | NM_198085 | −0.27 | 0.10 | 0.017 |
| 3832256 | SPINT2 | NM_021102 // SPINT2 // serine peptidase inhibitor, Kunitz type, 2 // 19q13.1 // | NM_021102 | −0.27 | 0.10 | 0.017 |
| 3371225 | CHST1 | NM_003654 // CHST1 // carbohydrate (keratan sulfate Gal-6) sulfotransferase 1 // | NM_003654 | −0.27 | 0.07 | 0.005 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3870494 | TFPT | NM_013342 // TFPT // TCF3 (E2A) fusion partner (in childhood Leukemia) // 19q13 | NM_013342 | −0.27 | 0.09 | 0.010 |
| 3863811 | PSG9 | NM_002784 // PSG9 // pregnancy specific beta-1-glycoprotein 9 // 19q13.2 // 5678 | NM_002784 | −0.28 | 0.09 | 0.011 |
| 3160175 | VLDLR | NM_003383 // VLDLR // very low density lipoprotein receptor // 9p24 // 7436 /// | NM_003383 | −0.28 | 0.08 | 0.007 |
| 2794704 | ASB5 | NM_080874 // ASB5 // ankyrin repeat and SOCS box-containing 5 // 4q34.2 // 14045 | NM_080874 | −0.28 | 0.11 | 0.019 |
| 3908901 | KCNB1 | NM_004975 // KCNB1 // potassium voltage-gated channel, Shab-related subfamily, m | NM_004975 | −0.28 | 0.09 | 0.009 |
| 3390852 | FLJ45803 | NM_207429 // FLJ45803 // FLJ45803 protein // 11q23.1 // 399948 /// ENST000003554 | NM_207429 | −0.28 | 0.10 | 0.015 |
| 2600689 | EPHA4 | NM_004438 // EPHA4 // EPH receptor A4 // 2q36.1 // 2043 /// ENST00000281821 // E | NM_004438 | −0.29 | 0.07 | 0.003 |
| 3469597 | NUAK1 | NM_014840 // NUAK1 // NUAK family, SNF1-like kinase, 1 // 12q23.3 // 9891 /// EN | NM_014840 | −0.29 | 0.09 | 0.009 |
| 3607232 | ISG20L1 | NM_022767 // ISG20L1 // interferon stimulated exonuclease gene 20 kDa-like 1 // 1 | NM_022767 | −0.29 | 0.10 | 0.015 |
| 2358426 | ADAMTSL4 | AK023606 // ADAMTSL4 // ADAMTS-like 4 // 1q21.2 // 54507 | AK023606 | −0.29 | 0.11 | 0.016 |
| 3853609 | CYP4F2 | NM_001082 // CYP4F2 // cytochrome P450, family 4, subfamily F, polypeptide 2 // | NM_001082 | −0.29 | 0.11 | 0.016 |
| 2936971 | KIF25 | NM_030615 // KIF25 // kinesin family member 25 // 6q27 // 3834 /// NM_005355 | NM_030615 | −0.30 | 0.09 | 0.008 |
| 2997272 | EEPD1 | NM_030636 // EEPD1 // endonuclease/exonuclease/ phosphatase family domain contain | NM_030636 | −0.30 | 0.09 | 0.010 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3961253 | RPS19BP1 | NM_194326 // RPS19BP1 // ribosomal protein S19 binding protein 1 // 22q13.1 // 9 | NM_194326 | −0.30 | 0.10 | 0.013 |
| 3082373 | VIPR2 | NM_003382 // VIPR2 // vasoactive intestinal peptide receptor 2 // 7q36.3 // 7434 | NM_003382 | −0.30 | 0.10 | 0.011 |
| 2340961 | IL12RB2 | NM_001559 // IL12RB2 // interleukin 12 receptor, beta 2 // 1p31.3-p31.2 // 3595 | NM_001559 | −0.30 | 0.08 | 0.005 |
| 2736462 | BMPR1B | NM_001203 // BMPR1B // bone morphogenetic protein receptor, type IB // 4q22-q24 | NM_001203 | −0.30 | 0.08 | 0.004 |
| 3774504 | — | — | | −0.30 | 0.11 | 0.016 |
| 3395958 | OR8B4 | NM_001005196 // OR8B4 // olfactory receptor, family 8, subfamily B, member 4 // | NM_001005196 | −0.30 | 0.11 | 0.018 |
| 2806231 | BXDC2 | NM_018321 // BXDC2 // brix domain containing 2 // 5p13.2 // 55299 /// ENST000003 | NM_018321 | −0.31 | 0.10 | 0.013 |
| 2396858 | NPPB | NM_002521 // NPPB // natriuretic peptide precursor B // 1p36.2 // 4879 /// ENST0 | NM_002521 | −0.31 | 0.11 | 0.016 |
| 3233322 | C10orf18 | NM_017782 // C10orf18 // chromosome 10 open reading frame 18 // 10p15.1 // 54906 | NM_017782 | −0.31 | 0.06 | 0.001 |
| 2439101 | FCRL1 | NM_052938 // FCRL1 // Fc receptor-like 1 // 1q21-q22 // 115350 /// ENST000003681 | NM_052938 | −0.31 | 0.06 | 0.001 |
| 2413907 | DHCR24 | NM_014762 // DHCR24 // 24-dehydrocholesterol reductase // 1p33-p31.1 // 1718 /// | NM_014762 | −0.31 | 0.11 | 0.014 |
| 3231186 | C9orf37 | NM_032937 // C9orf37 // chromosome 9 open reading frame 37 // 9q34.3 // 85026 // | NM_032937 | −0.31 | 0.09 | 0.008 |
| 2669955 | XIRP1 | NM_194293 // XIRP1 // xin actin-binding repeat containing 1 // 3p22.2 // 165904 | NM_194293 | −0.32 | 0.11 | 0.013 |
| 3345222 | AMOTL1 | NM_130847 // AMOTL1 // angiomotin like 1 // 11q14.3 // 154810 /// ENST0000031782 | NM_130847 | −0.32 | 0.11 | 0.012 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2573326 | FLJ14816 | BC112205 // FLJ14816 // hypothetical protein FLJ14816 // 2q14.2 // 84931 /// BC1 | BC112205 | −0.32 | 0.11 | 0.016 |
| 3349437 | UNQ2550 | AY358815 // UNQ2550 // SFVP2550 // 11q23.1 // 100130653 | AY358815 | −0.32 | 0.09 | 0.005 |
| 3951117 | ACR | NM_001097 // ACR // acrosin // 22q13-qter\|22q13.33 // 49 /// ENST00000216139 // | NM_001097 | −0.32 | 0.12 | 0.017 |
| 2489140 | — | — | — | −0.32 | 0.07 | 0.002 |
| 2562115 | LSM3 | CR457185 // LSM3 // LSM3 homolog, U6 small nuclear RNA associated (*S. cerevisiae* | CR457185 | −0.32 | 0.11 | 0.011 |
| 3572975 | NGB | NM_021257 // NGB // neuroglobin // 14q24.3 // 58157 /// ENST00000298352 // NGB / | NM_021257 | −0.33 | 0.09 | 0.004 |
| 2439350 | OR6N1 | NM_001005185 // OR6N1 // olfactory receptor, family 6, subfamily N, member 1 // | NM_001005185 | −0.33 | 0.10 | 0.009 |
| 3590275 | CHAC1 | NM_024111 // CHAC1 // ChaC, cation transport regulator homolog 1 (*E. coli*) // 15 | NM_024111 | −0.33 | 0.12 | 0.014 |
| 2397898 | HSPB7 | NM_014424 // HSPB7 // heat shock 27 kDa protein family, member 7 (cardiovascular) | NM_014424 | −0.33 | 0.12 | 0.015 |
| 2364677 | PBX1 | NM_002585 // PBX1 // pre-B-cell leukemia homeobox 1 // 1q23 // 5087 /// ENST0000 | NM_002585 | −0.34 | 0.07 | 0.001 |
| 2474409 | DNAJC5G | NM_173650 // DNAJC5G // DnaJ (Hsp40) homolog, subfamily C, member 5 gamma // 2p2 | NM_173650 | −0.34 | 0.09 | 0.004 |
| 3581373 | — | — | — | −0.34 | 0.12 | 0.014 |
| 3508330 | HSPH1 | NM_006644 // HSPH1 // heat shock 105 kDa/110 kDa protein 1 // 13q12.3 // 10808 /// | NM_006644 | −0.34 | 0.13 | 0.019 |
| 3751164 | DHRS13 | NM_144683 // DHRS13 // dehydrogenase/reductase (SDR family) member 13 // 17q11.2 | NM_144683 | −0.35 | 0.10 | 0.006 |
| 2908179 | VEGFA | NM_001025366 // VEGFA // vascular endothelial growth factor A // 6p12 // 7422 // | NM_001025366 | −0.35 | 0.13 | 0.016 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3962448 | dJ222E13.2 | NR_002184 // dJ222E13.2 // similar to CGI-96 // 22q13.2 // 91695 /// BC073834 // | NR_002184 | −0.35 | 0.12 | 0.014 |
| 3747638 | LOC201164 | BC031263 // LOC201164 // similar to CG12314 gene product // 17p11.2 // 201164 // | BC031263 | −0.35 | 0.09 | 0.004 |
| 2821981 | TMEM157 | NM_198507 // TMEM157 // transmembrane protein 157 // 5q21.1 // 345757 /// ENST00 | NM_198507 | −0.35 | 0.12 | 0.015 |
| 3123675 | PPP1R3B | NM_024607 // PPP1R3B // protein phosphatase 1, regulatory (inhibitor) subunit 3B | NM_024607 | −0.35 | 0.12 | 0.014 |
| 2656837 | ST6GAL1 | NM_173216 // ST6GAL1 // ST6 beta-galactosamide alpha-2,6-sialyltranferase 1 // 3 | NM_173216 | −0.35 | 0.13 | 0.016 |
| 3746574 | PMP22 | NM_000304 // PMP22 // peripheral myelin protein 22 // 17p12-p11.2 // 5376 /// NM | NM_000304 | −0.36 | 0.09 | 0.004 |
| 2771342 | EPHA5 | NM_004439 // EPHA5 // EPH receptor A5 // 4q13.1 // 2044 /// NM_182472 // EPHA5 / | NM_004439 | −0.36 | 0.09 | 0.003 |
| 2888674 | MXD3 | NM_031300 // MXD3 // MAX dimerization protein 3 // 5q35.3 // 83463 /// ENST00000 | NM_031300 | −0.36 | 0.12 | 0.012 |
| 2353477 | ATP1A1 | NM_000701 // ATP1A1 // ATPase, Na+/K+ transporting, alpha 1 polypeptide // 1p21 | NM_000701 | −0.36 | 0.11 | 0.007 |
| 3956984 | ZMAT5 | NM_019103 // ZMAT5 // zinc finger, matrin type 5 // 22cen-q12.3 // 55954 /// NM_ | NM_019103 | −0.36 | 0.11 | 0.009 |
| 2551651 | ATP6V1E2 | NM_080653 // ATP6V1E2 // ATPase, H+ transporting, lysosomal 31 kDa, V1 subunit E2 | NM_080653 | −0.37 | 0.13 | 0.017 |
| 3578069 | C14orf139 | BC008299 // C14orf139 // chromosome 14 open reading frame 139 // 14q32.13 // 796 | BC008299 | −0.37 | 0.13 | 0.016 |
| 2428501 | SLC16A1 | NM_003051 // SLC16A1 // solute carrier family 16, member 1 (monocarboxylic acid | NM_003051 | −0.37 | 0.14 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3061621 | TFPI2 | NM_006528 // TFPI2 // tissue factor pathway inhibitor 2 // 7q22 // 7980 /// ENST | NM_006528 | −0.37 | 0.09 | 0.002 |
| 3705516 | LOC100131454 | AF229804 // LOC100131454 // similar to hCG1646635 // 17p13.3 // 100131454 /// EN | AF229804 | −0.38 | 0.11 | 0.008 |
| 3306299 | XPNPEP1 | NM_020383 // XPNPEP1 // X-prolyl aminopeptidase (aminopeptidase P) 1, soluble // | NM_020383 | −0.38 | 0.14 | 0.018 |
| 2763550 | PPARGC1A | NM_013261 // PPARGC1A // peroxisome proliferator-activated receptor gamma, coact | NM_013261 | −0.38 | 0.13 | 0.012 |
| 2769063 | USP46 | NM_022832 // USP46 // ubiquitin specific peptidase 46 // 4q12 // 64854 /// ENST0 | NM_022832 | −0.38 | 0.13 | 0.013 |
| 3806459 | ST8SIA5 | NM_013305 // ST8SIA5 // ST8 alpha-N-acetyl-neuraminide alpha-2,8-sialyltransfera | NM_013305 | −0.38 | 0.10 | 0.004 |
| 3190151 | SLC25A25 | NM_001006641 // SLC25A25 // solute carrier family 25 (mitochondrial carrier; pho | NM_001006641 | −0.39 | 0.09 | 0.003 |
| 2489172 | MTHFD2 | NM_001040409 // MTHFD2 // methylenetetrahydrofolate dehydrogenase (NADP+ depende | NM_001040409 | −0.39 | 0.05 | 0.000 |
| 2952065 | PPIL1 | NM_016059 // PPIL1 // peptidylprolyl isomerase (cyclophilin)-like 1 // 6p21.1 // | NM_016059 | −0.39 | 0.10 | 0.005 |
| 3382015 | CHRDL2 | NM_015424 // CHRDL2 // chordin-like 2 // 11q14 // 25884 /// ENST00000263671 // C | NM_015424 | −0.39 | 0.10 | 0.003 |
| 2711139 | ATP13A5 | NM_198505 // ATP13A5 // ATPase type 13A5 // 3q29 // 344905 /// ENST00000342358 / | NM_198505 | −0.40 | 0.11 | 0.005 |
| 2633917 | RG9MTD1 | NM_017819 // RG9MTD1 // RNA (guanine-9-) methyltransferase domain containing 1 / | NM_017819 | −0.41 | 0.14 | 0.013 |
| 2974671 | C6orf192 | NM_052831 // C6orf192 // chromosome 6 open reading frame 192 // 6q22.3-q23.3 // | NM_052831 | −0.41 | 0.15 | 0.018 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 2982270 | FLJ27255 | ENST00000355047 // FLJ27255 // hypothetical LOC401281 // 6q25.3 // 401281 /// AK | ENST00000355047 | −0.41 | 0.12 | 0.007 |
| 2778273 | PGDS | NM_014485 // PGDS // prostaglandin D2 synthase, hematopoietic // 4q22.3 // 27306 | NM_014485 | −0.41 | 0.08 | 0.001 |
| 3005332 | RCP9 | NM_014478 // RCP9 // calcitonin gene-related peptide-receptor component protein | NM_014478 | −0.41 | 0.14 | 0.013 |
| 2650393 | PPM1L | NM_139245 // PPM1L // protein phosphatase 1 (formerly 2C)-like // 3q26.1 // 1517 | NM_139245 | −0.42 | 0.12 | 0.006 |
| 3463056 | CSRP2 | NM_001321 // CSRP2 // cysteine and glycine-rich protein 2 // 12q21.1 // 1466 /// | NM_001321 | −0.42 | 0.11 | 0.005 |
| 2459405 | — | — | — | −0.43 | 0.10 | 0.003 |
| 2570238 | NPHP1 | NM_000272 // NPHP1 // nephronophthisis 1 (juvenile) // 2q13 // 4867 /// NM_20718 | NM_000272 | −0.43 | 0.06 | 0.000 |
| 2840616 | NPM1 | NM_002520 // NPM1 // nucleophosmin (nucleolar phosphoprotein B23, numatrin) // 5 | NM_002520 | −0.43 | 0.14 | 0.010 |
| 3601051 | NEO1 | NM_002499 // NEO1 // neogenin homolog 1 (chicken) // 15q22.3-q23 // 4756 /// ENS | NM_002499 | −0.43 | 0.09 | 0.002 |
| 3936515 | TUBA8 | NM_018943 // TUBA8 // tubulin, alpha 8 // 22q11.1 // 51807 /// ENST00000330423 / | NM_018943 | −0.43 | 0.10 | 0.002 |
| 2725013 | UCHL1 | NM_004181 // UCHL1 // ubiquitin carboxyl-terminal esterase L1 (ubiquitin thioles | NM_004181 | −0.44 | 0.11 | 0.004 |
| 2380590 | TGFB2 | NM_003238 // TGFB2 // transforming growth factor, beta 2 // 1q41 // 7042 /// ENS | NM_003238 | −0.44 | 0.16 | 0.017 |
| 2496382 | NPAS2 | NM_002518 // NPAS2 // neuronal PAS domain protein 2 // 2q11.2 // 4862 /// ENST00 | NM_002518 | −0.46 | 0.10 | 0.002 |
| 3841574 | LILRB1 | NM_006669 // LILRB1 // leukocyte immunoglobulin-like receptor, subfamily B (with | NM_006669 | −0.46 | 0.16 | 0.015 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3726960 | NME2 | NM_001018137 // NME2 // non-metastatic cells 2, protein (NM23B) expressed in // | NM_001018137 | −0.47 | 0.16 | 0.013 |
| 2649367 | PTX3 | NM_002852 // PTX3 // pentraxin-related gene, rapidly induced by IL-1 beta // 3q2 | NM_002852 | −0.47 | 0.11 | 0.002 |
| 2909483 | GPR111 | NM_153839 // GPR111 // G protein-coupled receptor 111 // 6p12.3 // 222611 /// EN | NM_153839 | −0.47 | 0.13 | 0.006 |
| 2881950 | SLC36A2 | NM_181776 // SLC36A2 // solute carrier family 36 (proton/amino acid symporter), | NM_181776 | −0.48 | 0.12 | 0.004 |
| 3441190 | FGF6 | NM_020996 // FGF6 // fibroblast growth factor 6 // 12p13 // 2251 /// ENST0000022 | NM_020996 | −0.48 | 0.12 | 0.004 |
| 3028911 | C7orf34 | NM_178829 // C7orf34 // chromosome 7 open reading frame 34 // 7q34 // 135927 /// | NM_178829 | −0.49 | 0.18 | 0.019 |
| 2830861 | EGR1 | NM_001964 // EGR1 // early growth response 1 // 5q31.1 // 1958 /// ENST000002399 | NM_001964 | −0.49 | 0.19 | 0.020 |
| 3323891 | GAS2 | NM_177553 // GAS2 // growth arrest-specific 2 // 11p14.3-p15.2 // 2620 /// NM_00 | NM_177553 | −0.49 | 0.16 | 0.011 |
| 2497252 | SLC9A2 | NM_003048 // SLC9A2 // solute carrier family 9 (sodium/hydrogen exchanger), memb | NM_003048 | −0.50 | 0.11 | 0.002 |
| 3018484 | GPR22 | NM_005295 // GPR22 // G protein-coupled receptor 22 // 7q22-q31.1 // 2845 /// EN | NM_005295 | −0.51 | 0.15 | 0.008 |
| 2712632 | TFRC | NM_003234 // TFRC // transferrin receptor (p90, CD71) // 3829 // 7037 /// ENST00 | NM_003234 | −0.51 | 0.12 | 0.003 |
| 3214451 | NFIL3 | NM_005384 // NFIL3 // nuclear factor, interleukin 3 regulated // 9q22 // 4783 // | NM_005384 | −0.53 | 0.14 | 0.004 |
| 2435981 | S100A12 | NM_005621 // S100A12 // S100 calcium binding protein A12 // 1q21 // 6283 /// ENS | NM_005621 | −0.54 | 0.19 | 0.014 |
| 3320675 | RIG | U32331 // RIG // regulated in glioma // 11p15.1 // 10530 | U32331 | −0.54 | 0.10 | 0.001 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3290746 | SLC16A9 | NM_194298 // SLC16A9 // solute carrier family 16, member 9 (monocarboxylic acid | NM_194298 | −0.54 | 0.15 | 0.006 |
| 3055703 | NSUN5C | NM_032158 // NSUN5C // NOL1/NOP2/Sun domain family, member 5C // 7q11.23 // 2602 | NM_032158 | −0.57 | 0.17 | 0.008 |
| 3265494 | TRUB1 | NM_139169 // TRUB1 // TruB pseudouridine (psi) synthase homolog 1 (*E. coli*) // 1 | NM_139169 | −0.57 | 0.17 | 0.008 |
| 3374213 | OR1S2 | NM_001004459 // OR1S2 // olfactory receptor, family 1, subfamily S, member 2 // | NM_001004459 | −0.58 | 0.20 | 0.013 |
| 3318253 | OR51L1 | NM_001004755 // OR51L1 // olfactory receptor, family 51, subfamily L, member 1 / | NM_001004755 | −0.59 | 0.18 | 0.009 |
| 3294280 | DNAJC9 | NM_015190 // DNAJC9 // DnaJ (Hsp40) homolog, subfamily C, member 9 // 10q22.2 // | NM_015190 | −0.59 | 0.22 | 0.018 |
| 2899095 | HIST1H4A | NM_003538 // HIST1H4A // histone cluster 1, H4a // 6p21.3 // 8359 /// ENST000003 | NM_003538 | −0.60 | 0.16 | 0.005 |
| 2378068 | G0S2 | NM_015714 // G0S2 // G0/G1switch 2 // 1q32.2-q41 // 50486 /// ENST00000367029 // | NM_015714 | −0.63 | 0.22 | 0.016 |
| 3737677 | LOC100129503 | AF218021 // LOC100129503 // hypothetical protein LOC100129503 // 17q25.3 // 1001 | AF218021 | −0.64 | 0.19 | 0.007 |
| 3300115 | PPP1R3C | NM_005398 // PPP1R3C // protein phosphatase 1, regulatory (inhibitor) subunit 3C | NM_005398 | −0.69 | 0.26 | 0.020 |
| 3279058 | ACBD7 | NM_001039844 // ACBD7 // acyl-Coenzyme A binding domain containing 7 // 10p13 // | NM_001039844 | −0.69 | 0.13 | 0.001 |
| 4031156 | RPS4Y2 | NM_001039567 // RPS4Y2 // ribosomal protein S4, Y-linked 2 // Yq11.223 // 140032 | NM_001039567 | −0.71 | 0.17 | 0.003 |
| 2979246 | RAET1L | NM_130900 // RAET1L // retinoic acid early transcript 1L // 6q25.1 // 154064 /// | NM_130900 | −0.75 | 0.26 | 0.013 |

TABLE 1-continued

FASTING-RESPONSIVE HUMAN MRNAS.

| Affymetrix ID | mRNA | Gene Assignment | Accession No. | Change (Fasting-Fed) | SEM | P |
|---|---|---|---|---|---|---|
| 3321150 | ARNTL | NM_001178 // ARNTL // aryl hydrocarbon receptor nuclear translocator-like // 11p | NM_001178 | −0.80 | 0.20 | 0.004 |
| 3862873 | CYP2A6 | NM_000762 // CYP2A6 // cytochrome P450, family 2, subfamily A, polypeptide 6 // | NM_000762 | −1.12 | 0.34 | 0.009 |

4. Identification of Ursolic Acid as an Inhibitor of Fasting-Induced Muscle Atrophy.

Figure 4:
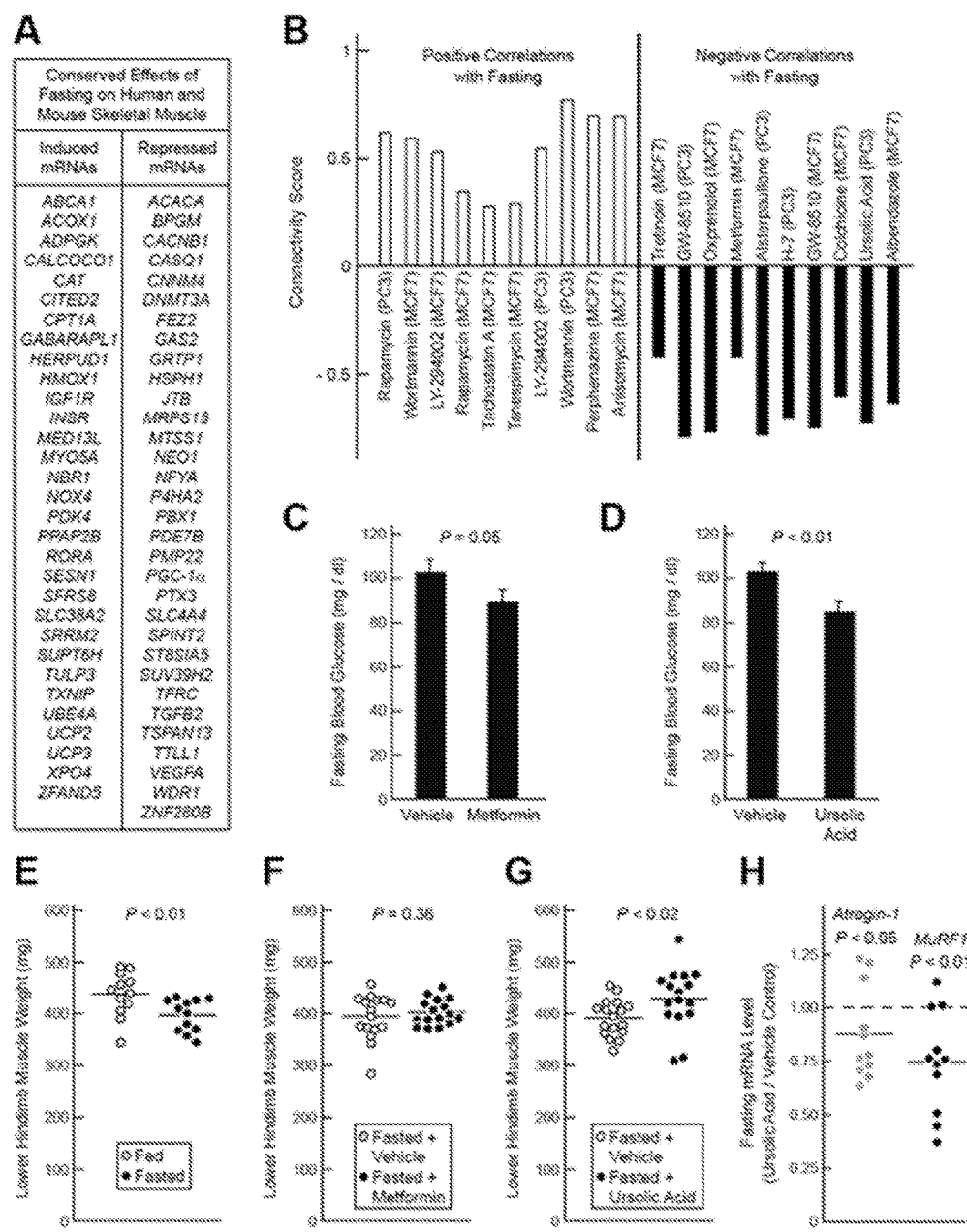
FIG. 4 shows representative data on the identification of ursolic acid as an inhibitor of fasting-induced skeletal muscle atrophy.

The Connectivity Map describes the effects of >1300 bioactive small molecules on global mRNA expression in several cultured cell lines, and contains search algorithms that permit comparisons between compound-specific mRNA expression signatures and mRNA expression signatures of interest (Lamb J, et al. (2006) *Science* (New York, N.Y. 313(5795):1929-1935). It was hypothesized herein that querying the Connectivity Map with the mRNA expression signature of fasting (atrophy signature-1) would identify inhibitors of atrophy-associated gene expression and thus, potential inhibitors of muscle atrophy. It was also reasoned herein that increasing the specificity of the query would enhance the output. To this end, as described herein, an evolutionarily conserved mRNA expression signature of fasting was discovered by comparing the effect of fasting on human skeletal muscle to the effect of a 24 h fast on mouse skeletal muscle. The mouse studies were described previously (Ebert S M, et al. (2010) *Molecular endocrinology* 24(4):790-799). Altogether, 35 mRNAs that were increased by fasting and 40 mRNAs that were decreased by fasting were identified in both human and mouse skeletal muscle (Table 2; the data in column labeled "Change" show mean changes in $\log_2$ hybridization signals between fasting and fed states for the species indicated, [Mean $\log_2$ mRNA levels for fasted] minus [Mean $\log_2$ mRNA levels in unfasted]; P-values were determined with paired t-tests). The data shown in Table 2 includes all mRNAs whose levels were increased by fasting in human muscle ($P \leq 0.02$) and in mouse muscle ($P \leq 0.05$), and all mRNAs whose levels were decreased by fasting in human muscle ($P \leq 0.02$) and in mouse muscle ($P \leq 0.05$). Of the mRNAs shown in Table 2, 63 mRNAs were represented on the HG-U133A arrays used in the Connectivity Map (FIG. 4A). These mRNAs (31 increased by fasting and 32 decreased by fasting) were used to query the Connectivity Map for candidate small molecule inhibitors of muscle atrophy.

TABLE 2

FASTING-REGULATED MRNAS COMMON TO HUMAN AND MOUSE SKELETAL MUSCLE.

| mRNA | Protein | Human Mean Log2 Change (Fasting - Fed) | P | Mouse Mean Log2 Change (Fasting - Fed) | P |
|---|---|---|---|---|---|
| PDK4 | pyruvate dehydrogenase kinase, isozyme 4 | 2.15 | 0.000 | 1.91 | 0.000 |
| TXNIP | thioredoxin interacting protein | 0.85 | 0.004 | 0.60 | 0.038 |
| FBXO32 | F-box protein 32 | 0.82 | 0.002 | 2.13 | 0.000 |
| SLC38A2 | solute carrier family 38, member 2 | 0.62 | 0.001 | 0.33 | 0.036 |
| UCP3 | uncoupling protein 3 (mitochondrial, proton carrier) | 0.59 | 0.000 | 1.02 | 0.001 |
| ZFAND5 | zinc finger, AN1-type domain 5 | 0.51 | 0.005 | 0.57 | 0.001 |
| HMOX1 | heme oxygenase (decycling) 1 | 0.46 | 0.006 | 0.17 | 0.035 |
| SESN1 | sestrin 1 | 0.46 | 0.004 | 1.51 | 0.001 |
| GABARAPL1 | GABA(A) receptor-associated protein like 1 | 0.39 | 0.004 | 1.18 | 0.000 |
| CAT | catalase | 0.39 | 0.003 | 0.85 | 0.001 |
| CITED2 | Cbp/p300-interacting transactivator, with Glu/Asp-rich carboxy-terminal domain | 0.37 | 0.005 | 0.29 | 0.010 |

TABLE 2-continued

FASTING-REGULATED MRNAS COMMON TO HUMAN AND MOUSE SKELETAL MUSCLE.

| mRNA | Protein | Human Mean Log2 Change (Fasting - Fed) | P | Mouse Mean Log2 Change (Fasting - Fed) | P |
|---|---|---|---|---|---|
| ABCA1 | ATP-binding cassette, sub-family A (ABC1), member 1 | 0.37 | 0.016 | 0.26 | 0.018 |
| FBXL20 | F-box and leucine-rich repeat protein 20 | 0.35 | 0.002 | 0.46 | 0.001 |
| XPO4 | exportin 4 | 0.31 | 0.009 | 0.22 | 0.022 |
| HERPUD1 | homocysteine-inducible, endoplasmic reticulum stress-inducible, ubiquitin-like domain 1 | 0.29 | 0.003 | 0.27 | 0.029 |
| ACOX1 | acyl-Coenzyme A oxidase 1, palmitoyl | 0.29 | 0.013 | 0.53 | 0.006 |
| NOX4 | NADPH oxidase 4 | 0.28 | 0.002 | 0.41 | 0.018 |
| UBE4A | ubiquitination factor E4A (UFD2 homolog, yeast) | 0.27 | 0.004 | 1.08 | 0.010 |
| INSR | insulin receptor | 0.24 | 0.014 | 0.58 | 0.003 |
| IGF1R | insulin-like growth factor 1 receptor | 0.23 | 0.013 | 0.40 | 0.001 |
| PANK1 | pantothenate kinase 1 | 0.21 | 0.007 | 0.78 | 0.000 |
| NBR1 | neighbor of BRCA1 gene 1 | 0.21 | 0.017 | 0.39 | 0.009 |
| RORA | RAR-related orphan receptor A | 0.21 | 0.006 | 0.39 | 0.006 |
| TMEM71 | transmembrane protein 71 | 0.21 | 0.009 | 0.40 | 0.008 |
| CPT1A | carnitine palmitoyltransferase 1A (liver) | 0.21 | 0.001 | 0.21 | 0.020 |
| UCP2 | uncoupling protein 2 (mitochondrial, proton carrier) | 0.20 | 0.005 | 0.33 | 0.024 |
| TULP3 | tubby like protein 3 | 0.19 | 0.008 | 0.22 | 0.008 |
| MED13L | mediator complex subunit 13-like | 0.18 | 0.000 | 0.23 | 0.011 |
| CALCOCO1 | calcium binding and coiled coil domain 1 | 0.16 | 0.010 | 0.31 | 0.028 |
| MYO5A | myosin VA (heavy chain 12, myoxin) | 0.14 | 0.006 | 0.36 | 0.012 |
| PPAP2B | phosphatidic acid phosphatase type 2B | 0.13 | 0.007 | 0.09 | 0.029 |
| SRRM2 | serine/arginine repetitive matrix 2 | 0.13 | 0.007 | 0.24 | 0.040 |
| ADPGK | ADP-dependent glucokinase | 0.13 | 0.007 | 0.16 | 0.009 |
| SUPT6H | suppressor of Ty 6 homolog (S. cerevisiae) | 0.11 | 0.005 | 0.26 | 0.036 |
| SFRS8 | splicing factor, arginine/serine-rich 8 | 0.08 | 0.016 | 0.13 | 0.011 |
| NFYA | nuclear transcription factor Y, alpha | −0.07 | 0.011 | −0.31 | 0.045 |
| MRPS15 | mitochondrial ribosomal protein S15 | −0.11 | 0.003 | −0.25 | 0.001 |
| PDE7B | phosphodiesterase 7B | −0.12 | 0.013 | −0.51 | 0.011 |
| WDR1 | WD repeat domain 1 | −0.14 | 0.019 | −0.21 | 0.047 |
| ACACA | acetyl-Coenzyme A carboxylase alpha | −0.15 | 0.010 | −0.22 | 0.041 |
| AXIN2 | axin 2 (conductin, axil) | −0.15 | 0.013 | −0.12 | 0.046 |
| CASQ1 | calsequestrin 1 (fast-twitch, skeletal muscle) | −0.16 | 0.015 | −0.26 | 0.015 |
| ZNF280B | zinc finger protein 280B | −0.16 | 0.005 | −0.34 | 0.046 |
| JTB | jumping translocation breakpoint | −0.16 | 0.014 | −0.42 | 0.030 |
| CACNB1 | calcium channel, voltage-dependent, beta 1 subunit | −0.17 | 0.013 | −0.43 | 0.003 |
| ALG2 | asparagine-linked glycosylation 2 homolog | −0.17 | 0.011 | −0.39 | 0.019 |
| TSPAN13 | tetraspanin 13 | −0.18 | 0.006 | −0.30 | 0.028 |
| P4HA2 | procollagen-proline, 2-oxoglutarate 4-dioxygenase, alpha II polypeptide | −0.18 | 0.007 | −0.12 | 0.012 |
| TTLL1 | tubulin tyrosine ligase-like family, member 1 | −0.18 | 0.001 | −0.29 | 0.043 |
| SUV39H2 | suppressor of variegation 3-9 homolog 2 (Drosophila) | −0.20 | 0.011 | −0.26 | 0.014 |

TABLE 2-continued

FASTING-REGULATED MRNAS COMMON TO HUMAN AND MOUSE SKELETAL MUSCLE.

| mRNA | Protein | Human Mean Log2 Change (Fasting - Fed) | P | Mouse Mean Log2 Change (Fasting - Fed) | P |
| --- | --- | --- | --- | --- | --- |
| SLC4A4 | solute carrier family 4, sodium bicarbonate cotransporter, member 4 | −0.20 | 0.007 | −0.69 | 0.003 |
| DNMT3A | DNA (cytosine-5-)-methyltransferase 3 alpha | −0.20 | 0.007 | −0.48 | 0.000 |
| FEZ2 | fasciculation and elongation protein zeta 2 (zygin II) | −0.21 | 0.000 | −0.50 | 0.019 |
| MTSS1 | metastasis suppressor 1 | −0.21 | 0.009 | −0.22 | 0.033 |
| TMTC4 | transmembrane and tetratricopeptide repeat containing 4 | −0.22 | 0.010 | −0.17 | 0.035 |
| PPM1J | protein phosphatase 1J (PP2C domain containing) | −0.23 | 0.003 | −0.30 | 0.012 |
| ARHGAP20 | Rho GTPase activating protein 20 | −0.23 | 0.003 | −0.22 | 0.013 |
| ABTB2 | ankyrin repeat and BTB (POZ) domain containing 2 | −0.25 | 0.010 | −0.18 | 0.005 |
| CNNM4 | cyclin M4 | −0.26 | 0.016 | −0.27 | 0.005 |
| GRTP1 | growth hormone regulated TBC protein 1 | −0.26 | 0.015 | −0.54 | 0.002 |
| RNF148 | ring finger protein 148 | −0.27 | 0.017 | −0.35 | 0.014 |
| SPINT2 | serine peptidase inhibitor, Kunitz type, 2 | −0.27 | 0.017 | −0.23 | 0.026 |
| PBX1 | pre-B-cell leukemia homeobox 1 | −0.34 | 0.001 | −0.22 | 0.000 |
| HSPH1 | heat shock 105 kDa/110 kDa protein 1 | −0.34 | 0.019 | −0.20 | 0.043 |
| VEGFA | vascular endothelial growth factor A | −0.35 | 0.016 | −0.26 | 0.002 |
| PMP22 | peripheral myelin protein 22 | −0.36 | 0.004 | −0.13 | 0.012 |
| PPARGC1A | peroxisome proliferative activated receptor, gamma, coactivator 1 alpha | −0.38 | 0.012 | −0.39 | 0.030 |
| ST8SIA5 | ST8 alpha-N-acetyl-neuraminide alpha-2,8-sialyltransferase 5 | −0.38 | 0.004 | −0.48 | 0.011 |
| PPIL1 | peptidylprolyl isomerase (cyclophilin)-like 1 | −0.39 | 0.005 | −0.52 | 0.016 |
| PPM1L | protein phosphatase 1 (formerly 2C)-like | −0.42 | 0.006 | −0.46 | 0.000 |
| NEO1 | neogenin homolog 1 (chicken) | −0.43 | 0.002 | −0.31 | 0.037 |
| TGFB2 | transforming growth factor, beta 2 | −0.44 | 0.017 | −0.30 | 0.003 |
| PTX3 | pentraxin-related gene, rapidly induced by IL-1 beta | −0.47 | 0.002 | −0.48 | 0.000 |
| GAS2 | growth arrest-specific 2 | −0.49 | 0.011 | −0.23 | 0.044 |
| TFRC | transferrin receptor (p90, CD71) | −0.51 | 0.003 | −1.37 | 0.011 |

The left side of FIG. 4B shows the 10 Connectivity Map instances (or data sets) with the most significant positive correlations (P<0.004) to the effect of fasting in skeletal muscle. The connectivity score, represented on the y-axis, is a measure of the strength of the correlation (Lamb J, et al. (2006) Science (New York, N.Y. 313(5795):1929-1935); the compound and cell-line is shown below the bar representing the Connectivity Score. Of these, 6 involved wortmannin or LY-294002 (inhibitors of phosphoinositide 3-kinase (PI3K)) or rapamycin (an inhibitor of the mammalian target of rapamycin complex 1 (mTORC1)). Since PI3K and mTORC1 mediate effects of insulin and IGF-I, and since insulin/IGF-I signaling inhibits muscle atrophy and atrophy-associated changes in skeletal muscle mRNA expression (Bodine S C, et al. (2001) Nat Cell Biol 3(11):1014-1019; Sandri M, et al. (2004) Cell 117(3):399-412), these results lent confidence that the Connectivity Map might be used to identify potential inhibitors of muscle atrophy. The right side of FIG. 4B shows the 10 Connectivity Map instances with the most significant negative correlations (P<0.004) to the effect of fasting in skeletal muscle. These compounds, whose effects on cultured cell lines were opposite to the effect of fasting on muscle, included metformin (an insulin-sensitizing agent widely used to treat type 2 diabetes), as well as ursolic acid. Further experiments focused on metformin and ursolic acid. To test the hypothesis that metformin and ursolic acid might reduce fasting-induced muscle atrophy, each compound was administered, or vehicle alone, via i.p. injection to C57BL/6 mice. The mice were then fasted, and after 12 hours of fasting, the mice received a second dose of the compound or vehicle. After 24 hours of fasting, the blood glucose was measured and muscles were harvested. The data shown in FIGS. 4C-4H are means±SEM from 16 mice. Both metformin (250 mg/kg) and ursolic acid (200 mg/kg) significantly reduced fasting blood glucose (FIGS. 4C and 4D). The effects of metformin and ursolic acid on fasting-induced muscle atrophy were also examined, i.e. the effect of 24 h fast (relative to ad lib feeding) on wet weight of lower hindlimb skeletal muscle (bilateral tibialis anterior ("TA" muscle), gastrocnemius, and soleus; see FIGS. 4E-4G). In the absence of metformin and ursolic acid, fasting reduced muscle weight by 9% (FIG. 4E). Although metformin did not alter muscle weight in fasted mice (FIG. 4F), ursolic acid increased it by 7±2% (FIG. 4G). Moreover, consistent with the predicted inhibitory effect on fasting-induced gene expression described herein, ursolic acid reduced fasting levels of atrogin-1 and MuRF1 mRNA levels in the TA muscles of fasted mice (FIG. 4H; the data shown are normalized to the levels in vehicle-treated mice, which were set at 1). In FIGS. 4E-4H, each data point represents one mouse and the horizontal bars denote the means. In FIGS. 4C-4H, P-values were determined using unpaired t-tests. Thus, ursolic acid, but not metformin, decreased fasting-induced muscle atrophy.

5. Ursolic Acid Reduces Denervation-Induced Muscle Atrophy.

The Connectivity Map was queried with a second mRNA expression signature, atrophy signature-2 (described above), to determine if this muscle atrophy signature would also correlate with ursolic acid, among other compounds. As described above, atrophy signature-2 was an mRNA expression signature identified as described herein for human skeletal muscle mRNAs that were induced or repressed by fasting and also by spinal cord injury ("SCI"). The studies of the effects of SCI on human skeletal muscle gene expression were described previously (Adams C M, et al. (2011) *Muscle Nerve*. 43(1):65-75). Using this approach with the muscle atrophy expression signatures described herein, there were 18 human mRNAs that were increased by fasting and SCI, and 17 human mRNAs that were decreased by fasting and SCI, and are shown in Table 3 ("Change" represents mean changes in $\log_2$ hybridization signals for pairs as indicated, e.g. fasting and fed states for column labeled "(Fasting-Fed)" or untrained and trained for the column labeled "(Untrained-Trained)"). The data in Table 3 include all mRNAs whose levels were increased by fasting ($P \leq 0.02$) and by SCI ($P \leq 0.05$), and all mRNAs whose levels were decreased by fasting ($P \leq 0.02$) and by SCI ($P \leq 0.05$). P-values in Table 3 were determined with paired t-tests.

TABLE 3

HUMAN SKELETAL MUSCLE MRNAS INDUCED OR REPRESSED BY FASTING AND SCI.

| | | EFFECT OF FASTING | | EFFECT OF SCI | |
|---|---|---|---|---|---|
| mRNA | Protein | Change (Fasting - Fed) | P | Change (Untrained - Trained) | P |
| OR1D4 | olfactory receptor, family 1, subfamily D, member 4 | 0.50 | 0.019 | 0.65 | 0.030 |
| RHOBTB1 | Rho-related BTB domain containing 1 | 0.48 | 0.001 | 0.71 | 0.032 |
| TSPAN8 | tetraspanin 8 | 0.39 | 0.015 | 1.79 | 0.023 |
| FLJ33996 | hypothetical protein FLJ33996 | 0.39 | 0.019 | 0.68 | 0.020 |
| NUPR1 | nuclear protein 1 | 0.35 | 0.007 | 0.65 | 0.030 |
| IRS2 | insulin receptor substrate 2 | 0.34 | 0.004 | 0.21 | 0.035 |
| NPC2 | Niemann-Pick disease, type C2 | 0.30 | 0.011 | 0.39 | 0.042 |
| KLF11 | Kruppel-like factor 11 | 0.29 | 0.011 | 0.22 | 0.034 |
| ZNF682 | zinc finger protein 682 | 0.28 | 0.017 | 0.72 | 0.013 |
| NOX4 | NADPH oxidase 4 | 0.28 | 0.002 | 0.56 | 0.007 |
| PLXDC2 | plexin domain containing 2 | 0.26 | 0.013 | 0.38 | 0.022 |
| CTDSP2 | CTD small phosphatase 2 | 0.25 | 0.003 | 0.34 | 0.021 |
| CAV3 | caveolin 3 | 0.24 | 0.007 | 0.56 | 0.020 |
| IGF1R | insulin-like growth factor 1 receptor | 0.23 | 0.013 | 0.63 | 0.040 |
| FLJ14154 | hypothetical protein FLJ14154 | 0.22 | 0.005 | 0.30 | 0.021 |
| CUGBP2 | CUG triplet repeat, RNA binding protein 2 | 0.21 | 0.004 | 0.14 | 0.034 |
| MLL | myeloid/lymphoid or mixed-lineage leukemia | 0.14 | 0.016 | 0.30 | 0.040 |
| SUPT6H | suppressor of Ty 6 homolog | 0.11 | 0.005 | 0.19 | 0.024 |
| MRPS15 | mitochondrial ribosomal protein S15 | −0.11 | 0.003 | −0.33 | 0.001 |
| RFXDC2 | regulatory factor X domain containing 2 | −0.12 | 0.012 | −0.10 | 0.037 |
| PDE7B | phosphodiesterase 7B | −0.12 | 0.013 | −0.39 | 0.011 |
| PFDN6 | prefoldin subunit 6 | −0.14 | 0.014 | −0.42 | 0.021 |
| ZNF280B | zinc finger protein 280B | −0.16 | 0.005 | −0.30 | 0.028 |
| TSPAN13 | tetraspanin 13 | −0.18 | 0.006 | −0.56 | 0.023 |
| TTLL1 | tubulin tyrosine ligase-like family, member 1 | −0.18 | 0.001 | −0.37 | 0.020 |
| CMAS | cytidine monophosphate N-acetylneuraminic acid synthetase | −0.21 | 0.000 | −0.22 | 0.025 |
| C8orf32 | chromosome 8 open reading frame 32 | −0.23 | 0.016 | −0.11 | 0.049 |

TABLE 3-continued

HUMAN SKELETAL MUSCLE MRNAS INDUCED OR REPRESSED BY FASTING AND SCI.

| mRNA | Protein | EFFECT OF FASTING Change (Fasting - Fed) | P | EFFECT OF SCI Change (Untrained - Trained) | P |
|---|---|---|---|---|---|
| GUCY1B3 | guanylate cyclase 1, soluble, beta 3 | −0.24 | 0.007 | −0.24 | 0.008 |
| ZNF32 | zinc finger protein 32 | −0.24 | 0.010 | −0.21 | 0.030 |
| VLDLR | very low density lipoprotein receptor | −0.28 | 0.007 | −0.16 | 0.015 |
| HSPB7 | heat shock 27 kDa protein family, member 7 (cardiovascular) | −0.33 | 0.015 | −0.77 | 0.032 |
| VEGFA | vascular endothelial growth factor A | −0.35 | 0.016 | −0.43 | 0.020 |
| SLC16A1 | solute carrier family 16, member 1 | −0.37 | 0.018 | −0.94 | 0.015 |
| PPARGC1A | peroxisome proliferative activated receptor, gamma, coactivator 1 alpha | −0.38 | 0.012 | −0.74 | 0.001 |
| C6orf192 | chromosome 6 open reading frame 192 | −0.41 | 0.018 | −0.39 | 0.042 |

Figure 5:
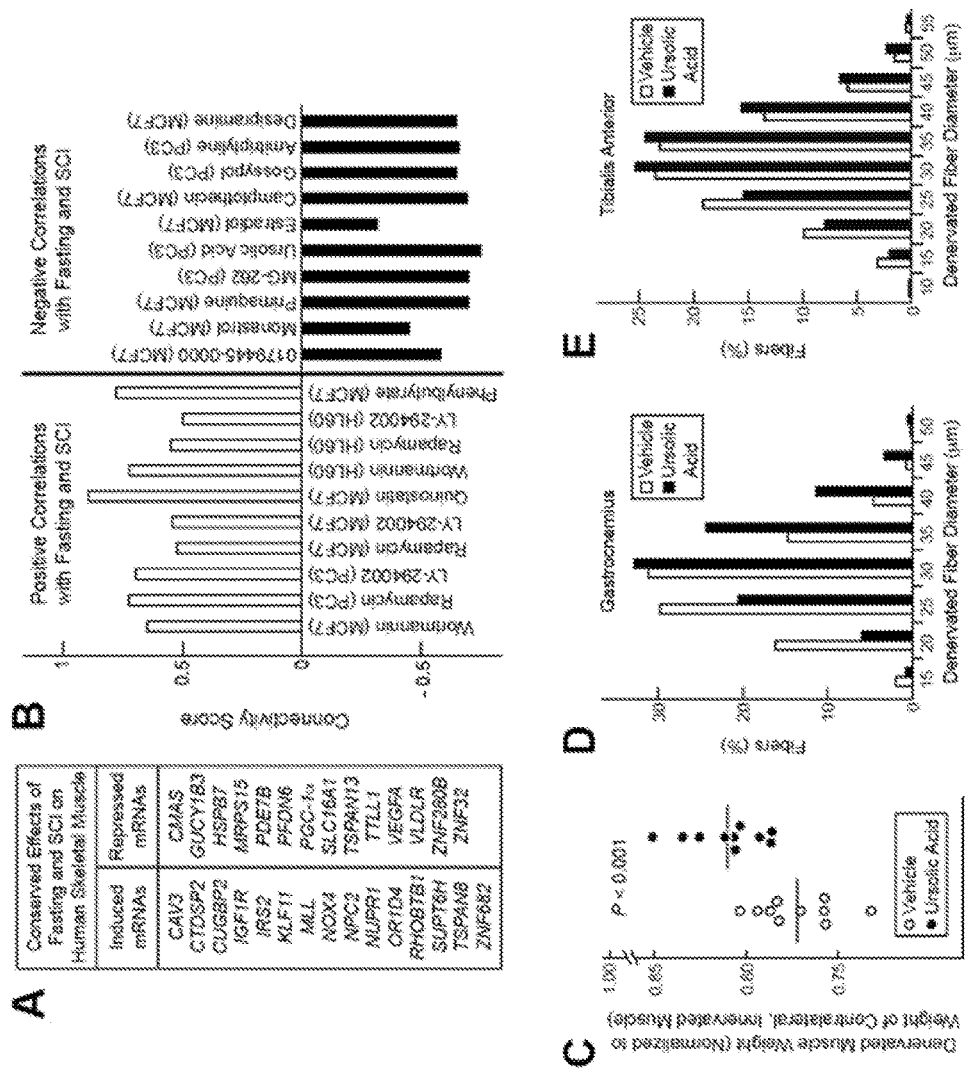
FIG. 5 shows representative data on the identification of ursolic acid as an inhibitor of denervation-induced muscle atrophy.

Of the mRNAs listed in Table 3, 29 were represented on the HG-U133A arrays used in the Connectivity Map (FIG. 5A), but only 10 were common to the 63 mRNAs used in the first Connectivity Map query described above for atrophy signature-1 (IGF-IR, NOX4, SUPT6H, MRPS15, PDE7B, PGC-1a, TSPAN13, TTLL1, VEGFA and ZNF280B). The mRNAs listed in FIG. 5A represent human muscle atrophy signature-2: mRNAs altered by both fasting and SCI in human muscle. These mRNAs, as described above, were used to query the Connectivity Map. Inclusion criteria were: P≤0.02 in fasted human muscle (by t-test), P≤0.05 in untrained, paralyzed muscle (by t-test), and the existence of complimentary probes on HG-U133A arrays. Connectivity Map instances with the most significant positive and negative correlations to the effect of fasting and SCI in human muscle. P≤0.005 for all compounds are shown in FIG. 5B. The results partially overlapped with the results of the first search: both search strategies identified LY-294002, wortmannin and rapamycin as predicted mimics of atrophy-inducing stress, and ursolic acid (but not metformin) as a predicted inhibitor (FIG. 5B).

Because atrophy signature-2 utilized data from SCI subjects, it was hypothesized that ursolic acid might reduce denervation-induced muscle atrophy. To test this, the left hindlimb muscles a denervation-induced skeletal muscle atrophy model in mouse was used. Briefly, on day 0, the left hindlimbs of C57BL/6 mice were denervated by transecting the left sciatic nerve. This approach allowed the right hindlimb to serve as an intra-subject control. Mice were then administered ursolic acid (200 mg/kg) or an equivalent volume of vehicle alone (corn oil) via i.p. injection twice daily for seven days. During this time, mice continued to have ad libitum access to food. On day 7, muscle tissues were harvested for analysis, and the left (denervated) and right (innervated) hindlimb muscles in both groups (ursolic acid vs. vehicle administration) were compared. Ursolic acid significantly decreased denervation-induced muscle loss (FIG. 5C). In FIG. 5C, weights of the left (denervated) lower hindlimb muscles were normalized to weights of the right (innervated) lower hindlimb muscles from the same mouse. Each data point represents one mouse, and horizontal bars denote the means and the P-value was determined using an unpaired t-test. Histologically, this effect of ursolic acid was reflected as an increase in the size of denervated skeletal muscle fiber diameter in denervated gastrocnemius (D) and TA (E) muscles (FIGS. 5D and 5E, respectively). The data shown in FIGS. 5D and 5E are from >2500 muscle fibers per condition; P<0.0001 by unpaired t-test. Thus, ursolic acid reduced denervation-induced muscle atrophy.

6. Ursolic Acid Induces Skeletal Muscle Hypertrophy.

The results from the denervation-induced muscle atrophy model suggested that ursolic acid reduced muscle atrophy, thus the hypothesis that ursolic acid might promote muscle hypertrophy in the absence of an atrophy-inducing stress was reasonable. Mice were provided ad lib access to either standard chow (control diet) or standard chow supplemented with 0.27% ursolic acid (ursolic acid diet) for 5 weeks before grip strength was measured and tissues were harvested. After five weeks, mice administered ursolic had increased lower hindlimb muscle weight (FIG. 6A), quadriceps weight (FIG. 6B), and upper forelimb muscle (triceps and biceps) weight (FIG. 6C). Each data point in FIGS. 6A-6C represents one mouse, and horizontal bars denote the means. The effect of ursolic acid in this study on skeletal muscle fiber size distribution is shown in FIG. 6D. Each distribution represents measurements of >800 triceps muscle fibers from 7 animals (>100 measurements/animal); P<0.0001. The effect of ursolic acid on peak grip strength (normalized to body weight) is shown in FIG. 6E. Each data point represents one mouse, and horizontal bars denote the means. Non-normalized grip strength data were 157±9 g (control diet) and 181±6 g (ursolic acid diet) (P=0.04).

Figure 6:
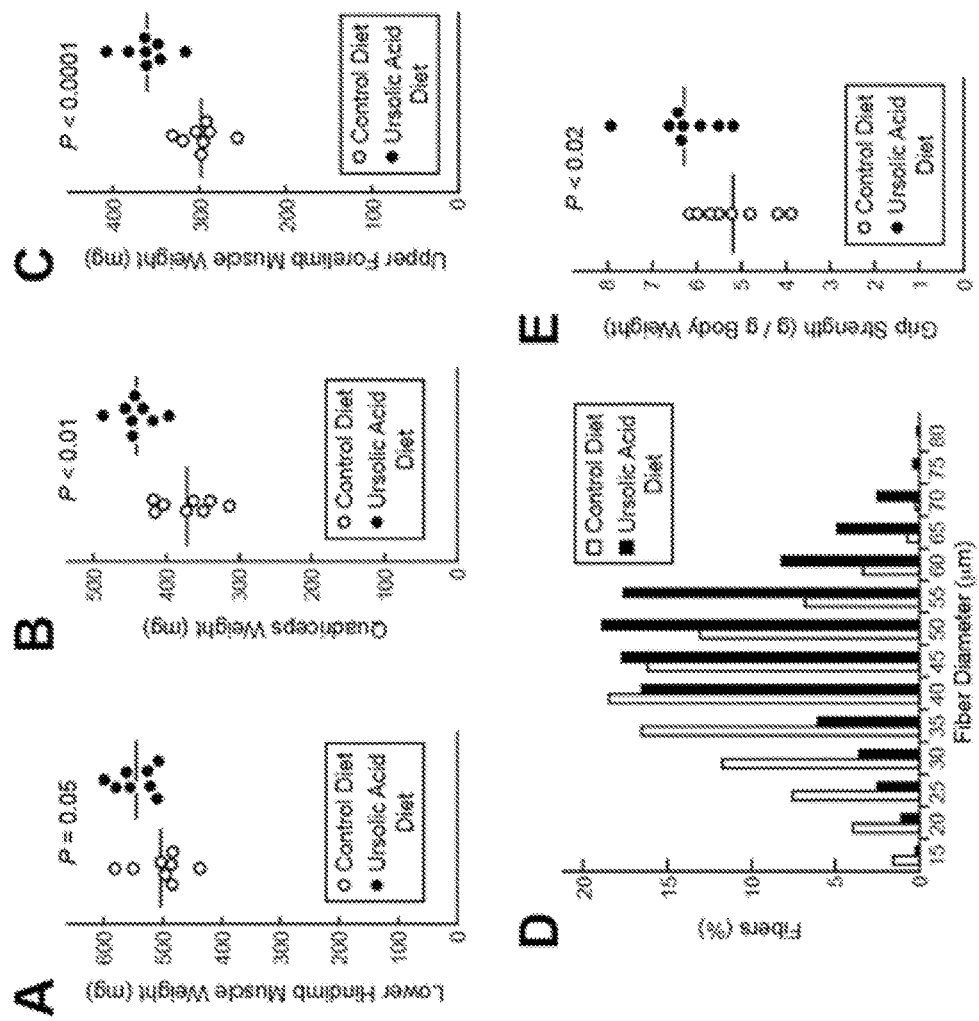
FIG. 6 shows representative data on ursolic acid-mediated induction of muscle hypertrophy.
Figure 7:
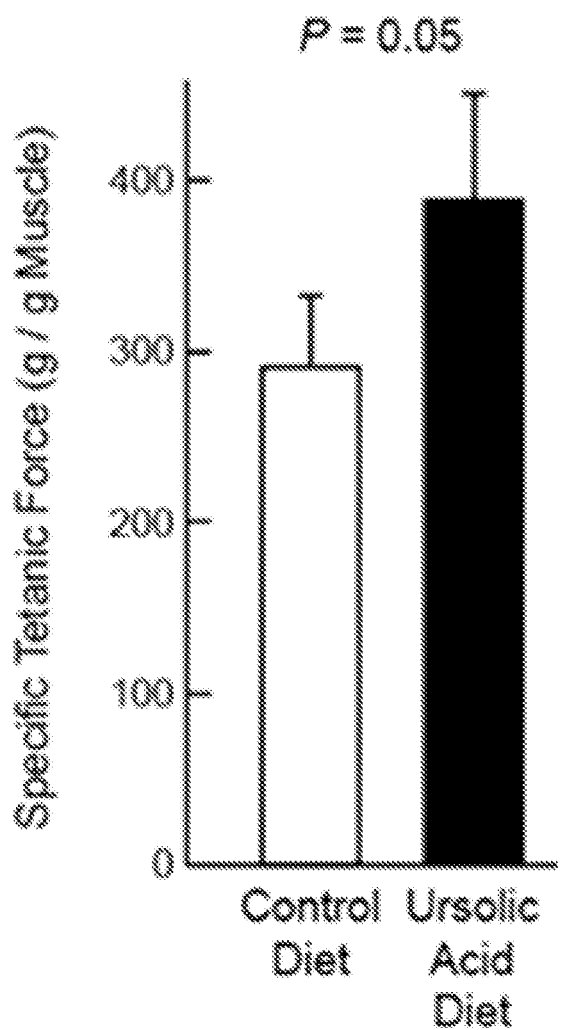
FIG. 7 shows representative data on the effect of ursolic acid on mouse skeletal muscle specific tetanic force.

Moreover, dietary ursolic acid increased the specific force generated by muscles ex vivo (FIG. 7). Briefly, six-week old male C57BL/6 mice were provided either standard diet or diet containing 0.27% ursolic acid for 16 weeks before being euthanized. The lower hindlimb was removed (by transecting the upper hindlimb mid-way through the femur), and placed in Krebs solution aerated with 95% O2 and 5% CO2. The gastrocnemius, soleus and tibialis anterior muscles, as well as the distal half of the tibia and fibula were then removed and discarded, leaving the extensor digitorum longus and peroneus muscles with their origins and insertions intact. A suture was placed through the proximal tendon and secured to the distal femur fragment. This ex vivo preparation was then mounted vertically in a water jacket bath (Aurora Scientific 1200A Intact Muscle Test System, filled with aerated Krebs solution) by attaching the suture to a servo-controlled lever (superiorly) and clamping the metatarsals (inferiorly). Passive muscle force was adjusted to a baseline of 1 g, and then muscles were stimulated with supramaximal voltage (80 V) at 100 Hz. The mean time from euthanasia to maximal force measurements was 10 min. After force measurements, muscles were removed and weighed in order to calculate specific titanic force. Maximal tetanic force and muscle weight did not differ between the two groups (P=0.20 and 0.26, respectively). Data are means±SEM from 5-6 mice per diet. P-values were determined with a t-test. Together, the data in FIGS. 6 and 7 provide morphological and functional evidence that ursolic acid induced skeletal muscle hypertrophy.

7. Ursolic Acid Induces Trophic Changes in Skeletal Muscle Gene Expression.

The foregoing results suggested that ursolic acid might alter skeletal muscle gene expression. To test this hypothesis, an unbiased approach was used, specifically exon expression arrays were used to analyze gastrocnemius muscle mRNA expression in mice that had been fed diets lacking or containing ursolic acid for 5 weeks. Mice were provided ad lib access to either standard chow (control diet) or standard chow supplemented with 0.27% ursolic acid (ursolic acid diet) for 5 weeks before gastrocnemius muscle RNA was harvested and analyzed by Affymetrix Mouse Exon 1.0 ST arrays (n=4 arrays per diet). Each array assessed pooled gastrocnemius RNA from two mice. Stringent criteria were used for ursolic acid-induced effects on mRNA levels (P<0.005), and mRNAs with low levels of expression were disregarded (i.e. only transcripts that were increased to a mean $\log_2$ hybridization signal≥8, or repressed from a mean $\log_2$ hybridization signal≥8 were included). The results were that ursolic acid decreased 18 mRNAs and increased 51 mRNAs (out of >16,000 mRNAs analyzed. The results are shown in Table 4 ("Change" is the meang $\log_2$ change or difference between mice on ursolic acid diet and control diet, i.e. [Mean $\log_2$ mRNA levels in ursolic acid diet] minus [Mean $\log_2$ mRNA levels in control diet]).

TABLE 4

MOUSE SKELETAL MUSCLE MRNAS INDUCED OR REPRESSED BY URSOLIC ACID.

| mRNA | Protein | Change | P |
| --- | --- | --- | --- |
| Smox | spermine oxidase | 0.81 | 0.001 |
| Lyz2 | lysozyme 2 | 0.71 | 0.001 |
| C3 | complement component 3 | 0.70 | 0.000 |
| Tyrobp | TYRO protein tyrosine kinase binding protein | 0.69 | 0.001 |
| Lum | lumican | 0.61 | 0.001 |
| Igf1 | insulin-like growth factor 1 | 0.56 | 0.005 |
| Fmo1 | flavin containing monooxygenase 1 | 0.47 | 0.000 |
| Ostn | osteocrin | 0.43 | 0.001 |
| Nampt | nicotinamide phosphoribosyltransferase | 0.41 | 0.003 |
| H19 | H19 fetal liver mRNA | 0.39 | 0.004 |
| Hipk2 | homeodomain interacting protein kinase 2 | 0.38 | 0.002 |
| Fbp2 | fructose bisphosphatase 2 | 0.37 | 0.003 |
| Gpx1 | glutathione peroxidase 1 | 0.36 | 0.001 |
| Sepp1 | selenoprotein P, plasma, 1 | 0.35 | 0.004 |
| Parp3 | poly (ADP-ribose) polymerase family, member 3 | 0.32 | 0.001 |
| Hspb8 | heat shock protein 8 | 0.32 | 0.000 |
| Musk | muscle, skeletal, receptor tyrosine kinase | 0.31 | 0.004 |
| Fhl3 | four and a half LIM domains 3 | 0.31 | 0.005 |
| Hsph1 | heat shock 105 kDa/110 kDa protein 1 | 0.30 | 0.001 |
| Arfgap2 | ADP-ribosylation factor GTPase activating protein 2 | 0.30 | 0.001 |
| Cd24a | CD24a antigen | 0.28 | 0.002 |
| Sepx1 | selenoprotein X 1 | 0.28 | 0.003 |
| Hk2 | hexokinase 2 | 0.26 | 0.003 |
| Ggct | gamma-glutamyl cyclotransferase | 0.24 | 0.005 |
| Trip10 | thyroid hormone receptor interactor 10 | 0.23 | 0.000 |
| Npc1 | Niemann Pick type C1 | 0.22 | 0.001 |
| Asb5 | ankyrin repeat and SOCs box-containing 5 | 0.21 | 0.001 |
| Vps29 | vacuolar protein sorting 29 (*S. pombe*) | 0.20 | 0.000 |
| Ahsa2 | AHA1, activator of heat shock protein ATPase homolog 2 | 0.18 | 0.001 |
| Lsm14a | LSM14 homolog A (SCD6, *S. cerevisiae*) | 0.18 | 0.004 |
| Pdha1 | pyruvate dehydrogenase E1 alpha 1 | 0.18 | 0.001 |
| Trappc2l | trafficking protein particle complex 2-like | 0.16 | 0.004 |
| Ube2l3 | ubiquitin-conjugating enzyme E2L 3 | 0.16 | 0.003 |
| Ctsb | cathepsin B | 0.16 | 0.003 |
| D0H4S114 | DNA segment, human D4S114 | 0.15 | 0.004 |
| Psma2 | proteasome (prosome, macropain) subunit, alpha type 2 | 0.15 | 0.005 |
| Mrpl46 | mitochondrial ribosomal protein L46 | 0.15 | 0.001 |
| Eef1e1 | eukaryotic translation elongation factor 1 epsilon 1 | 0.15 | 0.002 |
| Krr1 | KRR1, small subunit (SSU) processome component, homolog | 0.15 | 0.005 |
| Ndufaf4 | NADH dehydrogenase (ubiquinone) 1 alpha subcomplex, assembly factor 4 | 0.14 | 0.005 |
| Ndufs2 | NADH dehydrogenase (ubiquinone) Fe—S protein 2 | 0.14 | 0.002 |
| 2610507B11Rik | RIKEN cDNA 2610507B11 gene | 0.14 | 0.000 |
| Ssr4 | signal sequence receptor, delta | 0.14 | 0.000 |
| Ndufs4 | NADH dehydrogenase (ubiquinone) Fe—S protein 4 | 0.14 | 0.003 |
| Sqstm1 | sequestosome 1 | 0.12 | 0.001 |
| Gfm1 | G elongation factor, mitochondrial 1 | 0.12 | 0.003 |
| 2310016M24Rik | RIKEN cDNA 2310016M24 gene | 0.12 | 0.004 |
| Sod2 | superoxide dismutase 2, mitochondrial | 0.12 | 0.001 |
| Prdx5 | peroxiredoxin 5 | 0.10 | 0.005 |
| BC004004 | cDNA sequence BC004004 | 0.06 | 0.001 |
| Ghitm | growth hormone inducible transmembrane protein | 0.05 | 0.005 |
| Foxn3 | forkhead box N3 | −0.09 | 0.000 |
| Klhl31 | kelch-like 31 (*Drosophila*) | −0.09 | 0.001 |
| Acadm | acyl-Coenzyme A dehydrogenase, medium chain | −0.11 | 0.001 |
| Eif4g3 | eukaryotic translation initiation factor 4 gamma, 3 | −0.12 | 0.005 |
| Nrap | nebulin-related anchoring protein | −0.14 | 0.003 |
| Golga4 | golgi autoantigen, golgin subfamily a, 4 | −0.14 | 0.003 |
| Paip2b | poly(A) binding protein interacting protein 2B | −0.16 | 0.000 |
| Pde4dip | phosphodiesterase 4D interacting protein (myomegalin) | −0.18 | 0.001 |

TABLE 4-continued

MOUSE SKELETAL MUSCLE MRNAS INDUCED OR REPRESSED BY URSOLIC ACID.

| mRNA | Protein | Change | P |
|---|---|---|---|
| Sfpq | splicing factor proline/glutamine rich | −0.18 | 0.005 |
| Pnn | pinin | −0.18 | 0.002 |
| D4Wsu53e | DNA segment, Chr 4, Wayne State University 53, expressed | −0.18 | 0.003 |
| Mlec | malectin | −0.19 | 0.003 |
| Cacna1s | calcium channel, voltage-dependent, L type, alpha 1S | −0.22 | 0.001 |
| Sfrs5 | splicing factor, arginine/serine-rich 5 (SRp40, HRS) | −0.22 | 0.005 |
| Nnt | nicotinamide nucleotide transhydrogenase | −0.24 | 0.002 |
| Adprhl1 | ADP-ribosylhydrolase like 1 | −0.26 | 0.002 |
| Ddit4l | DNA-damage-inducible transcript 4-like | −0.32 | 0.000 |
| Fbxo32 | F-box protein 32 (Atrogin-1) | −0.35 | 0.001 |

Figure 8:
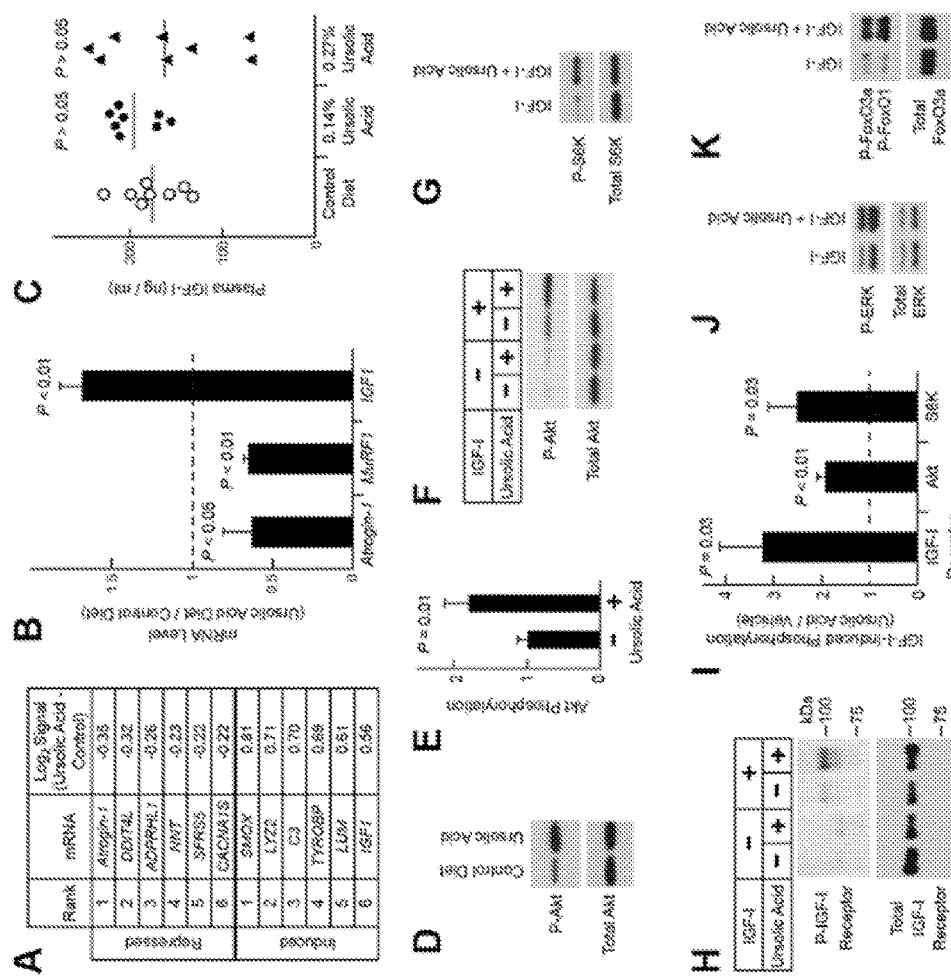
FIG. 8 shows representative data on the effect of ursolic acid on muscle growth, atrophic gene expression, trophic gene expression, and skeletal muscle IGF-I signaling.
Figure 9:
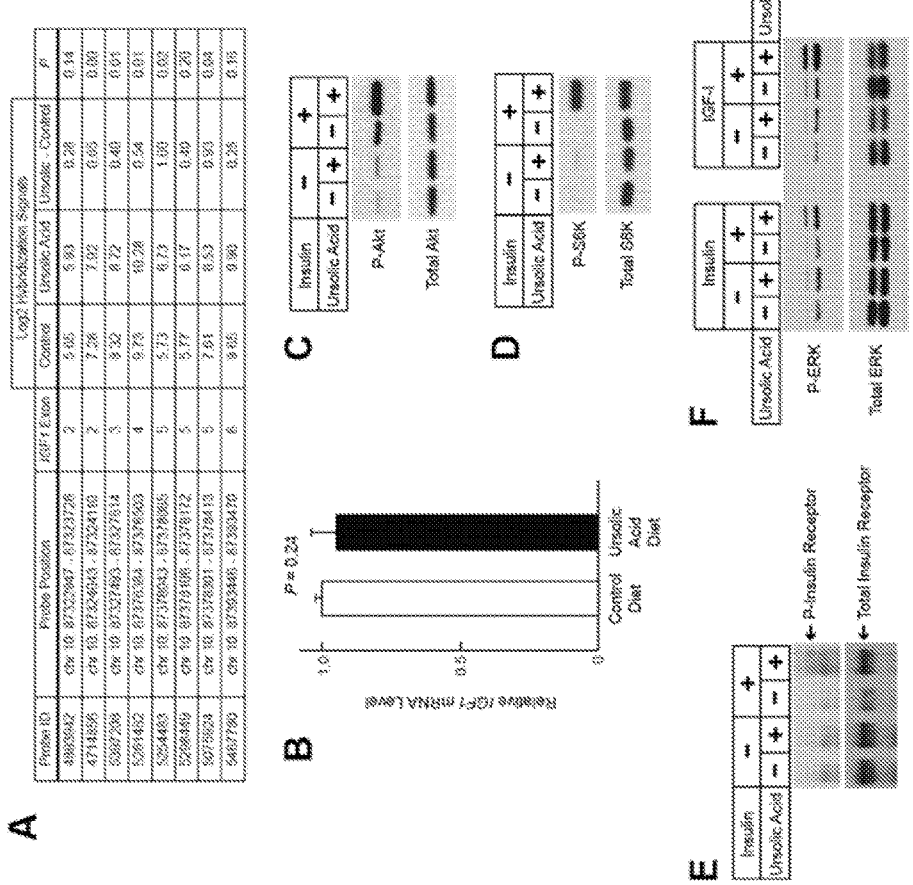
FIG. 9 shows representative data on the effect of ursolic acid on skeletal muscle expression of IGF1 gene exons, adipose IGF1 mRNA expression, and skeletal muscle insulin signaling.

As discussed above, atrogin-1 and MuRF1 are transcriptionally up-regulated by atrophy-inducing stresses (see FIG. 2B and Sacheck J M, et al. (2007) Faseb J 21(1):140-155), and they are required for muscle atrophy (Bodine S C, et al. (2001) Science (New York, N.Y. 294(5547):1704-1708). Moreover, in the studies of fasted mice as described herein above, ursolic acid reduced atrogin-1 and MuRF1 mRNAs (FIG. 4H). Consistent with that finding, the arrays indicated that dietary ursolic acid reduced atrogin-1 mRNA, which was the most highly repressed mRNA (FIG. 8A). The results shown in FIG. 8A represent a subset of the mRNAs from Table 4 which had the greatest increase or decrease in expression level in response to ursolic acid. Although MuRF1 mRNA was not measured by the arrays used in these experiments, qPCR analysis confirmed that dietary ursolic acid repressed both atrogin-1 and MuRF1 mRNAs (FIG. 8B; data are means±SEM). Interestingly, one of the most highly up-regulated muscle mRNAs was IGF1 (FIGS. 8A and 8B), which encodes insulin-like growth factor-I (IGF-I), a locally generated autocrine/paracrine hormone. IGF1 mRNA is known to be transcriptionally induced in hypertrophic muscle (Hameed M, et al. (2004) The Journal of physiology 555(Pt 1):231-240; Adams G R & Haddad F (1996) J Appl Physiol 81(6):2509-2516; Gentile M A, et al. (2010) Journal of molecular endocrinology 44(1):55-73). In addition, increased skeletal muscle IGF1 expression reduces denervation-induced muscle atrophy (Shavlakadze T, et al. (2005) Neuromuscul Disord 15(2):139-146), and stimulates muscle hypertrophy (Barton-Davis E R, et al. (1998) Proceedings of the National Academy of Sciences of the United States of America 95(26):15603-15607; Musarò A, et al. (2001) Nature Genetics 27(2):195-200). Moreover, by stimulating skeletal muscle insulin/IGF-I signaling, IGF-I represses atrogin-1 and MuRF mRNAs (Sacheck J M, et al. (2004) Am J Physiol Endocrinol Metab 287(4):E591-601; Frost R A, et al. (2009) J Cell Biochem 108(5):1192-1202.), as well as DDIT4L mRNA (ibid), which, after atrogin-1 mRNA, was the second most highly repressed mRNA in muscle from ursolic acid-treated mice (FIG. 8A). Thus, 5 weeks of dietary ursolic acid altered skeletal muscle gene expression in a manner known to reduce atrophy and promote hypertrophy, and muscle-specific IGF1 induction emerged as a likely contributing mechanism in ursolic acid-induced muscle hypertrophy. The effect of ursolic acid on plasma IGF-I levels was also determined, which primarily reflect growth hormone-mediated hepatic IGF-I production (Yakar S, et al. (1999) Proceedings of the National Academy of Sciences of the United States of America 96(13):7324-7329). Although diets containing 0.14% or 0.27% ursolic acid increased muscle mass (described in greater detail below; FIG. 10A), neither increased plasma IGF-I (FIG. 8C). For the data in FIG. 8C, mice were provided ad lib access to either standard chow (control diet) or standard chow supplemented with the indicated concentration of ursolic acid for 7 weeks before plasma IGF-I levels were measured. Each data point represents one mouse, and horizontal bars denote the means. P-values were determined by one-way ANOVA with Dunnett's post-test. Of note, exon expression arrays indicated that ursolic acid increased levels of all measured IGF1 exons (exons 2-6; FIG. 9A). The data in FIG. 9A are mean exon-specific $\log_2$ hybridization signals from the arrays described in Table 2. However, ursolic acid did not alter levels of mRNAs encoding myostatin (which reduces muscle mass, for example see Lee S J (2004) Annu Rev Cell Dev Biol 20:61-86), or twist or myogenin (which are induced by IGF-I during development, for example see Dupont J, et al. (2001) The Journal of biological chemistry 276(28):26699-26707; Tureckova J, et al. (2001) The Journal of biological chemistry 276(42):39264-39270). Moreover, ursolic acid did not alter the amount of IGF1 mRNA in adipose tissue (FIG. 9B). Briefly, the data shown in FIG. 9B were obtained as follows: mice were provided ad lib access to either standard chow (control diet) or standard chow supplemented with 0.27% ursolic acid (ursolic acid diet) for 7 weeks before retroperitoneal adipose tissue was harvested for qPCR quantification of IGF1 mRNA. The data shown are means±SEM from 5 mice per group. Without wishing to be bound by a particular theory, ursolic acid-mediated IGF1 induction may be localized to skeletal muscle.

8. Ursolic Acid Enhances Skeletal Muscle IGF-I Signaling.

Although muscle-specific IGF1 induction is characteristic of, and contributes to, muscle hypertrophy, it may be a relatively late event that promotes hypertrophy after it has been initiated by other stimuli (Adams G R, et al. (1999) J Appl Physiol 87(5):1705-1712). Without wishing to be bound by a particular theory, it is possible that ursolic acid might have a more proximal effect on insulin/IGF-I signaling. In a previous study of non-muscle cell lines (CHO/IR and 3T3-L1 cells), ursolic acid enhanced insulin-mediated Akt activation (Jung S H, et al. (2007) The Biochemical journal 403(2):243-250). To determine whether ursolic acid might have a similar effect in skeletal muscle, the level of phosphorylated Akt was assessed in quadriceps muscles of mice fed diets lacking or containing ursolic acid. Briefly, mice were provided ad lib access to either standard chow (control diet) or standard chow supplemented with 0.27% ursolic acid for 16 weeks. Total protein extracts from quadriceps muscles were subjected to SDS-PAGE, followed by immunoblot analysis for phosphorylated and total Akt, as indicated. A representative immunoblot is shown in FIG. 8D. Immunoblot data were quantitated as follows: in each mouse, the level of phospho-Akt was normalized to the level of total Akt; these ratios were then normalized to the average phospho-Akt/total Akt ratio from control mice and the results are shown in FIG. 8E (data are means±SEM from 9 mice per diet. P-value was determined by unpaired t-test). The data show that in quadriceps, ursolic acid increased Akt phosphorylation by 1.8-fold.

The effect of ursolic acid on Akt activation was examined in C2C12 skeletal myotubes, a well-established in vitro model of skeletal muscle (Sandri M, et al. (2004) Cell 117(3):399-412; Stitt T N, et al. (2004) *Mol Cell* 14(3):395-403). Use of an in vitro system, such as C2C12 skeletal myotubes, circumvented potentially confounding effects from non-muscle tissues, and enabled a determination of whether IGF-I or insulin was required for ursolic acid's effect. The latter consideration was important because circulating IGF-I and insulin are always present in healthy animals. Use of an in vitro system also allowed testing of a clearly defined concentration of ursolic acid (10 μM, similar what was used in the Connectivity Map (8.8 μM)) for a clearly defined time of incubation (20 min). These considerations were important because the in vivo pharmacokinetic properties of ursolic acid are not yet known.

For the data shown in FIGS. 8F-8K, serum-starved C2C12 myotubes were treated in the absence or presence of ursolic acid (10 μM) and/or IGF-I (10 nM), as indicated. For studies of the IGF-I receptor, cells were harvested 2 min later, and protein extracts were subjected to immunoprecipitation with anti-IGF-I receptor β antibody, followed by immunoblot analysis with anti-phospho-tyrosine or anti-IGF-I receptor β antibodies to assess phospho- and total IGF-I receptor, respectively. For other studies, cells were harvested 20 min after addition of ursolic acid and/or IGF-I, and immunoblot analyses were performed using total cellular protein extracts and antibodies specific for the phosphorylated or total proteins indicated. Representative immunoblots showing effect of ursolic acid on IGF-1-mediated phosphorylation of Akt (FIG. 8F), S6K (FIG. 8G) and IGF-I receptor (FIG. 8H). Data from immunoblots was quantitated as follows: levels in the presence of ursolic acid and IGF-I were normalized to levels in the presence of IGF-I alone, which were set at 1 and are indicated by the dashed line. The data shown in FIG. 8I are means±SEM from ≥3 experiments.

For the data shown in FIGS. 9C-9F, serum-starved C2C12 myotubes were treated in the absence or presence of ursolic acid (10 μM), insulin (10 nM) and/or IGF-I (10 nM), as indicated. For studies of the insulin receptor, cells were harvested 2 min later, and protein extracts were subjected to immunoprecipitation with anti-insulin receptor β antibody, followed by immunoblot analysis with anti-phospho-insulin receptor β (Y1162/1163) or anti-insulin receptor β antibodies to assess phospho- and total insulin receptor, respectively. For other studies, cells were harvested 20 min after addition of ursolic acid, insulin and/or IGF-I, and immunoblot analyses were performed using total cellular protein extracts and antibodies specific for the phosphorylated or total proteins indicated.

When serum-starved myotubes were treated with ursolic acid alone, Akt phosphorylation did not increase (FIG. 8F). However, in the presence of IGF-I, ursolic acid increased Akt phosphorylation by 1.9-fold (FIGS. 8F and 8I). Ursolic acid also increased Akt phosphorylation in the presence of insulin (FIG. 9C). Thus, ursolic acid enhanced IGF-1-mediated and insulin-mediated Akt phosphorylation. The finding that ursolic acid enhanced muscle Akt activity in vivo and in vitro was consistent with the finding that ursolic acid's mRNA expression signature negatively correlated with the mRNA expression signatures of LY-294002 and wortmannin (FIGS. 4B and 5B), which inhibit insulin/IGF-I signaling upstream of Akt. However, ursolic acid's signature also negatively correlated with the signature of rapamycin, which inhibits insulin/IGF-I signaling downstream of Akt.

Although ursolic acid alone did not increase S6K phosphorylation (FIG. 9D), it enhanced IGF-I-mediated and insulin-mediated S6K phosphorylation (FIGS. 8G, 8I and 9D). To further investigate the mechanism, the effect of ursolic acid on the IGF-I receptor was examined. Ursolic acid increased IGF-I receptor phosphorylation in the presence but not the absence of IGF-I (FIGS. 8H and 8I). Similarly, ursolic acid increased insulin receptor phosphorylation in the presence but not the absence of insulin (FIG. 9E). Both of these effects were rapid, occurring within 2 minutes after the addition of ursolic acid and either IGF-I or insulin. Consistent with enhanced signaling at the level of the IGF-I and insulin receptors, ursolic acid also enhanced IGF-I-mediated and insulin-mediated ERK phosphorylation (FIGS. 8J and 9F). Moreover, ursolic acid enhanced IGF-I-mediated phosphorylation (inhibition) of FoxO transcription factors, which activate transcription of atrogin-1 and MuRF1 mRNAs (FIG. 8K; Sandri M, et al. (2004) *Cell* 117(3):399-412; Stitt T N, et al. (2004) *Mol Cell* 14(3):395-403.). Without wishing to be bound by a particular theory, ursolic acid represses atrophy-associated gene expression and promotes muscle hypertrophy by increasing activity of the IGF-I and insulin receptors.

9. Ursolic Acid Reduces Adiposity.

Figure 10:
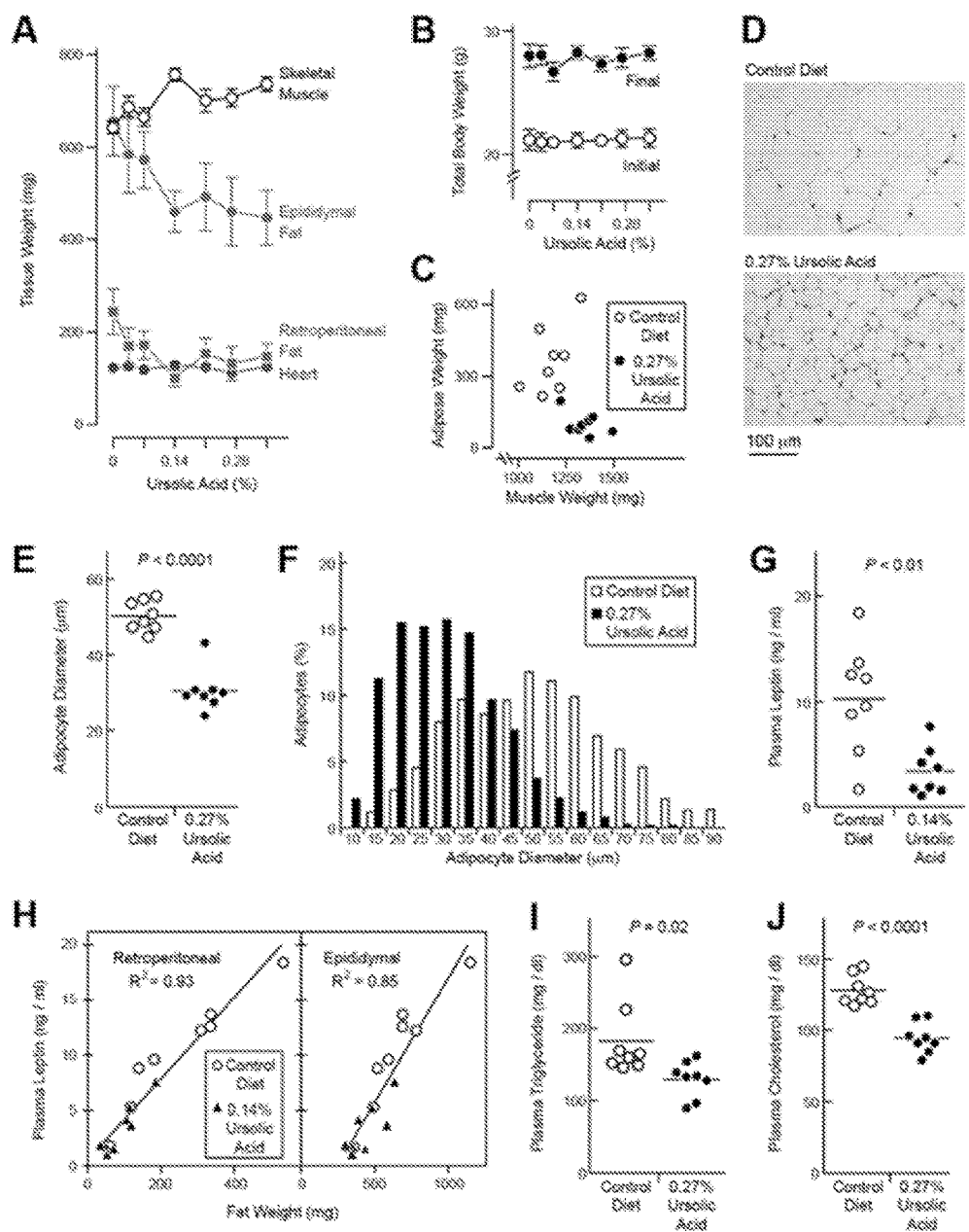
FIG. 10 shows representative data on the effect of ursolic acid on adiposity.

Mice were provided ad lib access to standard chow supplemented with the indicated concentration (weight percent in chow, either 0.14% or 0.28% as indicated in FIG. 10) of ursolic acid for 7 weeks before tissues were harvested for analysis. Data are means±SEM from 10 mice per diet. Data for the effects of ursolic acid on weights of skeletal muscle (quadriceps+triceps), epididymal fat, retroperitoneal fat and heart are shown in FIG. 10A. The P-values, determined by one-way ANOVA with post-test for linear trend, were <0.001 for muscle; 0.01 and 0.04 for epididymal and retroperitoneal fat, respectively; and 0.46 for heart. The data show that 7 weeks of dietary ursolic acid increased skeletal muscle weight in a dose-dependent manner, with a peak effect at 0.14% ursolic acid. Interestingly, although ursolic acid increased muscle weight, it did not increase total body weight (FIG. 10B; P-values were 0.71 and 0.80 for initial and final weights, respectively).

The data in FIG. 10A also show that 7 weeks of dietary ursolic acid reduced the weight of epididymal and retroperitoneal fat depots, with a peak effect at 0.14%. In another study, mice were provided ad lib access to either standard chow (control diet) or standard chow supplemented with 0.27% ursolic acid (ursolic acid diet) for 5 weeks. The relationship between skeletal muscle weight (quadriceps, triceps, biceps, TA, gastrocnemius and soleus) and retroperitoneal adipose weight is shown in FIG. 10C. Each data point in FIG. 10C represents one mouse; P<0.001 for both muscle and adipose by unpaired t-test. The data show that 5 weeks of ursolic acid administration (0.14%) also reduced adipose weight. Thus, muscle and fat weights were inversely related. Without wishing to be bound by a particular theory, ursolic acid-treated mice contain less fat because, in part, ursolic acid increases Akt activity (see FIGS. 8 and 9), and muscle-specific increases in Akt activity reduce adiposity as a secondary consequence of muscle hypertrophy (Lai K M, et al. (2004) *Molecular and cellular biology* 24(21):9295-9304; Izumiya Y, et al. (2008) *Cell metabolism* 7(2):159-172).

Ursolic acid reduced adipose weight by reducing adipocyte size as shown by data in FIGS. 10D-10F. FIG. 10D shows a representative H&E stain of retroperitoneal fat for animals feed a control data or a chow with 0.27% ursolic acid as indicated. The data in FIG. 10D are shown quantitatively in FIG. 10E in terms of adipocyte diameter, where data point represents the average diameter of ≥125 retroperitoneal adipocytes from one mouse. The retroperitoneal adipocyte size distribution. Each distribution represents combined adipocyte measurements (>1000 per diet) from FIG. 10E.

Figure 11:
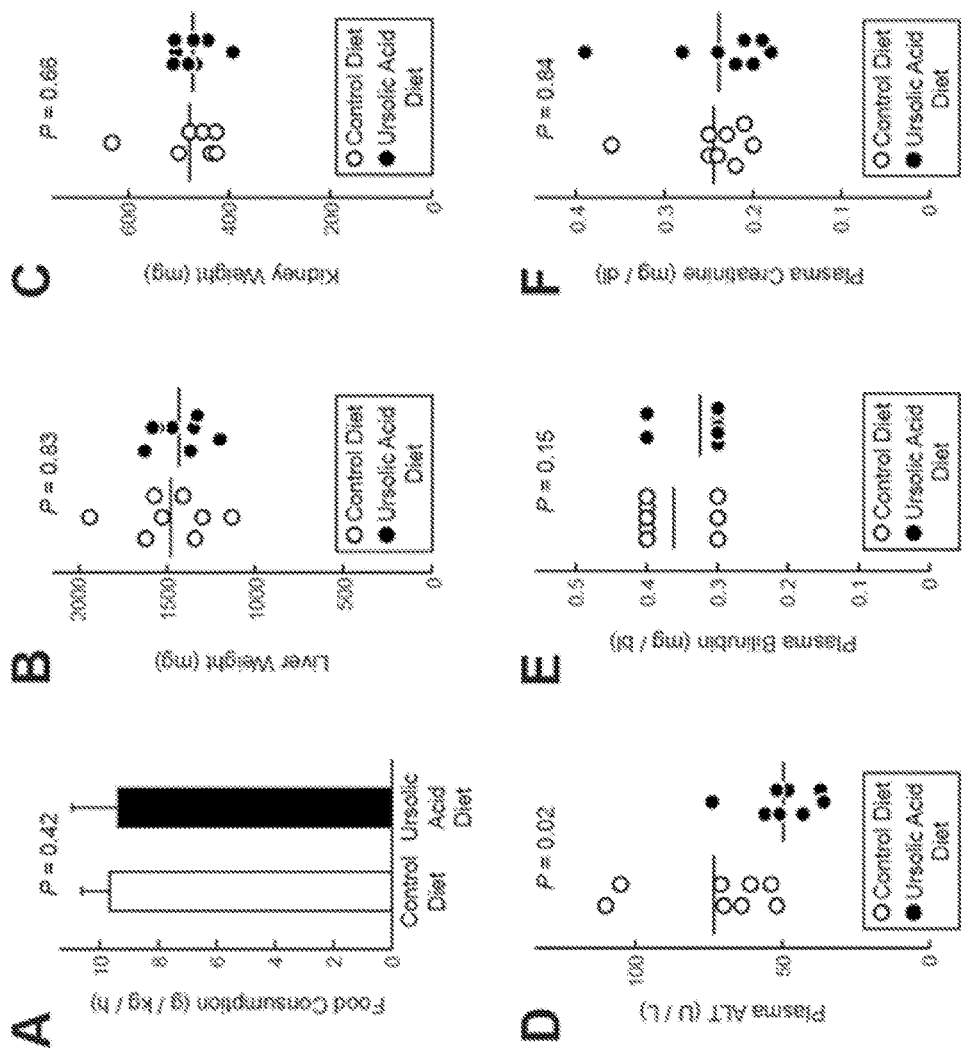
FIG. 11 shows representative data on the effect of ursolic acid on food consumption, liver weight, kidney weight, and plasma ALT, bilirubin, and creatinine concentrations.

The changes in adipocyte size were accompanied by a significant reduction in plasma leptin levels, which correlated closely with adipose weight (see FIGS. 10G and 10H). In FIG. 10G, each data point represents one mouse, and horizontal bars denote the means. P-values were determined by t-test. In FIG. 10H, each data point represents one mouse. Importantly, ursolic acid also significantly reduced plasma triglyceride (FIG. 10I) and cholesterol (FIG. 10J). In FIGS. 10I and 10J, each data point represents one mouse, and horizontal bars denote the means. P-values were determined by unpaired t-test. Although ursolic acid reduced leptin, it did not alter food intake (FIG. 11A). In this study, mice were provided ad lib access to either standard chow (control diet) or standard chow supplemented with 0.27% ursolic acid (ursolic acid diet) for 4 weeks. Mice were then moved to a comprehensive animal metabolic monitoring system (CLAMS; Columbus Instruments, Columbus, Ohio) and provided with ad lib access to the same diets. Food consumption was measured for 48 hours. Data are means±SEM from 6 mice per group. However, ursolic acid did not alter weights of heart (FIG. 10A), liver or kidney (FIGS. 11B and 11C), nor did it elevate plasma markers of hepatotoxicity or nephrotoxicity (alanine aminotransferase, bilirubin and creatinine; see FIGS. 11D-11F). The data in FIGS. 11B-11F were obtained as follows: mice were provided ad lib access to either standard chow (control diet) or standard chow supplemented with 0.27% ursolic acid (ursolic acid diet) for 5 weeks before tissues and plasma were harvested for the indicated measurements; each data point represents one mouse, and horizontal bars denote the means. For FIG. 11, P-values were determined with unpaired t-tests. Thus, dietary ursolic acid had two major effects: skeletal muscle hypertrophy and reduced adiposity.

10. Ursolic Acid Reduces Weight Gain and White Adipose Tissue.

Figure 12:
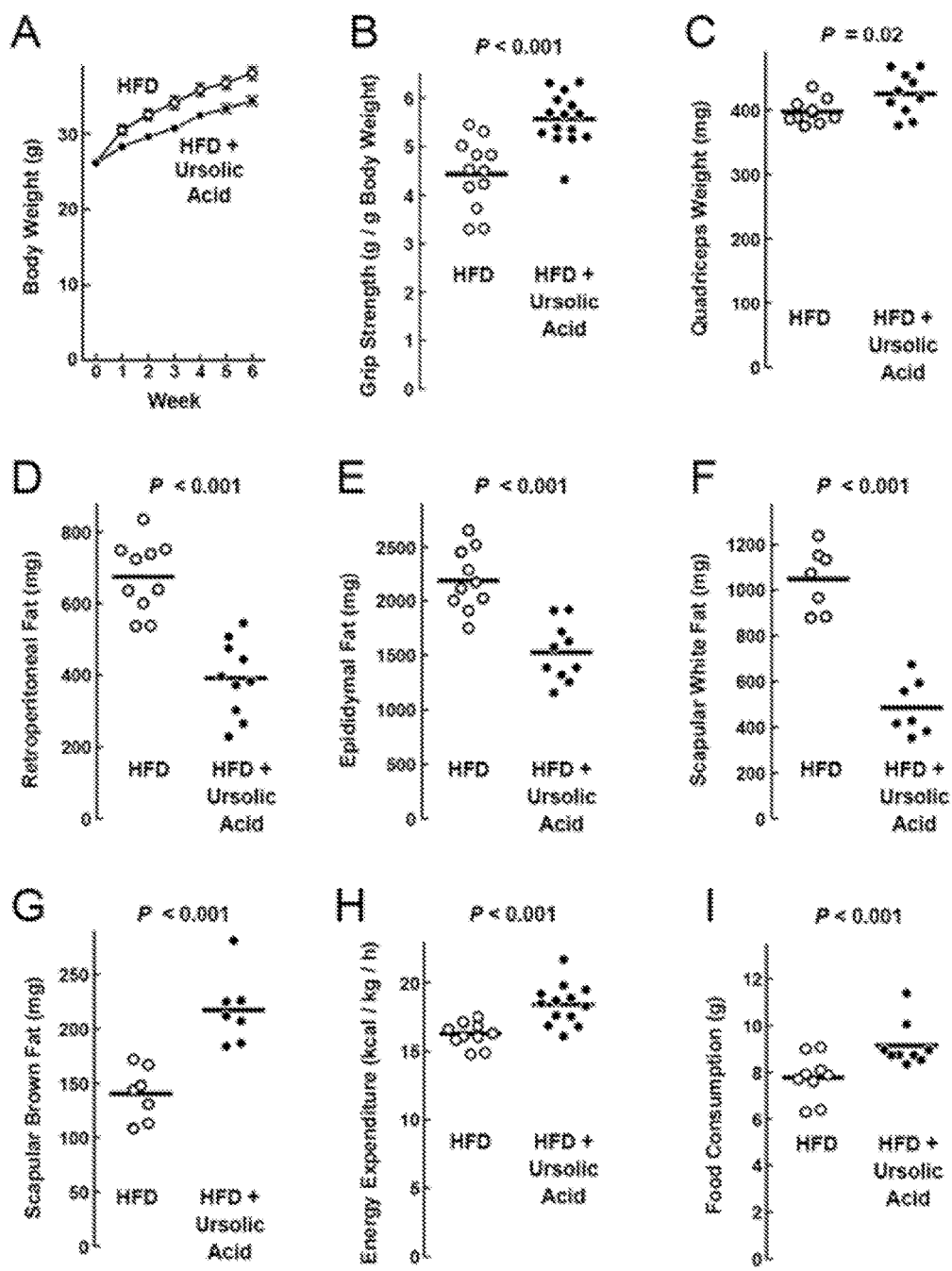
FIG. 12 shows representative data on the effect of ursolic acid on weight gain, white adipose tissue weight, skeletal muscle weight, brown adipose tissue weight and energy expenditure in a mouse model of obesity and metabolic syndrome.

The findings that ursolic acid increased skeletal muscle and decreased adiposity suggested that ursolic acid might increase energy expenditure, which would lead to obesity resistance. To test this, C57BL/6 mice were given ad libitum access to a high fat diet (HFD; Teklad TD.93075; 55% calories from fat) lacking or containing 0.27% ursolic acid. After 7 weeks, mice from each group were studied for three days in comprehensive lab animal monitoring systems ("CLAMS"; Columbus Instruments). In the CLAMS, mice were maintained on the same diet they had been eating since the beginning of the experiment. Following CLAMS, tissues were harvested for analysis. In high fat-fed mice, ursolic acid dramatically reduced weight gain, and this effect was apparent within one week (FIG. 12A). As previously observed in mice fed ursolic acid and standard chow (FIG. 6), ursolic acid increased grip strength and muscle mass (FIGS. 12B and 12C). Moreover, ursolic acid reduced retroperitoneal and epididymal fat (FIGS. 12D and 12E). Interestingly, in the scapular fat pad, which contains a mixture of white and thermogenic brown fat, ursolic acid reduced white fat (FIG. 12F), but increased brown fat (FIG. 12G). Importantly, increased skeletal muscle and brown adipose tissue would be predicted to increase energy expenditure. Indeed, CLAMS revealed that ursolic acid increased energy expenditure (FIG. 12H), providing an explanation for how ursolic acid reduces adiposity and obesity. Remarkably, CLAMS analysis revealed that ursolic acid-treated mice consumed more food (FIG. 12I), even though they gained less weight (FIG. 12A). For the data shown in FIG. 12A, data are means±SEM from 12 control mice and 15 treated mice, but it should be noted that some error bars are too small to see; P<0.01 at 1 wk and each subsequent time point. In FIGS. 12B-12I, each data point represents one mouse and horizontal bars denote the means. P-values were determined with unpaired t-tests.

11. Ursolic Acid Reduces Obesity-Related Pre-Diabetes, Diabetes, Fatty Liver Disease and Hypercholesterolemia.

Figure 13:
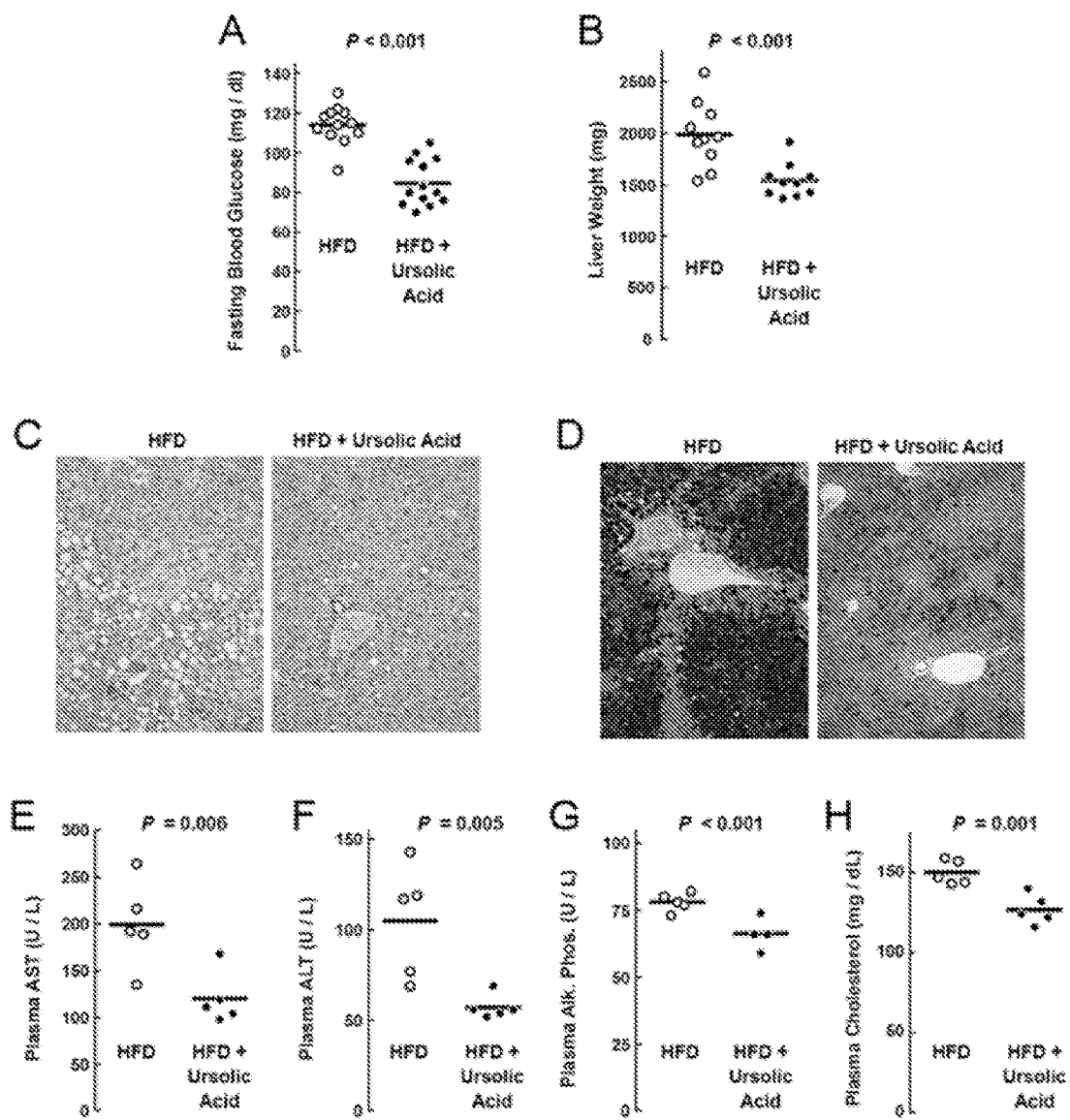
FIG. 13 shows representative data on the effect of ursolic acid on obesity-related pre-diabetes, diabetes, fatty liver disease and hyperlipidemia in a mouse model of obesity and metabolic syndrome.

The study was carried out as follows: C57BL/6 mice were given ad libitum access to a high fat diet ("HFD"; Teklad TD.93075; 55% calories from fat) lacking or containing 0.27% ursolic acid. After 5 weeks, mice were fasted for 16 h before blood glucose was measured via the tail vein (FIG. 13A). Normal fasting blood glucose: ≤100 mg/dl. (B-I) After 7 weeks, liver and plasma were harvested for analysis (FIGS. 13B-13I). The data shown in FIG. 13A suggest that most mice fed HFD without ursolic acid for 6 weeks developed impaired fasting glucose (pre-diabetes) or diabetes. Importantly, this was prevented by ursolic acid (FIG. 13A). In addition, mice fed HFD without ursolic acid developed fatty liver disease, as evidenced by increased liver weight (>30% increase above normal mouse liver weight of 1500 mg; FIG. 13B), hepatocellular lipid accumulation (FIG. 13C, H&E stain at 20× magnification; FIG. 13D, lipid-staining osmium at 10× magnification), and elevated plasma liver function tests (FIG. 13E, AST; 13F, ALT; 13G, alkaline phosphatase (labeled as "Alk. Phos. in figure); and, 13H, cholesterol). However, ursolic acid prevented all of these hepatic changes (FIG. 13B-13G). In addition, ursolic acid reduced obesity-related hypercholesterolemia (FIG. 13H). In FIGS. 13A, 13B, and 13E-13H, each data point represents one mouse and horizontal bars denote the means.

12. Oleanolic Acid does not Increase Skeletal Muscle Mass.

The effect of ursolic acid on skeletal muscle weight and liver weight was compared to the effects by oleanolic acid and metformin. Metformin was a compound identified from atrophy signature-1, but not atrophy signature-2. Oleanolic acid, like ursolic acid is a pentacyclic acid triterpane. This is a structurally similar compound to ursolic acid. However, the two compounds are distinct: oleanolic acid has two methyl groups at position 20, whereas ursolic acid has a single methyl group at each of positions 19 and 20 (compare FIGS. 14A and 14D). Both ursolic acid and oleanolic acid reduce blood glucose, adiposity and hepatic steatosis (Wang Z H, et al. (2010) *European journal of pharmacology* 628(1-3):255-260; Jayaprakasam B, et al. (2006) *J Agric Food Chem* 54(1):243-248; de Melo C L, et al. (2010) *Chem Biol Interact* 185(1):59-65). In addition, both ursolic acid and oleanolic acid possess a large number of cellular effects and biochemical targets, including nearly equivalent inhibition of protein tyrosine phosphatases ("PTPs"; see Zhang W, et al. (2006) *Biochimica et biophysica acta* 1760(10):1505-1512; Qian S, et al. (2010) *J Nat Prod* 73(11):1743-1750; Zhang Y N, et al. (2008) *Bioorg Med Chem* 16(18):8697-8705). However, the effects of these compounds on skeletal muscle mass were not known.

Because some PTPs (particularly PTP1B) dephosphorylate (inactivate) the insulin receptor, PTP inhibition represented a potential mechanism to explain ursolic acid-mediated enhancement of insulin signaling. Thus, because oleanolic acid and ursolic acid inhibit PTP1B and other PTPs with similar efficacy and potency in vitro (Qian S, et al. (2010) *Nat Prod* 73(11):1743-1750; Zhang Y N, et al. (2008) *Bioorg Med Chem* 16(18):8697-8705), testing oleanolic acid's effects on skeletal mass tests the potential role of PTP inhibition. It should be noted that neither ursolic acid nor oleanolic acid is known to inhibit PTPs in vivo, and neither of these compounds are known to enhance IGF-I signaling. Moreover, ursolic acid's capacity to inhibit PTPs has been disputed based on ursolic acid's failure to delay insulin receptor de-phosphorylation in cultured cells (Jung S H, et al. (2007) *The Biochemical journal* 403(2):243-250), and ursolic acid's capacity to act as an insulin mimetic (Jung S H, et al. (2007) *The Biochemical journal* 403(2):243-250). In addition, global and muscle-specific PTP1B knockout mice do not possess increased muscle mass, although they are resistant to obesity and obesity-related disorders(Delibegovic M, et al. (2007) *Molecular and cellular biology* 27(21):7727-7734; Klaman L D, et al. (2000) *Molecular and cellular biology* 20(15):5479-5489). Furthermore, ursolic acid increases pancreatic beta cell mass and serum insulin levels in vivo, perhaps via its anti-inflammatory effects (Wang Z H, et al. (2010) *European journal of pharmacology* 628(1-3):255-260; Jayaprakasam B, et al. (2006) *J Agric Food Chem* 54(1):243-248; de Melo C L, et al. (2010) *Chem Biol Interact* 185(1):59-65). Importantly, inflammation is now recognized as a central pathogenic mechanism in muscle atrophy, metabolic syndrome, obesity, fatty liver disease and type 2 diabetes. Thus, the existing data suggest at least four mechanisms to explain ursolic acid's capacity to increase insulin signaling in vivo: PTP inhibition, direct stimulation of the insulin receptor, increased insulin production, and reduced inflammation. Of these four potential mechanisms, only the latter three have been demonstrated in vivo.

Figure 14:
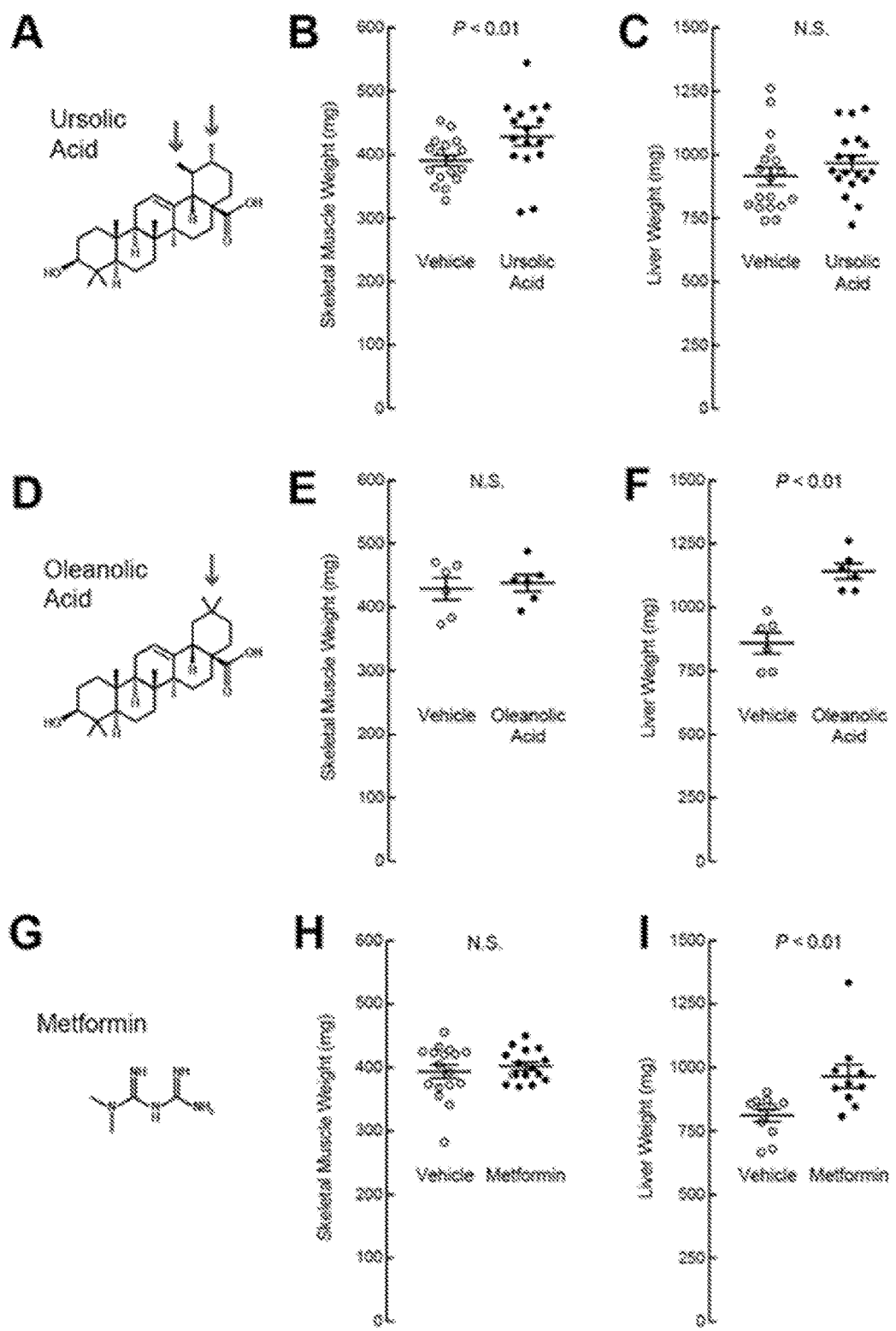
FIG. 14 shows representative data on the effect of oleanolic acid on skeletal muscle mass.

To compare the effects of ursolic acid and oleanolic acid on skeletal muscle and liver weight, C57BL/6 mice were administered ursolic acid (200 mg/kg), oleanolic acid (200 mg/kg), or vehicle alone (corn oil) via i.p. injection. Mice were then fasted, and after 12 hours of fasting, mice received a second dose of ursolic acid, oleanolic acid, or vehicle. After 24 hours of fasting, lower hindlimb skeletal muscles and liver were harvested and weighed. As shown previously, ursolic acid increased skeletal muscle weight (FIG. 14B), but not liver weight (FIG. 14C). In contrast, oleanolic acid increased liver weight (FIG. 14F), but not skeletal muscle weight (FIG. 14E). Interestingly, metformin (250 mg/kg) resembled oleanolic acid in biological effect: it increased liver weight (FIG. 14I), but not muscle weight (FIG. 14H). Without wishing to be bound by a particular theory, ursolic acid increases skeletal muscle and inhibit muscle atrophy by a pathway that does not involve PTP inhibition.

13. Targeted Inhibition of PTP1B does not Induce Skeletal Muscle Hypertrophy.

To further rule out the potential role of PTP1B inhibition in skeletal muscle hypertrophy, PTP1B expression was specifically reduced in mouse skeletal muscle by transfecting plasmid DNA constructed to express RNA interference constructs. Briefly, C57BL/6 mouse tibialis anterior muscles were transfected with 20 µg pCMV-miR-control (control plasmid transfected in the left TA) or either 20 µg pCMV-miR-PTP1B #1 (encoding miR-PTP1B #1; transfected in the right TA) or 20 µg pCMV-miR-PTP1B #2 (encoding miR-PTP1B #2; transfected in the right TA). miR-PTP1B #1 and miR-PTP1B #2 encode two distinct RNA interference (RNAi) constructs targeting distinct regions of PTP1B mRNA. Tissue was harvested 10 days following transfection.

Figure 15:
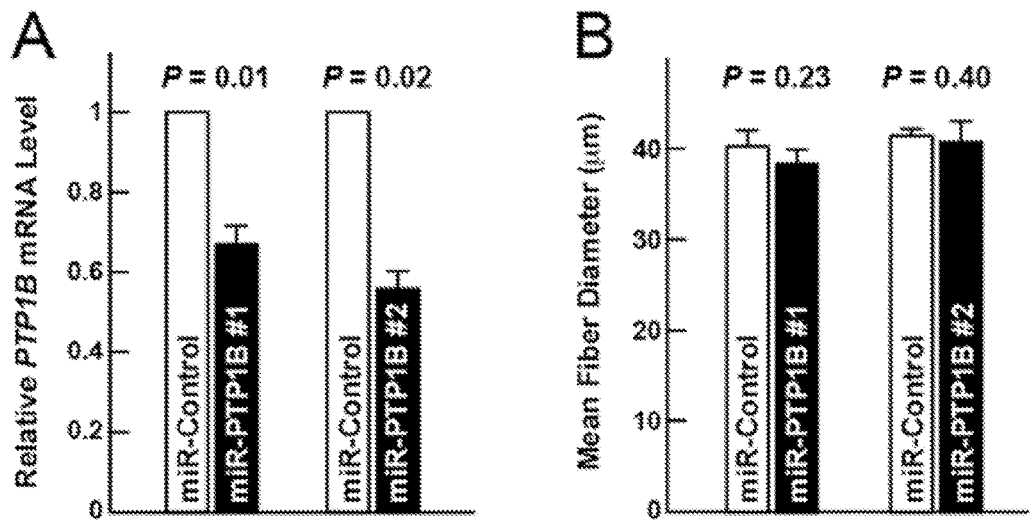
FIG. 15 shows representative data on the effect of targeted inhibition of PTP1B on skeletal muscle growth.

Of note with regard to FIG. 15A, mRNA measurements were taken from the entire TA muscle. Because electroporation transfects only a portion of muscle fibers, the data underestimate PTP1B knockdown in transfected muscle fibers. In FIG. 15A, mRNA levels in the right TA were normalized to levels in the left TA, which were set at 1; data are means±SEM from 3 mice. In FIG. 15B, in each TA muscle, the mean diameter of >300 transfected fibers was determined; data are means±SEM from 3 TA muscles per condition. For both FIGS. 15A and 15B, P-values were determined with one-tailed paired t-tests.

Although both miR-PTP1B constructs reduced PTP1B mRNA (FIG. 15A), neither increased skeletal muscle fiber diameter (FIG. 15B). These data demonstrate that targeted PTP1B inhibition does not cause muscle fiber hypertrophy. Without wishing to be bound by a particular theory, ursolic acid does not increase skeletal muscle by inhibiting PTP1B.

14. Ursolic Acid Serum Levels Associated with Increased Muscle Mass and Decreased Adiposity.

Figure 16:
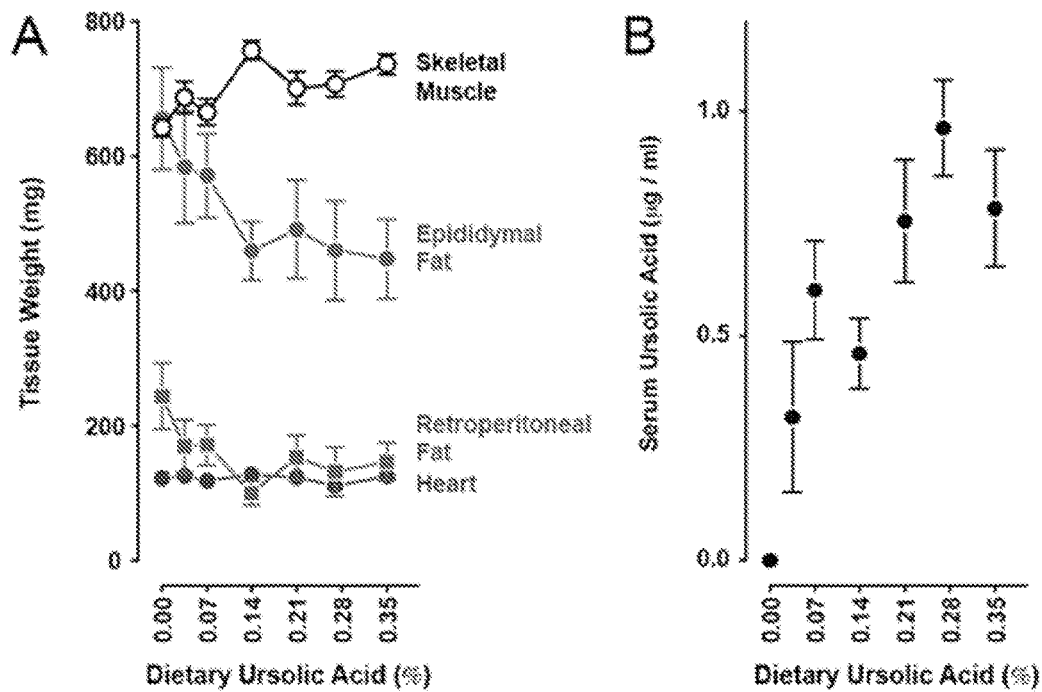
FIG. 16 shows representative data on the effect of ursolic acid serum concentration on muscle mass and adiposity.

To determine the dose-response relationship between dietary ursolic acid and muscle and adipose weight, C57BL/6 mice were fed standard chow containing varying amounts of ursolic acid for 7 weeks. Serum ursolic acid levels from mice were determined as described above. As shown previously in FIG. 10A, ursolic acid increased skeletal muscle weight and decreased weight of retroperitoneal and epididymal fat pads in a dose-dependent manner, but did not alter heart weight (FIG. 16A; data are means±SEM). These effects of ursolic acid were discernable at 0.035% ursolic acid and were maximal at doses ≥0.14% ursolic acid. Serum was collected from these same mice at the time of necropsy, and then measured random serum ursolic acid levels via ultra high performance liquid chromatography (UPLC). The data indicate that ursolic acid serum levels in the range of 0.25-0.5 µg/ml are sufficient to increase muscle mass and decrease adiposity (FIG. 16B; data are means±SEM). Of note, 0.5 µg/ml equals 1.1 µM ursolic acid, close to the dose used in the Connectivity Map (8.8 µM) and in the C2C12 experiments (10 µM) described above.

The data described herein indicate that ursolic acid reduced muscle atrophy and stimulated muscle hypertrophy in mice. Importantly, ursolic acid's effects on muscle were accompanied by reductions in adiposity, fasting blood glucose and plasma leptin, cholesterol and triglycerides, as well as increases in the ratio of skeletal muscle to fat, the amount of brown fat, the ratio of brown fat to white fat, and increased energy expenditure. Without wishing to be bound by a particular theory, ursolic acid reduced muscle atrophy and stimulated muscle hypertrophy by enhancing skeletal muscle IGF-I expression and IGF-I signaling, and inhibiting atrophy-associated skeletal muscle mRNA expression.

All of the compositions and/or methods disclosed and claimed herein can be made and executed without undue experimentation in light of the present disclosure. It will be apparent to those skilled in the art that various modifications and variations can be made in the present invention without departing from the scope or spirit of the invention.

More specifically, certain agents which are both chemically and physiologically related can be substituted for the agents described herein while the same or similar results can be achieved. All such similar substitutes and modifications apparent to those skilled in the art are deemed to be within the spirit, scope and concept of the invention as defined by the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

G. REFERENCES

The following references, to the extent that they provide exemplary procedural or other details supplementary to those set forth herein, are specifically incorporated herein by reference.

1. Bodine S C, et al. (2001) Akt/mTOR pathway is a crucial regulator of skeletal muscle hypertrophy and can prevent muscle atrophy in vivo. *Nat Cell Biol* 3(11):1014-1019.
2. Sandri M, et al. (2004) Foxo transcription factors induce the atrophy-related ubiquitin ligase atrogin-1 and cause skeletal muscle atrophy. *Cell* 117(3):399-412.
3. Stitt T N, et al. (2004) The IGF-1/PI3K/Akt pathway prevents expression of muscle atrophy-induced ubiquitin ligases by inhibiting FOXO transcription factors. *Mol Cell* 14(3):395-403.
4. Hu Z, et al. (2009) Endogenous glucocorticoids and impaired insulin signaling are both required to stimulate muscle wasting under pathophysiological conditions in mice. *The Journal of clinical investigation* 119(10):3059-3069.
5. Dobrowolny G, et al. (2005) Muscle expression of a local Igf-1 isoform protects motor neurons in an ALS mouse model. *The Journal of cell biology* 168(2):193-199.
6. Kandarian S C & Jackman R W (2006) Intracellular signaling during skeletal muscle atrophy. *Muscle & nerve* 33(2):155-165.
7. Hirose M, et al. (2001) Long-term denervation impairs insulin receptor substrate-1-mediated insulin signaling in skeletal muscle. *Metabolism: clinical and experimental* 50(2):216-222.
8. Pallafacchina G, et al. (2002) A protein kinase B-dependent and rapamycin-sensitive pathway controls skeletal muscle growth but not fiber type specification. *Proceedings of the National Academy of Sciences of the United States of America* 99(14):9213-9218.
9. Sandri M (2008) Signaling in muscle atrophy and hypertrophy. *Physiology* (Bethesda) 23:160-170.
10. Glass DJ (2005) Skeletal muscle hypertrophy and atrophy signaling pathways. *The international journal of biochemistry & cell biology* 37(10):1974-1984.
11. Lecker S H, et al. (2004) Multiple types of skeletal muscle atrophy involve a common program of changes in gene expression. *Faseb J* 18(1):39-51.
12. Sacheck J M, et al. (2007) Rapid disuse and denervation atrophy involve transcriptional changes similar to those of muscle wasting during systemic diseases. *Faseb J* 21(1): 140-155.
13. Jagoe R T, et al. (2002) Patterns of gene expression in atrophying skeletal muscles: response to food deprivation. *Faseb J* 16(13):1697-1712.
14. Sandri M, et al. (2006) PGC-1alpha protects skeletal muscle from atrophy by suppressing FoxO3 action and atrophy-specific gene transcription. *Proceedings of the National Academy of Sciences of the United States of America* 103(44):16260-16265.
15. Wenz T, et al. (2009) Increased muscle PGC-1alpha expression protects from sarcopenia and metabolic disease during aging. *Proceedings of the National Academy of Sciences of the United States of America* 106(48): 20405-20410.
16. Bodine S C, et al. (2001) Identification of ubiquitin ligases required for skeletal muscle atrophy. *Science* (New York, N.Y. 294(5547):1704-1708.
17. Lagirand-Cantaloube J, et al. (2008) The initiation factor eIF3-f is a major target for atrogin1/MAFbx function in skeletal muscle atrophy. *The EMBO journal* 27(8):1266-1276.
18. Cohen S, et al. (2009) During muscle atrophy, thick, but not thin, filament components are degraded by MuRF1-dependent ubiquitylation. *The Journal of cell biology* 185(6):1083-1095.
19. Adams V, et al. (2008) Induction of MuRF1 is essential for TNF-alpha-induced loss of muscle function in mice. *Journal of molecular biology* 384(1):48-59.
20. Leger B, et al. (2006) Human skeletal muscle atrophy in amyotrophic lateral sclerosis reveals a reduction in Akt and an increase in atrogin-1. *Faseb J* 20(3):583-585.
21. Doucet M, et al. (2007) Muscle atrophy and hypertrophy signaling in patients with chronic obstructive pulmonary disease. *American journal of respiratory and critical care medicine* 176(3):261-269.
22. Levine S, et al. (2008) Rapid disuse atrophy of diaphragm fibers in mechanically ventilated humans. *The New England journal of medicine* 358(13):1327-1335.
23. Adams C M, et al. (2011) Altered mRNA expression after long-term soleus electrical stimulation training in humans with paralysis. *Muscle & nerve* 43(1):65-75.
24. Ebert S M, et al. (2010) The transcription factor ATF4 promotes skeletal myofiber atrophy during fasting. *Molecular endocrinology* 24(4):790-799.
25. Lamb J, et al. (2006) The Connectivity Map: using gene-expression signatures to connect small molecules, genes, and disease. *Science* (New York, N.Y. 313(5795): 1929-1935.
26. Frighetto R T S, et al. (2008) Isolation of ursolic acid from apple peels by high speed counter-current chromatography. *Food Chemistry* 106:767-771.
27. Liu J (1995) Pharmacology of oleanolic acid and ursolic acid. *Journal of ethnopharmacology* 49(2):57-68.
28. Liu J (2005) Oleanolic acid and ursolic acid: research perspectives. *Journal of ethnopharmacology* 100(1-2):92-94.
29. Wang Z H, et al. (2010) Anti-glycative effects of oleanolic acid and ursolic acid in kidney of diabetic mice. *European journal of pharmacology* 628(1-3):255-260.
30. Jang S M, et al. (2009) Ursolic acid enhances the cellular immune system and pancreatic beta-cell function in streptozotocin-induced diabetic mice fed a high-fat diet. *Int Immunopharmacol* 9(1):113-119.
31. Jung S H, et al. (2007) Insulin-mimetic and insulin-sensitizing activities of a pentacyclic triterpenoid insulin receptor activator. *The Biochemical journal* 403(2):243-250.
32. Zhang W, et al. (2006) Ursolic acid and its derivative inhibit protein tyrosine phosphatase 1B, enhancing insulin receptor phosphorylation and stimulating glucose uptake. *Biochimica et biophysica acta* 1760(10): 1505-1512.
33. Goldstein B J, et al. (2000) Tyrosine dephosphorylation and deactivation of insulin receptor substrate-1 by protein-tyrosine phosphatase 1B. Possible facilitation by the formation of a ternary complex with the Grb2 adaptor protein. *The Journal of biological chemistry* 275(6):4283-4289.
34. Delibegovic M, et al. (2007) Improved glucose homeostasis in mice with muscle-specific deletion of protein-tyrosine phosphatase 1B. *Molecular and cellular biology* 27(21):7727-7734.
35. Zabolotny J M, et al. (2004) Transgenic overexpression of protein-tyrosine phosphatase 1B in muscle causes insulin resistance, but overexpression with leukocyte antigen-related phosphatase does not additively impair insulin action. *The Journal of biological chemistry* 279(23): 24844-24851.
36. Sivakumar G, et al. (2009) Plant-based corosolic acid: future anti-diabetic drug? *Biotechnol J* 4(12):1704-1711.
37. Ebert S M, et al. (2010) The transcription factor ATF4 promotes skeletal myofiber atrophy during fasting. *Molecular Endocrinology* 24(4):790-799.
38. Dubowitz V, et al. (2007) *Muscle biopsy: a practical approach* (Saunders Elsevier, Philadelphia) 3rd Ed pp XIII, 611 s.
39. Hishiya A, et al. (2006) A novel ubiquitin-binding protein ZNF216 functioning in muscle atrophy. *The EMBO journal* 25(3):554-564.
40. Adams C M, et al. (2011) Altered mRNA expression after long-term soleus electrical stimulation training in humans with paralysis. *Muscle Nerve.* 43(1):65-75
41. Hameed M, et al. (2004) The effect of recombinant human growth hormone and resistance training on IGF-I mRNA expression in the muscles of elderly men. *The Journal of physiology* 555(Pt 1):231-240.
42. Adams G R & Haddad F (1996) The relationships among IGF-1, DNA content, and protein accumulation during skeletal muscle hypertrophy. *J Appl Physiol* 81(6):2509-2516.
43. Gentile M A, et al. (2010) Androgen-mediated improvement of body composition and muscle function involves a novel early transcriptional program including IGF1, mechano growth factor, and induction of {beta}-catenin. *Journal of molecular endocrinology* 44(1):55-73.
44. Shavlakadze T, et al. (2005) Insulin-like growth factor I slows the rate of denervation induced skeletal muscle atrophy. *Neuromuscul Disord* 15(2):139-146.
45. Sacheck J M, et al. (2004) IGF-I stimulates muscle growth by suppressing protein breakdown and expression of atrophy-related ubiquitin ligases, atrogin-1 and MuRF1. *Am J Physiol Endocrinol Metab* 287 (4):E591-601.
46. Frost R A, et al. (2009) Regulation of REDD1 by insulin-like growth factor-I in skeletal muscle and myotubes. *J Cell Biochem* 108(5):1192-1202.
47. Lee SJ (2004) Regulation of muscle mass by myostatin. *Annu Rev Cell Dev Biol* 20:61-86.
48. Dupont J, et al. (2001) Insulin-like growth factor 1 (IGF-1)-induced twist expression is involved in the anti-apoptotic effects of the IGF-1 receptor. *The Journal of biological chemistry* 276(28):26699-26707.
49. Tureckova J, et al. (2001) Insulin-like growth factor-mediated muscle differentiation: collaboration between phosphatidylinositol 3-kinase-Akt-signaling pathways and myogenin. *The Journal of biological chemistry* 276 (42):39264-39270.
50. Yakar S, et al. (1999) Normal growth and development in the absence of hepatic insulin-like growth factor I. *Proceedings of the National Academy of Sciences of the United States of America* 96(13):7324-7329.
51. Adams G R, et al. (1999) Time course of changes in markers of myogenesis in overloaded rat skeletal muscles. *J Appl Physiol* 87(5):1705-1712.
52. Lai K M, et al. (2004) Conditional activation of akt in adult skeletal muscle induces rapid hypertrophy. *Molecular and cellular biology* 24(21):9295-9304.
53. Izumiya Y, et al. (2008) Fast/Glycolytic muscle fiber growth reduces fat mass and improves metabolic parameters in obese mice. *Cell metabolism* 7(2):159-172.
54. Jayaprakasam B, et al. (2006) Amelioration of obesity and glucose intolerance in high-fat-fed C57BL/6 mice by anthocyanins and ursolic acid in Cornelian cherry (*Cornus mas*). *J Agric Food Chem* 54(1):243-248.
55. de Melo C L, et al. (2010) Oleanolic acid, a natural triterpenoid improves blood glucose tolerance in normal mice and ameliorates visceral obesity in mice fed a high-fat diet. *Chem Biol Interact* 185(1):59-65.
56. Qian S, et al. (2010) Synthesis and biological evaluation of oleanolic acid derivatives as inhibitors of protein tyrosine phosphatase 1B. *J Nat Prod* 73(11):1743-1750.
57. Zhang Y N, et al. (2008) Oleanolic acid and its derivatives: new inhibitor of protein tyrosine phosphatase 1B with cellular activities. *Bioorg Med Chem* 16(18):8697-8705.
58. Klaman L D, et al. (2000) Increased energy expenditure, decreased adiposity, and tissue-specific insulin sensitivity in protein-tyrosine phosphatase 1B-deficient mice. *Molecular and cellular biology* 20(15):5479-5489.
59. Reagan-Shaw S, Nihal M, & Ahmad N (2008) Dose translation from animal to human studies revisited. *Faseb J* 22(3):659-661.
60. Barton-Davis E R, et al. (1998) Viral mediated expression of insulin-like growth factor I blocks the aging-related loss of skeletal muscle function. *Proceedings of the National Academy of Sciences of the United States of America* 95 (26): 15603-15607.
61. Musarò A, et al. (2001) Localized Igf-1 transgene expression sustains hypertrophy and regeneration in senescent skeletal muscle. *Nature Genetics* 27(2):195-200.
62. Zhou X, et al. (2010) Reversal of cancer cachexia and muscle wasting by ActRIIB antagonism leads to prolonged survival. *Cell* 142(4):531-43.

What is claimed is:

1. A method for increasing skeletal muscle mass in an animal, the method comprising administering to the animal ursolic acid, or a pharmaceutically acceptable salt, hydrate, or solvate thereof, wherein said animal is selected from the group consisting of a primate, domesticated fish, domesticated crustacean, domesticated mollusk, poultry, rabbit, dog, cat, and livestock.

2. The method of claim 1, wherein the ursolic acid or pharmaceutically acceptable salt, hydrate, or solvate thereof is administered to the animal in an amount of greater than or equal to 100 mg per day.

3. The method of claim 1, wherein the animal is a mammal.

4. The method of claim 1, wherein the animal is a human.

5. The method of claim 1, wherein the animal is selected from the group consisting of a dog, cat, pig, cow, horse, goat, bison, sheep, chicken, turkey, duck, goose, and domesticated fish.

6. The method of claim 1, wherein the ursolic acid is present as a pharmaceutically acceptable salt selected from salts derived from aluminum, ammonium, calcium, copper (-ic and -ous), ferric, ferrous, lithium, magnesium, manganese, potassium, sodium, or zinc; salts of primary, secondary, and tertiary amines; and salts derived from arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholinc, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, or tromethamine.

7. The method of claim 1, wherein the ursolic acid or pharmaceutically acceptable salt, hydrate, or solvate thereof is administered to the animal in an amount of greater than 200 mg per day.

8. The method of claim 1, wherein the ursolic acid or pharmaceutically acceptable salt, hydrate, or solvate thereof is administered to the animal in an amount of greater than 300 mg per day.

9. The method of claim 1, wherein the ursolic acid or pharmaceutically acceptable salt, hydrate, or solvate thereof is administered to the animal in an amount of greater than 400 mg per day.

10. The method of claim 1, wherein the ursolic acid or pharmaceutically acceptable salt, hydrate, or solvate thereof is administered to the animal in an amount of greater than 500 mg per day.

11. The method of claim 1, wherein the ursolic acid or pharmaceutically acceptable salt, hydrate, or solvate thereof is administered to the animal in an amount of greater than 750 mg per day.

12. The method of claim 1, wherein the ursolic acid or pharmaceutically acceptable salt, hydrate, or solvate thereof is administered to the animal in an amount of greater than 1000 mg per day.

13. The method of claim 1, wherein the ursolic acid or pharmaceutically acceptable salt, hydrate, or solvate thereof is administered to the animal in composition that further comprises one or more adjuvants.

14. The method of claim 1, wherein the ursolic acid or pharmaceutically acceptable salt, hydrate, or solvate thereof is administered to the animal in a dosage of from about 0.1 to about 50 mg/kg per day.

15. The method of claim 4, wherein the ursolic acid or pharmaceutically acceptable salt, hydrate, or solvate thereof is administered to the animal in a dosage of from about 0.1 to about 50 mg/kg per day.

16. The method of claim 7, wherein the ursolic acid or pharmaceutically acceptable salt, hydrate, or solvate thereof is administered to the animal in a dosage of from about 0.1 to about 50 mg/kg per day.

17. The method of claim 1, wherein the ursolic acid or pharmaceutically acceptable salt, hydrate, or solvate thereof is administered to the animal in a composition that further comprises a preservative.

18. The method of claim 17, wherein the ursolic acid or pharmaceutically acceptable salt, hydrate, or solvate thereof is administered to the animal in an amount of greater than or equal to 2100 mg per day.

19. The method of claim 17, wherein the animal is selected from a domesticated fish, poultry, pig, cow, horse, goat, bison, sheep, dog, cat, and bison.

20. The method of claim 18, wherein the animal is selected from a domesticated fish, poultry, pig, cow, horse, goat, bison, sheep, dog, cat, and bison.

* * * * *

UNITED STATES PATENT AND TRADEMARK OFFICE
CERTIFICATE OF CORRECTION

PATENT NO. : 9,856,204 B2
APPLICATION NO. : 13/698645
DATED : January 2, 2018
INVENTOR(S) : Adams et al.

It is certified that error appears in the above-identified patent and that said Letters Patent is hereby corrected as shown below:

In the Claims

Column 202, Line 21: Claim 18, Delete "equal to 2100 mg per day" and insert -- equal to 100 mg per day --

Signed and Sealed this
First Day of May, 2018

Andrei Iancu
*Director of the United States Patent and Trademark Office*